US011434502B2

(12) United States Patent
Sah et al.

(10) Patent No.: US 11,434,502 B2
(45) Date of Patent: Sep. 6, 2022

(54) TREATMENT OF AMYOTROPHIC LATERAL SCLEROSIS (ALS)

(71) Applicant: VOYAGER THERAPEUTICS, INC., Cambridge, MA (US)

(72) Inventors: Dinah Wen-Yee Sah, Hopkinton, MA (US); Qingmin Chen, Belmont, MA (US); Holger Patzke, Cambridge, MA (US); Jinzhao Hou, Cambridge, MA (US)

(73) Assignee: Voyager Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/756,586

(22) PCT Filed: Oct. 16, 2018

(86) PCT No.: PCT/US2018/055999
§ 371 (c)(1),
(2) Date: Apr. 16, 2020

(87) PCT Pub. No.: WO2019/079240
PCT Pub. Date: Apr. 25, 2019

(65) Prior Publication Data
US 2020/0239912 A1    Jul. 30, 2020

Related U.S. Application Data

(60) Provisional application No. 62/572,702, filed on Oct. 16, 2017.

(51) Int. Cl.
| | | |
|---|---|---|
| C07H 21/02 | (2006.01) | |
| C07H 21/04 | (2006.01) | |
| C12N 15/86 | (2006.01) | |
| A61P 25/28 | (2006.01) | |
| A61K 31/713 | (2006.01) | |
| C12N 15/113 | (2010.01) | |

(52) U.S. Cl.
CPC ............ *C12N 15/86* (2013.01); *A61K 31/713* (2013.01); *A61P 25/28* (2018.01); *C12N 15/113* (2013.01)

(58) Field of Classification Search
CPC .......................... C12N 15/113; C12N 2310/14
See application file for complete search history.

(56) References Cited

U.S. PATENT DOCUMENTS

| | | |
|---|---|---|
| 5,064,764 A | 11/1991 | Besnainon |
| 5,171,680 A | 12/1992 | Mullenbach et al. |
| 5,474,935 A | 12/1995 | Chatterjee |
| 5,587,308 A | 12/1996 | Carter |
| 5,652,224 A | 7/1997 | Wilson |
| 5,658,785 A | 8/1997 | Johnson |
| 5,688,676 A | 11/1997 | Zhou |
| 5,691,176 A | 11/1997 | Lebkowski |
| 5,693,531 A | 12/1997 | Chiorini |
| 5,741,683 A | 4/1998 | Zhou |
| 5,756,283 A | 5/1998 | Wilson |
| 5,856,152 A | 1/1999 | Wilson |
| 5,858,351 A | 1/1999 | Podsakoff |
| 5,858,775 A | 1/1999 | Johnson |
| 5,866,552 A | 2/1999 | Wilson |
| 5,866,696 A | 2/1999 | Carter |
| 5,871,982 A | 2/1999 | Wilson |
| 5,952,221 A | 9/1999 | Kurtzman |
| 5,962,313 A | 10/1999 | Podsakoff |
| 5,989,540 A | 11/1999 | Carter |
| 6,083,716 A | 7/2000 | Wilson |
| 6,143,548 A | 11/2000 | ORiordan |
| 6,143,567 A | 11/2000 | Van Agthoven |
| 6,146,874 A | 11/2000 | Zolotukhin |
| 6,156,303 A | 12/2000 | Russell |
| 6,174,527 B1 | 1/2001 | Wilson |
| 6,180,613 B1 | 1/2001 | Kaplitt |
| 6,194,191 B1 | 2/2001 | Zhang |
| 6,200,560 B1 | 3/2001 | Couto |
| 6,204,059 B1 | 3/2001 | Samulski |
| 6,211,163 B1 | 4/2001 | Podsakoff |
| 6,251,677 B1 | 6/2001 | Wilson |
| 6,258,595 B1 | 7/2001 | Gao |
| 6,261,551 B1 | 7/2001 | Wilson |
| 6,265,389 B1 | 7/2001 | Burke |
| 6,270,996 B1 | 8/2001 | Wilson |
| 6,274,354 B1 | 8/2001 | Wilson |
| 6,281,010 B1 | 8/2001 | Gao |
| 6,325,998 B1 | 12/2001 | Podsakoff |
| 6,335,011 B1 | 1/2002 | Podsakoff |

(Continued)

FOREIGN PATENT DOCUMENTS

| | | |
|---|---|---|
| AU | 2007201330 A1 | 4/2007 |
| CA | 2453183 A1 | 1/2003 |

(Continued)

OTHER PUBLICATIONS

Elbashir et al. (The EMBO Journal, vol. 20, No. 23, pp. 6877-6888, 2001).*
Arnold et al., ALS-linked TDP-43 mutations produce aberrant RNA splicing and adult-onset motor neuron disease without aggregation or loss of nuclear TDP-43. Proc Natl Acad Sci U S A. Feb. 19, 2013;110(8):E736-45.
Ayala et al., TDP-43 regulates retinoblastoma protein phosphorylation through the repression of cyclin-dependent kinase 6 expression. Proc Natl Acad Sci U S A. Mar. 11, 2008;105(10):3785-9.
Bali et al., Defining SOD1 ALS natural history to guide therapeutic clinical trial design. J Neurol Neurosurg Psychiatry. Feb. 2017;88(2):99-105.
Battistini et al., SOD1 mutations in amyotrophic lateral sclerosis. Results from a multicenter Italian study. J Neurol. Jul. 2005;252(7):782-8.

(Continued)

*Primary Examiner* — Amy H Bowman
(74) *Attorney, Agent, or Firm* — Nelson Mullins Riley & Scarborough LLP; Jane E. Remillard, Esq.; Cynthia L. Kanik

(57) ABSTRACT

The present invention relates to AAVs encoding a SOD1 targeting polynucleotide which may be used to treat amyotrophic lateral sclerosis (ALS) and/or canine degenerative myelopathy (DM).

16 Claims, 6 Drawing Sheets

Specification includes a Sequence Listing.

(56) References Cited

U.S. PATENT DOCUMENTS

| | | |
|---|---|---|
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,933,310 B1 | 8/2005 | Ikeda |
| 6,943,019 B2 | 9/2005 | Wilson |
| 6,953,690 B1 | 10/2005 | Gao |
| 6,984,517 B1 | 1/2006 | Chiorini |
| 6,995,006 B2 | 2/2006 | Atkinson |
| 7,015,026 B2 | 3/2006 | ORiordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,097,980 B2 | 8/2006 | Barany et al. |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,166,434 B2 | 1/2007 | Barany et al. |
| 7,169,612 B2 | 1/2007 | Kostenis |
| 7,186,552 B2 | 3/2007 | Wilson |
| 7,198,951 B2 | 4/2007 | Gao |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,312,039 B2 | 12/2007 | Barany et al. |
| 7,319,002 B2 | 1/2008 | Wilson |
| 7,320,865 B2 | 1/2008 | Barany et al. |
| 7,326,555 B2 | 2/2008 | Konz |
| 7,332,285 B2 | 2/2008 | Barany et al. |
| 7,342,111 B2 | 3/2008 | Lewin et al. |
| 7,344,872 B2 | 3/2008 | Gao |
| 7,364,858 B2 | 4/2008 | Barany et al. |
| 7,419,817 B2 | 9/2008 | Chiorini |
| 7,419,956 B2 | 9/2008 | Ohtaki |
| 7,429,453 B2 | 9/2008 | Barany et al. |
| 7,445,930 B2 | 11/2008 | Zhang |
| 7,459,547 B2 | 12/2008 | Zamore et al. |
| 7,465,583 B2 | 12/2008 | Samulski et al. |
| 7,479,554 B2 | 1/2009 | Chiorini |
| 7,491,508 B2 | 2/2009 | Roy |
| 7,498,316 B2 | 3/2009 | Xu et al. |
| 7,510,872 B2 | 3/2009 | Clark |
| 7,510,875 B2 | 3/2009 | Zhang |
| 7,556,924 B2 | 7/2009 | Barany et al. |
| 7,579,181 B2 | 8/2009 | ORiordan |
| 7,625,570 B1 | 12/2009 | Schaffer |
| 7,632,938 B2 | 12/2009 | Khvorova et al. |
| 7,638,120 B2 | 12/2009 | Liu |
| 7,662,627 B2 | 2/2010 | Johnson |
| 7,678,895 B2 | 3/2010 | Bennett et al. |
| 7,691,995 B2 | 4/2010 | Zamore et al. |
| 7,704,492 B2 | 4/2010 | Podsakoff |
| 7,704,721 B2 | 4/2010 | Wright |
| 7,732,129 B1 | 6/2010 | Zhang |
| 7,732,593 B2 | 6/2010 | Zamore et al. |
| 7,772,203 B2 | 8/2010 | Zamore et al. |
| 7,790,154 B2 | 9/2010 | Samulski et al. |
| 7,790,449 B2 | 9/2010 | Gao |
| 7,794,443 B2 | 9/2010 | Nelson et al. |
| 7,794,692 B2 | 9/2010 | Chakrabartty et al. |
| 7,803,622 B2 | 9/2010 | Engelhardt |
| 7,838,277 B2 | 11/2010 | Gao |
| 7,867,484 B2 | 1/2011 | Samulski et al. |
| 7,887,803 B2 | 2/2011 | Cashman |
| 7,888,096 B2 | 2/2011 | Wu |
| 7,892,809 B2 | 2/2011 | Bowles et al. |
| 7,893,036 B2 | 2/2011 | Zamore et al. |
| 7,901,921 B2 | 3/2011 | Coffey |
| 7,906,111 B2 | 3/2011 | Wilson |
| 7,951,784 B2 | 5/2011 | Rana et al. |
| 7,968,333 B2 | 6/2011 | Yu |
| 7,977,314 B2 | 7/2011 | Cashman |
| 8,008,271 B2 | 8/2011 | Xu et al. |
| 8,039,610 B2 | 10/2011 | Khvorova et al. |
| 8,090,542 B2 | 1/2012 | Khvorova et al. |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,173,614 B2 | 5/2012 | Burright et al. |
| 8,183,219 B2 | 5/2012 | Burright |
| 8,231,880 B2 | 7/2012 | Roy |
| 8,232,260 B2 | 7/2012 | Zamore et al. |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,304,530 B2 | 11/2012 | Zamore et al. |
| 8,309,533 B2 | 11/2012 | Xu |
| 8,309,705 B2 | 11/2012 | Zamore et al. |
| 8,318,480 B2 | 11/2012 | Gao |
| 8,318,687 B2 | 11/2012 | Tabira |
| 8,329,892 B2 | 12/2012 | Zamore et al. |
| 8,361,457 B2 | 1/2013 | Samulski et al. |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Hermens |
| 8,513,387 B2 | 8/2013 | Chakrabartty et al. |
| 8,524,219 B2 | 9/2013 | Roy |
| 8,524,446 B2 | 9/2013 | Gao |
| 8,530,438 B2 | 9/2013 | Zamore et al. |
| 8,557,785 B2 | 10/2013 | Zamore et al. |
| 8,586,554 B2 | 11/2013 | Bhanot et al. |
| 8,603,459 B2 | 12/2013 | Wilson |
| 8,614,101 B2 | 12/2013 | VanDine |
| 8,632,764 B2 | 1/2014 | Xiao et al. |
| 8,637,255 B2 | 1/2014 | Wilson |
| 8,642,314 B2 | 2/2014 | Bakker |
| 8,685,734 B2 | 4/2014 | Coffey |

(56) References Cited

U.S. PATENT DOCUMENTS

| | | |
|---|---|---|
| 8,697,417 B2 | 4/2014 | Bakker |
| 8,697,665 B2 | 4/2014 | Rom |
| 8,709,422 B2 | 4/2014 | Cashman et al. |
| 8,734,809 B2 | 5/2014 | Gao et al. |
| 8,778,885 B2 | 7/2014 | Cashman et al. |
| 8,784,799 B2 | 7/2014 | Samulski et al. |
| 8,834,863 B2 | 9/2014 | Roy |
| 8,846,030 B2 | 9/2014 | Engelhardt |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,012,224 B2 | 4/2015 | Bowles et al. |
| 9,051,542 B2 | 6/2015 | Wright |
| 9,056,892 B2 | 6/2015 | Pun |
| 9,080,183 B2 | 7/2015 | Klein |
| 9,089,667 B2 | 7/2015 | Bankiewicz |
| 9,101,645 B2 | 8/2015 | Watts |
| 9,102,943 B2 | 8/2015 | Shinmura |
| 9,102,949 B2 | 8/2015 | Gao et al. |
| 9,115,373 B2 | 8/2015 | Hermens |
| 9,163,260 B2 | 10/2015 | Wilson |
| 9,175,287 B2 | 11/2015 | Zamore et al. |
| 9,186,419 B2 | 11/2015 | Xiao et al. |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,284,357 B2 | 3/2016 | Gao et al. |
| 9,402,921 B2 | 8/2016 | Xiao et al. |
| 9,439,979 B2 | 9/2016 | Chiorini |
| 9,441,206 B2 | 9/2016 | Grieger |
| 9,441,244 B2 | 9/2016 | Schaffer |
| 9,447,433 B2 | 9/2016 | Hirsch |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,487,779 B2 | 11/2016 | Davidson |
| 9,493,788 B2 | 11/2016 | Gao |
| 9,506,083 B2 | 11/2016 | Arbetman |
| 9,528,126 B2 | 12/2016 | Qu |
| 9,539,307 B2 | 1/2017 | Kaspar |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,636,370 B2 | 5/2017 | McCown |
| 9,670,507 B2 | 6/2017 | Xiao |
| 9,677,088 B2 | 6/2017 | Nakai |
| 9,677,089 B2 | 6/2017 | Gao |
| 9,701,984 B2 | 7/2017 | Gao |
| 9,719,106 B2 | 8/2017 | Wilson |
| 9,850,487 B2 | 12/2017 | Zamore et al. |
| 10,035,825 B2 | 7/2018 | Gao et al. |
| 10,041,090 B2 | 8/2018 | Gao |
| 10,597,660 B2 | 3/2020 | Sah et al. |
| 10,689,420 B2 | 6/2020 | Gao et al. |
| 10,731,155 B2 | 8/2020 | Zamore et al. |
| 10,731,178 B2 | 8/2020 | Gao et al. |
| 10,920,227 B2 | 2/2021 | Sah et al. |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0100115 A1 | 5/2003 | Raj |
| 2003/0119191 A1 | 6/2003 | Gao |
| 2003/0138772 A1 | 7/2003 | Gao |
| 2003/0180756 A1 | 9/2003 | Shi |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0059005 A1 | 3/2005 | Tuschl |
| 2005/0130184 A1 | 6/2005 | Xu et al. |
| 2005/0255086 A1* | 11/2005 | Davidson ............ C12N 15/113 424/93.2 |
| 2005/0255487 A1 | 11/2005 | Khvorova et al. |
| 2005/0261218 A1 | 11/2005 | Esau |
| 2006/0003451 A1 | 1/2006 | Gao |
| 2006/0009402 A1 | 1/2006 | Zamore et al. |
| 2006/0041022 A1 | 2/2006 | Pasinetti |
| 2006/0204479 A1 | 9/2006 | Wilson |
| 2006/0229268 A1 | 10/2006 | Benjamin |
| 2006/0246517 A1 | 11/2006 | Cashman |
| 2007/0003977 A1 | 1/2007 | Cashman et al. |
| 2007/0004042 A1 | 1/2007 | Gao |
| 2008/0008684 A1 | 1/2008 | Wilson |
| 2008/0050343 A1 | 2/2008 | Wilson |
| 2008/0050345 A1 | 2/2008 | Wilson |
| 2008/0075737 A1 | 3/2008 | Gao |
| 2008/0113375 A1 | 5/2008 | Khvorova |
| 2009/0098151 A1 | 4/2009 | Cashman |
| 2009/0143764 A1 | 6/2009 | Nelson |
| 2009/0215871 A1 | 8/2009 | Wilson |
| 2009/0275107 A1 | 11/2009 | Lock |
| 2009/0317417 A1 | 12/2009 | Vandenberghe |
| 2010/0004320 A1 | 1/2010 | Elmen |
| 2010/0013351 A1 | 1/2010 | Gas et al. |
| 2010/0036107 A1 | 2/2010 | Clawson |
| 2010/0130594 A1 | 5/2010 | Barkats |
| 2010/0132060 A1 | 5/2010 | Burright |
| 2010/0240739 A1 | 9/2010 | Barkats |
| 2010/0247490 A1 | 9/2010 | Roy |
| 2010/0278791 A1 | 11/2010 | Wilson |
| 2010/0286378 A1 | 11/2010 | Li |
| 2011/0020816 A1 | 1/2011 | Chen |
| 2011/0039914 A1 | 2/2011 | Pavco |
| 2011/0104120 A1 | 5/2011 | Xiao et al. |
| 2011/0105517 A1 | 5/2011 | Ikeda et al. |
| 2011/0111496 A1 | 5/2011 | Li |
| 2011/0124018 A1 | 5/2011 | Cashman et al. |
| 2011/0135673 A1 | 6/2011 | Cashman |
| 2011/0136227 A1 | 6/2011 | Bakker |
| 2011/0171262 A1 | 7/2011 | Bakker |
| 2011/0223135 A1 | 9/2011 | Roy |
| 2011/0229971 A1 | 9/2011 | Knop |
| 2011/0251258 A1 | 10/2011 | Samarsky et al. |
| 2011/0263680 A1 | 10/2011 | Khvorova et al. |
| 2012/0015850 A1 | 1/2012 | Khvorova et al. |
| 2012/0046349 A1 | 2/2012 | Bell |
| 2012/0058102 A1 | 3/2012 | Wilson |
| 2012/0077212 A1 | 3/2012 | Cashman |
| 2012/0093853 A1 | 4/2012 | Wilson |
| 2012/0137379 A1 | 5/2012 | Gao |
| 2012/0258046 A1 | 10/2012 | Mutzke |
| 2012/0309050 A1 | 12/2012 | Kumon |
| 2013/0019580 A1 | 1/2013 | Anderson et al. |

(56) References Cited

U.S. PATENT DOCUMENTS

| | | |
|---|---|---|
| 2013/0023033 A1 | 1/2013 | Wilson |
| 2013/0045186 A1 | 2/2013 | Gao |
| 2013/0101558 A1 | 4/2013 | Gao |
| 2013/0171726 A1 | 7/2013 | Roelvink |
| 2013/0195801 A1 | 8/2013 | Gao |
| 2013/0225642 A1 | 8/2013 | Inoue et al. |
| 2013/0296532 A1 | 11/2013 | Hermens |
| 2013/0323226 A1 | 12/2013 | Wilson |
| 2013/0323302 A1 | 12/2013 | Constable |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia |
| 2014/0234274 A1 | 8/2014 | Xiao et al. |
| 2014/0243783 A1 | 8/2014 | Raghavan et al. |
| 2014/0335054 A1 | 11/2014 | Gao et al. |
| 2014/0335538 A1 | 11/2014 | Cashman |
| 2014/0336245 A1 | 11/2014 | Mingozzi |
| 2014/0341852 A1 | 11/2014 | Srivastava |
| 2014/0342434 A1 | 11/2014 | Hermens |
| 2014/0348822 A1 | 11/2014 | Cashman et al. |
| 2015/0005369 A1 | 1/2015 | Muzyczka |
| 2015/0023924 A1 | 1/2015 | High |
| 2015/0065562 A1 | 3/2015 | Yazicioglu |
| 2015/0111955 A1 | 4/2015 | High et al. |
| 2015/0118201 A1 | 4/2015 | Xiao et al. |
| 2015/0118287 A1 | 4/2015 | Hammond |
| 2015/0139952 A1 | 5/2015 | Webster |
| 2015/0159173 A1 | 6/2015 | Vandenberghe |
| 2015/0197751 A1 | 7/2015 | Roelvink |
| 2015/0232840 A1 | 8/2015 | Aronin |
| 2015/0238610 A1 | 8/2015 | Sista |
| 2015/0267189 A1 | 9/2015 | Angel et al. |
| 2015/0275193 A1 | 10/2015 | Angel et al. |
| 2015/0307898 A2 | 10/2015 | Hermens |
| 2015/0315610 A1 | 11/2015 | Nishie |
| 2015/0322813 A1 | 11/2015 | Tralshawala et al. |
| 2015/0374803 A1 | 12/2015 | Wolfe |
| 2016/0032319 A1 | 2/2016 | Wright |
| 2016/0102309 A1 | 4/2016 | Zamore et al. |
| 2016/0108373 A1 | 4/2016 | Bennett |
| 2016/0153992 A1 | 6/2016 | Buening |
| 2016/0166709 A1 | 6/2016 | Davidson |
| 2016/0251653 A1 | 9/2016 | Davidson |
| 2016/0264994 A1 | 9/2016 | Lawrence |
| 2016/0271192 A1 | 9/2016 | Roy |
| 2016/0272976 A1 | 9/2016 | Kaspar |
| 2016/0273058 A1 | 9/2016 | Akashika |
| 2016/0281084 A1 | 9/2016 | Davidson |
| 2016/0289275 A1 | 10/2016 | Chiorini |
| 2016/0289676 A1 | 10/2016 | Kaspar |
| 2016/0296694 A1 | 10/2016 | Bankiewicz |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0340393 A1 | 11/2016 | Schaffer |
| 2016/0340692 A1 | 11/2016 | Wang |
| 2016/0348106 A1 | 12/2016 | Harper |
| 2016/0355808 A1 | 12/2016 | Khvorova |
| 2016/0361439 A1 | 12/2016 | Agbandje-McKenna |
| 2016/0369298 A1 | 12/2016 | Marsic |
| 2016/0369299 A1 | 12/2016 | Boye |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0007669 A1 | 1/2017 | Sarkar |
| 2017/0007720 A1 | 1/2017 | Boye |
| 2017/0009304 A1 | 1/2017 | Zhuo |
| 2017/0022498 A1 | 1/2017 | Cullen |
| 2017/0028082 A1 | 2/2017 | Wilson |
| 2017/0037410 A1 | 2/2017 | Swayze |
| 2017/0044504 A1 | 2/2017 | Schaffer |
| 2017/0044530 A1 | 2/2017 | Kay |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088858 A1 | 3/2017 | Gao |
| 2017/0096646 A1 | 4/2017 | Roy |
| 2017/0105927 A1 | 4/2017 | Thorne |
| 2017/0112946 A1 | 4/2017 | Ikeda |
| 2017/0114340 A1 | 4/2017 | Mueller |
| 2017/0121734 A1 | 5/2017 | Cairns |
| 2017/0128594 A1 | 5/2017 | Wright |
| 2017/0130208 A1 | 5/2017 | Potter |
| 2017/0130245 A1 | 5/2017 | Kotin |
| 2017/0145440 A1 | 5/2017 | Hermens |
| 2017/0151348 A1 | 6/2017 | Kaspar |
| 2017/0151416 A1 | 6/2017 | Kutikov |
| 2017/0152517 A1 | 6/2017 | Barkats |
| 2017/0152525 A1 | 6/2017 | Hermens |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0216458 A1 | 8/2017 | Kaspar |
| 2017/0232117 A1 | 8/2017 | Arbetman |
| 2017/0304464 A1 | 10/2017 | Kugler |
| 2017/0306355 A1 | 10/2017 | Davidson |
| 2017/0314028 A1 | 11/2017 | Hou et al. |
| 2018/0230490 A1 | 8/2018 | O'Riordan |
| 2018/0237772 A1 | 8/2018 | Yu |
| 2018/0282732 A1 | 10/2018 | Sah et al. |
| 2018/0298380 A1 | 10/2018 | Gao |
| 2019/0169616 A1 | 6/2019 | Sah et al. |
| 2019/0194688 A1 | 6/2019 | Gao et al. |
| 2019/0194689 A1 | 6/2019 | Gao et al. |
| 2019/0276848 A1 | 9/2019 | Gao et al. |
| 2019/0276849 A1 | 9/2019 | Gao et al. |
| 2020/0123574 A1 | 4/2020 | Sah et al. |
| 2020/0149045 A1 | 5/2020 | Sah et al. |
| 2020/0157547 A1 | 5/2020 | Sah et al. |
| 2020/0199597 A1 | 6/2020 | Hou et al. |
| 2020/0237799 A1 | 7/2020 | Sah et al. |
| 2020/0239912 A1 | 7/2020 | Sah et al. |
| 2020/0270635 A1 | 8/2020 | Hou et al. |
| 2020/0377554 A1 | 12/2020 | Gao et al. |
| 2021/0139915 A1 | 5/2021 | Sah et al. |
| 2021/0163985 A1 | 6/2021 | Sah et al. |
| 2021/0230632 A1 | 7/2021 | Sah et al. |
| 2021/0254103 A1 | 8/2021 | Sah et al. |
| 2021/0361318 A1 | 11/2021 | Patzke et al. |

FOREIGN PATENT DOCUMENTS

| | | |
|---|---|---|
| CA | 3077426 A1 | 4/2019 |
| CN | 102016036 A | 4/2011 |
| EP | 1015619 A1 | 7/2000 |
| EP | 1046711 | 10/2000 |
| EP | 1078096 A1 | 2/2001 |
| EP | 1164195 | 12/2001 |
| EP | 1183380 A1 | 3/2002 |
| EP | 1218035 | 7/2002 |
| EP | 1240345 | 9/2002 |
| EP | 1279740 | 1/2003 |
| EP | 1412371 A1 | 4/2004 |
| EP | 1453547 | 9/2004 |
| EP | 1692262 B1 | 8/2006 |
| EP | 1696036 | 8/2006 |
| EP | 1847614 | 10/2007 |
| EP | 1849872 | 10/2007 |
| EP | 1857552 | 11/2007 |
| EP | 1900815 | 3/2008 |
| EP | 1944043 | 7/2008 |
| EP | 2007795 | 12/2008 |
| EP | 2164967 | 3/2010 |

(56) References Cited

FOREIGN PATENT DOCUMENTS

| | | |
|---|---|---|
| EP | 2172549 | 4/2010 |
| EP | 2198016 | 6/2010 |
| EP | 2213738 A2 | 8/2010 |
| EP | 2220241 | 8/2010 |
| EP | 2220242 | 8/2010 |
| EP | 2292779 | 3/2011 |
| EP | 2325298 | 5/2011 |
| EP | 2359866 | 8/2011 |
| EP | 2360251 | 8/2011 |
| EP | 2383346 | 11/2011 |
| EP | 2453735 | 5/2012 |
| EP | 2497500 | 9/2012 |
| EP | 2524037 | 11/2012 |
| EP | 2531604 | 12/2012 |
| EP | 2561073 A1 | 2/2013 |
| EP | 2572661 A1 | 3/2013 |
| EP | 2660325 | 11/2013 |
| EP | 2699270 | 2/2014 |
| EP | 2737071 | 6/2014 |
| EP | 2814958 | 12/2014 |
| EP | 2826860 A1 | 1/2015 |
| EP | 2871239 | 5/2015 |
| EP | 2879719 | 6/2015 |
| EP | 2906580 | 8/2015 |
| EP | 2933336 | 10/2015 |
| EP | 3058959 | 8/2016 |
| EP | 3067417 | 9/2016 |
| EP | 2176283 | 11/2016 |
| EP | 3108000 | 12/2016 |
| EP | 3117005 | 1/2017 |
| EP | 3134431 | 3/2017 |
| EP | 3168298 | 5/2017 |
| EP | 3174981 | 6/2017 |
| EP | 3209311 | 8/2017 |
| EP | 3235827 | 10/2017 |
| JP | 2013-143917 A | 7/2013 |
| WO | 1989012677 A1 | 12/1989 |
| WO | 1993009239 | 5/1993 |
| WO | 1995028493 A1 | 10/1995 |
| WO | 1995034670 | 12/1995 |
| WO | 1996017947 | 6/1996 |
| WO | 1996023810 | 8/1996 |
| WO | 1996030540 | 10/1996 |
| WO | 1997045559 A1 | 12/1997 |
| WO | 1998010088 | 3/1998 |
| WO | 1999027110 | 6/1999 |
| WO | 1999043360 | 9/1999 |
| WO | 1999058700 | 11/1999 |
| WO | 1999061595 | 12/1999 |
| WO | 1999060146 | 5/2000 |
| WO | 2000024916 | 5/2000 |
| WO | 2000066780 | 11/2000 |
| WO | 2000075353 | 12/2000 |
| WO | 2001014539 | 3/2001 |
| WO | 2001023001 | 4/2001 |
| WO | 2001025465 | 4/2001 |
| WO | 2001032711 | 5/2001 |
| WO | 2001036623 | 5/2001 |
| WO | 2001042444 | 6/2001 |
| WO | 2001068888 | 9/2001 |
| WO | 2001075164 A1 | 10/2001 |
| WO | 2001092551 A2 | 12/2001 |
| WO | 2001096587 | 12/2001 |
| WO | 2002012525 | 2/2002 |
| WO | 2002014487 | 2/2002 |
| WO | 2002020748 | 3/2002 |
| WO | 2002070719 | 9/2002 |
| WO | 2002071843 | 9/2002 |
| WO | 2003/006477 A1 | 1/2003 |
| WO | 2003010320 | 2/2003 |
| WO | 2003024502 | 3/2003 |
| WO | 2003042397 | 5/2003 |
| WO | 03080807 A2 | 10/2003 |
| WO | 2003087382 | 10/2003 |
| WO | 2003087383 | 10/2003 |
| WO | 2004027030 A2 | 4/2004 |
| WO | 2004044003 | 5/2004 |
| WO | 2004045543 A2 | 6/2004 |
| WO | 2004083441 | 9/2004 |
| WO | 2004108922 | 12/2004 |
| WO | 2004111191 A2 | 12/2004 |
| WO | 2004111248 | 12/2004 |
| WO | 2005001043 A2 | 1/2005 |
| WO | 2005005610 | 1/2005 |
| WO | 2005007875 A2 | 1/2005 |
| WO | 2005012537 | 2/2005 |
| WO | 2005019828 A1 | 3/2005 |
| WO | 2005027980 A1 | 3/2005 |
| WO | 2005062937 A2 | 7/2005 |
| WO | 2005096781 A2 | 10/2005 |
| WO | 2005111220 | 11/2005 |
| WO | 2006006948 A2 | 1/2006 |
| WO | 2006066066 A2 | 6/2006 |
| WO | 2006066203 A2 | 6/2006 |
| WO | 2006075434 A1 | 7/2006 |
| WO | 2006102072 | 9/2006 |
| WO | 2007044362 A2 | 4/2007 |
| WO | 2007089632 A2 | 8/2007 |
| WO | 2007/109097 A2 | 9/2007 |
| WO | 2007098607 A1 | 9/2007 |
| WO | 2007130519 | 11/2007 |
| WO | 2008086079 A2 | 7/2008 |
| WO | 2007148971 | 7/2009 |
| WO | WO 2009/102427 A2 * | 8/2009 ............ C12N 15/113 |
| WO | 2009134681 | 11/2009 |
| WO | 2009137006 A2 | 11/2009 |
| WO | 2010011346 A1 | 1/2010 |
| WO | 2010138263 A2 | 12/2010 |
| WO | 2011038187 | 3/2011 |
| WO | 2011054976 | 5/2011 |
| WO | 2011122950 | 10/2011 |
| WO | 2011133890 A1 | 10/2011 |
| WO | 2010109053 | 11/2011 |
| WO | 2012057363 | 5/2012 |
| WO | 2012114090 | 8/2012 |
| WO | 2012123430 A1 | 9/2012 |
| WO | 2012144446 | 10/2012 |
| WO | 2012149646 A1 | 11/2012 |
| WO | 2013078199 | 5/2013 |
| WO | 2013123503 A1 | 8/2013 |
| WO | 2013164793 | 11/2013 |
| WO | 2013170078 | 11/2013 |
| WO | 2014016817 A2 | 1/2014 |
| WO | 2014071219 A1 | 5/2014 |
| WO | 2014144486 A2 | 9/2014 |
| WO | 2014160092 | 10/2014 |
| WO | 2014168953 | 10/2014 |
| WO | 2014170470 | 10/2014 |
| WO | 2014170480 | 10/2014 |
| WO | 2014172669 | 10/2014 |
| WO | 2014186579 | 11/2014 |
| WO | 2014194132 | 12/2014 |
| WO | 2014201252 | 12/2014 |
| WO | 2015012924 | 1/2015 |
| WO | 2015013148 | 1/2015 |
| WO | 2015013313 A2 | 1/2015 |
| WO | 2015018503 | 2/2015 |
| WO | 2015023503 A2 | 2/2015 |
| WO | 2014186746 | 3/2015 |
| WO | 2015031392 | 3/2015 |
| WO | 2015031686 | 4/2015 |
| WO | 2015044292 | 4/2015 |
| WO | 2015060722 | 4/2015 |
| WO | 2015069647 A1 | 5/2015 |
| WO | 2015084254 A1 | 6/2015 |
| WO | 2015108610 | 7/2015 |
| WO | 2015114365 | 8/2015 |
| WO | 2015121501 | 8/2015 |
| WO | 2015124546 | 8/2015 |
| WO | 2015137802 | 9/2015 |
| WO | 2015143078 A1 | 9/2015 |
| WO | 2015143078 A1 | 9/2015 |
| WO | 2015153800 A2 | 10/2015 |
| WO | 2015127128 | 11/2015 |

(56) References Cited

FOREIGN PATENT DOCUMENTS

| | | |
|---|---|---|
| WO | 2015196179 | 12/2015 |
| WO | 2016/016449 A1 | 2/2016 |
| WO | 2016019364 | 2/2016 |
| WO | 2016040347 | 3/2016 |
| WO | 2016054554 | 4/2016 |
| WO | 2016054557 | 4/2016 |
| WO | 2016065001 | 4/2016 |
| WO | 2016077607 A1 | 5/2016 |
| WO | 2016077687 A1 | 5/2016 |
| WO | 2016077687 A1 | 5/2016 |
| WO | 2016077689 A1 | 5/2016 |
| WO | 2016077689 A1 | 5/2016 |
| WO | 2016081811 | 5/2016 |
| WO | 2016081927 | 5/2016 |
| WO | WO 2016/077689 A1 * | 5/2016 ........... C12N 15/113 |
| WO | 2016115382 | 7/2016 |
| WO | 2016115503 A1 | 7/2016 |
| WO | 2016122791 | 8/2016 |
| WO | 2016126857 | 8/2016 |
| WO | 2016130591 | 8/2016 |
| WO | 2016137949 | 9/2016 |
| WO | 2016154055 | 9/2016 |
| WO | 2016154344 | 9/2016 |
| WO | 2016164609 | 10/2016 |
| WO | 2016168728 | 10/2016 |
| WO | 2016172008 | 10/2016 |
| WO | 2016172155 | 10/2016 |
| WO | 2016179496 | 11/2016 |
| WO | 2016183297 | 11/2016 |
| WO | 2016191418 | 12/2016 |
| WO | 2016196328 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 | 2/2017 |
| WO | 2017019994 | 2/2017 |
| WO | 2017058892 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017083423 | 5/2017 |
| WO | 2017093330 | 6/2017 |
| WO | 2017096039 | 6/2017 |
| WO | 2017100671 | 6/2017 |
| WO | 2017100674 | 6/2017 |
| WO | 2017100676 | 6/2017 |
| WO | 2017100704 | 6/2017 |
| WO | 2017161273 | 9/2017 |
| WO | 2017/201258 A1 | 11/2017 |
| WO | 2017189963 A1 | 11/2017 |
| WO | 2017192699 | 11/2017 |
| WO | 2017192750 | 11/2017 |
| WO | 2018/204786 A1 | 11/2018 |
| WO | 2018/204797 A1 | 11/2018 |
| WO | 2018220211 A1 | 12/2018 |
| WO | 2019/028306 A2 | 2/2019 |
| WO | 2019/079242 A1 | 4/2019 |
| WO | 2019079240 A1 | 4/2019 |
| WO | 2019222329 A1 | 11/2019 |
| WO | 2020/010035 A1 | 1/2020 |
| WO | 2020/010042 A1 | 1/2020 |
| WO | 2020077165 A1 | 4/2020 |
| WO | 2020223296 A1 | 11/2020 |

OTHER PUBLICATIONS

Berry JD et al., New considerations in the design of clinical trials for amyotrophic lateral sclerosis. Clin Investig (Lond). Oct. 2011;1(10):1375-1389.

Bevan AK et al., Systemic gene delivery in large species for targeting spinal cord, brain, and peripheral tissues for pediatric disorders. Mol Ther. Nov. 2011;19(11):1971-80.

Van Blitterswijk et al., Anti-superoxide dismutase antibodies are associated with survival in patients with sporadic amyotrophic lateral sclerosis. Amyotroph Lateral Scler. Nov. 2011;12(6):430-8.

Boillée S et al., Onset and progression in inherited ALS determined by motor neurons and microglia. Science. Jun. 2, 2006;312(5778):1389-92.

Borchelt DR et al., Superoxide dismutase 1 with mutations linked to familial amyotrophic lateral sclerosis possesses significant activity. Proc Natl Acad Sci U S A. Aug. 16, 1994;91(17):8292-6.

Bosco DA et al., Wild-type and mutant SOD1 share an aberrant conformation and a common pathogenic pathway in ALS. Nat Neurosci. Nov. 2010;13(11):1396-403.

Brown et al. Analysis of mutant SOD1 electrophoretic mobility by Blue Native gel electrophoresis; evidence for soluble multimeric assemblies. PLoS One. Aug. 14, 2014;9(8):e104583.

Cedarbaum JM et al., The ALSFRS-R: a revised ALS functional rating scale that incorporates assessments of respiratory function. BDNF ALS Study Group (Phase III). J Neurol Sci. Oct. 31, 1999;169(1-2):13-21.

Chung et al., Cu/Zn superoxide dismutase can form pore-like structures. Biochem Biophys Res Commun. Dec. 26, 2003;312(4):873-6.

Clement et al., Wild-type nonneuronal cells extend survival of SOD1 mutant motor neurons in ALS mice. Science. Oct. 3, 2003;302(5642):113-7.

Cudkowicz et al., Epidemiology of mutations in superoxide dismutase in amyotrophic lateral sclerosis. Ann Neurol. Feb. 1997;41(2):210-21.

De Boer et al., Genetic validation of a therapeutic target in a mouse model of ALS. Sci Transl Med. Aug. 6, 2014;6(248):248ra104.

De la Maza. Molecular sturcture of adeno-associated virus variant DNA. JBC. Apr. 1980;255(7):3194-3203.

Deng et al., FUS-immunoreactive inclusions are a common feature in sporadic and non-SOD1 familial amyotrophic lateral sclerosis. Ann Neurol. Jun. 2010;67(6):739-48.

Di Giorgio et al., Non-cell autonomous effect of glia on motor neurons in an embryonic stem cell-based ALS model. Nat Neurosci. May 2007;10(5):608-14.

Dirren et al., SOD1 silencing in motoneurons or glia rescues neuromuscular function in ALS mice. Ann Clin Transl Neurol. Feb. 2015; 2(2):167-184.

Dupuis L et al., Differential screening of mutated SOD1 transgenic mice reveals early up-regulation of a fast axonal transport component in spinal cord motor neurons. Neurobiol Dis. Aug. 2000;7(4):274-85.

Elchuri et al., CuZnSOD deficiency leads to persistent and widespread oxidative damage and hepatocarcinogenesis later in life. Oncogene. Jan. 13, 2005;24(3):367-80.

Estévez et al., Induction of nitric oxide-dependent apoptosis in motor neurons by zinc-deficient superoxide dismutase. Science. Dec. 24, 1999;286(5449):2498-500.

Gurney et al., Motor neuron degeneration in mice that express a human Cu,Zn superoxide dismutase mutation. Science. Jun. 17, 1994;264(5166):1772-5.

Haidet-Phillips et al., Astrocytes from familial and sporadic ALS patients are toxic to motor neurons. Nat Biotechnol. Aug. 11, 2011;29(9):824-8.

Johnston et al., Amyotrophic lateral sclerosis in an urban setting: a population based study of inner city London. J Neurol. Dec. 2006;253(12):1642-3.

Jonsson el al., Minute quantities of misfolded mutant superoxide dismutase-1 cause amyotrophic lateral sclerosis. Brain. Jan. 2004;127(Pt 1):73-88.

Kanning et al., Motor neuron diversity in development and disease. Annu Rev Neurosci. 2010;33:409-40.

Ly CV et al., Emerging antisense oligonucleotide and viral therapies for amyotrophic lateral sclerosis. Curr Opin Neurol. Oct. 2018;31(5):648-654.

Challis et al., Systemic AAV vectors for widespread and targeted gene delivery in rodents. Nat Protoc. Feb. 2019;14(2):379-414.

(56) References Cited

OTHER PUBLICATIONS

Powell et al., Viral Expression Cassette Elements to Enhance Transgene Target Specificity and Expression in Gene Therapy. Discov Med. Jan. 2015;19(102):49-57.
Lee SH et al., Intrathecal delivery of recombinant AAV1 encoding hepatocyte growth factor improves motor functions and protects neuromuscular system in the nerve crush and SOD1-G93A transgenic mouse models. Acta Neuropathol Commun. Jun. 12, 2019;7(1):14.
Leyton-Jaimes et al., AAV2/9-mediated overexpression of MIF inhibits SOD1 misfolding, delays disease onset, and extends survival in mouse models of ALS. Proc Natl Acad Sci U S A. Jul. 1, 2019.
Bofill-De Ros et al. Guidelines for the optimal design of miRNA-based shRNAs. Methods. Jul. 1, 2016;103:157-66.
Miyagishi et al. Optimization of an siRNA-expression system with an improved hairpin and its significant suppressive effects in mammalian cells. The Journal of Gene Medicine: A cross-disciplinary journal for research on the science of gene transfer and its clinical applications. Jul. 2004;6(7):715-23.
Du et al. Design of expression vectors for RNA interference based on miRNAs and RNA splicing. The FEBS journal. Dec. 2006;273(23):5421-7.
Calloni et al. Scaffolds for artificial miRNA expression in animal cells. Human gene therapy methods. Aug. 27, 2015;26(5):162-74.
Schopman et al. Optimization of shRNA inhibitors by variation of the terminal loop sequence. Antiviral research. May 1, 2010;86(2):204-11.
Bravo-Hernandez et al., Spinal subpial delivery of AAV9 enables widespread gene silencing and blocks motoneuron degeneration in ALS. Nat Med. Dec. 23, 2019.
Lim et al., Treatment of a Mouse Model of ALS by In Vivo Base Editing. Mol Ther. Jan. 14, 2020. [Epub ahead of print].
Cornetta et al., The National Gene Vector Biorepository: Eleven Years of Providing Resources to the Gene Therapy Community. Hum Gene Ther. Feb. 2020;31(3-4):145-150.
Khosravi et al., Cell-to-cell transmission of C9orf72 poly-(Gly-Ala) triggers key features of ALS/FTD. EMBO J. Mar. 16, 2020:e102811. [Epub ahead of print].
Bey et al., Intra-CSF AAV9 and AAVrh10 administration in non-human primates: promising routes and vectors for what neurological diseases? Molecular Therapy Methods & Clinical Development. Apr. 11, 2020.
Hinderer et al., Translational feasibility of lumbar puncture for intrathecal AAV administration. Molecular Therapy Methods & Clinical Development. Apr. 17, 2020.
Lind et al., Intralingual administration of AAVrh10-miR SOD1 improves respiratory but not swallowing function in a SOD1 mouse model of ALS. Human Gene Therapy. Jun. 5, 2020.
Mueller et al., SOD1 Suppression With Adeno-Associated Virus and MicroRNA in Familial ALS. N Engl J Med. Jul. 9, 2020;383(2):151-158.
"Stoica L et al. Adeno Associated Viral Vector Delivered RNAi for Gene Therapy of SOD1 Amyotrophic Lateral Sclerosis.Front Mol Neurosci. Aug. 2, 2016;9:56."
Mieizsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.
Mieizsch M, et al. OneBac 2.0: Sf9 cell lines for production of AAV5 vectors with enhanced infectivity and minimal encapsidation of foreign DNA. Hum Gene Ther. Oct. 2015 26(10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.
Pacouret S, et al. AAV-ID: A Rapid and Robust Assay for Batch-to-Batch Consistency Evaluation of AAV Preparations. Mol Ther. Apr. 17, 2017. Epub ahead of print.
Penaud-Budloo M, et al. Accurate identification and quantification of DNA species by next-generation sequencing in adeno-associated viral vectors produced in insect cells. Hum Gene Ther Methods. May 2, 2017. Epub ahead of print.
Ruffing M, et al. Assembly of viruslike particles by recombinant structural proteins of adeno-associated virus type 2 in insect cells. J Virol. Dec. 1992;66(12):6922-30.
Samulski RJ, et al. Helper-free stocks of recombinant adeno-associated viruses: normal integration does not require viral gene expression. J Virol. Sep. 1989;63(9):3822-8.
Smith RH, et al. A simplified baculovirus-AAV expression vector system coupled with one-step affinity purification yields high-titer rAAV stocks from insect cells. Mol Ther. Nov. 2009; 17(11):1888-96. doi: 10.1038/mt.2009.128. Epub Jun. 16, 2009.
Urabe M, et al. Scalable generation of high-titer recombinant adeno-associated virus type 5 in insect cells. J Virol. Feb. 2006;80(4):1874-85.
Van Der Loo JCM, et al. Progress and challenges in viral vector manufacturing. Hum Mol Genet. Apr. 2016;25(R1):R42-52.
Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.
Zhao KN, et al. BPV1 E2 protein enhances packaging of full-length plasmid DNA in BPV1 pseudovirions. Virology. Jul. 5, 2000;272(2):382-93.
Pierson EE, et al. Resolving adeno-associated viral particle diversity with charge detection mass spectrometry. Anal Chem. Jul. 2016;88(13):6718-25.
Rashnonejad A, et al. Large-Scale Production of Adeno-Associated Viral Vector Serotype-9 Carrying the Human Survival Motor Neuron Gene. Mol Biotechnol. Jan. 2016;58(1):30-6.
Ling C, et al. Strategies to generate high-titer, high-potency recombinant AAV3 serotype vectors. Mol Ther Methods Clin Dev. May 2016;3:16029.
Afione S, et al. Identification and Mutagenesis of the Adeno-Associated Virus 5 Sialic Acid Binding Region.J Virol. Feb. 2015, 89(3):1660-72.
Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.
Halder S, et al. Structure of neurotropic adeno-associated virus AAVrh.8. J Struct Biol. Oct. 2015;192(1):21-36.
Huang LY, et al. Characterization of the adeno-associated virus 1 and 6 sialic acid binding site. J Virol. May 2016;90(11):5219-30.
Miao Y, et al. Single point mutation in adeno-associated viral vectors—DJ capsid leads to improvement for gene delivery in vivo BMC Biotechnol. Jan. 2016;16:1.
Marsic D et al. Altering Tropism of rAAV by Directed Evolution. Methods of Mol Biol. 2016;1382:151-73.
Tu MY, et al. Role of capsid proteins in parvoviruses infection. Virol J. Aug. 4, 2015;12:114.
Zeng C, et al. Probing the Link between Genomic Cargo, Contact Mechanics and Nanoindentation in Recombinant Adeno-Associated Virus 2. J Phys Chem B. Mar. 2017;121(8):1843-1853.
Zinn E, et al. In Silico Reconstruction of the Viral Evolutionary Lineage Yields a Potent Gene Therapy Vector. Cell Rep. Aug. 2015, 12(6):1056-68.
Grimm D, et al. E Pluribus Unum: 50 years of research, millions of viruses and one goal—tailored acceleration of AAV evolution. Mol Ther. Dec. 2015;23(12):1819-1831.
Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.
Ling C, et al. Development of Optimized AAV Serotype Vectors for High-Efficiency Transduction at Further Reduced Doses. Hum Gene Ther Methods. Aug. 2016;27(4):143-9.
Pillay S, et al. An essential receptor for adeno-associated virus infection. Nature. Feb. 2016;530(7588):108-12.

(56) References Cited

OTHER PUBLICATIONS

Li BZ, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Shen S, et al. Functional Analysis of the Putative Integrin Recognition Motif on Adeno-associated virus 9. J Biol Chem. Jan. 2015, 290(3):1496-504.
Steines B, et al. CFTR gene transfer with AAV improves early cystic fibrosis pig phenotypes. JCI Insight. Sep. 2016;1(14):e88728.
Bensky MJ, et al. Targeted gene delivery to the enteric nervous system using AAV: a comparison across serotypes and capsid mutants.Mol Ther. Mar. 2015;23(3):488-500.
Castle MJ, et al. Controlling AAV Tropism in the Nervous System with Natural and Engineered Capsids. Methods Mol Biol. 2016;1382:133-49.
Choudhury SR, et al. Widespread CNS gene transfer and silencing after systemic delivery of novel AAV-AS vectors. Mol Ther. Apr. 2016;24(4):726-35.
Davis AS, et al. Rational design and engineering of a modified adeno-associated virus (AAV1)-based vector system tor enhanced retrograde gene delivery. Neurosurgery. Feb. 2015;76(2):216-25.
Deverman BE et al. Cre-dependent selection yields AAV variants for widespread gene transfer to the adult brain. Nat Biotechnol. Feb. 2016;34(2):204-9.
Powell SK et al. Characterization of a novel adeno-associated viral vector with preferential oligodendrocyte tropism. Gene Ther. Sep. 15, 2016.
Tervo et al. A Designer AAV Variant Permits Efficient Retrograde Access to Projection Neurons. Neuron. Oct. 19, 2016;92(2):372-382.
Choudhury et al. In Vivo Selection Yields AAV-B1 Capsid for Central Nervous System and Muscle Gene Therapy. Mol Ther. Aug. 2016;24(7):1247-57.
Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gene Ther Methods. Feb. 2017;28(1):49-59.
Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol.Mar. 2015, 6:120.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Xie J, et al. Short DNA Hairpins Compromise Recombinant Adeno-Associated Virus Genome Homogeneity. Mol Ther. Jun. 7, 2017;25(6):1363-1374.
Davidsson M, et al. A novel process of viral vector barcoding and library preparation enables high-diversity library generation and recombination-free paired-end sequencing. Sci Rep. Nov. 2016;6:3563.
Chamberlain K, et al. Expressing transgenes that exceed the packaging capacity of AAV capsids. Hum Gene Ther Methods. Feb. 2016;27(1):1-12.
Conlon EG, et al. Unexpected similarities between C9ORF72 and sporadic forms of ALS/FTD suggest a common disease mechanism. Elife Jul. 13, 2018;7.
Iannitti T, et al. Translating SOD1 Gene Silencing toward the Clinic: A Highly Efficacious, Off-Target-free, and Biomarker-Supported Strategy for fALS. Mol Ther Nucleic Acids. Sep. 7, 2018.
Chandran JS, et al. Gene therapy in the nervous system: failures and successes. Adv Exp Med Biol. 2017;1007:241-257.
Tse LV, et al. Mapping and engineering function domains of the assembly-activating protein of adeno-associated viruses. J. Virol. Jun. 29, 2018;92(14).
Albright BH, et al. Mapping the Structural Determinants Required for AAVrh. 10 Transport across the Blood-Brain Barrier. Mol Ther. Feb. 7, 2018;26(2):510-523.
Gaj T, et al. In vivo genome editing improves motor function and extends survival in a mouse model of ALS. Sci Adv. Dec. 20, 2017;3(12):eaar3952.
Auyeung VC, et al. Beyond secondary structure: primary sequence determinants license pri-miRNA hairpins for processing. Cell. Feb. 2013;152(4):844-858.
Fellman C, et al. An optimized microRNA backbone for effective single-copy RNAi. Cell Rep. Dec. 2013;5(6):1704-1713.
Medinas DB, et al. Endoplasmic reticulum stress leads to accumulation of wild-type SOD1 aggregates associated with sporadic amyotrophic lateral sclerosis. Proc Natl Acad Sci USA Aug. 17, 2018;115(32):8209-8214.
Balendra R and Issacs AM. C9orf72-mediated ALS and FTD: multiple pathways to disease. Nat Rev Neurol. Aug. 17, 2018 Epub ahead of print.
Gowanlock D, et al. A designer AAV variant permits efficient retrograde access to projection neurons. Neuron. Oct. 19, 2016;92(2):372-382.
Ha et al., Regulation of microRNA biogenesis. Nat Rev Mol Cell Bio, Aug. 2014, vol. 15, No. 8, pp. 509-524.
Hardcastle N. AAV gene delivery to the spinal cord: serotypes, methods, candidate diseases and clinical trials. Expert Opinion on Biological Therapy. Mar. 2018;18(3):293-307.
Boudreau RL, et al. Artificial microRNAs as siRNA shuttles: improved safety as compared to shRNAs in vitro and in vivo. The American Society of Gene Therapy. 2009; 17(1):169-175.
Dirren JA, et al. SOD1 silencing in motor neurons or glia rescues neuromuscular function in ALS mice. Annals of Clinical and Translational Neurology 2015;2(2):167-184.
Federici T, et al. Surgical technique for spinal cord delivery of therapies: demonstration of procedure in gottingen minipigs. J Vis Exp Dec. 7, 2012;(70):e4371.
Foust KD et al. Therapeutic AAV9 mediated suppression of mutant SOD1 slows disease progression and extends survival in models of inherited ALS. Mol Ther Dec. 21, 2013(12):2148-59.
Ralph GS et al. Silencing mutant SOD1 using RNAi protects against neurodegeneration and extends survival in an ALS model. Nature Medicine. Apr. 11, 2005(4):429-33.
Raoul C et al. Lentiviral-mediated silencing of SOD1 through RNA interference retards disease onset and progression in a mouse model of ALS. Nature Medicine, vol. 11, No. 4, Apr. 2005, pp. 423-428.
Wang H, et al. Widespread spinal cord transduction by intrathecal injection of rAAV delivers efficacious RNAi therapy for amyotrophic lateral sclerosis. Hum Mol Genet Feb. 1, 2014; 23(3):668-81.
Borel, F et al. Safe and effective superoxide dismutase 1 silencing using artificial microRNA in macaques. Sci Transl Med. Oct. 31, 2018;10(465).
Paré B, et al. Misfolded SOD1 pathology in sporadic Amyotrophic Lateral Sclerosis. Sci Rep. Sep. 21, 2018;8(1):14223.
Mondo E, et al. Selective Neuronal Uptake and Distribution of AAVrh8, AAV9, and AAVrh10 in Sheep After Intra-Striatal Administration. Selective Neuronal Uptake and Distribution of AAVrh8, AAV9, and AAVrh10 in Sheep After Intra-Striatal Administration. J Huntingtons Dis. 2018;7(4):309-319.
Wang D, et al. Adeno-associated virus vector as a platform for gene therapy delivery. Nat Rev Drug Discov. Feb. 1, 2019. doi: 10.1038/S41573-019-0012-9. [Epub ahead of print] Review.

(56) References Cited

OTHER PUBLICATIONS

Martier R, et al. Artificial microRNAs targeting C9ORF72 have the potential to reduce accumulation of the intra-nuclear transcripts in ALS and FTD patients. Molecular Therapy Nucleic Acids. Jan. 22, 2019. DOI: https.//doi.org/10.1016 [Epub ahead of print] Review.
Buning and Srivastava. Capsid Modifications for Targeting and Improving the Efficacy of AAV Vectors. vol. 12, p. 248-265, Mar. 15, 2019.
Hudry E, Vandenberghe LH. Therapeutic AAV Gene Transfer to the Nervous System: A Clinical Reality. Neuron. Mar. 6, 2019;101(5):839-862.
Betancur JG et al., miRNA-like duplexes as RNAi triggers with improved specificity. Front Genet. Jul. 12, 2012;3:127.
Cullen BR. Induction of stable RNA interference in mammalian cells. Gene Ther. Mar. 2006;13(6):503-8.
Fellmann C. et al., Functional identification of optimized RNAi triggers using a massivelyparallel sensor assay. Mol Cell. Mar. 18, 2011;41(6):733-46.
Gu S et al., The loop position of shRNAs and pre-miRNAs is critical for the accuracy of dicer processing in vivo. Cell. Nov. 9, 2012;151(4):900-911.
Han J. et al., Molecular basis for the recognition of primary microRNAs by the Drosha-DGCR8 complex. Cell. Jun. 2, 2006;125(5):887-901.
Park JE et al., Dicer recognizes the 5' end of RNA for efficient and accurate processing. Nature. Jul. 13, 2011;475(7355):201-5.
Schwarz DS et al., Asymmetry in the assembly of the RNAi enzyme complex. Cell. Oct. 17, 2003;115(2):199-208.
Seitz H et al., A 5'-uridine amplifies miRNA/miRNA* asymmetry in *Drosophila* by promoting RNA-induced silencing complex formation. Silence. Jun. 7, 2011;2:4.
Maniatis S et al., Spatiotemporal dynamics of molecular pathology in amyotrophic lateral sclerosis.Science Apr. 5, 2019: vol. 364, Issue 6435, pp. 89-93.
Borel F et al., Recombinant AAV as a platform for translating the therapeutic potential of RNA interference .Mol Ther. Apr. 2014;22(4):692-701.
Pfeifer A et al., Pharmacological potential of RNAi—focus on miRNA. Pharmacol Ther. Jun. 2010;126(3):217-27.
Poesen et al., Neurofilament markers for ALS correlate with extent of upper and lower motor neuron disease. Neurology. Jun. 13, 2017; 88(24):2302-2309. Epub May 12, 2017.
Toedebusch et al., Cerebrospinal Fluid Levels of Phosphorylated Neurofilament Heavy as a Diagnostic Marker of Canine Degenerative Myelopathy. J Vet Intern Med. Mar.-Apr. 2017; 31(2): 513-520. Published online Feb. 10, 2017.
Nardone et al., Canine degenerative myelopathy: a model of human amyotrophic lateral sclerosis. Zoology (Jena). Feb. 2016;119(1):64-73. Epub Sep. 21, 2015.
Crisp et al., Canine degenerative myelopathy: Biochemical characterization of superoxide dismutase 1 in the first naturally occurring. Exp Neurol. Oct. 2013; 248:1-9 Epub May 23, 2013.
Awano et al., Genome-wide association analysis reveals a SOD1 mutation in canine degenerative myelopathy that resembles amyotrophic lateral sclerosis. Proc Natl Acad Sci U S A. Feb. 24, 2009; 106(8): 2794-2799. Published online Feb. 2, 2009.
Al-Chalabi et al., Deletions of the heavy neurofilament subunit tail in amyotrophic lateral sclerosis. Hum Mol Genet. Feb. 1999;8(2):157-64.
Al-Chalabi et al., The epidemiology of ALS: a conspiracy of genes, environment and time. Nat Rev Neurol. Nov. 2013;9(11):617-28.
Alonso et al., Incidence and lifetime risk of motor neuron disease in the United Kingdom: a population-based study. Eur J Neurol. Jun. 2009;16(6):745-51.
Armon et al., Sports and trauma in amyotrophic lateral sclerosis revisited. J Neurol Sci. Nov. 15, 2007;262(1-2):45-53.
Maniatis T. et al.,Molecular Cloning. CSH Laboratory, NY, N.Y. (1982).
Merten OW, et al. Viral vectors for gene therapy and gene modification approaches. Biochem Eng J. Apr. 2016;108:98-115.

Muzyczka N, et al. AAV's Golden Jubilee. Mol Ther. May 2015;23(5):807-8.
Philiport, et al. Liposomes as tools in Basic Research and Industry. CRC Press, Ann Arbor, Mich. (1995).
Kailasan S, et al. Parvovirus Family Conundrum: What makes a killer? Annu Rev Virol. Nov. 2015;2(1):425-50.
Rutledge EA, et al. Infectious clones and vectors derived from adeno-associated virus (AAV) serotypes other than AAV type 2. J Virol. Jan. 1998;72(1):309-19.
Pillay S, et al. An essential receptor for adeno-associated virus infection. Nature. Nov. 17, 2016;539(7629):456.
Platt MP, et al. Embryonic disruption of the candidate dyslexia susceptibility gene homolog Kiaa0319-like results in neuronal migration disorders. Neuroscience. Sep. 17, 2013;248:585-93.
Poon MW, et al. Distribution of Kiaa0319-like immunoreactivity in the adult mouse brain—a novel protein encoded by the putative dyslexia susceptibility gene KIAA0319-like Histol Histopathol. Aug. 2011;26(8):953-63.
Poon MW, et al. Dyslexia-associated kiaa0319-like protein interacts with axon guidance receptor nogo receptor 1. Cell Mol Neurobiol. Jan. 2011;31(1):27-35.
Myers EW, et al. Optimal alignments in linear space. Comput Appl Biosci. Mar. 1988;4(1):11-7.
Smith DW, et al. Biocomputing: Informatics and Genome Projects. Academic Press, New York, 1993.
Kozak M. Interpreting cDNA sequences: some insights from studies on translation. Mamm Genome. Aug. 1996;7(8):563-74.
Kozak M. Point mutations define a sequence flanking the AUG initiator codon that modulates translation by eukaryotic ribosomes. Cell. Jan. 31, 1986;44(2):283-92.
Kozak M. The scanning model for translation: an update. J Cell Biol. Feb. 1989;108(2):229-41.
Heim R, et al. Engineering green fluorescent protein for improved brightness, longer wavelengths and fluorescence resonance energy transfer. Curr Biol. Feb. 1, 1996;6(2):178-82.
Heim R,et al. Improved green fluorescence Nature 373, 663-664 (Feb. 23, 1995); doi:10.1038/373663b0.
Nygaard S, et al. A universal system to select gene-modified hepatocytes in vivo. Sci Transl Med. Jun. 2016;8(342):342ra79.
Smith RH, et al. Germline viral "fossils" guide in silico reconstruction of a mid-Cenozoic era marsupial adeno-associated virus. Sci Rep. Jul. 2016;6:28965.
Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.
O'Reilly DR, et al. Baculovirus expression vectors: a laboratory manual. Oxford University Press, 1994.
Oliva B, et al. An automated classification of the structure of protein loops. J Mol Biol. Mar. 7, 1997;266(4):814-30.
Samaranch L, et al. MR-guided parenchymal delivery of adeno-associated viral vector serotype 5 in non-human primate brain. Gene Ther. Apr. 2017;24(4):253-261.
Petit L, et al. Rod Outer Segment Development Influences AAV-Mediated Photoreceptor Transduction After Subretinal Injection. Hum Gene Ther. May 16, 2017. Epub ahead of print.
Hinderer C et al. Delivery of an Adeno-Associated Virus Vector into CSF Attenuates Central Nervous System Disease in Mucopolysaccharidosis Type II Mice. Hum Gene Ther. Aug. 10, 2016.
Hordeaux J., et al. Efficient central nervous system AAVrh10-mediated intrathecal gene transfers in adult and neonate rats. Gene Ther.Apr. 2015, 22(4):316-24.
Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.
Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.
Muralidharan G , et al. Unique glycan signatures regulate adeno-associated virus tropism in the developing brain. J Virol. Apr. 2015;89(7):3976-87.

(56) References Cited

OTHER PUBLICATIONS

Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Nonhuman Primates. Hum Gene Ther Methods. Feb. 2016;27(1):13-6.
Saraiva J et al. Gene Therapy for the CNS Using AAVs: The Impact of Systemic Delivery by AAV9. J Control Release. Nov. 16, 2016;241:94-109.
Shen F, et al. Inhibition of pathological brain angiogenesis through systemic delivery of AAV vector expressing soluble FLT1. Gene Therapy. Nov. 2015 22(11):893-900.
Hinderer C, et al. Neonatal Systemic AAV Induces Tolerance to CNS Gene Therapy in MPS I Dogs and Nonhuman Primates. Mol Ther. Aug. 2015, 23(8):1298-307.
Ojala DS, et al. Adeno-associated virus vectors and neurological gene therapy. Neuroscientist. Feb. 2015;21(1):84-98.
Katz ML, et al. AAV gene transfer delays disease onset in a TPP1-deficient canine model of the late infantile form of Batten Disease. Sci Transl Med. Nov. 2015;7(313):313ra180.
Kothari P, et al. Iodine-124 Labeled Adeno-Associated Virus: A Promising Tool for Tracking Gene Therapy. Journal of Nuclear Medicine. May 2015, 56 (supplement 3), 494-494.
Landegger LD, et al. A synthetic AAV vector enables safe and efficient gene transfer to the mammalian inner ear. Nat Biotechnol. Mar. 2017;35(3):280-284.
Mason JB, et al. Delivery and evaluation of recombinant adeno-associated viral vectors in the equine distal extremity for the treatment of laminitis. Equine Vet J. Jan. 2017;49(1):79-86.
Jeong D, et al. Matricellular Protein CCN5 Reverses Established Cardiac Fibrosis. J Am Coll Cardiol. Apr. 5, 2016;67(13):1556-68.
Knezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.
Ibrahim S, et al. Stable liver specific expression of human IDOL in humanized mice raises plasma cholesterol. Cardiovasc Res. May 2016;110(1):23-9.
Li Sy, et al. Efficient and targeted transduction of nonhuman primate liver with systemically delivered optimized AAV3B vectors. Mol Ther. Dec. 2015;23(12):1867-76.
Heller KN, et al. Human alpha 7 integrin gene (ITGA7) delivered by adeno-associated virus extends survival of severely affected dystrophin/utrophin deficient mice. Oct. 2015;26(10):647-56.
Mendell JR, et al. Follistatin Gene Therapy for Sporadic Inclusion Body Myositis Improves Functional Outcomes. Mol Ther. Apr. 2017;25(4):870-879.
Schnepp BC, et al. Recombinant adeno-associated virus vector genomes take the form of long-lived transcriptionally competent episomes in human muscle. Hum Gene Ther. Jan. 2016;27(1):32-42.
Murlidharan G et al. Glymphatic Fluid Transport Controls Paravascular Clearance of AAV Vectors from the Brain. JCI Insight. Sep. 8, 2016;1(14).
Neuberger EWI, et al. Establishment of two quantitative nested qPCR assays targeting the human EPO transgene. Gene Ther. Apr. 2016;23(4):330-9.
Lentz TB, et al. Insight into the Mechanism of Inhibition of Adeno-Associated Virus by the Mre11/Rad50/Nbs1 Complex. J Virol. Jan. 2015, 89(1):181-94.
Nicolson SC, et al. Identification and validation of small molecules that enhance recombinant Adeno-associated virus transduction following high throughput screen. J Virol. Jul. 2016;90(16):7019-31.
Wang M, et al. Direct interaction of human serum proteins with AAV virions to enhance AAV transduction: Immediate impact on clinical applications. Gene Ther. Jan. 2017;24(1):49-59.

Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction. Hum Gene Ther. Apr. 2016;27(4):309-24.
Hudry EM, et al. Exosome-associated AAV vector as a robust and convenient neurosocience tool. Gene Ther. Apr. 2016;23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem. Jan. 2016;136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep. Jun. 20, 2016;6:28272.
Kothari P, et al. Radioiodinated Capsids Facilitate In Vivo Non-lnvasive Tracking of Adeno-Associated Gene Transfer Vectors. Sci Rep. Jan. 2017;7:39594.
Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017;5:1-12.
Srivastava A. Adeno-Associated Virus: The Naturally Occurring Virus Versus the Recombinant Vector. Hum Gene Ther. Jan. 2016;27(1):1-6.
Thorne B, et al. Gene Therapy. Adv Biochem Eng Biotechnol. Mar. 14, 2017 Epub ahead of print.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Von Heinje G. Sequence Analysis in Molecular Biology. Academic Press, 1987.
Stahl PH, et al. Pharmaceutical Salts: Properties, Selection, and Use. Wiley-VCH, 2008.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28(4):314-322.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.
Wang S, et al. Direct brain infusion can be enhanced with focused ultrasound and microbubbles. J Cereb Blood Flow Metab. Feb. 2017;37(2):706-714.
Wang et al., Noninvasive, neuron-specific gene therapy can be facilitated by focused ultrasound and recombinant adeno-associated virus. Gene Therapy. Nov. 22, 2014, 104-110.
Weber-Adrian D, et al. Gene delivery to the spinal cord using MRI-guided focused ultrasound. Gene Ther. Jul. 2015, 22(7):568-77.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Zhu W, et al. Soluble FLT1 Gene Therapy Alleviates Brain Arteriovenous Malformation Severity. Stroke. May 2017;48(5):1420-1423.

(56) References Cited

OTHER PUBLICATIONS

Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Suzuki J, et al. Cochlear gene therapy with ancestral AAV in adult mice: complete transduction of inner hair cells without cochlear dysfunction. Apr. 3, 2017;7:45524.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016,90(21):9878-9888.
Wang LL, et al. Comparative study of liver gene transfer with AAV vectors based on endogenous and engineered AAV capsids. Mol Ther. Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. Curr Opin Virol. Sep. 2, 2016;21:75-80.
Adamson-Small L, et al. Sodium chloride enhances rAAV production in a serum-free suspension manufacturing platform using the Herpes Simplex Virus System. Hum Gene Ther Methods. Feb. 2017;28(1):1-14.
Ai J, et al. A Scalable and Accurate Method for Quantifying Vector Genomes of Recombinant Adeno-Associated Viruses in Crude Lysate. Hum Gene Ther Methods. Apr. 13, 2017. Epub ahead of print.
Buclez PO, et al. Rapid, scalable, and low-cost purification of recombinant adeno-associated virus produced by baculovirus expression vector system. Mol Ther Methods Clin Dev. May 2016;3:16035.
Burnham B, et al. Analytical ultracentrifugation as an approach to characterize recombinant adeno-associated viral vectors. Hum Gene Ther Methods. Dec. 2015;26(6):228-42.
Clement N, et al. Manufacturing of recombinant adeno-associated viral vectors for clinical trials. Mol Ther Methods Clin Dev. Mar. 2016;3:16002.
D'Costa S, et al. Practical utilization of recombinant AAV vector reference standards: focus on vector genome titration by free ITR qPCR. Mol Ther Methods Clin Dev. Mar. 2016;5:16019.
Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.
Kajigaya S, et al. Self-assembled B19 parvovirus capsids, produced in a baculovirus system, are antigenically and immunogenically similar to native virions. Proc Natl Acad Sci U S A. Jun. 1, 1991,88(11):4646-50.
Kirnbauer R, et al. Virus-like particles of bovine papillomavirus type 4 in prophylactic and therapeutic immunization. Virology. May 1, 1996;219(1):37-44.
Kohlbrenner E, et al. Production and Characterization of Vectors Based on the Cardiotropic AAV Serotype 9. Methods Mol Biol. 2017;1521:91-107.
Kotin RM, et al. Large-scale recombinant adeno-associated virus production. Hum Mol Genet. Apr. 15, 2011;20(R1): R2-6 doi: 10.1093/hmg/ddr141. Epub Apr. 29, 2011.
Kotin RM, et al. Manufacturing clinical grade recombinant adeno-associated virus using invertebrate cell lines. Hum Gene Ther. Mar. 28, 2017. Epub ahead of print.
Kotterman Ma, et al. Enhanced cellular secretion of AAV2 by expression of foreign viral envelope proteins. Biochemical Engineering Journal, vol. 93, Jan. 15, 2015, pp. 108-114.

Methods in Molecular Biology, ed. Richard, Humana Press, NJ (1995).
Carter BJ. Adeno-associated virus and the development of adeno-associated virus vectors: a historical perspective. Mol Ther. Dec. 2004;10(6):981-9.
G. S. Banker, Modern Pharmaceutics, Drugs and the Pharmaceutical Sciences, v. 72, Marcel Dekker, New York, Inc., 1996.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Hastie E, et al. Adeno-Associated Virus at 50: A Golden Anniversary of Discovery, Research, and Gene Therapy Success—A Personal Perspective. Hum Gene Ther. May 2015, 26(5):257-65.
Aydemir F, et al. Mutants at the 2-fold interface of AAV2 structural proteins suggest a role in viral transcription for AAV capsids. J Virol. Jul. 2016;90(16):7196-204.
Bantel-Schaal U, et al. Human adeno-associated virus type 5 is only distantly related to other known primate helper-dependent parvoviruses. J Virol. Feb. 1999;73(2):939-47.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.
Ding C, et al., Biochemical Characterization of Junonia Coenia Densovirus Nonstructural Protein NS-1. J. Virol., 76(1):338-345 2002.
Adachi K, et al. Drawing a high-resolution functional map of adeno-associated virus capsid by massively parallel sequencing. Nat Commun. 2014;5:3075. doi: 10.1038/ncomms4075.
Altschul SF, et al. Basic local alignment search tool. J Mol Biol. Oct. 5, 1990;215(3):403-10.
Carillo H, et al. The Multiple Sequence Alignment Problem in Biology. SIAM J. Appl. Math. 48-5 (1988), pp. 1073-1082.
Devereux J A comprehensive set of sequence analysis programs for the VAX. Nucleic Acids Res. Jan. 11, 1984;12(1 Pt 1):387-95.
Gribskov M, et al. Sequence Analysis Primer. M Stockton Press, New York, 1991.
Griffin AM, et al. Computer Analysis of Sequence Data, Part I. Humana Press, New Jersey, 1994.
Berge SM Pharmaceutical salts. J Pharm Sci. Jan. 1977;66(1):1-19.
Bell P, et al. Effects of self-complementarity, codon optimization, transgene, and dose on liver transduction with AAV8. Hum Gene Ther Methods. Dec. 2016;27(6):228-237.
Heim et al., Wavelength mutations and posttranslational autoxidation of green fluorescent protein. Proc. Natl. Acad. Sci. USA (1994).
Hastie E, et al. Recombinant adeno-associated virus vectors in the treatment of rare diseases. Expert Opin Orphan Drugs. 2015;3(6):675-689.
Fargnoli AS, et al. Liquid jet delivery method featuring S100A1 gene therapy in the rodent model following acute myocardial infarction. Gene Ther. Feb. 2016;23(2):151-7.
Aubourg P. Gene therapy for rare central nervous system diseases comes to age. Endocr Dev. 2016;30:141-6.
Bankiewicz KS et al. AAV Viral Vector Delivery to the Brain by Shape-conforming MR-guided Infusions. J Control Release. Oct. 28, 2016;240:434-442.
Bey K, et al. Efficient CNS targeting in adult mice by intrathecal infusion of single-stranded AAV9-GFP for gene therapy of neurological disorders. Gene Ther. Apr. 20, 2017. Epub ahead of print.

(56) References Cited

OTHER PUBLICATIONS

Brulet R, et al. NEUROD1 Instructs Neuronal Conversion in Non-Reactive Astrocytes. Stem Cell Reports. May 11, 2017. Epub ahead of print.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.
Chandler RJ, et al. Systemic AAV9 gene therapy improves the lifespan of mice with Niemann-Pick disease, type C1. Hum Mol Genet. Jan. 2017;26(1):52-64.
Dang CH, et al. In vivo dynamics of AAV-mediated gene delivery to sensory neurons of the trigeminal ganglia. Sci Rep. Apr. 19, 2017;7(1):927.
Dimidschstein J, et al. A viral strategy for targeting and manipulating interneurons across vertebrate species. Nat Neurosci. Dec. 2016;19(12):1743-1749.
Donsante A et al. Intracerebroventricular delivery of self-complementary adeno-associated virus serotype 9 to the adult rat brain. Gene Ther. May 2016;23(5):401-7.
El-Shamayleh Y, et al. Strategies for targeting primate neural circuits with viral vectors. J Neurophysiol. Jul. 2016;116(1):122-34.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Gessler DJ et al. Gene Therapy for the Treatment of Neurological Disorders: Metabolic Disorders. Methods Mol Biol. 2016;1382:429-65.
Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016;1382:231-7.
Burda BL, et al. Evaluation of AAV-mediated gene therapy for central nervous system disease in canine mucopolysaccharidosis VII. Mol Ther. Feb. 2016;24(2):206-16.
Ahmed SS, et al. rAAV gene therapy in a Canavan's disease mouse model reveals immune impairments and an extended pathology beyond the central nervous system. Mol Ther. Jun. 2016;24(6):1030-41.
Dashkoff J, et al. Tailored transgene expression to specific cell types in the central nervous system after peripheral injection with AAV9. Mol Ther Methods Clin Dev. Dec. 2016;3:16081.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Greig JA, et al. Impact of intravenous infusion time on AAV8 vector pharmacokinetics, safety, and liver transduction in cynomolgus macaques. Mol Ther Methods Clin Dev. Dec. 2016;3:16079.
Gruntman AM, et al. Delivery of Adeno-associated virus gene therapy by intravascular limb infusion methods. Hum Gene Ther Clin Dev Sep. 2015;26(3):159-64.
Hagg A, et al. Using AAV vectors expressing the beta 2-adrenoceptor or associated G alpha proteins to modulate skeletal muscle mass and muscle fiber size. Sci Rep. Mar. 2016;6:23042.
Greig JA, et al. Intramuscular administration of AAV overcomes pre-existing neutralizing antibodies in rhesus macaques. Vaccine. Dec. 2016;34(50):6323-6329.
Ai J, et al. Adeno-associated virus serotype rh.10 displays strong muscle tropism following intraperitoneal delivery. Sci Rep. Jan. 2017;7:40336.
Baum BJ, et al. Advances in salivary gland gene therapy—oral and systemic implications. Expert Opinion on Biological Therapy. 2015;15(10):1443-54.

Hai B, et al. Long-term transduction of miniature pig parotid glands using serotype 2 adeno-associated viral vectors. J Gene Med. Jun. 2009;11(6):506-14.
De Leeuw CN et al. rAAV-compatible MiniPromoters for Restricted Expression in the Brain and Eye. Mol Brain. May 10, 2016;9(1):52.
Hirsch ML, et al. Delivering Transgenic DNA Exceeding the Carrying Capacity of AAV Vectors. Methods Mol Biol. 2016;1382:21-39.
Lu J, et al. A 5'non-coding exon containing engineered intron enhances transgene expression from recombinant AAV vectors in vivo. Hum Gene Ther. Jan. 2017;28(1):125-134.
Powell SK, et al. Viral expression cassette elements to enhance transgene target specificity and expression in gene therapy. Discov Med. Jan. 2015;19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan Zy, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP.B. Front Mol Neurosci. Nov. 2016;6:116.
WcClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Med. Oct. 1997;3(10):1145-9.
Reid CA, et al. miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep. Jun. 13, 2016;6:27758.
Lukashcuk V et al. AAV9-mediated central nervous system-targeted gene delivery via cisterna magna route in mice. Mol Ther Methods Clin Dev. Feb. 17, 2016;3:15055.
Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Siu JJ, et al. Improved gene delivery to adult mouse spinal cord through the use of engineered hybrid adeno-associated viral serotypes. Gene Ther. Apr. 25, 2017. Epub ahead of print.
Deng XF, et al. Replication of an autonomous human parvovirus in non-dividing human airway epithelium is facilitated through the DNA damage and repair pathways. PLoS Pathog. Jan. 2016;12(1):e1005399.
Kailasan S, et al. Structure of an Enteric Pathogen, Bovine Parvovirus.J Virol. Mar. 2015, 89(5):2603-14.
Alton EW, et al. Repeated nebulisation of non-viral CFIR gene therapy in patients with cystic fibrosis: a randomised, double-blind, placebo-controlled, phase 2b trial. Lancet Respir Med. Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.
Shen W, et al. Analysis of the Cis and Trans Requirements for DNA Replication at the Right End Hairpin of the Human Bocavirus 1 Genome. J Virol. Aug. 2016;90(17):7761-77.
Ren J, et al. Noninvasive tracking of gene transcript and neuroprotection after gene therapy. Gene Ther. Jan. 2016;23(1):1-9.

(56) References Cited

OTHER PUBLICATIONS

Loring HS, et al. Development of rAAV2-CFTR: History of the First rAAV Vector Product to be Used in Humans. Hum Gene Ther Methods. Apr. 2016;27(2):49-58.
Valdmanis P, et al. Future of rAAV gene therapy: Platform for RNAi, Gene Editing and Beyond. Hum Gene Ther. Apr. 2017;28(4):361-372.
Cirulli ET, et al. Exome sequencing in amyotrophic lateral sclerosis identifies risk genes and pathways. Science. Mar. 27, 2015;347(6229):1436-41.
Häggmark A, et al. Plasma profiling reveals three proteins associated to amyotrophic lateral sclerosis. Ann Clin Transl Neurol. Aug. 2014;1(8):544-53.
Jackson KL, et al. Preservation of forelimb function by UPF1 gene therapy in a rat model of TDP-43-induced motor paralysis. Gene Ther.Jan. 2015, 22(1):20-8.
Jara JH, et al. Healthy and diseased corticospinal motor neurons are selectively transduced upon direct AAV2-2 injection into the motor cortex. Gene Ther. Mar. 2016;23(3):272-82.
Borel F et al.Therapeutic rAAVrh10 Mediated SOD1 Silencing in Adult SOD1(G93A) Mice and Nonhuman Primates. Hum Gene Ther. Jan. 2016;27(1):19-31.
Frakes AE, et al. Additive amelioration of ALS by co-targeting independent pathogenic mechanisms. Ann Clin Transl Neurol. Jan. 2017;4(2):76-86.
Van Zundert B et al. Silencing Strategies for Therapy of SOD1-Mediated ALS. Neurosci Lett. Aug. 6, 2016.
Stoica et al. Adeno-associated virus-delivered artificial microRNA extends survival and delays paralysis in an amyotrophic lateral sclerosis mouse model. Ann Neurol. Apr. 2016;79(4):687-700.
Picher-Martel V et al. From Animal Models to Human Disease: A Genetic Approach for Personalized Medicine in ALS. Acta Neuropathol Commun. Jul. 11, 2016;4(1):70.
Hocquemiller M et al. Adeno-Associated Virus-Based Gene Therapy for CNS Diseases. Hum Gene Ther. Jul. 2016;27(7):478-96.
Xie J et al. Adeno-Associated Virus-Mediated MicroRNA Delivery and Therapeutics. Semin Liver Dis. Feb. 2015, 35(1):81-8.
Enomoto M, et al. Efficient Gene Suppression in Dorsal Root Ganglia and Spinal Cord Using Adeno-Associated Virus Vectors Encoding Short-Hairpin RNA. Methods Mol Biol. 2016;1364:77-90.
Tse LV, et al. Structure-guided evolution of antigenically distinct adeno-associated virus variants for immune evasion. Proc Natl Acad Sci U S A. May 30, 2017. Epub ahead of print.
Li D, et al. Slow intrathecal injection of rAAVrh10 enhances its transduction of spinal cord and therapeutic efficacy in a mutant SOD1 model of ALS. Neuroscience. Oct. 9, 2017 Epub ahead of print.
Hinderer C, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.
Hinderer C, et al. Evaluation of intrathecal routes of administration for adeno-associated virus vectors in large animals. Hum Gene Ther. Aug. 15, 2017. doi: 10.1089/hum.2017.026.
Timothy M. Miller et al: "Virus-delivered small RNA silencing sustains strength in amyotrophic lateral sclerosis", Annals of Neurology., vol. 57, No. 5, May 1, 2005 (May 1, 2005), pp. 773-776.
Chris Towne et al: "Systemic AAV6 Delivery Mediating RNA Interference Against SOD1: Neuromuscular Transduction Does Not Alter Disease Progression in fALS Mice", Molecular Therapy: The Journal of the American Society of Gene Therapy, vol. 16, No. 6, Jun. 1, 2008 (Jun. 1, 2008), pp. 1018-1025.
Takayuki Kubodera et al: "In Vivo Application of an RNAi Strategy for the Selective Suppression of a Mutant Allele", Human Gene Therapy, vol. 22, No. 1, Jan. 1, 2011 (Jan. 1, 2011), pp. 27-34.
Yuki Saito et al: "Transgenic Small Interfering RNA Halts Amyotrophic Lateral Sclerosis in a Mouse Model", Journal of Biological Chemistry, vol. 280, No. 52, Oct. 12, 2005 (Oct. 12, 2005), pp. 42826-42830.
Rui Wu et al: "Nerve Injection of Viral Vectors Efficiently Transfers Transgenes into Motor Neurons and Delivers RNAi Therapy Against ALS", Antioxidants and Redox Signaling, vol. 11, No. 7, Jul. 1, 2009 (Jul. 1, 2009), pp. 1523-1534.
H. Zhou: "An RNA polymerase II construct synthesizes short-hairpin RNA with a quantitative indicatorand mediates highly efficien RNAi", Nucleic Acids Research, vol. 33, No. 6, Mar. 23, 2005 (Mar. 23, 2005), pp. e62-e62.
Monica Nizzardo et al: "Research advances in gene therapy approaches for the treatment of amyotrophic lateral sclerosis", CMLS Cellular and Molecular Life Sciences, Birkhauser-Verlag, BA, vol. 69, No. 10, Nov. 18, 2011 (Nov. 18, 2011), pp. 1641-1650.
Ly CV and Miller TM. Emerging antisense olgionucleotide and viral therapies for amyotrophic lateral sclerosis. Curr Opin. Neurol. Jul. 19, 2018 Epub ahead of print.
Larson TC, et al. Amyotrophic Lateral Sclerosis Mortality in the United States, 2011-2014. Neuroepidemiology. Jul. 10, 2018;51(1-2):96-103.
McCampbell A, et al. Antisense oligonucleotides extend survival and reverse decrement in muscle response in ALS models. J Clin Invest. Jul. 16, 2018 Epub ahead of print.
Raffaele Nardone et al: "Canine degenerative myelopathy: a model of human amyotrophic lateral sclerosis", Zoology, vol. 119, No. 1, Feb. 1, 2016 (Feb. 1, 2016), pp. 64-73.
Koen Poeesen et al: "Neurofilament markers for ALS correlate with extent of upper and lower motor neuron disease", Neurology, vol. 88, No. 24, Jun. 13, 2017 (Jun. 13, 2017), pp. 2302, 2309.
C.M. Toedebusch et al: "Cerebrospinal Fluid Levels of Phosphorylated Neurofilament Heavy as a Diagnostic Marker of Canine Degenerative Myelopathy", Journal of Veterinary Internal Medicine, vol. 31, No. 2, Mar. 1, 2017 (Mar. 1, 2017), pp. 513-520.
International Search Report and Written Opinion dated Jan. 28, 2019 received in corresponding International Application No. PCT/US2018/055999.
U.S. Appl. No. 15/526,690, filed May 12, 2017, Dinah Wen-Yee Sah, U.S. Pat. No. 10,597,660.
U.S. Appl. No. 16/774,493, filed Jan. 28, 2020, Dinah Wen-Yee Sah, U.S. Pat. No. 10,920,227.
U.S. Appl. No. 17/143,036, filed Jan. 6, 2021, Dinah Wen-Yee Sah, US 2021-0139915.
U.S. Appl. No. 16/611,054, filed Nov. 5, 2019, Dinah Wen-Yee Sah, US 2020-0123574.
U.S. Appl. No. 16/756,595, filed Apr. 16, 2020, Dinah Wen-Yee Sah, US 2020-0237799.
U.S. Appl. No. 17/252,584, filed Dec. 15, 2020, Dinah Wen-Yee Sah, US 2021-0254103.
U.S. Appl. No. 17/606,733, filed Oct. 26, 2021, Dinah Wen-Yee Sah.
U.S. Appl. No. 17/257,418, filed Dec. 31, 2020, Dinah Wen-Yee Sah, US 2021-0361318.
U.S. Appl. No. 15/526,697, filed May 12, 2017, Jinzhao Hou, US 2017-0314028.
U.S. Appl. No. 16/302,146, filed Nov. 16, 2018, , Dinah Wen-Yee Sah, US 2019-0169616.
Bensimon G et al., "A study of riluzole in the treatment of advanced stage or elderly patients with amyotrophic lateral sclerosis," J Neurol., vol. 249: 609-615 (2002).
Brown, J. et al., Intraparenchymal Spinal Cord Delivery of AAV VY-SOD102 Reduces Disease Burden in the G93A Mouse Model of ALS-SOD1, ASGCT—2020 Annual Meeting, May 12-15, 2020, 1 page.
BY999593, GenBank EST No. BY999593, BY999593 human cDNA library, immortalized cell line of corneal epithelial cells *Homo sapiens* cDNA clone cp1739 3, mRNA sequence, Apr. 14, 2008 [online]. [Retrieved on Apr. 5, 2016], Retrieved from the internet <URL: http://www.ncbi.nlm.nih.gov/nucest/BY999593>.
Ding H et al., "Design of functional small interfering RNAs targeting amyotrophic lateral sclerosis-associated mutant alleles," Chinese Medical J., vol. 124(1): 106-110 (2011).
Extended European Search Report, European Application No. 15859973, dated Apr. 30, 2018, 8 pages.
Foust, K. et al., "Therapeutic AAV9-mediated Suppression of Mutant SOD1 Slows Disease Progression and Extends Survival in Models

(56) References Cited

OTHER PUBLICATIONS of Inherited ALS," Molecular Therapy, The Journal of the American Society of Gene Therapy, vol. 21(12):2148-2159 (2013).
Fujita, Y. et al., "The Golgi apparatus is fragmented in spinal cord motor neurons of amyotrophic lateral sclerosis with basophilic inclusions," Acta Neuropathol., vol. 103:243-247 (2002).
Ghatak et al., "Anterior horn changes of motor neuron disease associated with demyelinating radiculopathy" J Neuropathol Exp Neurol., vol. 45: 385-395 (1986).
Holger Patzke, "Robust SOD1 Knockdown in Large Mammal Spinal Cord Using a Novel Delivery Paradigm With AAV Gene Therapy Targeting SOD1 for the Treatment of SOD1-ALS," ALSMND Dec. 7-9, 2018.
International Search Report & Written Opinion, PCT/US2015/60562, dated Apr. 19, 2016, 15 pages.
International Search Report and Written Opinion, PCT/US2018/056001, dated Jan. 24, 2019, 19 pages.
International Search Report and Written Opinion, PCT/US2019/040222, dated Sep. 10, 2020, 14 pages.
International Search Report and Written Opinion, PCT/US2019/040230, dated Dec. 12, 2019, 24 pages.
International Search Report and Written Opinion, PCT/US2020/030393, dated Sep. 10, 2020, 12 pages.
Kawamata, T. et al., "Immunologic reactions in amyotrophic lateral sclerosis brain and spinal cord tissue," Am J Pathol., vol. 140:691-707 (1992).
Kim C., et al., "Amyotrophic lateral sclerosis—cell based therapy and novel therapeutic development," Exp. Neurobiol., vol. 23(3): 207-214 (2014).
Lepore. et al., "Intraparenchymal spinal cord delivery of adeno-associated virus IGF-1 is protective in the SOD1 G93A model of ALS," Brain Research, vol. 1185: 256-265 (2007).
Maekawa, S. et al., Cortical selective vulnerability in motor neuron disease: a morphometric study Brain, vol. 27:1237-1251 (2004).
Matsumoto et al., "Ubiquitin-positive inclusion in anterior horn cells in subgroups of motor neuron diseases: a comparative study of adult-onset amyotrophic lateral sclerosis, juvenile amyotrophic lateral sclerosis and Werdnig-Hoffmann disease," J Neurol Sci., vol. 115: 208-213 (1993).
Maxwell MM et al., "RNA interference-mediated silencing of mutant superoxide dismutase rescues cyclosporin A-induced death in cultured neuroblastoma cells," PNAS, vol. 101(9):3178-3183 (2004).
McBride, J. et al., "Preclinical Safety of RNAi-Mediated HTT Suppression in the Rhesus Macaque as a Potential Therapy for Huntington's Disease," Molecular Therapy, vol. 19(12):2152-2162 (2011).
Mitroshina, EV et al., "Ration of Recombinant Adenoassociated Viruses for Transduction of Cell Cultures," The State University of Nizhny Novgorod (2013) No English Translation available.
Miyanohara, A.et al., "Potent spinal parenchymal AAV9-mediated gene delivery by subpial injection in adult rats and pigs," Molecular Therapy Methods & Clinical Develop., vol. 3: p. 16046, 10 pages (2016).
Partial European Search Report, European Application No. 18/794,385, dated Feb. 1, 2021, 13 pages.
Philips, T, and J D Rothstein. "Glial cells in amyotrophic lateral sclerosis." Experimental Neurology, vol. 262 Pt B (2014): 111-20. doi:10.1016/j.expneurol.2014.05.015.

Renton, A. et al., "State of play in amyotrophic lateral sclerosis genetics," Nat. Neurosci., vol. 17:17-23 (2014).
Rizvanov AA et al., "Retrogradely transported siRNA silences human mutant SOD1 in spinal cord motor neurons," Exp. Brain Res., vol. 195(1): 1-4 (2009).
Robberecht and Philip, "The changing scene of amyotrophic lateral sclerosis," Nat. Rev. Neurosci., vol. 14: 248-264 (2013).
Rosen DR et al., "Mutations in Cu/Zn superoxide dismutase gene are associated with familial amyotrophic lateral sclerosis," Nature, vol. 362: 59-62 (1993).
Rotunno MS and Bosco DA, "An emerging role for misfolded wild-type SOD1 in sporadic ALS pathogenesis," Front Cell Neurosci., vol. 16 (7): 253 (2013).
Rowland LP and Shneibder, "Amyotrophic lateral sclerosis," NA, N Engl. J. Med., vol. 344: 1688-1700 (2001).
Sasaki and Maruyama, "Immunocytochemical and ultrastructural studies of the motor cortex in amyotrophic lateral sclerosis" Acta Neuropathol., vol. 87: 578-585 (1994).
Schiffer D. et al., "Reactive astrogliosis of the spinal cord in amyotrophic lateral sclerosis," J Neurol Sci., vol. 139: 27-33 (1996).
Schwarz DS et al., "Designing siRNA that distinguish between genes that differ by a single nucleotide," Plos Genet., vol. 2(9): e140 (2006).
Thomsen, G.M., et al.,"Delayed Disease Onset and Extended Survival in the SOD1G93A Rat Model of Amyotrophic Lateral Sclerosis after Suppression of Mutant SOD1 in the Motor Cortex," The Journal of Neuroscience, vol. 34 (47):15587-15600 (2014).
Toedebusch, C.M. et al., "CerebrospinalFluid Levels of Phosphorylated Neurofilament Heavy as a Diagnostic Marker of Canine Degenerative Myelopathy," Journal of Veterinary Internal Medicine, vol. 31(2):513-520 (2017).
Towne C et al., "Neuroprotection by gene therapy targeting mutant SOD1 in individual pools of motor neurons does not translate into therapeutic benefit in fALS mice," Mol Ther., vol. 19(2): 274-283 (2011).
Udaka et al., "Degeneration of Betz cells in motor neuron disease. A Golgi study," Acta Neuropathol., vol. 70:289-295 (1986).
Vehvilainen P et al., "Mechanisms of mutant SOD1 induced mitochondrial toxicity in amyotrophic lateral sclerosis," Front Cell Neurosci., vol. 8: 126 (2014).
Voyager Therapeutics: "Intravenous Delivery of Novel AAV Capsids," Oct. 20, 2017 (Oct. 20, 2017), XP055630466, Retrieved from the Internet: URL:https://www.voyagertherapeutics.com/wp-content/uploads/2017/10/ESGCT_slides.pdf [retrieved on Oct. 9, 2019].
Wang H et al., "Therapeutic gene silencing delivered by a chemically modified small interfering RNA against mutant SOD1 slows amyotrophic lateral sclerosis progression," J Biol. Chem., vol. 283(23):15845-15852 (2008).
Wang, H. et al., "Widespread spinal cord transduction by intrathecal injection of rAAV delivers efficacious RNAi therapy for amyotrophic lateral sclerosis," Human Molecular Genetics, vol. 23(3):668-681 (2014).
Wroe R et al., "ALSOD: the Amyotrophic Lateral Sclerosis Online Database," Amyotroph Lateral Scler., vol. 9:249-250 (2008).
Xue, J. et al., "Epigenetics: Principles, Protocols and practices," 121-122 (2006) No English Translation available.
Yacila and Sari, "Potential therapeutic drugs and methods for the treatment of amyotrophic lateral sclerosis," Curr Med Chem., vol. 21(31): 3583-3593 (2014).

\* cited by examiner

SEQUENCE LISTING

<160> NUMBER OF SEQ ID NOS: 147

<210> SEQ ID NO 1
<211> LENGTH: 981
<212> TYPE: DNA
<213> ORGANISM: Homo sapiens

<400> SEQUENCE: 1

```
gtttggggcc agagtgggcg aggcgcggag gtctggccta taaagtagtc gcggagacgg      60
ggtgctggtt tgcgtcgtag tctcctgcag cgtctggggt ttccgttgca gtcctcggaa     120
ccaggacctc ggcgtggcct agcgagttat ggcgacgaag gccgtgtgcg tgctgaaggg     180
cgacggccca gtgcagggca tcatcaattt cgagcagaag gaaagtaatg gaccagtgaa     240
ggtgtgggga agcattaaag gactgactga aggcctgcat ggattccatg ttcatgagtt     300
tggagataat acagcaggct gtaccagtgc aggtcctcac tttaatcctc tatccagaaa     360
acacggtggg ccaaaggatg aagagaggca tgttggagac ttgggcaatg tgactgctga     420
caaagatggt gtggccgatg tgtctattga agattctgtg atctcactct caggagacca     480
ttgcatcatt ggccgcacac tggtggtcca tgaaaaagca gatgacttgg gcaaaggtgg     540
aaatgaagaa agtacaaaga caggaaacgc tggaagtcgt ttggcttgtg gtgtaattgg     600
gatcgcccaa taaacattcc cttggatgta gtctgaggcc ccttaactca tctgttatcc     660
tgctagctgt agaaatgtat cctgataaac attaaacact gtaatcttaa aagtgtaatt     720
gtgtgacttt ttcagagttg cttttaaagta cctgtagtga gaaactgatt tatgatcact     780
tggaagattt gtatagtttt ataaaactca gttaaaatgt ctgtttcaat gacctgtatt     840
ttgccagact taaatcacag atgggtatta aacttgtcag aatttctttg tcattcaagc     900
ctgtgaataa aaaccctgta tggcacttat tatgaggcta ttaaaagaat ccaaattcaa     960
actaaaaaaa aaaaaaaaa a                                                981
```

<210> SEQ ID NO 2
<211> LENGTH: 465

```
<212> TYPE: DNA
<213> ORGANISM: Macaca fascicularis

<400> SEQUENCE: 2
atggcgatga aggccgtgtg cgtgttgaag ggcgacagcc cagtgcaggg caccatcaat      60
ttcgagcaga aggaaagtaa tggaccagtg aaggtgtggg gaagcattac aggattgact     120
gaaggcctgc atggattcca tgttcatcag tttggagata atacacaagg ctgtaccagt     180
gcaggtcctc actttaatcc tctatccaga caacacggtg ggccaaagga tgaagagagg     240
catgttggag acctgggcaa tgtgactgct ggcaaagatg gtgtggccaa ggtgtctttc     300
gaagattctg tgatctcgct ctcaggagac cattccatca ttggccgcac attggtggtc     360
catgaaaaag cagatgactt gggcaaaggt ggaaatgaag aaagtaaaaa gacaggaaac     420
gctggaggtc gtctggcttg tggtgtaatt gggatcgccc aataa                      465

<210> SEQ ID NO 3
<400> SEQUENCE: 3

000

<210> SEQ ID NO 4
<211> LENGTH: 474
<212> TYPE: DNA
<213> ORGANISM: Canis lupus familiaris
<220> FEATURE:
<221> NAME/KEY: misc_feature
<222> LOCATION: (165)..(165)
<223> OTHER INFORMATION: n is a, c, g, or t

<400> SEQUENCE: 4
cgagtcatgg agatgaaggc cgtgtgcgtg ttgaagggcc agggcccggt ggagggcacc      60
atccacttcg tgcagaaggg aagtgggcct gttgtggtat caggaaccat tacagggctg     120
actgaaggcg agcatggatt ccacgtccat cagtttgaag ataanacaca aggctgtact     180
agtgcaggtc ctcactttaa tcctctgtcc aaaaaacatg gtgggccaaa agatcaagag     240
aggcatgttg gagacctggg caatgtgact gctggcaagg atggcgtggc cattgtgtcc     300
atagaagatt ctctgattgc actctcagga gactattcca tcattggccg caccatggtg     360
gtccacgaga aacgagatga cttgggcaaa ggtgacaatg aagaaagtac acagacagga     420
aacgccggga gtcgtttggc ttgtggtgtc attgggatcg cccaataaac attc            474

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
ucaccacaag ccaaacgacu u                                                21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6
```

```
ugauuaaagu gaggaccugu u                                          21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
uauuaaagug aggaccugcu u                                          21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
uacaccacaa gccaaacgau u                                          21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9
gauuaaagug aggaccugcu u                                          21

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10
ucaccacaag ccaaacgacu uu                                         22

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
ugccagcagu cacauugccu u                                          21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 12
```
uaacagauga guuaagggu u                       21

```
<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 13
```
uauuaaagug aggaccugcn n                       21

```
<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 14
```
uacaccacaa gccaaacgan n                       21

```
<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 15
```
uuguuuauug ggcgaucccn n                       21

```
<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 16
```
uguuuauugg gcgaucccan n                       21

```
<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
```

```
<221> NAME/KEY: misc_feature
<222> LOCATION: (20)..(21)
<223> OTHER INFORMATION: nn is a deoxythymidine dinucleotide

<400> SEQUENCE: 17
ucaccacaag ccaaacgacn n                                              21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 18
ugauuaaagu gaggaccugn n                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 19
uuuuauuggg cgaucccaan n                                              21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 20
ugucagcagu cacauugccn n                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 21
ugcgauccca auuacaccan n                                              21

<210> SEQ ID NO 22
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 22
gucguuuggc uugugguggc u                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 23
cagguccuca cuuuaaucgc u                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 24
gcagguccuc acuuuaaugc c                                              21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 25
gcagguccuc acuuuaaugc u                                              21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 26
ucguuuggcu uguggugugc u                                              21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 27
gcagguccuc acuuuaaucc c                                              21

<210> SEQ ID NO 28
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      polynucleotide

<400> SEQUENCE: 28
gucguuuggc uuguggaggc c                                              21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 29
cagguccuca cuuuaaucgc c                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 30
ucguuuggcu uguggugugc c                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 31
ggcaauguga cugcuggugc c                                              21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 32
ggcaauguga cugcuggauc c                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 33
ggcaaugugu cugcuggauc c                                              21

<210> SEQ ID NO 34
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      polynucleotide

<400> SEQUENCE: 34
ggcaauguga cugcuggccc c                                              21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 35
gcagguccuc acuuuaauuc c                                              21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 36
gcagguccug acuuuaaucc c                                              21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 37
ccccuuaacu cauuuguucc c                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 38
gcagguccuc acuuuaaucn n                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 39
```
ucguuuggcu uguggugucn n                                      21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 40
gggaucgccc aauaaacacn n                                      21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 41
ugggaucgcc caauaaaccn n                                      21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 42
gucguuuggc uuguggugcn n                                      21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 43
cagguccuca cuuuaauccn n                                      21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:

-continued

```
<221> NAME/KEY: misc_feature
<222> LOCATION: (20)..(21)
<223> OTHER INFORMATION: nn is a deoxythymidine dinucleotide

<400> SEQUENCE: 44
uugggaucgc ccaauaaacn n                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 45
ggcaauguga cugcugaccn n                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (20)..(21)
<223> OTHER INFORMATION: nn is a deoxythymidine dinucleotide

<400> SEQUENCE: 46
ugguguaauu gggaucgccn n                                              21

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
ctcccgcaga acaccatgcg ctccacggaa                                     30

<210> SEQ ID NO 48
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gaagcaaaga aggggcagag ggagcccgtg agctgagtgg gccagggact gggagaagga    60
gtgaggaggc agggccggca tgcctctgct gctggccaga                         100

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 49
gtgctgggcg gggggcggcg ggccctcccg cagaacacca tgcgctcttc ggaa       54

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gtggccactg agaag                                                  15

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gtctgcacct gtcactag                                               18

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
tgtgacctgg                                                        10

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
tgtgatttgg                                                        10

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
ctgaggagcg ccttgacagc agccatggga gggcc                            35

<210> SEQ ID NO 55
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
```

```
tggccgtgta gtgctaccca gcgctggctg cctcctcagc attgcaattc ctctcccatc    60
tgggcaccag tcagctaccc tggtgggaat ctgggtagcc                         100
```

<210> SEQ ID NO 56
<211> LENGTH: 99
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
ggccgtgtag tgctacccag cgctggctgc ctcctcagca ttgcaattcc tctcccatct    60
gggcaccagt cagctaccct ggtgggaatc tgggtagcc                          99
```

<210> SEQ ID NO 57
<211> LENGTH: 52
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
ctgaggagcg ccttgacagc agccatggga gggccgcccc ctacctcagt ga           52
```

<210> SEQ ID NO 58
<211> LENGTH: 52
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
ctgtggagcg ccttgacagc agccatggga gggccgcccc ctacctcagt ga           52
```

<210> SEQ ID NO 59
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gtgctgggcg gggggcggcg ggccctcccg cagaacacca tgcgctcttc ggaagcaggt    60 cctcactta atgcctgtga cctgggatta aagtgaggac ctgcttctga ggagcgcctt   120
gacagcagcc atgggagggc cgccccctac ctcagtga                          158
```

<210> SEQ ID NO 60
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
gtgctgggcg gggggcggcg ggccctcccg cagaacacca tgcgctcttc ggaaggcaat    60
gtgactgctg gccctgtga cctggtgcca gcagtcacat tgccttctga ggagcgcctt   120
gacagcagcc atgggagggc cgccccctac ctcagtga                          158
```

<210> SEQ ID NO 61
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gtgctgggcg gggggcggcg ggccctcccg cagaacacca tgcgctcttc ggaagcaggt    60
cctcacttta attcctgtga cctgggatta aagtgaggac ctgcttctga ggagcgcctt   120
gacagcagcc atgggagggc cgcccctac ctcagtga                            158

<210> SEQ ID NO 62
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
ctcccgcaga acaccatgcg ctccacggaa gcaggtcctc actttaatgc tgtggccact    60
gagaagtatt aaagtgagga cctgcttctg aggagcgcct tgacagcagc catgggaggg   120
cc                                                                  122

<210> SEQ ID NO 63
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
ctcccgcaga acaccatgcg ctccacggaa caggtcctca ctttaatcgc tgtggccact    60
gagaagtgat taaagtgagg acctgttctg aggagcgcct tgacagcagc catgggaggg   120
cc                                                                  122

<210> SEQ ID NO 64
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gtgctgggcg gggggcggcg ggccctcccg cagaacacca tgcgctcttc ggaaggcaat    60
gtgactgctg gtgcctgtga cctggtgcca gcagtcacat tgccttctga ggagcgcctt   120
gacagcagcc atgggagggc cgcccctac ctcagtga                            158

<210> SEQ ID NO 65
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
ctcccgcaga acaccatgcg ctccacggaa gtcgtttggc ttgtggtggc tgtggccact    60
gagaagtcac cacaagccaa acgacttctg aggagcgcct tgacagcagc catgggaggg   120
cc                                                                  122

<210> SEQ ID NO 66
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
ctcccgcaga acaccatgcg ctccacggaa tcgtttggct tgtggtgtgc tgtggccact    60
gagaagtaca ccacaagcca aacgattctg aggagcgcct tgacagcagc catgggaggg   120
cc                                                                  122

<210> SEQ ID NO 67
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gtgctgggcg gggggcggcg ggccctcccg cagaacacca tgcgctcttc ggaagcaggt    60
cctcacttta atccctgtga tttgggatta aagtgaggac ctgcttctga ggagcgcctt   120
gacagcagcc atgggagggc cgcccctac ctcagtga                            158

<210> SEQ ID NO 68
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gtgctgggcg gggggcggcg ggccctcccg cagaacacca tgcgctcttc ggaaggcaat    60
gtgactgctg gtacctgtga tttggtgcca gcagtcacat tgccttctga ggagcgcctt   120
gacagcagcc atgggagggc cgcccctac ctcagtga                            158

<210> SEQ ID NO 69
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gtgctgggcg gggggcggcg ggccctcccg cagaacacca tgcgctcttc ggaagcaggt    60 cctgactta atccctgtga cctgggatta aagtgaggac ctgcttctgt ggagcgcctt   120
gacagcagcc atgggagggc cgcccctac ctcagtga                            158

<210> SEQ ID NO 70
<211> LENGTH: 158
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 70
gtgctgggcg gggggcggcg ggccctcccg cagaacacca tgcgctcttc ggaaggcaat      60
gtgtctgctg gtacctgtga cctggtgcca gcagtcacat tgccttctgt ggagcgcctt     120
gacagcagcc atgggagggc cgcccccctac ctcagtga                            158

<210> SEQ ID NO 71
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gtgctgggcg gggggcggcg ggccctcccg cagaacacca tgcgctcttc ggaagcaggt      60
cctcacttta atccctgtga cctgggatta aagtgaggac ctgcttctgt ggagcgcctt    120
gacagcagcc atgggagggc cgcccccctac ctcagtga                            158

<210> SEQ ID NO 72
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gtgctgggcg gggggcggcg ggccctcccg cagaacacca tgcgctcttc ggaaggcaat      60
gtgactgctg gtacctgtga cctggtgcca gcagtcacat tgccttctgt ggagcgcctt    120
gacagcagcc atgggagggc cgcccccctac ctcagtga                            158

<210> SEQ ID NO 73
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gaagcaaaga aggggcagag ggagcccgtg agctgagtgg gccagggact gggagaagga      60
gtgaggaggc agggccggca tgcctctgct gctggccaga gcaggtcctc actttaatcc    120
cgtctgcacc tgtcactagg attaaagtga ggacctgctt tggccgtgta gtgctaccca    180
gcgctggctg cctcctcagc attgcaattc ctctcccatc tgggcaccag tcagctaccc    240
tggtgggaat ctgggtagcc                                                 260

<210> SEQ ID NO 74
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gaagcaaaga aggggcagag ggagcccgtg agctgagtgg gccagggact gggagaagga    60
gtgaggaggc agggccggca tgcctctgct gctggccaga gcaggtcctc actttaatgc   120
cgtctgcacc tgtcactagt attaaagtga ggacctgctt tggccgtgta gtgctaccca   180
gcgctggctg cctcctcagc attgcaattc ctctcccatc tgggcaccag tcagctaccc   240
tggtgggaat ctgggtagcc                                               260

<210> SEQ ID NO 75
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gaagcaaaga aggggcagag ggagcccgtg agctgagtgg gccagggact gggagaagga    60
gtgaggaggc agggccggca tgcctctgct gctggccaga caggtcctca ctttaatcgc   120
cgtctgcacc tgtcactagt gattaaagtg aggacctgtt tggccgtgta gtgctaccca   180
gcgctggctg cctcctcagc attgcaattc ctctcccatc tgggcaccag tcagctaccc   240
tggtgggaat ctgggtagcc                                               260

<210> SEQ ID NO 76
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
gaagcaaaga aggggcagag ggagcccgtg agctgagtgg gccagggact gggagaagga    60
gtgaggaggc agggccggca tgcctctgct gctggccaga ggcaatgtga ctgctggtac   120
cgtctgcacc tgtcactagt gccagcagtc acattgcctt tggccgtgta gtgctaccca   180
gcgctggctg cctcctcagc attgcaattc ctctcccatc tgggcaccag tcagctaccc   240
tggtgggaat ctgggtagcc                                               260

<210> SEQ ID NO 77
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gaagcaaaga aggggcagag ggagcccgtg agctgagtgg gccagggact gggagaagga    60
gtgaggaggc agggccggca tgcctctgct gctggccaga gtcgtttggc ttgtggtggc   120
cgtctgcacc tgtcactagt caccacaagc caaacgactt tggccgtgta gtgctaccca   180
gcgctggctg cctcctcagc attgcaattc ctctcccatc tgggcaccag tcagctaccc   240
tggtgggaat ctgggtagcc                                               260

<210> SEQ ID NO 78
<211> LENGTH: 260
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 78
gaagcaaaga aggggcagag ggagcccgtg agctgagtgg gccagggact gggagaagga      60
gtgaggaggc agggccggca tgcctctgct gctggccaga tcgtttggct tgtggtgtgc     120
cgtctgcacc tgtcactagt acaccacaag ccaaacgatt tggccgtgta gtgctaccca    180
gcgctggctg cctcctcagc attgcaattc ctctcccatc tgggcaccag tcagctaccc    240
tggtgggaat ctgggtagcc                                                 260

<210> SEQ ID NO 79
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
gaagcaaaga aggggcagag ggagcccgtg agctgagtgg gccagggact gggagaagga      60
gtgaggaggc agggccggca tgcctctgct gctggccaga ccccttaact catttgttcc    120
cgtctgcacc tgtcactagt aacagatgag ttaaggggtt tggccgtgta gtgctaccca    180
gcgctggctg cctcctcagc attgcaattc ctctcccatc tgggcaccag tcagctaccc    240
tggtgggaat ctgggtagcc                                                 260

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gcaggtcctc actttaatgc c                                                21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
ggcaatgtga ctgctggccc c                                                21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
gcaggtcctc actttaattc c                                                21

<210> SEQ ID NO 83
<211> LENGTH: 21
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 83
gcaggtcctc actttaatgc t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
caggtcctca ctttaatcgc t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
ggcaatgtga ctgctggtgc c                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gtcgtttggc ttgtggtggc t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
tcgtttggct tgtggtgtgc t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gcaggtcctc actttaatcc c                                              21

<210> SEQ ID NO 89
<211> LENGTH: 21
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 89
ggcaatgtga ctgctggtac c                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
gcaggtcctg actttaatcc c                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
ggcaatgtgt ctgctggtac c                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gcaggtcctc actttaatcc c                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
ggcaatgtga ctgctggtac c                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gcaggtcctc actttaatcc c                                              21

<210> SEQ ID NO 95
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 95
gcaggtcctc actttaatgc c                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
caggtcctca ctttaatcgc c                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
ggcaatgtga ctgctggtac c                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gtcgtttggc ttgtggtggc c                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99
tcgtttggct tgtggtgtgc c                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
ccccttaact catttgttcc c                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 101
gattaaagtg aggacctgct t                                          21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
tgccagcagt cacattgcct t                                          21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gattaaagtg aggacctgct t                                          21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
tattaaagtg aggacctgct t                                          21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
tgattaaagt gaggacctgt t                                          21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
tgccagcagt cacattgcct t                                          21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 107
tcaccacaag ccaaacgact t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
tacaccacaa gccaaacgat t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
gattaaagtg aggacctgct t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
tgccagcagt cacattgcct t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gattaaagtg aggacctgct t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
tgccagcagt cacattgcct t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 113
gattaaagtg aggacctgct t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
tgccagcagt cacattgcct t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
gattaaagtg aggacctgct t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
tattaaagtg aggacctgct t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
tgattaaagt gaggacctgt t                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
tgccagcagt cacattgcct t                                              21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
```
tcaccacaag ccaaacgact tt                                              22

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
tacaccacaa gccaaacgat t                                               21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
taacagatga gttaaggggt t                                               21

<210> SEQ ID NO 122
<211> LENGTH: 1453
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
aagatcaatt caattcacgc gtcgacattg attattgact agttattaat agtaatcaat    180
tacggggtca ttagttcata gcccatatat ggagttccgc gttacataac ttacggtaaa    240
tggcccgcct ggctgaccgc ccaacgaccc ccgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca gtacgccccc tattgacgt     420
caatgacggt aaatggcccg cctggcatta tgcccagtac atgaccttat gggactttcc    480
tacttggcag tacatctacg tattagtcat cgctattacc atgtcgaggc cacgttctgc    540
ttcactctcc ccatctcccc cccctcccca ccccaatttt gtatttatt tattttttaa    600
ttattttgtg cagcgatggg ggcggggggg ggggcgcgc gccaggcggg gcggggcggg    660
gcgaggggcg gggcggggcg aggcggagag gtgcggcggc agccaatcag agcggcgcgc    720
tccgaaagtt tccttttatg gcgaggcggc ggcggcggcg gccctataaa aagcgaagcg    780
cgcggcgggc gggagcaagc ttgaactgaa aaaccagaaa gttaactggt aagtttagtc    840
tttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg taccgagctc tcccgcagaa caccatgcgc   1020
tccacggaag tcgtttggct tgtggtggct gtggccactg agaagtcacc acaagccaaa   1080
cgacttctga ggagcgccctt gacagcagcc atggagggc tcgaggacg gggtgaacta    1140
cgcctgagga tccgatcttt ttccctctgc caaaaattat ggggacatca tgaagcccct   1200

```
tgagcatctg acttctggct aataaaggaa atttattttc attgcaatag tgtgttggaa      1260
ttttttgtgt ctctcactcg gcctaggtag ataagtagca tggcgggtta atcattaact      1320
acaaggaacc cctagtgatg gagttggcca ctccctctct gcgcgctcgc tcgctcactg      1380
aggccgggcg accaaaggtc gcccgacgcc cgggctttgc ccgggcggcc tcagtgagcg      1440
agcgagcgcg cag                                                         1453
```

<210> SEQ ID NO 123
<211> LENGTH: 1453
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

```
ctgcgcgctc gctcgctcac tgaggccgcc cgggcaaagc ccgggcgtcg ggcgaccttt       60
ggtcgcccgg cctcagtgag cgagcgagcg cgcagagagg gagtgtagcc atgctctagg      120
aagatcaatt caattcacgc gtcgacattg attattgact agttattaat agtaatcaat      180 tacgggtca ttagttcata gcccatatat ggagttccgc gttacataac ttacggtaaa       240
tggcccgcct ggctgaccgc ccaacgaccc ccgcccattg acgtcaataa tgacgtatgt      300
tcccatagta acgccaatag ggactttcca ttgacgtcaa tgggtggagt atttacggta      360
aactgcccac ttggcagtac atcaagtgta tcatatgcca gtacgcccc ctattgacgt       420 caatgacggt aaatggcccg cctggcatta tgcccagtac atgaccttat ggactttcc      480 tacttggcag tacatctacg tattagtcat cgctattacc atgtcgaggc cacgttctgc      540
ttcactctcc ccatctcccc ccctcccca ccccaattt tgtatttatt tatttttaa        600 ttattttgtg cagcgatggg ggcggggggg ggggcgcgc gccaggcggg gcggggcggg      660
gcgaggggcg gggcggggcg aggcggagag gtgcggcggc agccaatcag agcggcgcgc      720
tccgaaagtt ccctttatg gcgaggcggc ggcggcggcg gccctataaa aagcgaagcg      780
cgcggcgggc gggagcaagc ttgaactgaa aaaccagaaa gttaactggt aagtttagtc      840
tttttgtctt ttatttcagg tcccggatcc ggtggtggtg caaatcaaag aactgctcct      900
cagtggatgt tgcctttact tctaggcctg tacggaagtg ttacttctgc tctaaaagct      960
gcggaattgt acccgcggcc gatccaccgg taccgagctc tcccgcagaa caccatgcgc     1020
tccacggaac aggtcctcac tttaatcgct gtggccactg agaagtgatt aaagtgagga     1080
cctgttctga ggagcgcctt gacagcagcc atgggagggc ctcgaggacg gggtgaacta     1140
cgcctgagga tccgatcttt ttccctctgc caaaaattat ggggacatca tgaagcccct     1200
tgagcatctg acttctggct aataaaggaa atttattttc attgcaatag tgtgttggaa     1260
ttttttgtgt ctctcactcg gcctaggtag ataagtagca tggcgggtta atcattaact     1320
acaaggaacc cctagtgatg gagttggcca ctccctctct gcgcgctcgc tcgctcactg     1380
aggccgggcg accaaaggtc gcccgacgcc cgggctttgc ccgggcggcc tcagtgagcg     1440
agcgagcgcg cag                                                        1453
```

<210> SEQ ID NO 124
<211> LENGTH: 1584
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt caattcacgc gtcgacattg attattgact agttattaat agtaatcaat | 180 |
| tacggggtca ttagttcata gcccatatat ggagttccgc gttacataac ttacggtaaa | 240 |
| tggcccgcct ggctgaccgc ccaacgaccc ccgcccattg acgtcaataa tgacgtatgt | 300 |
| tcccatagta acgccaatag ggactttcca ttgacgtcaa tgggtggagt atttacggta | 360 |
| aactgcccac ttggcagtac atcaagtgta tcatatgcca agtacgcccc ctattgacgt | 420 |
| caatgacggt aaatggcccg cctggcatta tgcccagtac atgaccttat gggactttcc | 480 |
| tacttggcag tacatctacg tattagtcat cgctattacc atgtcgaggc cacgttctgc | 540 |
| ttcactctcc ccatctcccc cccctcccca ccccaatttt gtatttatt tattttttaa | 600 |
| ttattttgtg cagcgatggg ggcggggggg ggggcgcgc gccaggcggg gcggggcggg | 660 |
| gcgaggggcg gggcggggcg aggcggagag gtgcggcggc agccaatcag agcggcgcgc | 720 |
| tccgaaagtt cccttttatg gcgaggcggc ggcggcggcg gccctataaa aagcgaagcg | 780 |
| cgcggcgggc gggagcaagc ttgaactgaa aaaccagaaa gttaactggt aagtttagtc | 840 |
| tttttgtctt ttatttcagg tcccggatcc ggtggtggtg caaatcaaag aactgctcct | 900 |
| cagtggatgt tgcctttact tctaggcctg tacggaagtg ttacttctgc tctaaaagct | 960 |
| gcggaattgt acccgcggcc gatccaccgg tgaagcaaag aagggcagag gggagcccgt | 1020 |
| gagctgagtg ggccagggac tgggagaagg agtgaggagg cagggccggc atgcctctgc | 1080 |
| tgctggccag agcaggtcct cactttaatg ccgtctgcac ctgtcactag tattaaagtg | 1140 |
| aggacctgct ttggccgtgt agtgctaccc agcgctggct gcctcctcag cattgcaatt | 1200 |
| cctctcccat ctgggcacca gtcagctacc ctggtgggaa tctgggtagc cctcgaggac | 1260 |
| ggggtgaact acgcctgagg atccgatctt tttccctctg ccaaaaatta tggggacatc | 1320 |
| atgaagcccc ttgagcatct gacttctggc taataaagga aatttatttt cattgcaata | 1380 |
| gtgtgttgga attttttgtg tctctcactc ggcctaggta gataagtagc atggcgggtt | 1440 |
| aatcattaac tacaaggaac ccctagtgat ggagttggcc actccctctc tgcgcgctcg | 1500 |
| ctcgctcact gaggccgggc gaccaaaggt cgcccgacgc ccgggctttg cccgggcggc | 1560 |
| ctcagtgagc gagcgagcgc gcag | 1584 |

<210> SEQ ID NO 125
<211> LENGTH: 1453
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 125

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt caattcacgc gtcgacattg attattgact agttattaat agtaatcaat | 180 |
| tacggggtca ttagttcata gcccatatat ggagttccgc gttacataac ttacggtaaa | 240 |
| tggcccgcct ggctgaccgc ccaacgaccc ccgcccattg acgtcaataa tgacgtatgt | 300 |

```
tcccatagta acgccaatag ggactttcca ttgacgtcaa tgggtggagt atttacggta      360
aactgcccac ttggcagtac atcaagtgta tcatatgcca agtacgcccc ctattgacgt      420
caatgacggt aaatggcccg cctggcatta tgcccagtac atgaccttat gggactttcc      480
tacttggcag tacatctacg tattagtcat cgctattacc atgtcgaggc cacgttctgc      540
ttcactctcc ccatctcccc ccctcccca ccccaatt tgtatttatt tattttttaa       600
ttattttgtg cagcgatggg ggcggggggg ggggcgcgc gccaggcggg gcggggcggg      660
gcgaggggcg gggcggggcg aggcggagag gtgcggcggc agccaatcag agcggcgcgc      720
tccgaaagtt tccttttatg gcgaggcggc ggcggcggcg gccctataaa agcgaagcg       780 cgcggcgggc gggagcaagc ttgaactgaa aaaccagaaa gttaactggt aagtttagtc      840
tttttgtctt ttatttcagg tcccggatcc ggtggtggtg caaatcaaag aactgctcct      900
cagtggatgt tgcctttact tctaggcctg tacggaagtg ttacttctgc tctaaaagct      960
gcggaattgt acccgcggcc gatccaccgg taccgagctc tcccgcagaa caccatgcgc     1020
tccacggaag caggtcctca ctttaatgct gtggccactg agaagtatta aagtgaggac     1080
ctgcttctga ggagcgcctt gacagcagcc atgggagggc ctcgaggacg gggtgaacta     1140
cgcctgagga tccgatcttt ttccctctgc caaaaattat ggggacatca tgaagcccct     1200
tgagcatctg acttctggct aataaaggaa atttatttc attgcaatag tgtgttggaa      1260
ttttttgtgt ctctcactcg gcctaggtag ataagtagca tggcgggtta atcattaact     1320
acaaggaacc cctagtgatg gagttggcca ctccctctct gcgcgctcgc tcgctcactg     1380
aggccgggcg accaaaggtc gcccgacgcc cgggctttgc ccgggcggcc tcagtgagcg     1440
agcgagcgcg cag                                                         1453

<210> SEQ ID NO 126
<211> LENGTH: 1453
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
ctgcgcgctc gctcgctcac tgaggccgcc cgggcaaagc ccgggcgtcg ggcgaccttt       60
ggtcgcccgg cctcagtgag cgagcgagcg cgcagagagg gagtgtagcc atgctctagg      120
aagatcaatt caattcacgc gtcgacattg attattgact agttattaat agtaatcaat      180
tacggggtca ttagttcata gcccatatat ggagttccgc gttacataac ttacggtaaa      240
tggcccgcct ggctgaccgc ccaacgaccc ccgcccattg acgtcaataa tgacgtatgt      300
tcccatagta acgccaatag ggactttcca ttgacgtcaa tgggtggagt atttacggta      360
aactgcccac ttggcagtac atcaagtgta tcatatgcca agtacgcccc ctattgacgt      420
caatgacggt aaatggcccg cctggcatta tgcccagtac atgaccttat gggactttcc      480
tacttggcag tacatctacg tattagtcat cgctattacc atgtcgaggc cacgttctgc      540
ttcactctcc ccatctcccc ccctcccca ccccaatt tgtatttatt tattttttaa       600
ttattttgtg cagcgatggg ggcggggggg ggggcgcgc gccaggcggg gcggggcggg      660
gcgaggggcg gggcggggcg aggcggagag gtgcggcggc agccaatcag agcggcgcgc      720
tccgaaagtt tccttttatg gcgaggcggc ggcggcggcg gccctataaa agcgaagcg       780 cgcggcgggc gggagcaagc ttgaactgaa aaaccagaaa gttaactggt aagtttagtc      840
```

```
ttttgtctt ttatttcagg tcccggatcc ggtggtggtg caaatcaaag aactgctcct      900
cagtggatgt tgcctttact tctaggcctg tacggaagtg ttacttctgc tctaaaagct      960
gcggaattgt acccgcggcc gatccaccgg taccgagctc tcccgcagaa caccatgcgc     1020
tccacggaat cgtttggctt gtggtgtgct gtggccactg agaagtacac cacaagccaa     1080
acgattctga ggagcgcctt gacagcagcc atgggagggc ctcgaggacg ggtgaacta      1140 cgcctgagga tccgatcttt ttccctctgc caaaaattat ggggacatca tgaagcccct     1200
tgagcatctg acttctggct aataaaggaa atttattttc attgcaatag tgtgttggaa     1260
ttttttgtgt ctctcactcg gcctaggtag ataagtagca tggcgggtta atcattaact     1320
acaaggaacc cctagtgatg gagttggcca ctccctctct gcgcgctcgc tcgctcactg     1380
aggccgggcg accaaaggtc gcccgacgcc cgggctttgc ccgggcggcc tcagtgagcg     1440
agcgagcgcg cag                                                         1453
```

<210> SEQ ID NO 127
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

```
ctgcgcgctc gctcgctcac tgaggccgcc cgggcaaagc ccgggcgtcg ggcgaccttt       60
ggtcgcccgg cctcagtgag cgagcgagcg cgcagagagg gagtgtagcc atgctctagg      120
aagatcaatt caattcacgc gtcgacattg attattgact agttattaat agtaatcaat      180
tacggggtca ttagttcata gcccatatat ggagttccgc gttacataac ttacggtaaa      240
tggcccgcct ggctgaccgc ccaacgaccc ccgcccattg acgtcaataa tgacgtatgt      300
tcccatagta acgccaatag ggactttcca ttgacgtcaa tgggtggagt atttacggta      360
aactgcccac ttggcagtac atcaagtgta tcatatgcca gtacgccccc ctattgacgt      420
caatgacggt aaatggcccg cctggcatta tgcccagtac atgaccttat gggactttcc      480
tacttggcag tacatctacg tattagtcat cgctattacc atgtcgaggc cacgttctgc      540
ttcactctcc ccatctcccc cccctcccca ccccaatttt gtatttatt tatttttaa       600 ttattttgtg cagcgatggg ggcggggggg ggggcgcgc gccaggcggg gcggggcggg      660
gcgaggggcg gggcggggcg aggcggagag gtgcggcggc agccaatcag agcggcgcgc      720
tccgaaagtt tccttttatg gcgaggcggc ggcggcggcg gccctataaa aagcgaagcg      780
cgcggcgggc gggagcaagc ttgaactgaa aaaccagaaa gttaactggt aagtttagtc      840
tttttgtctt ttatttcagg tcccggatcc ggtggtggtg caaatcaaag aactgctcct      900
cagtggatgt tgcctttact tctaggcctg tacggaagtg ttacttctgc tctaaaagct      960
gcggaattgt acccgcggcc gatccaccgg tgaagcaaag aagggcagag gggagcccgt     1020
gagctgagtg ggccagggac tgggagaagg agtgaggagg cagggccggc atgcctctgc     1080
tgctggccag agcaggtcct cactttaatc ccgtctgcac ctgtcactag gattaaagtg     1140
aggacctgct ttggccgtgt agtgctaccc agcgctggct gcctcctcag cattgcaatt     1200
cctctcccat ctgggcacca gtcagctacc ctggtgggaa tctgggtagc cctcgaggac     1260
ggggtgaact acgcctgagg atccgatctt tttccctctg ccaaaaatta tggggacatc     1320
atgaagcccc ttgagcatct gacttctggc taataaagga aatttatttt cattgcaata     1380
```

```
gtgtgttgga attttttgtg tctctcactc ggcctaggta gataagtagc atggcgggtt    1440
aatcattaac tacaaggaac ccctagtgat ggagttggcc actccctctc tgcgcgctcg    1500
ctcgctcact gaggccgggc gaccaaaggt cgcccgacgc ccgggctttg cccgggcggc    1560
ctcagtgagc gagcgagcgc gcag                                          1584
```

<210> SEQ ID NO 128
<211> LENGTH: 1406
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
ctgcgcgctc gctcgctcac tgaggccgcc cgggcaaagc ccgggcgtcg ggcgaccttt     60
ggtcgcccgg cctcagtgag cgagcgagcg cgcagagagg gagtgtagcc atgctctagg    120
aagatcaatt caattcacgc gtccatggct tagaaggcaa gaatcctggc tgtggaaaga    180
tacctaaagg atcaacagct cctggggatt tggggttgct ctggaaaact catttgcacc    240
actgctgtgc cttggaatgc tagttggagt aataaatctc tggaacagat ttggaatcac    300
acgacctgga tggagtggga cagagaaatt aacaattaca caagcttaat acactcctta    360
attgaagaat cgcaaaacca gcaagaaaag aatgaacaag aattattgga attagataaa    420
tgggcaagtt tgtggaattg gtttaacata acaaattggc tgtggtatat aaaattattc    480
ataatgatag taggaggctt ggtaggttta agaatagttt ttgctgtact ttctatagtg    540
aatagagtta ggcagggata ttcaccatta tcgtttcaga cccacctccc aaccccgagg    600
ggacccgaca ggcccgaagg aatagaagaa gaaggtggag agagagacag agacagatcc    660
attcgattag tgaacggatc tcgacggtat cgatcacgag actagcctcg agcggccgca    720
attcgaacgc tgacgtcatc aacccgctcc aaggaatcgc gggcccagtg tcactaggcg    780
ggaacaccca gcgcgcgtgc gccctggcag gaagatggct gtgagggaca gggagtggcg    840
ccctgcaata tttgcatgtc gctatgtgtt ctgggaaatc accataaacg tgaaatgtct    900
ttggatttgg gaatcttata agttctgtat gagaccacac cggtaccgag ctctcccgca    960
gaacaccatg cgctccacgg aagcaggtcc tcactttaat gctgtggcca ctgagaagta   1020
ttaaagtgag gacctgcttc tgaggagcgc cttgacagca gccatgggag ggcctcgagg   1080
acggggtgaa ctacgcctga ggatccgatc ttttccctc tgccaaaaat tatgggaca    1140 tcatgaagcc ccttgagcat ctgacttctg gctaataaag gaaatttatt ttcattgcaa   1200
tagtgtgttg gaatttttg tgtctctcac tcggcctagg tagataagta gcatggcggg   1260
ttaatcatta actacaagga acccctagtg atggagttgg ccactccctc tctgcgcgct   1320
cgctcgctca ctgaggccgg gcgaccaaag gtcgcccgac gcccgggctt tgcccgggcg   1380
gcctcagtga gcgagcgagc gcgcag                                       1406
```

<210> SEQ ID NO 129
<211> LENGTH: 1406
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129

```
ctgcgcgctc gctcgctcac tgaggccgcc cgggcaaagc ccgggcgtcg ggcgaccttt     60
```

```
ggtcgcccgg cctcagtgag cgagcgagcg cgcagagagg gagtgtagcc atgctctagg      120
aagatcaatt caattcacgc gtccatggct tagaaggcaa gaatcctggc tgtggaaaga      180
tacctaaagg atcaacagct cctggggatt tggggttgct ctggaaaact catttgcacc      240
actgctgtgc cttggaatgc tagttggagt aataaatctc tggaacagat ttggaatcac      300
acgacctgga tggagtggga cagagaaatt aacaattaca caagcttaat acactcctta      360
attgaagaat cgcaaaacca gcaagaaaag aatgaacaag aattattgga attagataaa      420
tgggcaagtt tgtggaattg gtttaacata acaaattggc tgtggtatat aaaattattc      480
ataatgatag taggaggctt ggtaggttta agaatagttt ttgctgtact ttctatagtg      540
aatagagtta ggcagggata ttcaccatta tcgtttcaga cccacctccc aaccccgagg      600
ggacccgaca ggcccgaagg aatagaagaa gaaggtggag agagacag agacagatcc       660 attcgattag tgaacggatc tcgacggtat cgatcacgag actagcctcg agcggccgca      720
attcgaacgc tgacgtcatc aacccgctcc aaggaatcgc gggcccagtg tcactaggcg      780
ggaacaccca gcgcgcgtgc gccctggcag gaagatggct gtgagggaca gggagtggcg      840
ccctgcaata tttgcatgtc gctatgtgtt ctgggaaatc accataaacg tgaaatgtct      900
ttggatttgg gaatcttata agttctgtat gagaccacac cggtaccgag ctctcccgca      960
gaacaccatg cgctccacgg aagtcgtttg gcttgtggtg gctgtggcca ctgagaagtc     1020
accacaagcc aaacgacttc tgaggagcgc cttgacagca gccatgggag ggcctcgagg     1080
acggggtgaa ctacgcctga ggatccgatc ttttcctc tgccaaaaat tatgggggaca     1140 tcatgaagcc ccttgagcat ctgacttctg gctaataaag gaaatttatt ttcattgcaa     1200
tagtgtgttg gaattttttg tgtctctcac tcggcctagg tagataagta gcatggcggg     1260
ttaatcatta actacaagga accctagtg atggagttgg ccactccctc tctgcgcgct      1320
cgctcgctca ctgaggccgg gcgaccaaag gtcgcccgac gcccgggctt tgcccgggcg     1380
gcctcagtga gcgagcgagc gcgcag                                          1406
```

<210> SEQ ID NO 130
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
ctgcgcgctc gctcgctcac tgaggccgcc cgggcaaagc ccgggcgtcg ggcgaccttt       60
ggtcgcccgg cctcagtgag cgagcgagcg cgcagagagg gagtgtagcc atgctctagg      120
aagatcaatt caattcacgc gtcgacattg attattgact agttattaat agtaatcaat      180
tacggggtca ttagttcata gcccatatat ggagttccgc gttacataac ttacggtaaa      240
tggcccgcct ggctgaccgc ccaacgaccc ccgcccattg acgtcaataa tgacgtatgt      300
tcccatagta acgccaatag ggactttcca ttgacgtcaa tgggtggagt atttacggta      360
aactgcccac ttggcagtac atcaagtgta tcatatgcca gtacgccccc tattgacgt      420 caatgacggt aaatggcccg cctggcatta tgcccagtac atgaccttat gggactttcc      480
tacttggcag tacatctacg tattagtcat cgctattacc atgtcgaggc cacgttctgc      540
ttcactctcc ccatctcccc cccctcccca ccccaatttt gtatttatt tattttttaa      600 ttattttgtg cagcgatggg ggcgggggggg ggggcgcgc gccaggcggg gcggggcggg     660
```

```
gcgaggggcg ggcggggcg aggcggagag gtgcggcggc agccaatcag agcggcgcgc    720
tccgaaagtt tccttttatg gcgaggcggc ggcggcggcg gccctataaa aagcgaagcg    780
cgcggcgggc gggagcaagc ttgaactgaa aaaccagaaa gttaactggt aagtttagtc    840
tttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg tgaagcaaag aagggcaga gggagcccgt   1020 gagctgagtg ggccagggac tgggagaagg agtgaggagg cagggccggc atgcctctgc   1080
tgctggccag agtcgtttgg cttgtggtgg ccgtctgcac ctgtcactag tcaccacaag   1140
ccaaacgact ttggccgtgt agtgctaccc agcgctggct gcctcctcag cattgcaatt   1200
cctctcccat ctgggcacca gtcagctacc ctggtgggaa tctgggtagc cctcgaggac   1260
ggggtgaact acgcctgagg atccgatctt tttccctctg ccaaaaatta tggggacatc   1320
atgaagcccc ttgagcatct gacttctggc taataaagga aatttatttt cattgcaata   1380
gtgtgttgga attttttgtg tctctcactc ggcctaggta gataagtagc atggcgggtt   1440
aatcattaac tacaaggaac ccctagtgat ggagttggcc actccctctc tgcgcgctcg   1500
ctcgctcact gaggccgggc gaccaaaggt cgcccgacgc ccgggctttg cccgggcggc   1560
ctcagtgagc gagcgagcgc gcag                                          1584

<210> SEQ ID NO 131
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
ctgcgcgctc gctcgctcac tgaggccgcc cgggcaaagc ccgggcgtcg ggcgaccttt     60
ggtcgcccgg cctcagtgag cgagcgagcg cgcagagagg gagtgtagcc atgctctagg    120
aagatcaatt caattcacgc gtcgacattg attattgact agttattaat agtaatcaat    180
tacggggtca ttagttcata gcccatatat ggagttccgc gttacataac ttacggtaaa    240
tggcccgcct ggctgaccgc ccaacgaccc cgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca gtacgcccc ctattgacgt    420 caatgacggt aaatggcccg cctggcatta tgcccagtac atgaccttat gggactttcc    480
tacttggcag tacatctacg tattagtcat cgctattacc atgtcgaggc cacgttctgc    540
ttcactctcc ccatctcccc ccctcccca ccccaattt tgtatttatt tatttttaa       600 ttatttgtg cagcgatggg ggcgggggg ggggcgcgc gccaggcggg gcgggcggg       660 gcgaggggcg ggcggggcg aggcggagag gtgcggcggc agccaatcag agcggcgcgc    720
tccgaaagtt tccttttatg gcgaggcggc ggcggcggcg gccctataaa aagcgaagcg    780
cgcggcgggc gggagcaagc ttgaactgaa aaaccagaaa gttaactggt aagtttagtc    840
tttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg tgaagcaaag aagggcaga gggagcccgt   1020 gagctgagtg ggccagggac tgggagaagg agtgaggagg cagggccggc atgcctctgc   1080
```

```
tgctggccag acaggtcctc actttaatcg ccgtctgcac ctgtcactag tgattaaagt    1140
gaggacctgt ttggccgtgt agtgctaccc agcgctggct gcctcctcag cattgcaatt    1200
cctctcccat ctgggcacca gtcagctacc ctggtgggaa tctgggtagc cctcgaggac    1260
ggggtgaact acgcctgagg atccgatctt tttccctctg ccaaaaatta tggggacatc    1320
atgaagcccc ttgagcatct gacttctggc taataaagga aatttatttt cattgcaata    1380
gtgtgttgga attttttgtg tctctcactc ggcctaggta gataagtagc atggcgggtt    1440
aatcattaac tacaaggaac ccctagtgat ggagttggcc actccctctc tgcgcgctcg    1500
ctcgctcact gaggccgggc gaccaaaggt cgcccgacgc ccgggctttg cccgggcggc    1560
ctcagtgagc gagcgagcgc gcag                                          1584
```

<210> SEQ ID NO 132
<211> LENGTH: 1584
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
ctgcgcgctc gctcgctcac tgaggccgcc cgggcaaagc ccgggcgtcg ggcgaccttt     60
ggtcgcccgg cctcagtgag cgagcgagcg cgcagagagg gagtgtagcc atgctctagg    120
aagatcaatt caattcacgc gtcgacattg attattgact agttattaat agtaatcaat    180 tacgggtca ttagttcata gcccatatat ggagttccgc gttacataac ttacggtaaa     240
tggcccgcct ggctgaccgc ccaacgaccc ccgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca agtacgcccc ctattgacgt    420
caatgacggt aaatggcccg cctggcatta tgcccagtac atgaccttat gggactttcc    480
tacttggcag tacatctacg tattagtcat cgctattacc atgtcgaggc cacgttctgc    540
ttcactctcc ccatctcccc cccctcccca ccccaatttt gtatttatt tattttttaa    600 ttattttgtg cagcgatggg ggcgggggg ggggcgcgc gccaggcggg gcggggcggg     660
gcgaggggcg gggcggggcg aggcggagag gtgcggcggc agccaatcag agcggcgcgc    720
tccgaaagtt tccttttatg gcgaggcggc ggcggcggcg gccctataaa aagcgaagcg    780
cgcggcgggc gggagcaagc ttgaactgaa aaaccagaaa gttaactggt aagtttagtc    840
tttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg tgaagcaaag aaggggcaga gggagcccgt    1020
gagctgagtg ggccagggac tgggagaagg agtgaggagg cagggccggc atgcctctgc    1080
tgctggccag atcgtttggc ttgtggtgtg ccgtctgcac ctgtcactag taccaccaa     1140 gccaaacgat ttggccgtgt agtgctaccc agcgctggct gcctcctcag cattgcaatt    1200
cctctcccat ctgggcacca gtcagctacc ctggtgggaa tctgggtagc cctcgaggac    1260
ggggtgaact acgcctgagg atccgatctt tttccctctg ccaaaaatta tggggacatc    1320
atgaagcccc ttgagcatct gacttctggc taataaagga aatttatttt cattgcaata    1380
gtgtgttgga attttttgtg tctctcactc ggcctaggta gataagtagc atggcgggtt    1440
aatcattaac tacaaggaac ccctagtgat ggagttggcc actccctctc tgcgcgctcg    1500
```

```
ctcgctcact gaggccgggc gaccaaaggt cgcccgacgc ccgggctttg cccgggcggc   1560
ctcagtgagc gagcgagcgc gcag                                          1584
```

<210> SEQ ID NO 133
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
ctgcgcgctc gctcgctcac tgaggccgcc cgggcaaagc ccgggcgtcg ggcgaccttt     60
ggtcgcccgg cctcagtgag cgagcgagcg cgcagagagg gagtgtagcc atgctctagg   120
aagatcaatt caattcacgc gtcgacattg attattgact agttattaat agtaatcaat   180
tacggggtca ttagttcata gcccatatat ggagttccgc gttacataac ttacggtaaa   240
tggcccgcct ggctgaccgc ccaacgaccc ccgcccattg acgtcaataa tgacgtatgt   300
tcccatagta acgccaatag ggactttcca ttgacgtcaa tgggtggagt atttacggta   360
aactgcccac ttggcagtac atcaagtgta tcatatgcca gtacgccccc tattgacgt    420 caatgacggt aaatggcccg cctggcatta tgcccagtac atgacctat gggactttcc    480 tacttggcag tacatctacg tattagtcat cgctattacc atgtcgaggc cacgttctgc   540
ttcactctcc ccatctcccc ccctccccca ccccaatttt gtatttatt tattttttaa    600 ttatttgtg cagcgatggg ggcggggggg ggggcgcgc gccaggcggg gcggggcggg     660
gcgaggggcg gggcggggcg aggcggagag gtgcggcggc agccaatcag agcggcgcgc   720
tccgaaagtt tccttttatg gcgaggcggc ggcggcggcg gccctataaa aagcgaagcg   780
cgcggcgggc gggagcaagc ttgaactgaa aaaccagaaa gttaactggt aagtttagtc   840
tttttgtctt ttatttcagg tcccggatcc ggtggtggtg caaatcaaag aactgctcct   900
cagtggatgt tgcctttact tctaggcctg tacggaagtg ttacttctgc tctaaaagct   960
gcggaattgt acccgcggcc gatccaccgg taccgagctg tgctgggcgg ggggcggcgg  1020
gccctcccgc agaacaccat gcgctcttcg gaaggcaatg tgactgctgg tgcctgtgac  1080
ctggtgccag cagtcacatt gccttctgag gagcgccttg acagcagcca tgggagggcc  1140
gccccctacc tcagtgactc gaggacgggg tgaactacgc ctgaggatcc gatctttttc  1200
cctctgccaa aaattatggg gacatcatga agccccttga gcatctgact tctggctaat  1260
aaaggaaatt tattttcatt gcaatagtgt gttggaattt tttgtgtctc tcactcggcc  1320
taggtagata agtagcatgg cgggttaatc attaactaca aggaaccct agtgatggag   1380 ttggccactc cctctctgcg cgctcgctcg ctcactgagg ccgggcgacc aaaggtcgcc  1440
cgacgcccgg gctttgcccg gcggcctca gtgagcgagc gagcgcgcag              1490
```

<210> SEQ ID NO 134
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

```
ctgcgcgctc gctcgctcac tgaggccgcc cgggcaaagc ccgggcgtcg ggcgaccttt     60
```

| | |
|---|---|
| ggtcgcccgg cctcagtgag cgagcgagcg cgcagagagg gagtgtagcc atgctctagg | 120 |
| aagatcaatt caattcacgc gtcgacattg attattgact agttattaat agtaatcaat | 180 |
| tacggggtca ttagttcata gcccatatat ggagttccgc gttacataac ttacggtaaa | 240 |
| tggcccgcct ggctgaccgc ccaacgaccc ccgcccattg acgtcaataa tgacgtatgt | 300 |
| tcccatagta acgccaatag ggactttcca ttgacgtcaa tgggtggagt atttacggta | 360 |
| aactgcccac ttggcagtac atcaagtgta tcatatgcca gtacgcccc ctattgacgt | 420 |
| caatgacggt aaatggcccg cctggcatta tgcccagtac atgaccttat gggactttcc | 480 |
| tacttggcag tacatctacg tattagtcat cgctattacc atgtcgaggc cacgttctgc | 540 |
| ttcactctcc ccatctcccc ccctcccca ccccaattt tgtatttatt tattttttaa | 600 |
| ttattttgtg cagcgatggg ggcggggggg ggggcgcgc gccaggcggg gcggggcggg | 660 |
| gcgaggggcg gggcggggcg aggcggagag gtgcggcggc agccaatcag agcggcgcgc | 720 |
| tccgaaagtt tccttttatg gcgaggcggc ggcggcggcg gccctataaa aagcgaagcg | 780 |
| cgcggcgggc gggagcaagc ttgaactgaa aaaccagaaa gttaactggt aagtttagtc | 840 |
| tttttgtctt ttatttcagg tcccggatcc ggtggtggtg caaatcaaag aactgctcct | 900 |
| cagtggatgt tgcctttact tctaggcctg tacggaagtg ttacttctgc tctaaaagct | 960 |
| gcggaattgt acccgcggcc gatccaccgg taccgagctg tgctgggcgg ggggcggcgg | 1020 |
| gccctcccgc agaacaccat cgctcttcg gaaggcaatg tgactgctgg tacctgtgat | 1080 |
| ttggtgccag cagtcacatt gccttctgag gagcgccttg acagcagcca tgggagggcc | 1140 |
| gcccctacc tcagtgactc gaggacgggg tgaactacgc tgaggatcc gatcttttc | 1200 |
| cctctgccaa aaattatggg gacatcatga agccccttga gcatctgact tctggctaat | 1260 |
| aaaggaaatt tattttcatt gcaatagtgt gttggaattt tttgtgtctc tcactcggcc | 1320 |
| taggtagata agtagcatgg cgggttaatc attaactaca aggaacccct agtgatggag | 1380 |
| ttggccactc cctctctgcg cgctcgctcg ctcactgagg ccgggcgacc aaaggtcgcc | 1440 |
| cgacgcccgg gctttgcccg gcggcctca gtgagcgagc gagcgcgcag | 1490 |

```
<210> SEQ ID NO 135
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
```

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt caattcacgc gtcgacattg attattgact agttattaat agtaatcaat | 180 |
| tacggggtca ttagttcata gcccatatat ggagttccgc gttacataac ttacggtaaa | 240 |
| tggcccgcct ggctgaccgc ccaacgaccc ccgcccattg acgtcaataa tgacgtatgt | 300 |
| tcccatagta acgccaatag ggactttcca ttgacgtcaa tgggtggagt atttacggta | 360 |
| aactgcccac ttggcagtac atcaagtgta tcatatgcca gtacgcccc ctattgacgt | 420 |
| caatgacggt aaatggcccg cctggcatta tgcccagtac atgaccttat gggactttcc | 480 |
| tacttggcag tacatctacg tattagtcat cgctattacc atgtcgaggc cacgttctgc | 540 |
| ttcactctcc ccatctcccc ccctcccca ccccaattt tgtatttatt tattttttaa | 600 |

```
ttatttttgtg cagcgatggg ggcgggggg ggggggcgcgc gccaggcggg gcggggcggg    660
gcgaggggcg gggcggggcg aggcggagag gtgcggcggc agccaatcag agcggcgcgc    720
tccgaaagtt tcctttatg gcgaggcggc ggcggcggcg gccctataaa aagcgaagcg    780
cgcggcgggc gggagcaagc ttgaactgaa aaaccagaaa gttaactggt aagtttagtc    840 ttttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg taccgagctg tgctgggcgg ggggcggcgg   1020
gccctcccgc agaacaccat gcgctcttcg gaaggcaatg tgactgctgg tacctgtgac   1080
ctggtgccag cagtcacatt gccttctgtg gagcgccttg acagcagcca tgggagggcc   1140 gcccctacc tcagtgactc gaggacgggg tgaactacgc ctgaggatcc gatcttttttc   1200 cctctgccaa aaattatggg gacatcatga agcccttga gcatctgact tctggctaat   1260
aaaggaaatt tattttcatt gcaatagtgt gttggaattt tttgtgtctc tcactcggcc   1320
taggtagata agtagcatgg cgggttaatc attaactaca aggaacccct agtgatggag   1380
ttggccactc cctctctgcg cgctcgctcg ctcactgagg ccgggcgacc aaaggtcgcc   1440
cgacgcccgg gctttgcccg gcggcctca gtgagcgagc gagcgcgcag                1490
```

<210> SEQ ID NO 136
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

```
ctgcgcgctc gctcgctcac tgaggccgcc cgggcaaagc ccgggcgtcg ggcgaccttt     60
ggtcgcccgg cctcagtgag cgagcgagcg cgcagagagg gagtgtagcc atgctctagg    120
aagatcaatt caattcacgc gtcgacattg attattgact agttattaat agtaatcaat    180
tacggggtca ttagttcata gcccatatat ggagttccgc gttacataac ttacggtaaa    240
tggcccgcct ggctgaccgc ccaacgaccc ccgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca gtacgcccc ctattgacgt    420 caatgacggt aaatggcccg cctggcatta tgcccagtac atgaccttat gggactttcc    480
tacttggcag tacatctacg tattagtcat cgctattacc atgtcgaggc cacgttctgc    540
ttcactctcc ccatctcccc ccccctcccca cccccaattt tgtatttatt tattttttaa    600 ttatttttgtg cagcgatggg ggcgggggg ggggggcgcgc gccaggcggg gcggggcggg    660
gcgaggggcg gggcggggcg aggcggagag gtgcggcggc agccaatcag agcggcgcgc    720
tccgaaagtt tcctttatg gcgaggcggc ggcggcggcg gccctataaa aagcgaagcg    780
cgcggcgggc gggagcaagc ttgaactgaa aaaccagaaa gttaactggt aagtttagtc    840 ttttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg taccgagctg tgctgggcgg ggggcggcgg   1020
gccctcccgc agaacaccat gcgctcttcg gaaggcaatg tgtctgctgg tacctgtgac   1080
ctggtgccag cagtcacatt gccttctgtg gagcgccttg acagcagcca tgggagggcc   1140
```

| | |
|---|---|
| gcccctacc tcagtgactc gaggacgggg tgaactacgc ctgaggatcc gatcttttc | 1200 |
| cctctgccaa aaattatggg gacatcatga agcccttga gcatctgact tctggctaat | 1260 |
| aaaggaaatt tattttcatt gcaatagtgt gttggaattt tttgtgtctc tcactcggcc | 1320 |
| taggtagata agtagcatgg cgggttaatc attaactaca aggaacccct agtgatggag | 1380 |
| ttggccactc cctctctgcg cgctcgctcg ctcactgagg ccgggcgacc aaaggtcgcc | 1440 |
| cgacgcccgg gctttgcccg ggcggcctca gtgagcgagc gagcgcgcag | 1490 |

<210> SEQ ID NO 137
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt caattcacgc gtcgacattg attattgact agttattaat agtaatcaat | 180 |
| tacggggtca ttagttcata gcccatatat ggagttccgc gttacataac ttacggtaaa | 240 |
| tggcccgcct ggctgaccgc ccaacgaccc cgcccattg acgtcaataa tgacgtatgt | 300 |
| tcccatagta acgccaatag ggactttcca ttgacgtcaa tgggtggagt atttacggta | 360 |
| aactgcccac ttggcagtac atcaagtgta tcatatgcca agtacgcccc ctattgacgt | 420 |
| caatgacggt aaatggcccg cctggcatta tgcccagtac atgaccttat gggactttcc | 480 |
| tacttggcag tacatctacg tattagtcat cgctattacc atgtcgaggc cacgttctgc | 540 |
| ttcactctcc ccatctcccc ccctcccca ccccaattt tgtatttatt tatttttaa | 600 |
| ttattttgtg cagcgatggg ggcggggggg ggggcgcgc gccaggcggg gcggggcggg | 660 |
| gcgaggggcg gggcggggcg aggcggagag gtgcggcggc agccaatcag agcggcgcgc | 720 |
| tccgaaagtt cctttttatg gcgaggcggc ggcggcggcg gccctataaa agcgaagcg | 780 |
| cgcggcgggc gggagcaagc ttgaactgaa aaaccagaaa gttaactggt aagtttagtc | 840 |
| ttttgtctt ttatttcagg tcccggatcc ggtggtggtg caaatcaaag aactgctcct | 900 |
| cagtggatgt tgcctttact tctaggcctg tacggaagtg ttacttctgc tctaaaagct | 960 |
| gcggaattgt acccgcggcc gatccaccgg taccgagctg tgctgggcgg ggggcggcgg | 1020 |
| gccctcccgc agaacaccat gcgctcttcg gaaggcaatg tgactgctgg ccctgtgac | 1080 |
| ctggtgccag cagtcacatt gccttctgag gagcgccttg acagcagcca tgggagggcc | 1140 |
| gcccctacc tcagtgactc gaggacgggg tgaactacgc ctgaggatcc gatcttttc | 1200 |
| cctctgccaa aaattatggg gacatcatga agcccttga gcatctgact tctggctaat | 1260 |
| aaaggaaatt tattttcatt gcaatagtgt gttggaattt tttgtgtctc tcactcggcc | 1320 |
| taggtagata agtagcatgg cgggttaatc attaactaca aggaacccct agtgatggag | 1380 |
| ttggccactc cctctctgcg cgctcgctcg ctcactgagg ccgggcgacc aaaggtcgcc | 1440 |
| cgacgcccgg gctttgcccg ggcggcctca gtgagcgagc gagcgcgcag | 1490 |

<210> SEQ ID NO 138
<211> LENGTH: 1490
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 138

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtgtagcc | atgctctagg | 120 |
| aagatcaatt | caattcacgc | gtcgacattg | attattgact | agttattaat | agtaatcaat | 180 |
| tacgggtca  | ttagttcata | gcccatatat | ggagttccgc | gttacataac | ttacggtaaa | 240 |
| tggcccgcct | ggctgaccgc | ccaacgaccc | ccgcccattg | acgtcaataa | tgacgtatgt | 300 |
| tcccatagta | acgccaatag | ggactttcca | ttgacgtcaa | tgggtggagt | atttacggta | 360 |
| aactgcccac | ttggcagtac | atcaagtgta | tcatatgcca | agtacgcccc | ctattgacgt | 420 |
| caatgacggt | aaatggcccg | cctggcatta | tgcccagtac | atgaccttat | gggactttcc | 480 |
| tacttggcag | tacatctacg | tattagtcat | cgctattacc | atgtcgaggc | cacgttctgc | 540 |
| ttcactctcc | ccatctcccc | ccctcccca  | ccccaattt  | tgtatttatt | tattttttaa | 600 |
| ttattttgtg | cagcgatggg | ggcgggggggg | ggggcgcgc | gccaggcggg | gcggggcggg | 660 |
| gcgaggggcg | gggcggggcg | aggcggagag | gtgcggcggc | agccaatcag | agcggcgcgc | 720 |
| tccgaaagtt | tccttttatg | gcgaggcggc | ggcggcggcg | gccctataaa | aagcgaagcg | 780 |
| cgcggcgggc | gggagcaagc | ttgaactgaa | aaaccagaaa | gttaactggt | aagtttagtc | 840 |
| tttttgtctt | ttatttcagg | tcccggatcc | ggtggtggtg | caaatcaaag | aactgctcct | 900 |
| cagtggatgt | tgcctttact | tctaggcctg | tacggaagtg | ttacttctgc | tctaaaagct | 960 |
| gcggaattgt | acccgcggcc | gatccaccgg | taccgagctg | tgctgggcgg | ggggcggcgg | 1020 |
| gccctcccgc | agaacaccat | gcgctcttcg | gaagcaggtc | ctcactttaa | ttcctgtgac | 1080 |
| ctgggattaa | agtgaggacc | tgcttctgag | gagcgccttg | acagcagcca | tgggagggcc | 1140 |
| gcccctacc  | tcagtgactc | gaggacgggg | tgaactacgc | ctgaggatcc | gatctttttc | 1200 |
| cctctgccaa | aaattatggg | gacatcatga | agccccttga | gcatctgact | tctggctaat | 1260 |
| aaaggaaatt | tattttcatt | gcaatagtgt | gttggaattt | tttgtgtctc | tcactcggcc | 1320 |
| taggtagata | agtagcatgg | cgggttaatc | attaactaca | aggaacccct | agtgatggag | 1380 |
| ttggccactc | cctctctgcg | cgctcgctcg | ctcactgagg | ccgggcgacc | aaaggtcgcc | 1440 |
| cgacgcccgg | gctttgcccg | ggcggcctca | gtgagcgagc | gagcgcgcag | | 1490 |

<210> SEQ ID NO 139
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtgtagcc | atgctctagg | 120 |
| aagatcaatt | caattcacgc | gtcgacattg | attattgact | agttattaat | agtaatcaat | 180 |
| tacgggtca  | ttagttcata | gcccatatat | ggagttccgc | gttacataac | ttacggtaaa | 240 |
| tggcccgcct | ggctgaccgc | ccaacgaccc | ccgcccattg | acgtcaataa | tgacgtatgt | 300 |
| tcccatagta | acgccaatag | ggactttcca | ttgacgtcaa | tgggtggagt | atttacggta | 360 |
| aactgcccac | ttggcagtac | atcaagtgta | tcatatgcca | agtacgcccc | ctattgacgt | 420 |

```
caatgacggt aaatggcccg cctggcatta tgcccagtac atgacctat gggactttcc      480 tacttggcag tacatctacg tattagtcat cgctattacc atgtcgaggc cacgttctgc      540
ttcactctcc ccatctcccc cccctcccca ccccaatttt tgtatttatt tattttttaa      600
ttattttgtg cagcgatggg ggcgggggggg ggggcgcgc gccaggcggg gcggggcggg      660
gcgaggggcg gggcggggcg aggcggagag gtgcggcggc agccaatcag agcggcgcgc      720
tccgaaagtt ccttttatg gcgaggcggc ggcggcggcg gccctataaa aagcgaagcg      780
cgcggcgggc gggagcaagc ttgaactgaa aaaccagaaa gttaactggt aagtttagtc      840
tttttgtctt ttatttcagg tcccggatcc ggtggtggtg caaatcaaag aactgctcct      900
cagtggatgt tgcctttact tctaggcctg tacgaagtg ttacttctgc tctaaaagct      960
gcggaattgt acccgcggcc gatccaccgg tgaagcaaag aagggcagag gggagcccgt     1020
gagctgagtg ggccagggac tgggagaagg agtgaggagg cagggccggc atgcctctgc     1080
tgctggccag aggcaatgtg actgctggta ccgtctgcac ctgtcactag tgccagcagt     1140
cacattgcct ttggccgtgt agtgctaccc agcgctggct gcctcctcag cattgcaatt     1200
cctctcccat ctgggcacca gtcagctacc ctggtgggaa tctgggtagc cctcgaggac     1260
ggggtgaact acgcctgagg atccgatctt tttccctctg ccaaaaatta tggggacatc     1320
atgaagcccc ttgagcatct gacttctggc taataaagga aatttatttt cattgcaata     1380
gtgtgttgga atttttgtg tctctcactc ggcctaggta gataagtagc atggcgggtt     1440
aatcattaac tacaaggaac ccctagtgat ggagttggcc actccctctc tgcgcgctcg     1500
ctcgctcact gaggccgggc gaccaaaggt cgcccgacgc ccgggctttg cccgggcggc     1560
ctcagtgagc gagcgagcgc gcag                                             1584
```

<210> SEQ ID NO 140
<211> LENGTH: 1491
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
ctgcgcgctc gctcgctcac tgaggccgcc cgggcaaagc ccgggcgtcg ggcgacctttt     60 ggtcgcccgg cctcagtgag cgagcgagcg cgcagagagg gagtgtagcc atgctctagg    120
aagatcaatt caattcacgc gtcgacattg attattgact agttattaat agtaatcaat    180 tacgggtca ttagttcata gcccatatat ggagttccgc gttacataac ttacggtaaa     240
tggcccgcct ggctgaccgc ccaacgaccc cgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca gtacgcccc ctattgacgt    420 caatgacggt aaatggcccg cctggcatta tgcccagtac atgaccttat gggactttcc    480
tacttggcag tacatctacg tattagtcat cgctattacc atgtcgaggc cacgttctgc    540
ttcactctcc ccatctcccc cccctcccca ccccaatttt tgtatttatt tattttttaa    600
ttattttgtg cagcgatggg ggcgggggggg ggggcgcgc gccaggcggg gcggggcggg    660
gcgaggggcg gggcggggcg aggcggagag gtgcggcggc agccaatcag agcggcgcgc    720
tccgaaagtt ccttttatg gcgaggcggc ggcggcggcg gccctataaa aagcgaagcg    780
cgcggcgggc gggagcaagc ttgaactgaa aaaccagaaa gttaactggt aagtttagtc    840
```

```
ttttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg taccgagctg gtgctgggcg ggggcggcg    1020 ggccctcccg cagaacacca tgcgctcttc ggaagcaggt cctcactta atccctgtga    1080 cctgggatta aagtgaggac ctgcttctgt ggagcgcctt gacagcagcc atggagggc    1140 cgcccctac ctcagtgact cgaggacggg gtgaactacg cctgaggatc cgatctttt    1200 ccctctgcca aaattatgg ggacatcatg aagccccttg agcatctgac ttctggctaa    1260
taaaggaaat ttattttcat tgcaatagtg tgttggaatt ttttgtgtct ctcactcggc    1320
ctaggtagat aagtagcatg gcgggttaat cattaactac aaggaacccc tagtgatgga    1380
gttggccact ccctctctgc gcgctcgctc gctcactgag gccgggcgac caaaggtcgc    1440
ccgacgcccg ggctttgccc gggcggcctc agtgagcgag cgagcgcgca g             1491

<210> SEQ ID NO 141
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
ctgcgcgctc gctcgctcac tgaggccgcc cgggcaaagc ccgggcgtcg gcgacctttt    60
ggtcgcccgg cctcagtgag cgagcgagcg cgcagagagg gagtgtagcc atgctctagg    120
aagatcaatt caattcacgc gtcgacattg attattgact agttattaat agtaatcaat    180 tacgggtca ttagttcata gcccatatat ggagttccgc gttacataac ttacggtaaa    240
tggcccgcct ggctgaccgc ccaacgaccc ccgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca agtacgcccc ctattgacgt    420
caatgacggt aaatggcccg cctggcatta tgcccagtac atgaccttat gggactttcc    480
tacttggcag tacatctacg tattagtcat cgctattacc atgtcgaggc cacgttctgc    540
ttcactctcc ccatctcccc cccctcccca ccccaatttt gtatttatt tattttttaa    600 ttatttgtg cagcgatggg ggcggggggg ggggcgcgc gccaggcggg gcggggcggg    660
gcgaggggcg gggcggggcg aggcggagag gtgcggcggc agccaatcag agcggcgcgc    720
tccgaaagtt tccttttatg gcgaggcggc ggcggcggcg gccctataaa aagcgaagcg    780
cgcggcgggc gggagcaagc ttgaactgaa aaaccagaaa gttaactggt aagtttagtc    840 ttttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg taccgagctg tgctgggcgg ggcggcgg    1020 gccctcccgc agaacaccat gcgctcttcg gaagcaggtc tgactttaa tccctgtgac    1080 ctgggattaa agtgaggacc tgcttctgtg gagcgcttg acagcagcca tgggagggcc    1140 gcccctacc tcagtgactc gaggacgggg tgaactacgc ctgaggatcc gatcttttc    1200 cctctgccaa aaattatggg gacatcatga agccccttga gcatctgact tctggctaat    1260
aaaggaaatt tattttcatt gcaatagtgt gttggaattt tttgtgtctc tcactcggcc    1320
taggtagata agtagcatgg cgggttaatc attaactaca aggaaccct agtgatggag    1380
```

```
ttggccactc cctctctgcg cgctcgctcg ctcactgagg ccgggcgacc aaaggtcgcc    1440
cgacgcccgg gctttgcccg ggcggcctca gtgagcgagc gagcgcgcag                1490
```

<210> SEQ ID NO 142
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142

```
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg    120
aagatcaatt caattcacgc gtcgacattg attattgact agttattaat agtaatcaat    180
tacggggtca ttagttcata gcccatatat ggagttccgc gttacataac ttacggtaaa    240
tggcccgcct ggctgaccgc ccaacgaccc ccgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca gtacgccccc tattgacgt    420 caatgacggt aaatggcccg cctggcatta tgcccagtac atgaccttat gggactttcc    480
tacttggcag tacatctacg tattagtcat cgctattacc atgtcgaggc cacgttctgc    540
ttcactctcc ccatctcccc cccctcccca ccccaatttt gtatttatt tatttttaa      600 ttattttgtg cagcgatggg ggcggggggg ggggcgcgc gccaggcggg gcggggcggg    660
gcgaggggcg gggcggggcg aggcggagag gtgcggcggc agccaatcag agcggcgcgc    720
tccgaaagtt cctttttatg gcgaggcggc ggcggcggcg gccctataaa aagcgaagcg    780
cgcggcgggc gggagcaagc ttgaactgaa aaaccagaaa gttaactggt aagtttagtc    840
tttttgtctt ttatttcagg tcccggatcc ggtggtggtg caaatcaaag aactgctcct    900
cagtggatgt tgcctttact tctaggcctg tacggaagtg ttacttctgc tctaaaagct    960
gcggaattgt acccgcggcc gatccaccgg taccgagctg tgctgggcgg ggggcggcgg    1020
gccctcccgc agaacaccat gcgctcttcg gaagcaggtc ctcactttaa tgcctgtgac   1080
ctgggattaa agtgaggacc tgcttctgag gagcgccttg acagcagcca tgggagggcc   1140 gcccctacc tcagtgactc gaggacgggg tgaactacgc ctgaggatcc gatcttttc     1200 cctctgccaa aaattatggg gacatcatga agccccttga gcatctgact tctggctaat   1260
aaaggaaatt tattttcatt gcaatagtgt gttggaattt tttgtgtctc tcactcggcc   1320
taggtagata agtagcatgg cgggttaatc attaactaca aggaaccct agtgatggag    1380 ttggccactc cctctctgcg cgctcgctcg ctcactgagg ccgggcgacc aaaggtcgcc   1440
cgacgcccgg gctttgcccg ggcggcctca gtgagcgagc gagcgcgcag               1490
```

<210> SEQ ID NO 143
<211> LENGTH: 1490
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143

```
ctgcgcgctc gctcgctcac tgaggccgcc cgggcaaagc ccgggcgtcg ggcgaccttt      60
```

| | |
|---|---|
| ggtcgcccgg cctcagtgag cgagcgagcg cgcagagagg gagtgtagcc atgctctagg | 120 |
| aagatcaatt caattcacgc gtcgacattg attattgact agttattaat agtaatcaat | 180 |
| tacggggtca ttagttcata gcccatatat ggagttccgc gttacataac ttacggtaaa | 240 |
| tggcccgcct ggctgaccgc ccaacgaccc ccgcccattg acgtcaataa tgacgtatgt | 300 |
| tcccatagta acgccaatag ggactttcca ttgacgtcaa tgggtggagt atttacggta | 360 |
| aactgcccac ttggcagtac atcaagtgta tcatatgcca gtacgcccc ctattgacgt | 420 |
| caatgacggt aaatggcccg cctggcatta tgcccagtac atgaccttat gggactttcc | 480 |
| tacttggcag tacatctacg tattagtcat cgctattacc atgtcgaggc cacgttctgc | 540 |
| ttcactctcc ccatctcccc ccctcccca ccccaattt tgtatttatt tatttttaa | 600 |
| ttattttgtg cagcgatggg ggcggggggg ggggcgcgc gccaggcggg gcggggcggg | 660 |
| gcgaggggcg gggcggggcg aggcggagag gtgcggcggc agccaatcag agcggcgcgc | 720 |
| tccgaaagtt tccttttatg gcgaggcggc ggcggcggcg gccctataaa aagcgaagcg | 780 |
| cgcggcgggc gggagcaagc ttgaactgaa aaaccagaaa gttaactggt aagtttagtc | 840 |
| tttttgtctt ttatttcagg tcccggatcc ggtggtggtg caaatcaaag aactgctcct | 900 |
| cagtggatgt tgcctttact tctaggcctg tacggaagtg ttacttctgc tctaaaagct | 960 |
| gcggaattgt acccgcggcc gatccaccgg taccgagctg tgctgggcgg ggggcggcgg | 1020 |
| gccctcccgc agaacaccat cgctcttcg gaagcaggtc tcactttaa tccctgtgat | 1080 |
| ttgggattaa agtgaggacc tgcttctgag gagcgccttg acagcagcca tgggagggcc | 1140 |
| gccccctacc tcagtgactc gaggacgggg tgaactacgc ctgaggatcc gatcttttc | 1200 |
| cctctgccaa aaattatggg gacatcatga agccccttga gcatctgact tctggctaat | 1260 |
| aaaggaaatt tattttcatt gcaatagtgt gttggaattt tttgtgtctc tcactcggcc | 1320 |
| taggtagata agtagcatgg cgggttaatc attaactaca aggaaccct agtgatggag | 1380 |
| ttggccactc cctctctgcg cgctcgctcg ctcactgagg ccgggcgacc aaaggtcgcc | 1440 |
| cgacgcccgg gctttgcccg gcggcctca gtgagcgagc gagcgcgcag | 1490 |

<210> SEQ ID NO 144
<211> LENGTH: 1584
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 144

| | |
|---|---|
| ctgcgcgctc gctcgctcac tgaggccgcc cgggcaaagc ccgggcgtcg ggcgacctt | 60 |
| ggtcgcccgg cctcagtgag cgagcgagcg cgcagagagg gagtgtagcc atgctctagg | 120 |
| aagatcaatt caattcacgc gtcgacattg attattgact agttattaat agtaatcaat | 180 |
| tacggggtca ttagttcata gcccatatat ggagttccgc gttacataac ttacggtaaa | 240 |
| tggcccgcct ggctgaccgc ccaacgaccc ccgcccattg acgtcaataa tgacgtatgt | 300 |
| tcccatagta acgccaatag ggactttcca ttgacgtcaa tgggtggagt atttacggta | 360 |
| aactgcccac ttggcagtac atcaagtgta tcatatgcca gtacgcccc ctattgacgt | 420 |
| caatgacggt aaatggcccg cctggcatta tgcccagtac atgaccttat gggactttcc | 480 |
| tacttggcag tacatctacg tattagtcat cgctattacc atgtcgaggc cacgttctgc | 540 |
| ttcactctcc ccatctcccc ccctcccca ccccaattt tgtatttatt tatttttaa | 600 |

| | |
|---|---|
| ttattttgtg cagcgatggg ggcgggggg ggggcgcgc gccaggcggg gcggggcggg | 660 |
| gcgaggggcg gggcggggcg aggcggagag gtgcggcggc agccaatcag agcggcgcgc | 720 |
| tccgaaagtt tccttttatg gcgaggcggc ggcggcggcg gccctataaa aagcgaagcg | 780 |
| cgcggcgggc gggagcaagc ttgaactgaa aaccagaaa gttaactggt aagtttagtc | 840 |
| ttttgtctt ttatttcagg tcccggatcc ggtggtggtg caaatcaaag aactgctcct | 900 |
| cagtggatgt tgcctttact tctaggcctg tacggaagtg ttacttctgc tctaaaagct | 960 |
| gcggaattgt acccgcggcc gatccaccgg tgaagcaaag aaggggcaga gggagcccgt | 1020 |
| gagctgagtg ggccagggac tgggagaagg agtgaggagg cagggccggc atgcctctgc | 1080 |
| tgctggccag acccctaac tcatttgttc ccgtctgcac ctgtcactag taacagatga | 1140 |
| gttaaggggt ttggccgtgt agtgctaccc agcgctggct gcctcctcag cattgcaatt | 1200 |
| cctctcccat ctgggcacca gtcagctacc ctggtgggaa tctgggtagc cctcgaggac | 1260 |
| ggggtgaact acgcctgagg atccgatctt tttccctctg ccaaaaatta tggggacatc | 1320 |
| atgaagcccc ttgagcatct gacttctggc taataaagga aatttatttt cattgcaata | 1380 |
| gtgtgttgga atttttgtg tctctcactc ggcctaggta gataagtagc atggcgggtt | 1440 |
| aatcattaac tacaaggaac ccctagtgat ggagttggcc actccctctc tgcgcgctcg | 1500 |
| ctcgctcact gaggccgggc gaccaaaggt cgcccgacgc ccgggctttg cccgggcggc | 1560 |
| ctcagtgagc gagcgagcgc gcag | 1584 |

<210> SEQ ID NO 145
<211> LENGTH: 1406
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtgtagcc atgctctagg | 120 |
| aagatcaatt caattcacgc gtccatggct agaaggcaa gaatcctggc tgtggaaaga | 180 |
| tacctaaagg atcaacagct cctggggatt tggggttgct ctggaaaact catttgcacc | 240 |
| actgctgtgc cttggaatgc tagttggagt aataaatctc tggaacagat ttggaatcac | 300 |
| acgacctgga tggagtggga cagagaaatt aacaattaca caagcttaat acactcctta | 360 |
| attgaagaat cgcaaaacca gcaagaaaag aatgaacaag aattattgga attagataaa | 420 |
| tgggcaagtt tgtggaattg gtttaacata acaaattggc tgtggtatat aaaattattc | 480 |
| ataatgatag taggaggctt ggtaggttta agaatagttt ttgctgtact ttctatagtg | 540 |
| aatagagtta ggcagggata ttcaccatta tcgtttcaga cccacctccc aaccccgagg | 600 |
| ggacccgaca ggcccgaagg aatagaagaa gaaggtggag agagacag agacagatcc | 660 |
| attcgattag tgaacggatc tcgacggtat cgatcacgag actagcctcg agcggccgca | 720 |
| attcgaacgc tgacgtcatc aacccgctcc aaggaatcgc gggcccagtg tcactaggcg | 780 |
| ggaacaccca gcgcgcgtgc gccctggcag gaagatggct gtgagggaca gggagtggcg | 840 |
| ccctgcaata tttgcatgtc gctatgtgtt ctgggaaatc accataaacg tgaaatgtct | 900 |
| ttggatttgg gaatcttata agttctgtat gagaccacac cggtaccgag ctctcccgca | 960 |
| gaacaccatg cgctccacgg aagcaggtcc tcactttaat gctgtggcca ctgagaagta | 1020 |

```
ttaaagtgag gacctgcttc tgaggagcgc cttgacagca gccatgggag ggcctcgagg    1080
acggggtgaa ctacgcctga ggatccgatc tttttccctc tgccaaaaat tatggggaca    1140
tcatgaagcc ccttgagcat ctgacttctg gctaataaag gaaatttatt ttcattgcaa    1200
tagtgtgttg gaattttttg tgtctctcac tcggcctagg tagataagta gcatggcggg    1260
ttaatcatta actacaagga acccctagtg atggagttgg ccactccctc tctgcgcgct    1320
cgctcgctca ctgaggccgg gcgaccaaag gtcgcccgac gcccgggctt tgcccgggcg    1380
gcctcagtga gcgagcgagc gcgcag                                        1406
```

<210> SEQ ID NO 146
<211> LENGTH: 1406
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

```
ctgcgcgctc gctcgctcac tgaggccgcc cgggcaaagc ccgggcgtcg ggcgacctt      60 ggtcgcccgg cctcagtgag cgagcgagcg cgcagagagg gagtgtagcc atgctctagg    120
aagatcaatt caattcacgc gtccatggct tagaaggcaa gaatcctggc tgtggaaaga    180
tacctaaagg atcaacagct cctggggatt tggggttgct ctggaaaact catttgcacc    240
actgctgtgc cttggaatgc tagttggagt aataaatctc tggaacagat ttggaatcac    300
acgacctgga tggagtggga cagagaaatt aacaattaca caagcttaat acactcctta    360
attgaagaat cgcaaaacca gcaagaaaag aatgaacaag aattattgga attagataaa    420
tgggcaagtt tgtggaattg gtttaacata acaaattggc tgtggtatat aaaattattc    480
ataatgatag taggaggctt ggtaggttta agaatagttt ttgctgtact ttctatagtg    540
aatagagtta ggcagggata ttcaccatta tcgtttcaga cccacctccc aaccccgagg    600
ggacccgaca ggcccgaagg aatagaagaa gaaggtggag agagagacag agacagatcc    660
attcgattag tgaacggatc tcgacggtat cgatcacgag actagcctcg agcggccgca    720
attcgaacgc tgacgtcatc aacccgctcc aaggaatcgc gggcccagtg tcactaggcg    780
ggaacaccca gcgcgcgtgc gccctggcag aagatggct gtgagggaca gggagtggcg    840
ccctgcaata tttgcatgtc gctatgtgtt ctggaaatc accataaacg tgaaatgtct    900
ttggatttgg gaatcttata agttctgtat gagaccacac cggtaccgag ctctcccgca    960
gaacaccatg cgctccacgg aagtcgtttg cttgtggtg gctgtggcca ctgagaagtc    1020
accacaagcc aaacgacttc tgaggagcgc cttgacagca gccatgggag ggcctcgagg    1080
acggggtgaa ctacgcctga ggatccgatc tttttccctc tgccaaaaat tatggggaca    1140
tcatgaagcc ccttgagcat ctgacttctg gctaataaag gaaatttatt ttcattgcaa    1200
tagtgtgttg gaattttttg tgtctctcac tcggcctagg tagataagta gcatggcggg    1260
ttaatcatta actacaagga acccctagtg atggagttgg ccactccctc tctgcgcgct    1320
cgctcgctca ctgaggccgg gcgaccaaag gtcgcccgac gcccgggctt tgcccgggcg    1380
gcctcagtga gcgagcgagc gcgcag                                        1406
```

<210> SEQ ID NO 147
<211> LENGTH: 2052
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 147

| | | | | | |
|---|---|---|---|---|---|
| ctgcgcgctc | gctcgctcac | tgaggccgcc | cgggcaaagc | ccgggcgtcg | ggcgaccttt | 60
| ggtcgcccgg | cctcagtgag | cgagcgagcg | cgcagagagg | gagtgtagcc | atgctctagg | 120
| aagatcaatt | caattcacgc | gtcgacattg | attattgact | agttattaat | agtaatcaat | 180
| tacggggtca | ttagttcata | gcccatatat | ggagttccgc | gttacataac | ttacggtaaa | 240
| tggcccgcct | ggctgaccgc | ccaacgaccc | ccgcccattg | acgtcaataa | tgacgtatgt | 300
| tcccatagta | acgccaatag | ggactttcca | ttgacgtcaa | tgggtggagt | atttacggta | 360
| aactgcccac | ttggcagtac | atcaagtgta | tcatatgcca | agtacgcccc | ctattgacgt | 420
| caatgacggt | aaatggcccg | cctggcatta | tgcccagtac | atgaccttat | gggactttcc | 480
| tacttggcag | tacatctacg | tattagtcat | cgctattacc | atgtcgaggc | cacgttctgc | 540
| ttcactctcc | ccatctcccc | cccctcccca | ccccaatttt | gtatttatt | tatttttaa | 600
| ttattttgtg | cagcgatggg | ggcggggggg | ggggcgcgc | gccaggcggg | gcggggcggg | 660
| gcgaggggcg | gggcggggcg | aggcggagag | gtgcggcggc | agccaatcag | agcggcgcgc | 720
| tccgaaagtt | tccttttatg | gcgaggcggc | ggcggcggcg | gccctataaa | aagcgaagcg | 780
| cgcggcgggc | gggagcaagc | ttgaactgaa | aaaccagaaa | gttaactggt | aagtttagtc | 840
| tttttgtctt | ttatttcagg | tcccggatcc | ggtggtggtg | caaatcaaag | aactgctcct | 900
| cagtggatgt | tgcctttact | tctaggcctg | tacggaagtg | ttacttctgc | tctaaaagct | 960
| gcggaattgt | acccgcggcc | gatccaccgg | tcaccatggt | gagcaagggc | gaggaggata | 1020
| acatggccat | catcaaggag | ttcatgcgct | tcaaggtgca | catggagggc | tccgtgaacg | 1080
| gccacgagtt | cgagatcgag | ggcgagggcg | agggccgccc | ctacgagggc | acccagaccg | 1140
| ccaagctgaa | ggtgaccaag | ggtggcccc | tgcccttcgc | ctgggacatc | ctgtcccctc | 1200
| agttcatgta | cggctccaag | gcctacgtga | agcaccccgc | cgacatcccc | gactacttga | 1260
| agctgtcctt | ccccgagggc | ttcaagtggg | agcgcgtgat | gaacttcgag | gacggcggcg | 1320
| tggtgaccgt | gacccaggac | tcctccctgc | aggacggcga | gttcatctac | aaggtgaagc | 1380
| tgcgcggcac | caacttcccc | tccgacggcc | ccgtaatgca | gaagaagacc | atgggctggg | 1440
| aggcctcctc | cgagcggatg | taccccgagg | acggcgccct | gaagggcgag | atcaagcaga | 1500
| ggctgaagct | gaaggacggc | ggccactacg | acgctgaggt | caagaccacc | tacaaggcca | 1560
| agaagcccgt | gcagctgccc | ggcgcctaca | acgtcaacat | caagttggac | atcacctccc | 1620
| acaacgagga | ctacaccatc | gtggaacagt | acgaacgcgc | cgagggccgc | cactccaccg | 1680
| gcggcatgga | cgagctgtac | aagtccggac | tcagatagtc | tcgaggacgg | ggtgaactac | 1740
| gcctgaggat | ccgatctttt | tccctctgcc | aaaaattatg | gggacatcat | gaagcccctt | 1800
| gagcatctga | cttctggcta | ataaaggaaa | tttattttca | ttgcaatagt | gtgttggaat | 1860
| tttttgtgtc | tctcactcgg | cctaggtaga | taagtagcat | ggcgggttaa | tcattaacta | 1920
| caaggaaccc | ctagtgatgg | agttggccac | tccctctctg | cgcgctcgct | cgctcactga | 1980
| ggccgggcga | ccaaaggtcg | cccgacgccc | gggctttgcc | cggcggcct | cagtgagcga | 2040
| gcgagcgcgc | ag | | | | | 2052

TREATMENT OF AMYOTROPHIC LATERAL SCLEROSIS (ALS)

CROSS REFERENCE TO RELATED APPLICATIONS

This application is a 35 U.S.C. § 371 U.S. National Stage Entry of International Application No. PCT/US2018/055999, filed Oct. 16, 2018 and entitled TREATMENT OF AMYOTROPHIC LATERAL SCLEROSIS (ALS); which claims priority to U.S. Provisional Patent Application No. 62/572,702, filed Oct. 16, 2017 and entitled TREATMENT OF AMYOTROPHIC LATERAL SCLEROSIS (ALS); the contents of each of which are herein incorporated by reference in their entirety.

REFERENCE TO SEQUENCE LISTING

The present application is being filed along with a Sequence Listing in electronic format. The Sequence Listing is provided as a file entitled 20571047US371SL.txt, created on Apr. 16, 2020, which is 93,331 bytes in size. The information in the electronic format of the sequence listing is incorporated herein by reference in its entirety.

FIELD OF THE INVENTION

The present invention relates to compositions, methods and processes for the design, preparation, manufacture and/or formulation of polynucleotides, including AAV vectors, small interfering RNA (siRNA) duplexes, shRNA, microRNA or precursors thereof which target or encode molecules which target the superoxide dismutase 1 (SOD1) gene to interfere with SOD1 gene expression and/or SOD1 enzyme production. In some embodiments, polynucleotides are inserted into recombinant adeno-associated virus (AAV) vectors. Methods for inhibiting SOD1 gene expression in a subject with a neurodegenerative disease are also disclosed. The method optionally introduces at least one polynucleotide into the subject with the neurodegenerative disease. Particularly, the disease is amyotrophic lateral sclerosis (ALS).

BACKGROUND OF THE INVENTION

Amyotrophic lateral sclerosis (ALS), also known as Lou Gehrig's disease, is a fatal progressive neurodegenerative disease, characterized by the predominant loss of motor neurons (MNs) in primary motor cortex, the brainstem, and the spinal cord. The loss of motor neurons devastates basic fundamental movements, such as breathing, and typically causes death to patients within 2~5 years after diagnosis. Progressive deterioration of motor function in patients severely disrupts their breathing ability, requiring some form of breathing aid for survival of the patients. Other symptoms also include muscle weakness in hands, arms, legs or the muscles of swallowing. Some patients (e.g., FTD-ALS) may also develop frontotemporal dementia.

According to the ALS Association, approximately 5,600 people in the United States of America are diagnosed with ALS each year. The incidence of ALS is two per 100,000 people, and it is estimated that as many as 30,000 Americans may have the disease at any given time.

Two forms of ALS have been described: one is sporadic ALS (sALS), which is the most common form of ALS in the United States of America and accounts for 90 to 95% of all cases diagnosed; the other is familial ALS (fALS), which occurs in a family lineage mainly with a dominant inheritance and only accounts for about 5 to 10% of all cases in the United States of America. sALS and fALS are clinically indistinguishable.

Pathological studies have shown that some of cellular processes occur after the disease onset, including increased ER stress, generation of free radicals (i.e., reactive oxygen species (ROS)), mitochondrial dysfunction, protein aggregation, apoptosis, inflammation and glutamate excitotoxicity, specifically in the motor neurons (MNs).

The causes of ALS are complicated and heterogeneous. In general, ALS is considered to be a complex genetic disorder in which multiple genes in combination with environmental exposures combine to render a person susceptible. More than dozen genes associated with ALS have been discovered, including, SOD-1 ($Cu^{2+}/Zn^{2+}$ superoxide dismutase), TDP-43 (TARDBP, TAR DNA binding protein-43), FUS (Fused in Sarcoma/Translocated in Sarcoma), ANG (Angiogenin), ATXN2 (Ataxin-2), valosin containing protein (VCP), OPTN (Optineurin) and an expansion of the non-coding GGGGCC hexanucleotide repeat in the chromosome 9, open reading frame 72 (C9ORF72). However, the exact mechanisms of motor neuron degeneration are still elusive.

Currently, there is no curative treatment for ALS. The only FDA approved drug is Riluzole, which antagonizes the glutamate response to reduce the pathology development of ALS. However, only about a three-month life span expansion for ALS patients in the early stages has been reported, and no therapeutic benefit for ALS patients in the late stages has been observed, indicating a lack of therapeutic options for the patients (Bensimon G et al., *J Neurol.* 2002, 249, 609-615). Therefore, new treatment strategy that can effectively prevent the disease progression is still in demand.

Mutations in the gene of $Cu^{2+}/Zn^{2+}$ superoxide dismutase type I (SOD1) are the most common cause of fALS, accounting for about 20 to 30% of all fALS cases. Recent reports indicate that SOD1 mutations may also be linked to about 4% of all sALS cases (Robberecht and Philip, *Nat. Rev. Neurosci.*, 2013, 14, 248-264). SOD1-linked fALS is most likely not caused by loss of the normal SOD1 activity, but rather by a gain of a toxic function. One of the hypotheses for mutant SOD1-linked fALS toxicity proposes that an aberrant SOD1 enzyme causes small molecules such as peroxynitrite or hydrogen peroxide to produce damaging free radicals. Other hypotheses for mutant SOD1 neurotoxicity include inhibition of the proteasome activity, mitochondrial damage, disruption of RNA processing and formation of intracellular aggregates. Abnormal accumulation of mutant SOD1 variants and/or wild-type SOD1 in ALS forms insoluble fibrillar aggregates which are identified as pathological inclusions. Aggregated SOD1 protein can induce mitochondria stress (Vehvilainen P et al., *Front Cell Neurosci.*, 2014, 8, 126) and other toxicity to cells, particularly to motor neurons.

These findings indicate that SOD1 can be a potential therapeutic target for both familial and sporadic ALS. A therapy that can reduce the SOD1 protein, whether wildtype or mutant, produced in the central nervous system of ALS patients may ameliorate the symptoms of ALS in patients such as motor neuron degeneration and muscle weakness and atrophy. Agents and methods that aim to prevent the formation of wild type and/or mutant SOD1 protein aggregation may prevent disease progression and allow for amelioration of ALS symptoms. RNA interfering (RNAi) mediated gene silencing has drawn researchers' interest in recent years. Small double stranded RNA (small interfering RNA) molecules that target SOD1 gene haven been taught in the art for their potential in treating ALS (See, e.g., U.S. Pat. No. 7,632,938 and U.S. Patent Publication No. 20060229268).

The present invention develops an RNA interference, or knock-down based approach to inhibit or prevent the expression of SOD1 gene in ALS patients for treatment of the disease.

The present invention provides novel polynucleotides, including double stranded RNA (dsRNA) constructs and/or siRNA constructs, shRNA constructs and/or microRNA constructs and methods of their design. In addition, these siRNA constructs may be synthetic molecules encoded in an expression vector (one or both strands) for delivery into cells. Such vectors include, but are not limited to adeno-associated viral vectors such as vector genomes of any of the AAV serotypes or other viral delivery vehicles such as lentivirus, etc.

SUMMARY OF THE INVENTION

The present invention provides AAV vectors encoding a SOD1 targeting polynucleotide to interfere SOD1 gene expression and/or SOD1 protein production and methods of use thereof. Methods for treating motor neuron degeneration diseases such as amyotrophic lateral sclerosis are also included in the present invention.

In one embodiment, SOD1 is suppressed 30% in a subject treated with an AAV encoding a SOD1 targeting polynucleotide as compared to an untreated subject. The subject may be administered the AAV in an infusion or as a bolus at a pre-determine dose level. As a non-limiting example, the suppression is seen in the C1 to L7 ventral horn region.

The present invention relates to RNA molecule mediated gene specific interference with gene expression and protein production. Methods for treating motor neuron degeneration diseases such as amyotrophic lateral sclerosis are also included in the present invention. The siRNA included in the compositions featured herein encompass a dsRNA having an antisense strand (the antisense strand) having a region that is 30 nucleotides or less, generally 19-24 nucleotides in length, that is substantially complementary to at least part of an mRNA transcript of the SOD1 gene.

The present invention provides short double stranded RNA molecules such as small interfering RNA (siRNA) duplexes that target SOD1 mRNA to interfere with SOD1 gene expression and/or SOD1 protein production. The siRNA duplexes of the present invention may interfere with both alleles of the SOD1 gene irrespective of any particular mutation in the SOD1 gene and may particularly interact with those found in ALS disease.

In some embodiments, such siRNA molecules, or a single strand of the siRNA molecules, are inserted into adeno-associated viral vectors to be introduced into cells, specifically motor neurons and/or other surrounding cells in the central nervous system.

The siRNA duplex of the present invention comprises an antisense strand and a sense strand hybridized together forming a duplex structure, wherein the antisense strand is complementary to the nucleic acid sequence of the targeted SOD1 gene, and wherein the sense strand is homologous to the nucleic acid sequence of the targeted SOD1 gene. In some aspects, the 5' end of the antisense strand has a 5' phosphate group and the 3' end of the sense strand contains a 3' hydroxyl group. In other aspects, there are none, one or 2 nucleotides overhangs at the 3' end of each strand.

According to the present invention, each strand of the siRNA duplex targeting the SOD1 gene is about 19-25 nucleotides in length, preferably about 19 nucleotides, 20 nucleotides, 21 nucleotides, 22 nucleotides, 23 nucleotides, 24 nucleotides, or 25 nucleotides in length. In some aspects, the siRNAs may be unmodified RNA molecules.

In other aspects, the siRNAs may contain at least one modified nucleotide, such as base, sugar or backbone modification.

In one embodiment, an siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding SOD1, and the region of complementarity is 30 nucleotides or less, and at least 15 nucleotides in length. Generally, the dsRNA is 19 to 24, e.g., 19 to 21 nucleotides in length. In some embodiments the dsRNA is from about 15 to about 25 nucleotides in length, and in other embodiments the dsRNA is from about 25 to about 30 nucleotides in length.

The dsRNA, either upon contacting with a cell expressing SOD1 or upon transcription within a cell expressing SOD1, inhibits or suppresses the expression of a SOD1 gene by at least 10%, at least 20%, at least 25%, at least 30%, at least 35% or at least 40% or more, such as when assayed by a method as described herein.

According to the present invention, AAV vectors comprising the nucleic acids encoding the siRNA duplexes, one strand of the siRNA duplex or the dsRNA targeting SOD1 gene are produced, the AAV vector serotype may be AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, AAV-PHP.B, AAV-PHP.A, G2B-26, G2B-13, TH1.1-32, TH1.1-35, AAVPHP.B2, AAVPHP.B3, AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, AAVG2B5 and variants thereof.

According to the present invention, siRNA duplexes or dsRNA targeting the SOD1 gene in ALS are selected from the siRNA duplexes listed in Table 4. Preferably, the siRNA duplexes or dsRNA targeting SOD1 gene in ALS are selected from the group consisting of siRNA duplexes: D-4000 to D-4025.

The present invention also provides pharmaceutical compositions comprising at least one siRNA duplex targeting the SOD1 gene and a pharmaceutically acceptable carrier. In some aspects, a nucleic acid sequence encoding the siRNA duplex is inserted into an AAV vector.

In some embodiments, the present invention provides methods for inhibiting/silencing SOD1 gene expression in a cell. Accordingly, the siRNA duplexes or dsRNA can be used to substantially inhibit SOD1 gene expression in a cell, in particular in a motor neuron. In some aspects, the inhibition of SOD1 gene expression refers to an inhibition by at least about 20%, preferably by at least about 30%, 40%, 50%, 60%, 70%, 80%, 85%, 90%, 95% and 100%. Accordingly, the protein product of the targeted gene may be inhibited by at least about 20%, preferably by at least about 30%, 40%, 50%, 60%, 70%, 80%, 85%, 90%, 95% and 100%. The SOD1 gene can be either a wild type gene or a mutated SOD1 gene with at least one mutation. Accordingly, the SOD1 protein is either wild type protein or a mutated polypeptide with at least one mutation.

In some embodiments, the present invention provides methods for treating, or ameliorating amyotrophic lateral sclerosis associated with abnormal SOD1 gene and/or SOD1 protein in a subject in need of treatment, the method comprising administering to the subject a pharmaceutically effective amount of at least one siRNA duplex targeting the SOD1 gene, delivering said siRNA duplex into targeted cells, inhibiting SOD1 gene expression and protein production, and ameliorating symptoms of ALS in the subject.

In some embodiments, an AAV vector comprising the nucleic acid sequence encoding at least one siRNA duplex targeting the SOD1 gene is administered to the subject in need for treating and/or ameliorating ALS. The AAV vector serotype may be selected from the group consisting of AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Cly1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, AAV-PHP.B, AAV-PHP.A, G2B-26, G2B-13, TH1.1-32, TH1.1-35, AAVPHP.B2, AAVPHP.B3, AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, AAVG2B5 and variants thereof.

In some aspects, ALS is familial ALS linked to SOD1 mutations. In other aspects, ALS is sporadic ALS which is characterized by abnormal aggregation of SOD1 protein or disruption of SOD1 protein function or localization, though not necessarily as a result of genetic mutation. The symptoms of ALS ameliorated by the present method may include motor neuron degeneration, muscle weakness, stiffness of muscles, slurred speech and/or difficulty in breathing.

In some embodiments, the siRNA duplexes or dsRNA targeting SOD1 gene or the AAV vectors comprising such siRNA-encoding molecules may be introduced directly into the central nervous system of the subject, for example, by intracranial injection.

In some embodiments, the pharmaceutical composition of the present invention is used as a solo therapy. In other embodiments, the pharmaceutical composition of the present invention is used in combination therapy. The combination therapy may be in combination with one or more neuroprotective agents such as small molecule compounds, growth factors and hormones which have been tested for their neuroprotective effect on motor neuron degeneration.

In some embodiments, the present invention provides methods for treating, or ameliorating amyotrophic lateral sclerosis (ALS) by administering to a subject in need thereof a therapeutically effective amount of a plasmid or AAV vector described herein. The ALS may be familial ALS or sporadic ALS.

In some embodiments, the present invention provides methods for treating, or ameliorating canine degenerative myelopathy (DM) by administering to a subject in need thereof a therapeutically effective amount of a plasmid or AAV vector described herein.

In some embodiment, the present invention provides methods for treating, or ameliorating amyotrophic lateral sclerosis (ALS) by administering to a subject in need thereof, a therapeutically effective amount of a plasmid or AAV vector described herein to reduce the levels of neurofilament light chain (NF-L) in a subject.

In some embodiment, the present invention provides methods for treating, or ameliorating canine degenerative myelopathy (DM) by administering to a subject in need thereof, a therapeutically effective amount of a plasmid or AAV vector described herein to reduce the levels of neurofilament light chain (NF-L) in a subject.

In some embodiment, the present invention provides methods for reducing the level of neurofilament light chain (NF-L) in a subject by administering to a subject in need thereof, a therapeutically effective amount of a plasmid or AAV vector described herein.

BRIEF DESCRIPTION OF THE DRAWINGS

The foregoing and other objects, features and advantages will be apparent from the following description of particular embodiments of the invention, as illustrated in the accompanying drawings. The drawings are not necessarily to scale, emphasis instead being placed upon illustrating the principles of various embodiments of the invention.

FIG. 2A shows the stability of NF-L in pg/ml and FIG. 2B shows the stability as a percent of the −80° C. control.

FIG. 3A shows the stability of NF-L in pg/ml and FIG. 3B shows the stability as a percent of the −80° C. control.

FIG. 4A shows the NF-L levels in CSF and FIG. 4B shows the NF-L levels in serum.

FIG. 5A shows the pNF-H level is increased in the CSF of DM-dogs. FIG. 5B shows that pNF-H level in the CSF does not correlate with disease severity. FIG. 5C shows that pNF-H in the CSF is specific to DM.

DETAILED DESCRIPTION OF THE INVENTION

Figure 1:
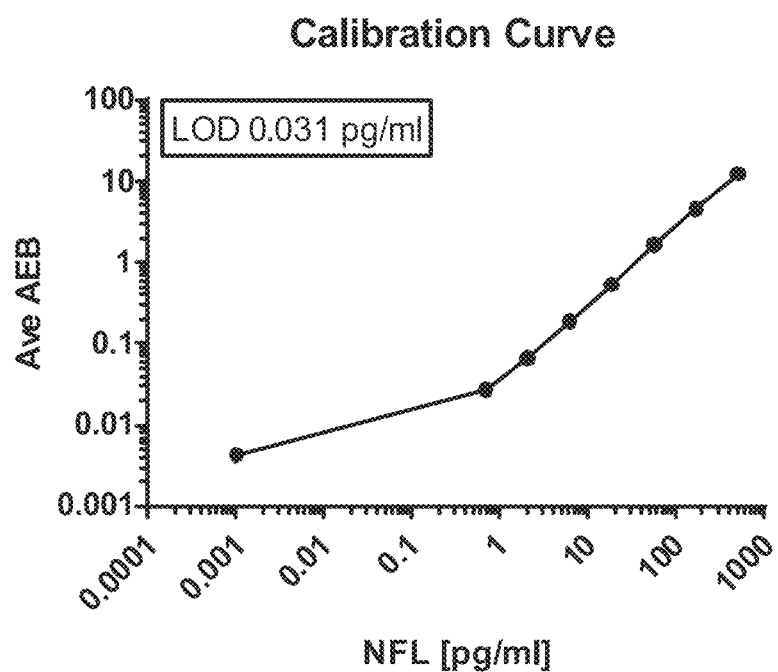
FIG. 1 shows a calibration curve for NF-L for the Quanterix Simoa hNF-L (Beta) assay.

The present invention relates to SOD1 targeting polynucleotides as therapeutic agents. RNA interfering mediated gene silencing can specifically inhibit gene expression. The present invention therefore provides polynucleotides such as small double stranded RNA (dsRNA) molecules (small interfering RNA, siRNA), shRNA, microRNA and precursors thereof targeting SOD1 gene, pharmaceutical compositions encompassing such polynucleotides, as well as processes of their design. The present invention also provides methods of their use for inhibiting SOD1 gene express and protein production, for treating neurodegenerative disease, in particular, amyotrophic lateral sclerosis (ALS).

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

Amyotrophic Lateral Sclerosis (ALS) and SOD1

Amyotrophic lateral sclerosis (ALS), an adult-onset neurodegenerative disorder, is a progressive and fatal disease characterized by the selective death of motor neurons in the motor cortex, brainstem and spinal cord. Patients diagnosed with ALS develop a progressive muscle phenotype characterized by spasticity, hyperreflexia or hyporeflexia, fasciculations, muscle atrophy and paralysis. These motor impairments are caused by the de-innervation of muscles due to the loss of motor neurons. The major pathological features of ALS include degeneration of the corticospinal tracts and extensive loss of lower motor neurons (LMNs) or anterior horn cells (Ghatak et al., *J Neuropathol Exp Neurol.,* 1986, 45, 385-395), degeneration and loss of Betz cells and other pyramidal cells in the primary motor cortex (Udaka et al., *Acta Neuropathol,* 1986, 70, 289-295; Maekawa et al., *Brain,* 2004, 127, 1237-1251) and reactive gliosis in the motor cortex and spinal cord (Kawamata et al., *Am J Pathol.,* 1992, 140, 691-707; and Schiffer et al., *J Neurol Sci.,* 1996, 139, 27-33). ALS is usually fatal within 3 to 5 years after the diagnosis due to respiratory defects and/or inflammation (Rowland L P and Shneibder N A, *N Engl. J. Med.,* 2001, 344, 1688-1700).

A cellular hallmark of ALS is the presence of proteinaceous, ubiquitinated, cytoplasmic inclusions in degenerating motor neurons and surrounding cells (e.g., astrocytes). Ubiquitinated inclusions (i.e., Lewy body-like inclusions or Skein-like inclusions) are the most common and specific type of inclusion in ALS and are found in LMNs of the spinal cord and brainstem, and in corticospinal upper motor neurons (UMNs) (Matsumoto et al., *J Neurol Sci.*, 1993, 115, 208-213; and Sasak and Maruyama, *Acta Neuropathol.*, 1994, 87, 578-585). A few proteins have been identified to be components of the inclusions, including ubiquitin, Cu/Zn superoxide dismutase 1 (SOD1), peripherin and Dorfin. Neurofilamentous inclusions are often found in hyaline conglomerate inclusions (HCIs) and axonal 'spheroids' in spinal cord motor neurons in ALS. Other types and less specific inclusions include Bunina bodies (cystatin C-containing inclusions) and Crescent shaped inclusions (SCIs) in upper layers of the cortex. Other neuropathological features seen in ALS include fragmentation of the Golgi apparatus, mitochondrial vacuolization and ultrastructural abnormalities of synaptic terminals (Fujita et al., *Acta Neuropathol.* 2002, 103, 243-247).

In addition, in frontotemporal dementia ALS (FTD-ALS), cortical atrophy (including the frontal and temporal lobes) is also observed, which may cause cognitive impairment in FTD-ALS patients.

ALS is a complex and multifactorial disease and multiple mechanisms hypothesized as responsible for ALS pathogenesis include dysfunction of protein degradation, glutamate excitotoxicity, mitochondrial dysfunction, apoptosis, oxidative stress, inflammation, protein misfolding and aggregation, aberrant RNA metabolism, and altered gene expression.

About 10% of ALS cases have family history of the disease, and these patients are referred to as familial ALS (fALS) or inherited patients, commonly with a Mendelian dominant mode of inheritance and high penetrance. The remainder (approximately 90%-95%) is classified as sporadic ALS (sALS), as they are not associated with a documented family history, which is thought to be due to other risk factors, including environmental factors, genetic polymorphisms, somatic mutations, and possibly gene-environmental interactions. In most cases, familiar (or inherited) ALS is inherited as autosomal dominant disease, but pedigrees with autosomal recessive and X-linked inheritance and incomplete penetrance exist. Sporadic and familial forms are clinically indistinguishable suggesting a common pathogenesis. The precise cause of the selective death of motor neurons in ALS remains elusive. Progress in understanding the genetic factors in fALS may shed light on both forms of the disease.

Recently, an explosion to genetic causes of ALS has discovered mutations in more than 10 different genes that are known to cause fALS. The most common ones are found in the genes encoding Cu/Zn superoxide dismutase 1 (SOD1; ~20%) (Rosen D R et al., *Nature*, 1993, 362, 59-62), fused in sarcoma/translated in liposarcoma (FUS/TLS; 1-5%) and TDP-43 (TARDBP; 1-5%). Recently, a hexanucleotide repeat expansion (GGGGCC)$_n$ in the C9orF72 gene was identified as the most frequent cause of fALS (~40%) in the Western population (reviewed by Renton et al., *Nat. Neurosci.*, 2014, 17, 17-23). Other genes mutated in ALS include alsin (ALS2), senataxin (SETX), vesicle-associated membrane protein (VAPB), angiogenin (ANG). fALS genes control different cellular mechanisms, suggesting that the pathogenesis of ALS is complicated and may be related to several different processes finally leading to motor neuron degeneration.

SOD1 is one of the three human superoxide dismutases identified and characterized in mammals: copper-zinc superoxide dismutase (Cu/ZnSOD or SOD1), manganese superoxide dismutase (MnSOD or SOD2), and extracellular superoxide dismutase (ECSOD or SOD3). SOD1 is a 32 kDa homodimer of a 153-residue polypeptide with one copper- and one zinc-binding site per subunit, which is encoded by SOD1 gene (NCBI Reference Sequence NM_000454.4; SEQ ID NO: 1) on human chromosome 21 (see Table 10). SOD1 catalyzes the reaction of superoxide anion ($O^{2-}$) into molecular oxygen ($O_2$) and hydrogen peroxide ($H_2O_2$) at a bound copper ion. The intracellular concentration of SOD1 is high (ranging from 10 to 100 µM), counting for 1% of the total protein content in central nervous system (CNS). The protein is localized not only in the cytoplasm but also in nucleus, lysosomes, peroxisomes, and mitochondrial intermembrane spaces in eukaryotic cells (Lindenau J et al., *Glia*, 2000, 29, 25-34).

Mutations in SOD1 gene are carried by 15-20% of fALS patients and by 1-2% of all ALS cases. Currently, at least 170 different mutations distributed throughout the 153-amino acid SOD1 polypeptide have been found to cause ALS, and an updated list can be found at the ALS online Genetic Database (ALSOD) (Wroe R et al., *Amyotroph Lateral Scler.*, 2008, 9, 249-250). Table 1 lists some examples of mutations in SOD1 in ALS. These mutations are predominantly single amino acid substitutions (i.e. missense mutations) although deletions, insertions, and C-terminal truncations also occur. Different SOD1 mutations display different geographic distribution patterns. For instance, about half of all Americans with ALS caused by SOD1 gene mutations have a particular mutation Ala4Val (or A4V). The A4V mutation is typically associated with more severe signs and symptoms. The I113T mutation is by far the most common mutation in the United Kingdom. The most prevalent mutation in Europe is D90A substitute.

TABLE 1

Examples of SOD1 mutations in ALS

| | Mutations |
|---|---|
| Exon1 (220 bp) | Q22L; E21K, G; F20C; N19S; G16A, S; V14M, S; G12R; G10G, V, R; L8Q, V; V7E; C6G, F; V5L; A4T, V, S |
| Exon2 (97 bp) | T54R; E49K; H48R, Q; V47F, A; H46R; F45C; H43R; G41S, D; G37R; V29, insA |
| Exon3 (70 bp) | D76Y, V; G72S, C; L67R; P66A; N65S; S59I, S |
| Exon4 (118 bp) | D124G, V; V118L, InsAAAAC; L117V; T116T; R115G; G114A; I113T, F; I112M, T; G108V; L106V, F; S106L, delTCACTC; I104F; D101G, Y, H, N; E100G, K; I99V; V97L, M; D96N, V; A95T, V; G93S, V, A, C, R, D; D90V, A; A89T, V; T88delACTGCTGAC; V87A, M; N86I, S, D, K; G85R, S; L84V, F; H80R |
| Exon5 (461 bp) | I151T, S; I149T; V148I, G; G147D, R; C146R, stop; A145T, G; L144F, S; G141E, stop; A140A, G; N139D, K, H, N; G138E; T137R; S134N; E133V, delGAA, insTT; E132insTT; G127R, InsTGGG; L126S, delITT, stop; D126, delTT |

To investigate the mechanism of neuronal death associated with SOD1 gene defects, several rodent models of SOD1-linked ALS were developed in the art, which express the human SOD1 gene with different mutations, including missense mutations, small deletions or insertions. Some examples of ALS mouse models include SOD1$^{G93A}$, SOD1$^{A4V}$, SOD1$^{G37R}$, SOD1$^{G85R}$, SOD1$^{D90A}$, SOD1$^{L84V}$, SOD1$^{I113T}$, SOD1$^{H36R/H48Q}$, SOD1$^{G127X}$, SOD1$^{L126X}$ and SOD1$^{L126delTT}$ There are two transgene rat models carrying two different human SOD1 mutations: SOD1$^{H46R}$ and SOD1$^{G93R}$. These rodent ALS models can develop muscle weakness similar to human ALS patients and other pathogenic features that reflect several characteristics of the human disease, in particular, the selective death of spinal motor neurons, aggregation of protein inclusions in motor neurons and microglial activation. It is well known in the art that the transgenic rodents are good models of human SOD1-associated ALS disease and provide models for studying disease pathogenesis and developing disease treatment.

Studies in animal and cellular models showed that SOD1 pathogenic variants cause ALS by gain of function. That is to say, the superoxide dismutase enzyme gains new but harmful properties when altered by SOD1 mutations. For example, some SOD1 mutated variants in ALS increase oxidative stress (e.g., increased accumulation of toxic superoxide radicals) by disrupting redox cycle. Other studies also indicate that some SOD1 mutated variants in ALS might acquire toxic properties that are independent of its normal physiological function (such as abnormal aggregation of misfolded SOD1 variants. In the aberrant redox chemistry model, mutant SOD1 is unstable and through aberrant chemistry interacts with nonconventional substrates causing reactive oxygen species (ROS) overproduction. In the protein toxicity model, unstable, misfolded SOD1 aggregates into cytoplasmic inclusion bodies, sequestering proteins crucial for cellular processes. These two hypotheses are not mutually exclusive. It has been shown that oxidation of selected histidine residues that bind metals in the active site mediates SOD1 aggregation.

The aggregated mutant SOD1 protein may also induce mitochondrial dysfunction (Vehvilainen P et al., *Front Cell Neurosci.,* 2014, 8, 126), impairment of axonal transport, aberrant RNA metabolism, glial cell pathology and glutamate excitotoxicity. In some sporadic ALS cases, misfolded wild-type SOD1 protein is found in diseased motor neurons which forms "toxic conformation" that is similar to familiar ALS-linked SOD1 variants (Rotunno M S and Bosco D A, *Front Cell Neurosci.,* 2013, 16, 7, 253). Such evidence suggests that ALS is a protein folding disease analogous to other neurodegenerative diseases such as Alzheimer's disease and Parkinson's disease.

Currently, no curative treatments are available for patients suffering from ALS. The only FDA approved drug Riluzole (also called Rilutek), an inhibitor of glutamate release, has a moderate effect on ALS, only extending survival by 2-3 months if it is taken for 18 months. Unfortunately, patients taking riluzole do not experience any slowing in disease progression or improvement in muscle function. Therefore, riluzole does not present a cure, or even an effective treatment. Researchers continue to search for better therapeutic agents.

One approach to inhibit abnormal SOD1 protein aggregation is to silence/inhibit SOD1 gene expression in ALS. It has been reported that small interfering RNAs for specific gene silencing of the mutated allele is therapeutically beneficial for the treatment of fALS (e.g., Ralgh G S et al., *Nat. Medicine,* 2005, 11(4), 429-433; and Raoul C et al., *Nat. Medicine,* 2005, 11(4), 423-428; and Maxwell M M et al., *PNAS,* 2004, 101(9), 3178-3183; and Ding H et al., *Chinese Medical J.,* 2011, 124(1), 106-110; and Scharz D S et al., *Plos Genet.,* 2006, 2(9), e140; the content of each of which is incorporated herein by reference in their entirety).

Many other RNA therapeutic agents that target SOD1 gene and modulate SOD1 expression in ALS are taught in the art, such RNA based agents include antisense oligonucleotides and double stranded small interfering RNAs. See, e.g., Wang H et al., *J Biol. Chem.,* 2008, 283(23), 15845-15852); U.S. Pat. Nos. 7,498,316; 7,632,938; 7,678, 895; 7,951,784; 7,977,314; 8,183,219; 8,309,533 and 8, 586, 554; and U.S. Patent publication Nos. 2006/0229268 and 2011/0263680; the content of each of which is herein incorporated by reference in their entirety.

The present invention employs viral vectors such as adeno-associated viral (AAV) vectors to deliver siRNA duplexes or SOD1 targeting polynucleotides into cells with high efficiency. The AAV vectors comprising RNAi molecules, e.g., siRNA molecules of the present invention may increase the delivery of active agents into motor neurons. SOD1 targeting polynucleotides may be able to inhibit SOD1 gene expression (e.g., mRNA level) significantly inside cells; therefore, ameliorating SOD1 expression induced stress inside the cells such as aggregation of protein and formation of inclusions, increased free radicals, mitochondrial dysfunction and RNA metabolism.

Such SOD1 targeting polynucleotides inhibition may be used for treating ALS. According to the present invention, methods for treating and/or ameliorating ALS in a patient comprises administering to the patient an effective amount of at least one SOD1 targeting polynucleotides encoding one or more siRNA duplexes into cells and allowing the inhibition/silence of SOD1 gene expression, are provided.

Compositions of the Invention

Vectors

In some embodiments, the siRNA molecules described herein can be inserted into, or encoded by, vectors such as plasmids or viral vectors. Preferably, the siRNA molecules are inserted into, or encoded by, viral vectors.

Viral vectors may be Herpesvirus (HSV) vectors, retroviral vectors, adenoviral vectors, adeno-associated viral vectors, lentiviral vectors, and the like. In some specific embodiments, the viral vectors are AAV vectors.

Retroviral Vectors

In some embodiments, the siRNA duplex targeting SOD1 gene may be encoded by a retroviral vector (See, e.g., U.S. Pat. Nos. 5,399,346; 5,124,263; 4,650,764 and 4,980,289; the content of each of which is incorporated herein by reference in their entirety).

Adenoviral Vectors

Adenoviruses are eukaryotic DNA viruses that can be modified to efficiently deliver a nucleic acid to a variety of cell types in vivo, and have been used extensively in gene therapy protocols, including for targeting genes to neural cells. Various replication defective adenovirus and minimum adenovirus vectors have been described for nucleic acid therapeutics (See, e.g., PCT Patent Publication Nos. WO199426914, WO 199502697, WO199428152, WO199412649, WO199502697 and WO199622378; the content of each of which is incorporated by reference in their entirety). Such adenoviral vectors may also be used to deliver siRNA molecules of the present invention to cells.

Adeno-Associated Viral (AAV) Vectors

An AAV is a dependent parvovirus. Like other parvoviruses, AAV is a single stranded, non-enveloped DNA virus, having a genome of about 5000 nucleotides in length containing two open reading frames that encode the proteins responsible for replication (Rep) and the structural protein of the capsid (Cap). The open reading frames are flanked by two Inverted Terminal Repeat (ITR) sequences, which serve as the origin of replication of viral genome. Furthermore, the AAV genome contains a packaging sequence, allowing packaging of the viral genome into an AAV capsid. The AAV vector requires co-helper (e.g., adenovirus) to undergo a productive infection in infected cells. In the absence of such helper functions, the AAV virions essentially enter host cells and integrate into cells' genome.

AAV vectors have been investigated for siRNA delivery because of its several unique features. These features include (i) ability to infect both dividing and non-dividing cells; (ii) a broad host range for infectivity, including human cells; (iii) wild-type AAV has never been associated with any disease and cannot replicate in infected cells; (iv) lack of cell-mediated immune response against the vector and (v) ability to integrate into a host chromosome or persist episomally, thereby creating potential for long-term expression. Moreover, infection with AAV vectors has minimal influence on changing the pattern of cellular gene expression (Stilwell and Samulski et al., *Biotechniques*, 2003, 34, 148).

Typically, AAV vectors for siRNA delivery may be recombinant viral vectors which are replication defective because of lacking sequences encoding functional Rep and Cap proteins in viral genome. In some cases, the defective AAV vectors may lack most of all coding sequences and essentially only contains one or two AAV ITR sequences and a packaging sequence.

AAV vectors may also comprise self-complementary AAV vectors (scAAVs). scAAV vectors contain both DNA strands which anneal together to form double stranded DNA. By skipping second strand synthesis, scAAVs allow for rapid expression in the cell.

Methods for producing/modifying AAV vectors are disclosed in the art such as pseudotyped AAV vectors (PCT Patent Publication Nos. WO200028004; WO200123001; WO2004112727; WO 2005005610 and WO 2005072364, the content of each of which is incorporated herein by reference in their entirety).

AAV vectors for delivering siRNA molecules into mammalian cells, may be prepared or derived from various serotypes of AAVs, including, but not limited to, AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 and AAV-DJ. In some cases, different serotypes of AAVs may be mixed together or with other types of viruses to produce chimeric AAV vectors.

AAV vectors for siRNA delivery may be modified to enhance the efficiency of delivery. Such modified AAV vectors containing the siRNA expression cassette can be packaged efficiently and can be used to infect successfully the target cells at high frequency and with minimal toxicity.

In some embodiments, the AAV vector for delivering siRNA duplexes of the present invention may be a human serotype AAV vector. Such human AAV vector may be derived from any known serotype, e.g., from any one of serotypes AAV1-AAV11. As non-limiting examples, AAV vectors may be vectors comprising an AAV1-derived genome in an AAV1-derived capsid; vectors comprising an AAV2-derived genome in an AAV2-derived genome; vectors comprising an AAV4-derived genome in an AAV4 derived capsid; vectors comprising an AAV6-derived genome in an AAV6 derived capsid or vectors comprising an AAV9-derived genome in an AAV9 derived capsid.

In other embodiments, the AAV vector for delivering siRNA duplexes of the present invention may be a pseudotyped AAV vector which contains sequences and/or components originating from at least two different AAV serotypes. Pseudotyped AAV vectors may be vectors comprising an AAV genome derived from one AAV serotype and a Capsid protein derived at least in part from a different AAV serotype. As non-limiting examples, such pseudotyped AAV vectors may be vectors comprising an AAV2-derived genome in an AAV1-derived capsid; or vectors comprising an AAV2-derived genome in an AAV6-derived capsid; or vectors comprising an AAV2-derived genome in an AAV4-derived capsid; or an AAV2-derived genome in an AAV9-derived capsid.

In other embodiments, AAV vectors may be used for delivering siRNA molecules to the central nervous system (e.g., U.S. Pat. No. 6,180,613; the content of which is herein incorporated by reference in its entirety).

In some aspects, the AAV vector for delivering siRNA duplexes of the present invention may further comprise a modified capsid including peptides from non-viral origin. In other aspects, the AAV vector may contain a CNS specific chimeric capsid to facilitate the delivery of siRNA duplexes into the brain and the spinal cord. For example, an alignment of cap nucleotide sequences from AAV variants exhibiting CNS tropism may be constructed to identify variable region (VR) sequence and structure.

Viral Genome

In one embodiment, as shown in an AAV particle comprises a viral genome with a payload region.

Viral Genome Size

In one embodiment, the viral genome which comprises a payload described herein, may be single stranded or double stranded viral genome. The size of the viral genome may be small, medium, large or the maximum size. Additionally, the viral genome may comprise a promoter and a polyA tail.

In one embodiment, the viral genome which comprises a payload described herein, may be a small single stranded viral genome. A small single stranded viral genome may be 2.7 to 3.5 kb in size such as about 2.7, 2.8, 2.9, 3.0, 3.1, 3.2, 3.3, 3.4, and 3.5 kb in size. As a non-limiting example, the small single stranded viral genome may be 3.2 kb in size. Additionally, the viral genome may comprise a promoter and a polyA tail.

In one embodiment, the viral genome which comprises a payload described herein, may be a small double stranded viral genome. A small double stranded viral genome may be 1.3 to 1.7 kb in size such as about 1.3, 1.4, 1.5, 1.6, and 1.7 kb in size. As a non-limiting example, the small double stranded viral genome may be 1.6 kb in size. Additionally, the viral genome may comprise a promoter and a polyA tail.

In one embodiment, the viral genome which comprises a payload described herein, may a medium single stranded viral genome. A medium single stranded viral genome may be 3.6 to 4.3 kb in size such as about 3.6, 3.7, 3.8, 3.9, 4.0, 4.1, 4.2 and 4.3 kb in size. As a non-limiting example, the medium single stranded viral genome may be 4.0 kb in size. Additionally, the viral genome may comprise a promoter and a polyA tail.

In one embodiment, the viral genome which comprises a payload described herein, may be a medium double stranded viral genome. A medium double stranded viral genome may be 1.8 to 2.1 kb in size such as about 1.8, 1.9, 2.0, and 2.1 kb in size. As a non-limiting example, the medium double stranded viral genome may be 2.0 kb in size. Additionally, the viral genome may comprise a promoter and a polyA tail.

In one embodiment, the viral genome which comprises a payload described herein, may be a large single stranded viral genome. A large single stranded viral genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded viral genome may be 4.7 kb in size. As another non-limiting example, the large single stranded viral genome may be 4.8 kb in size. As yet another non-limiting example, the large single stranded viral genome may be 6.0 kb in size. Additionally, the viral genome may comprise a promoter and a polyA tail.

In one embodiment, the viral genome which comprises a payload described herein, may be a large double stranded viral genome. A large double stranded viral genome may be 2.2 to 3.0 kb in size such as about 2.2, 2.3, 2.4, 2.5, 2.6, 2.7, 2.8, 2.9 and 3.0 kb in size. As a non-limiting example, the large double stranded viral genome may be 2.4 kb in size. Additionally, the viral genome may comprise a promoter and a polyA tail.

Viral Genome Component: Inverted Terminal Repeats (ITRs)

The AAV particles of the present invention comprise a viral genome with at least one ITR region and a payload region. In one embodiment the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes of the invention may be comprised of naturally occurring polynucleotide sequences or recombinantly derived polynucleotide sequences.

The ITRs may be derived from the same serotype as the capsid, selected from any of the serotypes herein, or a derivative thereof. The ITR may be of a different serotype from the capsid. In one embodiment the AAV particle has more than one ITR. In a non-limiting example, the AAV particle has a viral genome comprising two ITRs. In one embodiment the ITRs are of the same serotype as one another. In another embodiment the ITRs are of different serotypes. Non-limiting examples include zero, one or both of the ITRs having the same serotype as the capsid. In one embodiment both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In one embodiment the ITRs are 140-142 nucleotides in length. Non-limiting examples of ITR length are 102, 140, 141, 142, 145 nucleotides in length, and those having at least 95% identity thereto.

In one embodiment, the AAV particle comprises a nucleic acid sequence encoding an siRNA molecule which may be located near the 5' end of the flip ITR in an expression vector. In another embodiment, the AAV particle comprises a nucleic acid sequence encoding an siRNA molecule may be located near the 3' end of the flip ITR in an expression vector. In yet another embodiment, the AAV particle comprises a nucleic acid sequence encoding an siRNA molecule may be located near the 5' end of the flop ITR in an expression vector. In yet another embodiment, the AAV particle comprises a nucleic acid sequence encoding an siRNA molecule may be located near the 3' end of the flop ITR in an expression vector. In one embodiment, the AAV particle comprises a nucleic acid sequence encoding an siRNA molecule may be located between the 5' end of the flip ITR and the 3' end of the flop ITR in an expression vector. In one embodiment, the AAV particle comprises a nucleic acid sequence encoding an siRNA molecule may be located between (e.g., half-way between the 5' end of the flip ITR and 3' end of the flop ITR or the 3' end of the flop ITR and the 5' end of the flip ITR), the 3' end of the flip ITR and the 5' end of the flip ITR in an expression vector. As a non-limiting example, the AAV particle comprises a nucleic acid sequence encoding an siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR) in an expression vector. As a non-limiting example, the AAV particle comprises a nucleic acid sequence encoding an siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR) in an expression vector. As another non-limiting example, the AAV particle comprises a nucleic acid sequence encoding an siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR) in an expression vector. As another non-limiting example, the AAV particle comprises a nucleic acid sequence encoding an siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR) in an expression vector. As a non-limiting example, the AAV particle comprises a nucleic acid sequence encoding an siRNA molecule may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR) in an expression vector. As another non-limiting example, the AAV particle comprises a nucleic acid sequence encoding an siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the 5' or 3' end of an ITR (e.g., Flip or Flop ITR) in an expression vector.

Viral Genome Component: Promoters

In one embodiment, the payload region of the viral genome comprises at least one element to enhance the transgene target specificity and expression (See e.g., Powell et al. Viral Expression Cassette Elements to Enhance Transgene Target Specificity and Expression in Gene Therapy, 2015; the contents of which are herein incorporated by reference in its entirety). Non-limiting examples of elements to enhance the transgene target specificity and expression include promoters, endogenous miRNAs, post-transcriptional regulatory elements (PREs), polyadenylation (PolyA) signal sequences and upstream enhancers (USEs), CMV enhancers and introns.

A person skilled in the art may recognize that expression of the polypeptides of the invention in a target cell may require a specific promoter, including but not limited to, a promoter that is species specific, inducible, tissue-specific, or cell cycle-specific (Parr et al., *Nat. Med.* 3:1145-9 (1997); the contents of which are herein incorporated by reference in their entirety).

In one embodiment, the promoter is deemed to be efficient when it drives expression of the polypeptide(s) encoded in the payload region of the viral genome of the AAV particle.

In one embodiment, the promoter is a promoter deemed to be efficient to drive the expression of the modulatory polynucleotide.

In one embodiment, the promoter is a promoter deemed to be efficient when it drives expression in the cell being targeted.

In one embodiment, the promoter drives expression of the payload for a period of time in targeted tissues. Expression driven by a promoter may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years.

In one embodiment, the promoter drives expression of the payload for at least 1 month, 2 months, 3 months, 4 months, 5 months, 6 months, 7 months, 8 months, 9 months, 10 months, 11 months, 1 year, 2 years, 3 years 4 years, 5 years, 6 years, 7 years, 8 years, 9 years, 10 years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 55 years, 60 years, 65 years, or more than 65 years.

Promoters may be naturally occurring or non-naturally occurring. Non-limiting examples of promoters include viral promoters, plant promoters and mammalian promoters. In some embodiments, the promoters may be human promoters. In some embodiments, the promoter may be truncated.

Promoters which drive or promote expression in most tissues include, but are not limited to, human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC). Tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes.

Non-limiting examples of muscle-specific promoters include mammalian muscle creatine kinase (MCK) promoter, mammalian desmin (DES) promoter, mammalian troponin I (TNNI2) promoter, and mammalian skeletal alpha-actin (ASKA) promoter (see, e.g. U.S. Patent Publication US 20110212529, the contents of which are herein incorporated by reference in their entirety)

Non-limiting examples of tissue-specific expression elements for neurons include neuron-specific enolase (NSE), platelet-derived growth factor (PDGF), platelet-derived growth factor B-chain (PDGF-β), synapsin (Syn), methyl-CpG binding protein 2 (MeCP2), $Ca^{2+}$/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2) promoters. Non-limiting examples of tissue-specific expression elements for astrocytes include glial fibrillary acidic protein (GFAP) and EAAT2 promoters. A non-limiting example of a tissue-specific expression element for oligodendrocytes includes the myelin basic protein (MBP) promoter.

In one embodiment, the promoter may be less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800 nucleotides. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components of the same or different starting or parental promoters such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. In one embodiment, the promoter is a combination of a 382 nucleotide CMV-enhancer sequence and a 260 nucleotide CBA-promoter sequence.

In one embodiment, the viral genome comprises a ubiquitous promoter. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3).

Yu et al. (Molecular Pain 2011, 7:63; the contents of which are herein incorporated by reference in their entirety) evaluated the expression of eGFP under the CAG, EF1α, PGK and UBC promoters in rat DRG cells and primary DRG cells using lentiviral vectors and found that UBC showed weaker expression than the other 3 promoters and only 10-12% glial expression was seen for all promoters. Soderblom et al. (E. Neuro 2015; the contents of which are herein incorporated by reference in its entirety) evaluated the expression of eGFP in AAV8 with CMV and UBC promoters and AAV2 with the CMV promoter after injection in the motor cortex. Intranasal administration of a plasmid containing a UBC or EF1α promoter showed a sustained airway expression greater than the expression with the CMV promoter (See e.g., Gill et al., Gene Therapy 2001, Vol. 8, 1539-1546; the contents of which are herein incorporated by reference in their entirety). Husain et al. (Gene Therapy 2009; the contents of which are herein incorporated by reference in its entirety) evaluated an HβH construct with a hGUSB promoter, an HSV-1LAT promoter and an NSE promoter and found that the HβH construct showed weaker expression than NSE in mouse brain. Passini and Wolfe (J. Virol. 2001, 12382-12392, the contents of which are herein incorporated by reference in its entirety) evaluated the long-term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in their entirety) when NFL and NFH promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650-nucleotide promoter and NFH is a 920 nucleotide promoter which are both absent in the liver but NFH is abundant in the sensory proprioceptive neurons, brain and spinal cord and NFH is present in the heart. Scn8a is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. *Identification of evolutionary conserved, functional noncoding elements in the promoter region of the sodium channel gene SCN8A*, Mamm Genome (2007) 18:723-731; and Raymond et al. *Expression of Alternatively Spliced Sodium Channel α-subunit genes*, Journal of Biological Chemistry (2004) 279(44) 46234-46241; the contents of each of which are herein incorporated by reference in their entireties).

Any of promoters taught by the aforementioned Yu, Soderblom, Gill, Husain, Passini, Xu, Drews or Raymond may be used in the present inventions.

In one embodiment, the promoter is not cell specific.

In one embodiment, the promoter is a ubiquitin c (UBC) promoter. The UBC promoter may have a size of 300-350 nucleotides. As a non-limiting example, the UBC promoter is 332 nucleotides.

In one embodiment, the promoter is a β-glucuronidase (GUSB) promoter. The GUSB promoter may have a size of 350-400 nucleotides. As a non-limiting example, the GUSB promoter is 378 nucleotides.

In one embodiment, the promoter is a neurofilament light (NFL) promoter. The NFL promoter may have a size of 600-700 nucleotides. As a non-limiting example, the NFL promoter is 650 nucleotides. As a non-limiting example, the construct may be AAV-promoter-CMV/globin intron-modulatory polynucleotide-RBG, where the AAV may be self-complementary and the AAV may be the DJ serotype.

In one embodiment, the promoter is a neurofilament heavy (NFH) promoter. The NFH promoter may have a size of 900-950 nucleotides. As a non-limiting example, the NFH promoter is 920 nucleotides. As a non-limiting example, the construct may be AAV-promoter-CMV/globin intron-modulatory polynucleotide-RBG, where the AAV may be self-complementary and the AAV may be the DJ serotype.

In one embodiment, the promoter is a scn8a promoter. The scn8a promoter may have a size of 450-500 nucleotides. As a non-limiting example, the scn8a promoter is 470 nucleotides. As a non-limiting example, the construct may be AAV-promoter-CMV/globin intron-modulatory polynucleotide-RBG, where the AAV may be self-complementary and the AAV may be the DJ serotype In one embodiment, the viral genome comprises a Pol III promoter.

In one embodiment, the viral genome comprises a P1 promoter.

In one embodiment, the viral genome comprises a FXN promoter.

In one embodiment, the promoter is a phosphoglycerate kinase 1 (PGK) promoter.

In one embodiment, the promoter is a chicken β-actin (CBA) promoter.

In one embodiment, the promoter is a CAG promoter which is a construct comprising the cytomegalovirus (CMV) enhancer fused to the chicken beta-actin (CBA) promoter.

In one embodiment, the promoter is a cytomegalovirus (CMV) promoter.

In one embodiment, the viral genome comprises a H1 promoter.

In one embodiment, the viral genome comprises a U6 promoter.

In one embodiment, the promoter is a liver or a skeletal muscle promoter. Non-limiting examples of liver promoters include human α-1-antitrypsin (hAAT) and thyroxine binding globulin (TBG). Non-limiting examples of skeletal muscle promoters include Desmin, MCK or synthetic C5-12.

In one embodiment, the promoter is an RNA pol III promoter. As a non-limiting example, the RNA pol III promoter is U6. As a non-limiting example, the RNA pol III promoter is H1.

In one embodiment, the viral genome comprises two promoters. As a non-limiting example, the promoters are an EF1α promoter and a CMV promoter.

In one embodiment, the viral genome comprises an enhancer element, a promoter and/or a 5'UTR intron. The enhancer element, also referred to herein as an "enhancer," may be, but is not limited to, a CMV enhancer, the promoter may be, but is not limited to, a CMV, CBA, UBC, GUSB, NSE, Synapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter, (9) GFAP promoter, (10) H1 promoter; and (11) U6 promoter.

In one embodiment, the viral genome comprises an engineered promoter.

In another embodiment the viral genome comprises a promoter from a naturally expressed protein.

Viral Genome Component: Untranslated Regions (UTRs)

By definition, wild type untranslated regions (UTRs) of a gene are transcribed but not translated. Generally, the 5' UTR starts at the transcription start site and ends at the start codon and the 3' UTR starts immediately following the stop codon and continues until the termination signal for transcription.

Features typically found in abundantly expressed genes of specific target organs may be engineered into UTRs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genomes of the AAV particles of the invention to enhance expression in hepatic cell lines or liver.

While not wishing to be bound by theory, wild-type 5' untranslated regions (UTRs) include features which play roles in translation initiation. Kozak sequences, which are commonly known to be involved in the process by which the ribosome initiates translation of many genes, are usually included in 5' UTRs. Kozak sequences have the consensus CCR(A/G)CCAUGG, where R is a purine (adenine or guanine) three bases upstream of the start codon (ATG), which is followed by another 'G'.

In one embodiment, the 5'UTR in the viral genome includes a Kozak sequence.

In one embodiment, the 5'UTR in the viral genome does not include a Kozak sequence.

While not wishing to be bound by theory, wild-type 3' UTRs are known to have stretches of Adenosines and Uridines embedded therein. These AU rich signatures are particularly prevalent in genes with high rates of turnover. Based on their sequence features and functional properties, the AU rich elements (AREs) can be separated into three classes (Chen et al, 1995, the contents of which are herein incorporated by reference in its entirety): Class I AREs, such as, but not limited to, c-Myc and MyoD, contain several dispersed copies of an AUUUA motif within U-rich regions. Class II AREs, such as, but not limited to, GM-CSF and TNF-a, possess two or more overlapping UUAUUUA(U/A)(U/A) nonamers. Class III ARES, such as, but not limited to, c-Jun and Myogenin, are less well defined. These U rich regions do not contain an AUUUA motif. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides. When engineering specific polynucleotides, e.g., payload regions of viral genomes, one or more copies of an ARE can be introduced to make polynucleotides less stable and thereby curtail translation and decrease production of the resultant protein. Likewise, AREs can be identified and removed or mutated to increase the intracellular stability and thus increase translation and production of the resultant protein.

In one embodiment, the 3' UTR of the viral genome may include an oligo(dT) sequence for templated addition of a poly-A tail.

In one embodiment, the viral genome may include at least one miRNA seed, binding site or full sequence. microRNAs (or miRNA or miR) are 19-25 nucleotide noncoding RNAs that bind to the sites of nucleic acid targets and down-regulate gene expression either by reducing nucleic acid molecule stability or by inhibiting translation. A microRNA sequence comprises a "seed" region, i.e., a sequence in the region of positions 2-8 of the mature microRNA, which sequence has perfect Watson-Crick complementarity to the miRNA target sequence of the nucleic acid.

In one embodiment, the viral genome may be engineered to include, alter or remove at least one miRNA binding site, sequence or seed region.

Any UTR from any gene known in the art may be incorporated into the viral genome of the AAV particle. These UTRs, or portions thereof, may be placed in the same orientation as in the gene from which they were selected, or they may be altered in orientation or location. In one embodiment, the UTR used in the viral genome of the AAV particle may be inverted, shortened, lengthened, made with one or more other 5' UTRs or 3' UTRs known in the art. As used herein, the term "altered" as it relates to a UTR, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides.

In one embodiment, the viral genome of the AAV particle comprises at least one artificial UTRs which is not a variant of a wild type UTR.

In one embodiment, the viral genome of the AAV particle comprises UTRs which have been selected from a family of transcripts whose proteins share a common function, structure, feature or property.

Viral Genome Component: Polyadenylation Sequence

In one embodiment, the viral genome of the AAV particles of the present invention comprise at least one polyadenylation sequence. The viral genome of the AAV particle may comprise a polyadenylation sequence between the 3' end of the payload coding sequence and the 5' end of the 3' ITR.

In one embodiment, the polyadenylation sequence or "polyA sequence" may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and 500 nucleotides in length.

In one embodiment, the polyadenylation sequence is 50-100 nucleotides in length.

In one embodiment, the polyadenylation sequence is 50-150 nucleotides in length.

In one embodiment, the polyadenylation sequence is 50-160 nucleotides in length.

In one embodiment, the polyadenylation sequence is 50-200 nucleotides in length.

In one embodiment, the polyadenylation sequence is 60-100 nucleotides in length.

In one embodiment, the polyadenylation sequence is 60-150 nucleotides in length.

In one embodiment, the polyadenylation sequence is 60-160 nucleotides in length.

In one embodiment, the polyadenylation sequence is 60-200 nucleotides in length.

In one embodiment, the polyadenylation sequence is 70-100 nucleotides in length.

In one embodiment, the polyadenylation sequence is 70-150 nucleotides in length.

In one embodiment, the polyadenylation sequence is 70-160 nucleotides in length.

In one embodiment, the polyadenylation sequence is 70-200 nucleotides in length.

In one embodiment, the polyadenylation sequence is 80-100 nucleotides in length.

In one embodiment, the polyadenylation sequence is 80-150 nucleotides in length.

In one embodiment, the polyadenylation sequence is 80-160 nucleotides in length.

In one embodiment, the polyadenylation sequence is 80-200 nucleotides in length.

In one embodiment, the polyadenylation sequence is 90-100 nucleotides in length.

In one embodiment, the polyadenylation sequence is 90-150 nucleotides in length.

In one embodiment, the polyadenylation sequence is 90-160 nucleotides in length.

In one embodiment, the polyadenylation sequence is 90-200 nucleotides in length.

In one embodiment, the AAV particle comprises a nucleic acid sequence encoding an siRNA molecule may be located upstream of the polyadenylation sequence in an expression vector. Further, the AAV particle comprises a nucleic acid sequence encoding an siRNA molecule may be located downstream of a promoter such as, but not limited to, CMV, U6, CAG, CBA or a CBA promoter with a SV40 intron or a human beta globin intron in an expression vector. As a non-limiting example, the AAV particle comprises a nucleic acid sequence encoding an siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the AAV particle comprises a nucleic acid sequence encoding an siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the AAV particle comprises a nucleic acid sequence encoding an siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the AAV particle comprises a nucleic acid sequence encoding an siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In one embodiment, the AAV particle comprises a rabbit globin polyadenylation (polyA) signal sequence.

In one embodiment, the AAV particle comprises a human growth hormone polyadenylation (polyA) signal sequence.

Viral Genome Component: Introns

In one embodiment, the payload region comprises at least one element to enhance the expression such as one or more introns or portions thereof. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron or intron portion may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The intron may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

In one embodiment, the AAV viral genome may comprise a promoter such as, but not limited to, CMV or U6. As a non-limiting example, the promoter for the AAV comprising the nucleic acid sequence for the siRNA molecules of the present invention is a CMV promoter. As another non-limiting example, the promoter for the AAV comprising the nucleic acid sequence for the siRNA molecules of the present invention is a U6 promoter.

In one embodiment, the AAV viral genome may comprise a CMV promoter.

In one embodiment, the AAV viral genome may comprise a U6 promoter.

In one embodiment, the AAV viral genome may comprise a CMV and a U6 promoter.

In one embodiment, the AAV viral genome may comprise a H1 promoter.

In one embodiment, the AAV viral genome may comprise a CBA promoter.

In one embodiment, the encoded siRNA molecule may be located downstream of a promoter in an expression vector such as, but not limited to, CMV, U6, H1, CBA, CAG, or a CBA promoter with an intron such as SV40 or others known in the art. Further, the encoded siRNA molecule may also be located upstream of the polyadenylation sequence in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

Viral Genome Component: Filler Sequence

In one embodiment, the viral genome comprises one or more filler sequences.

In one embodiment, the viral genome comprises one or more filler sequences in order to have the length of the viral genome be the optimal size for packaging. As a non-limiting example, the viral genome comprises at least one filler sequence in order to have the length of the viral genome be about 2.3 kb. As a non-limiting example, the viral genome comprises at least one filler sequence in order to have the length of the viral genome be about 4.6 kb.

In one embodiment, the viral genome comprises one or more filler sequences in order to reduce the likelihood that a hairpin structure of the vector genome (e.g., a modulatory polynucleotide described herein) may be read as an inverted terminal repeat (ITR) during expression and/or packaging. As a non-limiting example, the viral genome comprises at least one filler sequence in order to have the length of the viral genome be about 2.3 kb. As a non-limiting example, the viral genome comprises at least one filler sequence in order to have the length of the viral genome be about 4.6 kb.

In one embodiment, the viral genome is a single stranded (ss) viral genome and comprises one or more filler sequences which have a length about between 0.1 kb-3.8 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, or 3.8 kb. As a non-limiting example, the total length filler sequence in the vector genome is 3.1 kb. As a non-limiting example, the total length filler sequence in the vector genome is 2.7 kb. As a non-limiting example, the total length filler sequence in the vector genome is 0.8 kb. As a non-limiting example, the total length filler sequence in the vector genome is 0.4 kb. As a non-limiting example, the length of each filler sequence in the vector genome is 0.8 kb. As a non-limiting example, the length of each filler sequence in the vector genome is 0.4 kb.

In one embodiment, the viral genome is a self-complementary (sc) viral genome and comprises one or more filler sequences which have a length about between 0.1 kb-1.5 kb, such as, but not limited to, 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, or 1.5 kb. As a non-limiting example, the total length filler sequence in the vector genome is 0.8 kb. As a non-limiting example, the total length filler sequence in the vector genome is 0.4 kb. As a non-limiting example, the length of each filler sequence in the vector genome is 0.8 kb. As a non-limiting example, the length of each filler sequence in the vector genome is 0.4 kb.

In one embodiment, the viral genome comprises any portion of a filler sequence. The viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of a filler sequence.

In one embodiment, the viral genome is a single stranded (ss) viral genome and comprises one or more filler sequences in order to have the length of the viral genome be about 4.6 kb. As a non-limiting example, the viral genome comprises at least one filler sequence and the filler sequence is located 3' to the 5' ITR sequence. As a non-limiting example, the viral genome comprises at least one filler sequence and the filler sequence is located 5' to a promoter sequence. As a non-limiting example, the viral genome comprises at least one filler sequence and the filler sequence is located 3' to the polyadenylation signal sequence. As a non-limiting example, the viral genome comprises at least one filler sequence and the filler sequence is located 5' to the 3' ITR sequence. As a non-limiting example, the viral genome comprises at least one filler sequence, and the filler sequence is located between two intron sequences. As a non-limiting example, the viral genome comprises at least one filler sequence, and the filler sequence is located within an intron sequence. As a non-limiting example, the viral genome comprises two filler sequences, and the first filler sequence is located 3' to the 5' ITR sequence and the second filler sequence is located 3' to the polyadenylation signal sequence. As a non-limiting example, the viral genome comprises two filler sequences, and the first filler sequence is located 5' to a promoter sequence and the second filler sequence is located 3' to the polyadenylation signal sequence. As a non-limiting example, the viral genome comprises two filler sequences, and the first filler sequence is located 3' to the 5' ITR sequence and the second filler sequence is located 5' to the 5' ITR sequence.

In one embodiment, the viral genome is a self-complementary (sc) viral genome and comprises one or more filler sequences in order to have the length of the viral genome be about 2.3 kb. As a non-limiting example, the viral genome comprises at least one filler sequence and the filler sequence is located 3' to the 5' ITR sequence. As a non-limiting example, the viral genome comprises at least one filler sequence and the filler sequence is located 5' to a promoter sequence. As a non-limiting example, the viral genome comprises at least one filler sequence and the filler sequence is located 3' to the polyadenylation signal sequence. As a non-limiting example, the viral genome comprises at least one filler sequence and the filler sequence is located 5' to the 3' ITR sequence. As a non-limiting example, the viral genome comprises at least one filler sequence, and the filler sequence is located between two intron sequences. As a non-limiting example, the viral genome comprises at least one filler sequence, and the filler sequence is located within an intron sequence. As a non-limiting example, the viral genome comprises two filler sequences, and the first filler sequence is located 3' to the 5' ITR sequence and the second filler sequence is located 3' to the polyadenylation signal sequence. As a non-limiting example, the viral genome comprises two filler sequences, and the first filler sequence is located 5' to a promoter sequence and the second filler sequence is located 3' to the polyadenylation signal sequence. As a non-limiting example, the viral genome comprises two filler sequences, and the first filler sequence is located 3' to the 5' ITR sequence and the second filler sequence is located 5' to the 5' ITR sequence.

In one embodiment, the viral genome may comprise one or more filler sequences between one of more regions of the viral genome. In one embodiment, the filler region may be located before a region such as, but not limited to, a payload region, an inverted terminal repeat (ITR), a promoter region, an intron region, an enhancer region, a polyadenylation signal sequence region, and/or an exon region. In one embodiment, the filler region may be located after a region such as, but not limited to, a payload region, an inverted terminal repeat (ITR), a promoter region, an intron region, an enhancer region, a polyadenylation signal sequence region, and/or an exon region. In one embodiment, the filler region may be located before and after a region such as, but not limited to, a payload region, an inverted terminal repeat (ITR), a promoter region, an intron region, an enhancer region, a polyadenylation signal sequence region, and/or an exon region.

In one embodiment, the viral genome may comprise one or more filler sequences which bifurcates at least one region of the viral genome. The bifurcated region of the viral genome may comprise 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 99% of the of the region to the 5' of the filler sequence region. As a non-limiting example, the filler sequence may bifurcate at least one region so that 10% of the region is located 5' to the filler sequence and 90% of the region is located 3' to the filler sequence. As a non-limiting example, the filler sequence may bifurcate at least one region so that 20% of the region is located 5' to the filler sequence and 80% of the region is located 3' to the filler sequence. As a non-limiting example, the filler sequence may bifurcate at least one region so that 30% of the region is located 5' to the filler sequence and 70% of the region is located 3' to the filler sequence. As a non-limiting example, the filler sequence may bifurcate at least one region so that 40% of the region is located 5' to the filler sequence and 60% of the region is located 3' to the filler sequence. As a non-limiting example, the filler sequence may bifurcate at least one region so that 50% of the region is located 5' to the filler sequence and 50% of the region is located 3' to the filler sequence. As a non-limiting example, the filler sequence may bifurcate at least one region so that 60% of the region is located 5' to the filler sequence and 40% of the region is located 3' to the filler sequence. As a non-limiting example, the filler sequence may bifurcate at least one region so that 70% of the region is located 5' to the filler sequence and 30% of the region is located 3' to the filler sequence. As a non-limiting example, the filler sequence may bifurcate at least one region so that 80% of the region is located 5' to the filler sequence and 20% of the region is located 3' to the filler sequence. As a non-limiting example, the filler sequence may bifurcate at least one region so that 90% of the region is located 5' to the filler sequence and 10% of the region is located 3' to the filler sequence.

In one embodiment, the viral genome comprises a filler sequence after the 5' ITR.

In one embodiment, the viral genome comprises a filler sequence after the promoter region. In one embodiment, the viral genome comprises a filler sequence after the payload region. In one embodiment, the viral genome comprises a filler sequence after the intron region. In one embodiment, the viral genome comprises a filler sequence after the enhancer region. In one embodiment, the viral genome comprises a filler sequence after the polyadenylation signal sequence region. In one embodiment, the viral genome comprises a filler sequence after the exon region.

In one embodiment, the viral genome comprises a filler sequence before the promoter region. In one embodiment, the viral genome comprises a filler sequence before the payload region. In one embodiment, the viral genome comprises a filler sequence before the intron region. In one embodiment, the viral genome comprises a filler sequence before the enhancer region. In one embodiment, the viral genome comprises a filler sequence before the polyadenylation signal sequence region. In one embodiment, the viral genome comprises a filler sequence before the exon region.

In one embodiment, the viral genome comprises a filler sequence before the 3' ITR.

In one embodiment, a filler sequence may be located between two regions, such as, but not limited to, the 5' ITR and the promoter region. In one embodiment, a filler sequence may be located between two regions, such as, but not limited to, the 5' ITR and the payload region. In one embodiment, a filler sequence may be located between two regions, such as, but not limited to, the 5' ITR and the intron region. In one embodiment, a filler sequence may be located between two regions, such as, but not limited to, the 5' ITR and the enhancer region. In one embodiment, a filler sequence may be located between two regions, such as, but not limited to, the 5' ITR and the polyadenylation signal sequence region.

In one embodiment, a filler sequence may be located between two regions, such as, but not limited to, the 5' ITR and the exon region.

In one embodiment, a filler sequence may be located between two regions, such as, but not limited to, the promoter region and the payload region. In one embodiment, a filler sequence may be located between two regions, such as, but not limited to, the promoter region and the intron region. In one embodiment, a filler sequence may be located between two regions, such as, but not limited to, the promoter region and the enhancer region. In one embodiment, a filler sequence may be located between two regions, such as, but not limited to, the promoter region and the polyadenylation signal sequence region. In one embodiment, a filler sequence may be located between two regions, such as, but not limited to, the promoter region and the exon region. In one embodiment, a filler sequence may be located between two regions, such as, but not limited to, the promoter region and the 3' ITR.

In one embodiment, a filler sequence may be located between two regions, such as, but not limited to, the payload region and the intron region. In one embodiment, a filler sequence may be located between two regions, such as, but not limited to, the payload region and the enhancer region. In one embodiment, a filler sequence may be located between two regions, such as, but not limited to, the payload region and the polyadenylation signal sequence region. In one embodiment, a filler sequence may be located between two regions, such as, but not limited to, the payload region and the exon region.

In one embodiment, a filler sequence may be located between two regions, such as, but not limited to, the payload region and the 3' ITR.

In one embodiment, a filler sequence may be located between two regions, such as, but not limited to, the intron region and the enhancer region. In one embodiment, a filler sequence may be located between two regions, such as, but not limited to, the intron region and the polyadenylation signal sequence region. In one embodiment, a filler sequence may be located between two regions, such as, but not limited to, the intron region and the exon region. In one embodiment, a filler sequence may be located between two regions, such as, but not limited to, the intron region and the 3' ITR. In one embodiment, a filler sequence may be located between two regions, such as, but not limited to, the enhancer region and the polyadenylation signal sequence region. In one embodiment, a filler sequence may be located between two regions, such as, but not limited to, the enhancer region and the exon region. In one embodiment, a filler sequence may be located between two regions, such as, but not limited to, the enhancer region and the 3' ITR.

In one embodiment, a filler sequence may be located between two regions, such as, but not limited to, the polyadenylation signal sequence region and the exon region. In one embodiment, a filler sequence may be located between two regions, such as, but not limited to, the polyadenylation signal sequence region and the 3' ITR.

In one embodiment, a filler sequence may be located between two regions, such as, but not limited to, the exon region and the 3' ITR.

Payloads of the Invention

The AAV particles of the present disclosure comprise at least one payload region. As used herein, "payload" or "payload region" refers to one or more polynucleotides or polynucleotide regions encoded by or within a viral genome or an expression product of such polynucleotide or polynucleotide region, e.g., a transgene, a polynucleotide encoding a polypeptide or multi-polypeptide or a modulatory nucleic acid or regulatory nucleic acid. Payloads of the present invention typically encode modulatory polynucleotides or fragments or variants thereof.

The payload region may be constructed in such a way as to reflect a region similar to or mirroring the natural organization of an mRNA.

The payload region may comprise a combination of coding and non-coding nucleic acid sequences.

In some embodiments, the AAV payload region may encode a coding or non-coding RNA.

In one embodiment, the AAV particle comprises a viral genome with a payload region comprising nucleic acid sequences encoding a siRNA, miRNA or other RNAi agent. In such an embodiment, a viral genome encoding more than one polypeptide may be replicated and packaged into a viral particle. A target cell transduced with a viral particle may express the encoded siRNA, miRNA or other RNAi agent inside a single cell.

Modulatory Polynucleotides

In one embodiment, modulatory polynucleotides, e.g., RNA or DNA molecules, may be used to treat neurodegenerative disease, in particular, amyotrophic lateral sclerosis (ALS). As used herein, a "modulatory polynucleotide" is any nucleic acid sequence(s) which functions to modulate (either increase or decrease) the level or amount of a target gene, e.g., mRNA or protein levels.

In one embodiment, the modulatory polynucleotides may comprise at least one nucleic acid sequence encoding at least one siRNA molecule. The nucleic acids may, independently if there is more than one, encode 1, 2, 3, 4, 5, 6, 7, 8, 9, or more than 9 siRNA molecules.

In one embodiment, the molecular scaffold may be located downstream of a CMV promoter, fragment or variant thereof.

In one embodiment, the molecular scaffold may be located downstream of a CBA promoter, fragment or variant thereof.

In one embodiment, the molecular scaffold may be a natural pri-miRNA scaffold located downstream of a CMV promoter. As a non-limiting example, the natural pri-miRNA scaffold is derived from the human miR155 scaffold.

In one embodiment, the molecular scaffold may be a natural pri-miRNA scaffold located downstream of a CBA promoter.

In one embodiment, the selection of a molecular scaffold and modulatory polynucleotide is determined by a method of comparing modulatory polynucleotides in pri-miRNA (see e.g., the method described by Miniarikova et al. *Design, Characterization, and Lead Selection of Therapeutic miR-NAs Targeting Huntingtin for Development of Gene Therapy for Huntington's Disease*. Molecular Therapy-Nucleic Acids (2016) 5, e297 and International Publication No. WO2016102664; the contents of each of which are herein incorporated by reference in their entireties). To evaluate the activities of the modulatory polynucleotides, the molecular scaffold used which may be used is a human pri-miRNA scaffold (e.g., miR155 scaffold) and the promoter may be CMV. The activity may be determined in vitro using HEK293T cells and a reporter (e.g., Luciferase).

In order to evaluate the optimal molecular scaffold for the modulatory polynucleotide, the modulatory polynucleotide is used in pri-miRNA scaffolds with a CAG promoter. The constructs are co-transfected with a reporter (e.g., luciferase reporter) at 50 ng. Constructs with greater than 80% knockdown at 50 ng co-transfection are considered efficient. In one aspect, the constructs with strong guide-strand activity are preferred. The molecular scaffolds can be processed in HEK293T cells by NGS to determine guide-passenger ratios, and processing variability.

To evaluate the molecular scaffolds and modulatory polynucleotides in vivo the molecular scaffolds comprising the modulatory polynucleotides are packaged in AAV (e.g., the serotype may be AAV5 (see e.g., the method and constructs described in WO2015060722, the contents of which are herein incorporated by reference in their entirety)) and administered to an in vivo model and the guide-passenger ratios, 5' and 3' end processing, ratio of guide to passenger strands, and knockdown can be determined in different areas of the model (e.g., tissue regions).

In one embodiment, the selection of a molecular scaffold and modulatory polynucleotide is determined by a method of comparing modulatory polynucleotides in natural pri-miRNA and synthetic pri-miRNA. The modulatory polynucleotide may, but it not limited to, targeting an exon other than exon 1. To evaluate the activities of the modulatory polynucleotides, the molecular scaffold is used with a CBA promoter. In one aspect, the activity may be determined in vitro using HEK293T cells, HeLa cell and a reporter (e.g., Luciferase) and knockdown efficient modulatory polynucleotides showed SOD1 knockdown of at least 80% in the cell tested. Additionally, the modulatory polynucleotides which are considered most efficient showed low to no significant passenger strand (p-strand) activity. In another aspect, the endogenous SOD1 knockdown efficacy is evaluated by transfection in vitro using HEK293T cells, HeLa cell and a reporter. Efficient modulatory polynucleotides show greater than 50% endogenous SOD1 knockdown. In yet another aspect, the endogenous SOD1 knockdown efficacy is evaluated in different cell types (e.g., HEK293, HeLa, primary astrocytes, U251 astrocytes, SH-SY5Y neuron cells and fibroblasts from ALS patients) by infection (e.g., AAV2). Efficient modulatory polynucleotides show greater than 60% endogenous SOD1 knockdown.

To evaluate the molecular scaffolds and modulatory polynucleotides in vivo the molecular scaffolds comprising the modulatory polynucleotides are packaged in AAV and administered to an in vivo model and the guide-passenger ratios, 5' and 3' end processing, ratio of guide to passenger strands, and knockdown can be determined in different areas of the model (e.g., tissue regions). The molecular scaffolds can be processed from in vivo samples by NGS to determine guide-passenger ratios, and processing variability.

In one embodiment, the modulatory polynucleotide is designed using at least one of the following properties: loop variant, seed mismatch/bulge/wobble variant, stem mismatch, loop variant and vassal stem mismatch variant, seed mismatch and basal stem mismatch variant, stem mismatch and basal stem mismatch variant, seed wobble and basal stem wobble variant, or a stem sequence variant.

The present invention relates, in part, to RNA interfering (RNAi) induced inhibition of gene expression for treating neurodegenerative disorders. Provided are siRNA duplexes or dsRNA that target SOD1 gene. Such siRNA duplexes or dsRNA can silence SOD1 gene expression in cells, for example, motor neurons, therefore, ameliorating symptoms of ALS such as motor death and muscle atrophy. The SOD1 siRNA may be encoded in polynucleotides of a recombinant AAV vector.

siRNA duplexes or dsRNA targeting a specific mRNA may be designed and synthesized as part of a target SOD1 targeting polynucleotide in vitro and introduced into cells for activating RNAi process.

siRNA Molecules

The present invention relates to RNA interference (RNAi) induced inhibition of gene expression for treating neurodegenerative disorders. Provided herein are siRNA duplexes or encoded dsRNA that target the gene of interest (referred to herein collectively as "siRNA molecules"). Such siRNA duplexes or encoded dsRNA can reduce or silence gene expression in cells, such as but not limited to, medium spiny neurons, cortical neurons and/or astrocytes.

RNAi (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2-nucleotide 3' overhangs and that match the nucleic acid sequence of the target gene. These short RNA species may be naturally produced in vivo by Dicer-mediated cleavage of larger dsRNAs and they are functional in mammalian cells.

Naturally expressed small RNA molecules, named microRNAs (miRNAs), elicit gene silencing by regulating the expression of mRNAs. The miRNAs containing RNA Induced Silencing Complex (RISC) targets mRNAs presenting a perfect sequence complementarity with nucleotides 2-7 in the 5' region of the miRNA which is called the seed region, and other base pairs with its 3' region. miRNA mediated down regulation of gene expression may be caused by cleavage of the target mRNAs, translational inhibition of the target mRNAs, or mRNA decay. miRNA targeting sequences are usually located in the 3'-UTR of the target mRNAs. A single miRNA may target more than 100 transcripts from various genes, and one mRNA may be targeted by different miRNAs.

siRNA duplexes or dsRNA targeting a specific mRNA may be designed and synthesized in vitro and introduced into cells for activating RNAi processes. Elbashir et al. demonstrated that 21-nucleotide siRNA duplexes (termed small interfering RNAs) were capable of effecting potent and specific gene knockdown without inducing immune response in mammalian cells (Elbashir S M et al., Nature, 2001, 411, 494-498). Since this initial report, post-transcriptional gene silencing by siRNAs quickly emerged as a powerful tool for genetic analysis in mammalian cells and has the potential to produce novel therapeutics.

RNAi molecules which were designed to target against a nucleic acid sequence that encodes poly-glutamine repeat proteins which cause poly-glutamine expansion diseases such as Huntington's Disease, are described in U.S. Pat. Nos. 9,169,483 and 9,181,544 and International Patent Publication No. WO2015179525, the content of each of which is herein incorporated by reference in their entirety. U.S. Pat. Nos. 9,169,483 and 9,181,544 and International Patent Publication No. WO2015179525 each provide isolated RNA duplexes comprising a first strand of RNA (e.g., 15 contiguous nucleotides) and second strand of RNA (e.g., complementary to at least 12 contiguous nucleotides of the first strand) where the RNA duplex is about 15 to 30 base pairs in length. The first strand of RNA and second strand of RNA may be operably linked by an RNA loop (~4 to 50 nucleotides) to form a hairpin structure which may be inserted into an expression cassette. Non-limiting examples of loop portions include SEQ ID NO: 9-14 of U.S. Pat. No. 9,169,483, the content of which is herein incorporated by reference in its entirety. Non-limiting examples of strands of RNA which may be used, either full sequence or part of the sequence, to form RNA duplexes include SEQ ID NO: 1-8 of U.S. Pat. No. 9,169,483 and SEQ ID NO: 1-11, 33-59, 208-210, 213-215 and 218-221 of U.S. Pat. No. 9,181,544, the contents of each of which is herein incorporated by reference in its entirety. Non-limiting examples of RNAi molecules include SEQ ID NOs: 1-8 of U.S. Pat. No. 9,169,483, SEQ ID NOs: 1-11, 33-59, 208-210, 213-215 and 218-221 of U.S. Pat. No. 9,181,544 and SEQ ID NOs: 1, 6, 7, and 35-38 of International Patent Publication No. WO2015179525, the contents of each of which is herein incorporated by reference in their entirety.

In vitro synthesized siRNA molecules may be introduced into cells in order to activate RNAi. An exogenous siRNA duplex, when it is introduced into cells, similar to the endogenous dsRNAs, can be assembled to form the RNA Induced Silencing Complex (RISC), a multiunit complex that interacts with RNA sequences that are complementary to one of the two strands of the siRNA duplex (i.e., the antisense strand). During the process, the sense strand (or passenger strand) of the siRNA is lost from the complex, while the antisense strand (or guide strand) of the siRNA is matched with its complementary RNA. In particular, the targets of siRNA containing RISC complexes are mRNAs presenting a perfect sequence complementarity. Then, siRNA mediated gene silencing occurs by cleaving, releasing and degrading the target.

The siRNA duplex comprised of a sense strand homologous to the target mRNA and an antisense strand that is complementary to the target mRNA offers much more advantage in terms of efficiency for target RNA destruction compared to the use of the single strand (ss)-siRNAs (e.g. antisense strand RNA or antisense oligonucleotides). In many cases, it requires higher concentration of the ss-siRNA to achieve the effective gene silencing potency of the corresponding duplex.

Any of the foregoing molecules may be encoded by a viral genome.

Design and Sequences of siRNA Duplexes Targeting Gene of Interest

The present invention provides small interfering RNA (siRNA) duplexes (and modulatory polynucleotides encoding them) that target mRNA to interfere with gene expression and/or protein production.

The encoded siRNA duplex of the present invention contains an antisense strand and a sense strand hybridized together forming a duplex structure, wherein the antisense strand is complementary to the nucleic acid sequence of the targeted gene, and wherein the sense strand is homologous to the nucleic acid sequence of the targeted gene. In some aspects, the 5' end of the antisense strand has a 5' phosphate group and the 3' end of the sense strand contains a 3' hydroxyl group. In other aspects, there are none, one or 2 nucleotide overhangs at the 3' end of each strand.

Some guidelines for designing siRNAs have been proposed in the art. These guidelines generally recommend generating a 19-nucleotide duplexed region, symmetric 2-3 nucleotide 3' overhangs, 5'-phosphate and 3'-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA molecules essential for suppressing mammalian target gene expression may be readily designed.

According to the present invention, siRNA molecules (e.g., siRNA duplexes or encoded dsRNA) that target the gene of interest are designed. Such siRNA molecules can specifically, suppress gene expression and protein production. In some aspects, the siRNA molecules are designed and used to selectively "knock out" gene variants in cells, i.e., mutated transcripts. In some aspects, the siRNA molecules are designed and used to selectively "knock down" gene variants in cells. In other aspects, the siRNA molecules are able to inhibit or suppress both the wild type and mutated version of the gene of interest.

In one embodiment, an siRNA molecule of the present invention comprises a sense strand and a complementary antisense strand in which both strands are hybridized together to form a duplex structure. The antisense strand has sufficient complementarity to the target mRNA sequence to direct target-specific RNAi, i.e., the siRNA molecule has a sequence sufficient to trigger the destruction of the target mRNA by the RNAi machinery or process.

In one embodiment, an siRNA molecule of the present invention comprises a sense strand and a complementary antisense strand in which both strands are hybridized together to form a duplex structure and where the start site of the hybridization to the mRNA is between nucleotide 10 and 1000 on the target mRNA sequence. As a non-limiting example, the start site may be between nucleotide 10-20, 20-30, 30-40, 40-50, 60-70, 70-80, 80-90, 90-100, 100-150, 150-200, 200-250, 250-300, 300-350, 350-400, 400-450, 450-500, 500-550, 550-600, 600-650, 650-700, 700-70, 750-800, 800-850, 850-900, 900-950, 950-1000, on the target mRNA sequence. As yet another non-limiting example, the start site may be nucleotide 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, and 1000 on the target mRNA sequence.

In some embodiments, the antisense strand and target mRNA sequences have 100% complementarity. The antisense strand may be complementary to any part of the target mRNA sequence.

In other embodiments, the antisense strand and target mRNA sequences comprise at least one mismatch. As a non-limiting example, the antisense strand and the target mRNA sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In one embodiment, an siRNA or dsRNA includes at least two sequences that are complementary to each other.

According to the present invention, the siRNA molecule has a length from about 10-50 or more nucleotides, i.e., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementarity to a target region. In one embodiment, each strand of the siRNA molecule has a length from about 19 to 25, 19 to 24 or 19 to 21 nucleotides. In one embodiment, at least one strand of the siRNA molecule is 19 nucleotides in length. In one embodiment, at least one strand of the siRNA molecule is 20 nucleotides in length. In one embodiment, at least one strand of the siRNA molecule is 21 nucleotides in length. In one embodiment, at least one strand of the siRNA molecule is 22 nucleotides in length. In one embodiment, at least one strand of the siRNA molecule is 23 nucleotides in length. In one embodiment, at least one strand of the siRNA molecule is 24 nucleotides in length. In one embodiment, at least one strand of the siRNA molecule is 25 nucleotides in length.

In some embodiments, the siRNA molecules of the present invention can be synthetic RNA duplexes comprising about 19 nucleotides to about 25 nucleotides, and two overhanging nucleotides at the 3'-end. In some aspects, the siRNA molecules may be unmodified RNA molecules. In other aspects, the siRNA molecules may contain at least one modified nucleotide, such as base, sugar or backbone modifications.

In one embodiment, the siRNA molecules of the present invention may comprise an antisense sequence and a sense sequence, or a fragment or variant thereof. As a non-limiting example, the antisense sequence and the sense sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In other embodiments, the siRNA molecules of the present invention can be encoded in plasmid vectors, AAV particles, viral genome or other nucleic acid expression vectors for delivery to a cell.

DNA expression plasmids can be used to stably express the siRNA duplexes or dsRNA of the present invention in cells and achieve long-term inhibition of the target gene expression. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

According to the present invention, AAV particles comprising the nucleic acids encoding the siRNA molecules targeting the mRNA are produced, the AAV serotypes may be any of the serotypes listed herein. Non-limiting examples of the AAV serotypes include, AAV1, AAV2, AAV3, AAV4, AAV5, AAV6, AAV7, AAV8, AAV9, AAV9.47, AAV9 (hu14), AAV10, AAV11, AAV12, AAVrh8, AAVrh10, AAV-DJ8, AAV-DJ, AAV-PHP.A, AAV-PHP.B, AAVPHP.B2, AAVPHP.B3, AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, AAVG2B5, and variants thereof.

In some embodiments, the siRNA duplexes or encoded dsRNA of the present invention suppress (or degrade) the target mRNA. Accordingly, the siRNA duplexes or encoded dsRNA can be used to substantially inhibit the gene expression in a cell, for example a neuron. In some aspects, the inhibition of the gene expression refers to an inhibition by at least about 20%, preferably by at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 90%, 95%, 99% and 100%, or at least 20-30%, 20-40%, 20-50%, 20-60%, 20-70%, 20-80%, 20-90%, 20-95%, 20-100%, 30-40%, 30-45%, 30-50%, 30-60%, 30-70%, 30-80%, 30-90%, 30-95%, 30-100%, 35-45%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 55-65%, 57-68%, 60-70%, 60-80%, 60-90%, 60-95%, 60-100%, 70-80%, 70-90%, 70-95%, 70-100%, 80-90%, 80-95%, 80-100%, 85-99%, 90-95%, 90-100% or 95-100%. Accordingly, the protein product of the targeted gene may be inhibited by at least about 20%, preferably by at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 90%, 95%, 99% and 100%, or at least 20-30%, 20-40%, 20-50%, 20-60%, 20-70%, 20-80%, 20-90%, 20-95%, 20-100%, 30-40%, 30-45%, 30-50%, 30-60%, 30-70%, 30-80%, 30-90%, 30-95%, 30-100%, 35-45%,40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 55-65%, 57-68%, 60-70%, 60-80%, 60-90%, 60-95%, 60-100%, 70-80%, 70-90%, 70-95%, 70-100%, 80-90%, 80-95%, 80-100%, 85-99%, 90-95%, 90-100% or 95-100%. As a non-limiting example, the inhibition may be 30-40%. As a non-limiting example, the inhibition may be 30-45%. As a non-limiting example, the inhibition may be 35-45%. As a non-limiting example, the inhibition may be greater than 50%. As a non-limiting example, the inhibition may be 50-60%. As a non-limiting example, the inhibition may be greater than 60%. As a non-limiting example, the inhibition may be 55-65%. As a non-limiting example, the inhibition may be 57-68%. As a non-limiting example, the inhibition may be 70-80%. As a non-limiting example, the inhibition may be 85-99%. As a non-limiting example, the inhibition may be 35%. As a non-limiting example, the inhibition may be 36%. As a non-limiting example, the inhibition may be 40%. As a non-limiting example, the inhibition may be 41%. As a non-limiting example, the inhibition may be 43%. As a non-limiting example, the inhibition may be 45%. As a non-limiting example, the inhibition may be 49%. As a non-limiting example, the inhibition may be 62%. As a non-limiting example, the inhibition may be 64%. As a non-limiting example, the inhibition may be 74%. As a non-limiting example, the inhibition may be 77%. As a non-limiting example, the inhibition may be 84%. As a non-limiting example, the inhibition may be 87%. As a non-limiting example, the inhibition may be 95%. As a non-limiting example, the inhibition may be 99%. As a non-limiting example, the inhibition may be 100%.

In one embodiment, the siRNA duplexes or encoded dsRNA of the present invention suppress (or degrade) the target mRNA in spinal cord motor neurons. In some aspects, the inhibition of the gene expression refers to suppression of at least about 20%, preferably by at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 90%, 95%, 99% and 100%, or at least 20-30%, 20-40%, 20-50%, 20-60%, 20-70%, 20-80%, 20-90%, 20-95%, 20-100%, 30-40%, 30-45%, 30-50%, 30-60%, 30-70%, 30-80%, 30-90%, 30-95%, 30-100%, 35-45%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 55-65%, 57-68%, 60-70%, 60-80%, 60-90%, 60-95%, 60-100%, 70-80%, 70-90%, 70-95%, 70-100%, 80-90%, 80-95%, 80-100%, 85-99%, 90-95%, 90-100% or 95-100%. Accordingly, the protein product of the targeted gene may be inhibited by at least about 20%, preferably by at least about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 90%, 95%, 99% and 100%, or at least 20-30%, 20-40%, 20-50%, 20-60%, 20-70%, 20-80%, 20-90%, 20-95%, 20-100%, 30-40%, 30-45%, 30-50%, 30-60%, 30-70%, 30-80%, 30-90%, 30-95%, 30-100%, 35-45%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 55-65%, 57-68%, 60-70%, 60-80%, 60-90%, 60-95%, 60-100%, 70-80%, 70-90%, 70-95%, 70-100%, 80-90%, 80-95%, 80-100%, 85-99%, 90-95%, 90-100% or 95-100%. As a non-limiting example, the suppression may be 30-45%. As a non-limiting example, the suppression may be 35-45%. As a non-limiting example, the suppression may be greater than 50%. As a non-limiting example, the suppression may be greater than 60%. As a non-limiting example, the suppression may be 50-60%. As a non-limiting example, the suppression may be 55-65%. As a non-limiting example, the suppression may be 57-68%. As a non-limiting example, the suppression may be 70-80%. As a non-limiting example, the suppression may be 85-99%. As a non-limiting example, the suppression may be 35%. As a non-limiting example, the suppression may be 36%. As a non-limiting example, the suppression may be 40%. As a non-limiting example, the suppression may be 41%. As a non-limiting example, the suppression may be 43%. As a non-limiting example, the suppression may be 45%. As a non-limiting example, the suppression may be 49%. As a non-limiting example, the suppression may be 62%. As a non-limiting example, the suppression may be 64%. As a non-limiting example, the suppression may be 74%. As a non-limiting example, the suppression may be 77%. As a non-limiting example, the suppression may be 84%. As a non-limiting example, the suppression may be 87%. As a non-limiting example, the suppression may be 95%. As a non-limiting example, the suppression may be 99%. As a non-limiting example, the suppression may be 100%.

In one embodiment, the siRNA duplexes or encoded dsRNA of the present invention suppress (or degrade) the target mRNA in spinal cord motor neurons by 78%.

In one embodiment, the siRNA duplexes or encoded dsRNA of the present invention suppress (or degrade) the target mRNA in spinal cord motor neurons by 45-55%.

In one embodiment, the siRNA duplexes or encoded dsRNA of the present invention suppress (or degrade) the target mRNA in vg+ cells of motor neuron morphology. In some aspects, the inhibition of the gene expression refers to an inhibition by at least about 20%, preferably by at least about 30%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 71%, 72%, 73%, 74%, 75%, 76%, 77%, 78%, 79%, 80%, 81%, 82%, 83%, 84%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 71%, 72%, 73%, 74%, 75%, 76%, 77%, 78%, 79%, 80%, 81%, 82%, 83%, 84%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 45-50%, 45-55%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In one embodiment, the siRNA duplexes or encoded dsRNA of the present invention suppress (or degrade) the target mRNA in vg+ cells of motor neuron morphology by 53%.

In one embodiment, the siRNA molecules comprise a miRNA seed match for the target located in the guide strand. In another embodiment, the siRNA molecules comprise a miRNA seed match for the target located in the passenger strand. In yet another embodiment, the siRNA duplexes or encoded dsRNA targeting the gene of interest do not comprise a seed match for the target located in the guide or passenger strand.

In one embodiment, the siRNA duplexes or encoded dsRNA targeting the gene of interest may have almost no significant full-length off target effects for the guide strand. In another embodiment, the siRNA duplexes or encoded dsRNA targeting the gene of interest may have almost no significant full-length off target effects for the passenger strand. The siRNA duplexes or encoded dsRNA targeting the gene of interest may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the passenger strand. In yet another embodiment, the siRNA duplexes or encoded dsRNA targeting the gene of interest may have almost no significant full-length off target effects for the guide strand or the passenger strand. The siRNA duplexes or encoded dsRNA targeting the gene of interest may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the guide or passenger strand.

In one embodiment, the siRNA duplexes or encoded dsRNA targeting the gene of interest may have high activity in vitro. In another embodiment, the siRNA molecules may have low activity in vitro. In yet another embodiment, the siRNA duplexes or dsRNA targeting the gene of interest may have high guide strand activity and low passenger strand activity in vitro.

In one embodiment, the siRNA molecules have a high guide strand activity and low passenger strand activity in vitro. The target knock-down (KD) by the guide strand may be at least 40%, 50%, 60%, 65%, 70%, 75%, 80%, 85%, 90%, 95%, 99%, 99.5% or 100%. The target knock-down by the guide strand may be 40-50%, 45-50%, 50-55%, 50-60%, 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%. As a non-limiting example, the target knock-down (KD) by the guide strand is greater than 70%. As a non-limiting example, the target knock-down (KD) by the guide strand is greater than 60%.

In one embodiment, the siRNA duplex is designed so there is no miRNA seed match for the sense or antisense sequence to the non-gene of interest sequence.

In one embodiment, the $IC_{50}$ of the guide strand for the nearest off target is greater than 100 multiplied by the $IC_{50}$ of the guide strand for the on-target gene. As a non-limiting example, if the $IC_{50}$ of the guide strand for the nearest off target is greater than 100 multiplied by the $IC_{50}$ of the guide strand for the target then the siRNA molecule is said to have high guide strand selectivity for inhibiting the gene of interest in vitro.

In one embodiment, the 5' processing of the guide strand has a correct start (n) at the 5' end at least 75%, 80%, 85%, 90%, 95%, 99% or 100% of the time in vitro or in vivo. As a non-limiting example, the 5' processing of the guide strand is precise and has a correct start (n) at the 5' end at least 99% of the time in vitro. As a non-limiting example, the 5' processing of the guide strand is precise and has a correct start (n) at the 5' end at least 99% of the time in vivo. As a non-limiting example, the 5' processing of the guide strand is precise and has a correct start (n) at the 5' end at least 90% of the time in vitro. As a non-limiting example, the 5' processing of the guide strand is precise and has a correct start (n) at the 5' end at least 90% of the time in vivo. As a non-limiting example, the 5' processing of the guide strand is precise and has a correct start (n) at the 5' end at least 85% of the time in vitro. As a non-limiting example, the 5' processing of the guide strand is precise and has a correct start (n) at the 5' end at least 85% of the time in vivo.

In one embodiment, the guide to passenger (G:P) (also referred to as the antisense to sense) strand ratio expressed is 1:10, 1:9, 1:8, 1:7, 1:6, 1:5, 1:4, 1:3, 1:2, 1;1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The guide to passenger ratio refers to the ratio of the guide strands to the passenger strands after intracellular processing of the pri-microRNA. For example, a 80:20 guide-to-passenger ratio would have 8 guide strands to every 2 passenger strands processed from the precursor. As a non-limiting example, the guide-to-passenger strand ratio is 8:2 in vitro. As a non-limiting example, the guide-to-passenger strand ratio is 8:2 in vivo. As a non-limiting example, the guide-to-passenger strand ratio is 9:1 in vitro. As a non-limiting example, the guide-to-passenger strand ratio is 9:1 in vivo.

In one embodiment, the guide to passenger (G:P) strand ratio is in a range of 1-99, 1.3-99, 5-99, 10-99, 15-99, 20-99, 25-99, 30-99, 35-99, 40-99, 45-99, 50-99, 55-99, 60-99, 65-99, 70-99, 75-99, 80-99, 85-99, 90-99, 95-99, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 10-15, 10-20, 10-25, 10-30, 10-35, 10-40, 10-45, 10-50, 10-55, 10-60, 10-65, 10-70, 10-75, 10-80, 10-85, 10-90, 10-95, 15-20, 15-25, 15-30, 15-35, 15-40, 15-45, 15-50, 15-55, 15-60, 15-65, 15-70, 15-75, 15-80, 15-85, 15-90, 15-95, 20-25, 20-30, 20-35, 20-40, 20-45, 20-50, 20-55, 20-60, 20-65, 20-70, 20-75, 20-80, 20-85, 20-90, 20-95, 25-30, 25-35, 25-40, 25-45, 25-50, 25-55, 25-60, 25-65, 25-70, 25-75, 25-80, 25-85, 25-90, 25-95, 30-35, 30-40, 30-45, 30-50, 30-55, 30-60, 30-65, 30-70, 30-75, 30-80, 30-85, 30-90, 30-95, 35-40, 35-45, 35-50, 35-55, 35-60, 35-65, 35-70, 35-75, 35-80, 35-85, 35-90, 35-95, 40-45, 40-50, 40-55, 40-60, 40-65, 40-70, 40-75, 40-80, 40-85, 40-90, 40-95, 45-50, 45-55, 45-60, 45-65, 45-70, 45-75, 45-80, 45-85, 45-90, 45-95, 50-55, 50-60, 50-65, 50-70, 50-75, 50-80, 50-85, 50-90, 50-95, 55-60, 55-65, 55-70, 55-75, 55-80, 55-85, 55-90, 55-95, 60-65, 60-70, 60-75, 60-80, 60-85, 60-90, 60-95, 65-70, 65-75, 65-80, 65-85, 65-90, 65-95, 70-75, 70-80, 70-85, 70-90, 70-95, 75-80, 75-85, 75-90, 75-95, 80-85, 80-90, 80-95, 85-90, 85-95, or 90-95. As a non-limiting example, the guide to passenger ratio is a range of 1.3 to 99. As a non-limiting example, the guide to passenger ratio is a range of 10 to 99.

In one embodiment, the guide to passenger (G:P) strand ratio is 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, 60.5, 61, 61.5, 62, 62.5, 63, 63.5, 64, 64.5, 65, 65.5, 66, 66.5, 67, 67.5, 68, 68.5, 69, 69.5, 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5, or 99. As a non-limiting example, the guide to passenger (G:P) strand ratio is 11.5. As a non-limiting example, the guide to passenger (G:P) strand ratio is 99.

In one embodiment, the guide to passenger (G:P) (also referred to as the antisense to sense) strand ratio expressed is greater than 1.

In one embodiment, the guide to passenger (G:P) (also referred to as the antisense to sense) strand ratio expressed is greater than 2.

In one embodiment, the guide to passenger (G:P) (also referred to as the antisense to sense) strand ratio expressed is greater than 5.

In one embodiment, the guide to passenger (G:P) (also referred to as the antisense to sense) strand ratio expressed is greater than 10.

In one embodiment, the guide to passenger (G:P) (also referred to as the antisense to sense) strand ratio expressed is greater than 20.

In one embodiment, the guide to passenger (G:P) (also referred to as the antisense to sense) strand ratio expressed is greater than 50.

In one embodiment, the guide to passenger (G:P) (also referred to as the antisense to sense) strand ratio expressed is greater than 300.

In one embodiment, the guide to passenger (G:P) (also referred to as the antisense to sense) strand ratio expressed is 314.

In one embodiment, the guide to passenger (G:P) (also referred to as the antisense to sense) strand ratio expressed is greater than 400.

In one embodiment, the guide to passenger (G:P) (also referred to as the antisense to sense) strand ratio expressed is 434.

In one embodiment, the guide to passenger (G:P) (also referred to as the antisense to sense) strand ratio expressed is at least 3:1.

In one embodiment, the guide to passenger (G:P) (also referred to as the antisense to sense) strand ratio expressed is at least 5:1.

In one embodiment, the guide to passenger (G:P) (also referred to as the antisense to sense) strand ratio expressed is at least 10:1.

In one embodiment, the guide to passenger (G:P) (also referred to as the antisense to sense) strand ratio expressed is at least 20:1.

In one embodiment, the guide to passenger (G:P) (also referred to as the antisense to sense) strand ratio expressed is at least 50:1.

In one embodiment, the passenger to guide (P:G) (also referred to as the sense to antisense) strand ratio expressed is 1:10, 1:9, 1:8, 1:7, 1:6, 1:5, 1:4, 1:3, 1:2, 1;1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The passenger to guide ratio refers to the ratio of the passenger strands to the guide strands after the intracellular processing of the pri-microRNA. For example, a 80:20 of passenger-to-guide ratio would have 8 passenger strands to every 2 guide strands processed from the precursor. As a non-limiting example, the passenger-to-guide strand ratio is 80:20 in vitro. As a non-limiting example, the passenger-to-guide strand ratio is 80:20 in vivo. As a non-limiting example, the passenger-to-guide strand ratio is 8:2 in vitro. As a non-limiting example, the passenger-to-guide strand ratio is 8:2 in vivo. As a non-limiting example, the passenger-to-guide strand ratio is 9:1 in vitro. As a non-limiting example, the passenger-to-guide strand ratio is 9:1 in vivo.

In one embodiment, the passenger to guide (P:G) strand ratio is in a range of 1-99, 1.3-99, 5-99, 10-99, 15-99, 20-99, 25-99, 30-99, 35-99, 40-99, 45-99, 50-99, 55-99, 60-99, 65-99, 70-99, 75-99, 80-99, 85-99, 90-99, 95-99, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 10-15, 10-20, 10-25, 10-30, 10-35, 10-40, 10-45, 10-50, 10-55, 10-60, 10-65, 10-70, 10-75, 10-80, 10-85, 10-90, 10-95, 15-20, 15-25, 15-30, 15-35, 15-40, 15-45, 15-50, 15-55, 15-60, 15-65, 15-70, 15-75, 15-80, 15-85, 15-90, 15-95, 20-25, 20-30, 20-35, 20-40, 20-45, 20-50, 20-55, 20-60, 20-65, 20-70, 20-75, 20-80, 20-85, 20-90, 20-95, 25-30, 25-35, 25-40, 25-45, 25-50, 25-55, 25-60, 25-65, 25-70, 25-75, 25-80, 25-85, 25-90, 25-95, 30-35, 30-40, 30-45, 30-50, 30-55, 30-60, 30-65, 30-70, 30-75, 30-80, 30-85, 30-90, 30-95, 35-40, 35-45, 35-50, 35-55, 35-60, 35-65, 35-70, 35-75, 35-80, 35-85, 35-90, 35-95, 40-45, 40-50, 40-55, 40-60, 40-65, 40-70, 40-75, 40-80, 40-85, 40-90, 40-95, 45-50, 45-55, 45-60, 45-65, 45-70, 45-75, 45-80, 45-85, 45-90, 45-95, 50-55, 50-60, 50-65, 50-70, 50-75, 50-80, 50-85, 50-90, 50-95, 55-60, 55-65, 55-70, 55-75, 55-80, 55-85, 55-90, 55-95, 60-65, 60-70, 60-75, 60-80, 60-85, 60-90, 60-95, 65-70, 65-75, 65-80, 65-85, 65-90, 65-95, 70-75, 70-80, 70-85, 70-90, 70-95, 75-80, 75-85, 75-90, 75-95, 80-85, 80-90, 80-95, 85-90, 85-95, or 90-95.

In one embodiment, the passenger to guide (P:G) strand ratio is 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, 60.5, 61, 61.5, 62, 62.5, 63, 63.5, 64, 64.5, 65, 65.5, 66, 66.5, 67, 67.5, 68, 68.5, 69, 69.5, 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5, or 99.

In one embodiment, the passenger to guide (P:G) (also referred to as the sense to antisense) strand ratio expressed is greater than 1.

In one embodiment, the passenger to guide (P:G) (also referred to as the sense to antisense) strand ratio expressed is greater than 2.

In one embodiment, the passenger to guide (P:G) (also referred to as the sense to antisense) strand ratio expressed is greater than 5.

In one embodiment, the passenger to guide (P:G) (also referred to as the sense to antisense) strand ratio expressed is greater than 10.

In one embodiment, the passenger to guide (P:G) (also referred to as the sense to antisense) strand ratio expressed is greater than 20.

In one embodiment, the passenger to guide (P:G) (also referred to as the sense to antisense) strand ratio expressed is greater than 50.

In one embodiment, the passenger to guide (P:G) (also referred to as the sense to antisense) strand ratio expressed is at least 3:1.

In one embodiment, the passenger to guide (P:G) (also referred to as the sense to antisense) strand ratio expressed is at least 5:1.

In one embodiment, the passenger to guide (P:G) (also referred to as the sense to antisense) strand ratio expressed is at least 10:1.

In one embodiment, the passenger to guide (P:G) (also referred to as the sense to antisense) strand ratio expressed is at least 20:1.

In one embodiment, the passenger to guide (P:G) (also referred to as the sense to antisense) strand ratio expressed is at least 50:1.

In one embodiment, a passenger-guide strand duplex is considered effective when the pri- or pre-microRNAs demonstrate, but methods known in the art and described herein, greater than 2-fold guide to passenger strand ratio when processing is measured. As a non-limiting examples, the pri- or pre-microRNAs demonstrate great than 2-fold, 3-fold, 4-fold, 5-fold, 6-fold, 7-fold, 8-fold, 9-fold, 10-fold, 11-fold, 12-fold, 13-fold, 14-fold, 15-fold, or 2 to 5-fold, 2 to 10-fold, 2 to 15-fold, 3 to 5-fold, 3 to 10-fold, 3 to 15-fold, 4 to 5-fold, 4 to 10-fold, 4 to 15-fold, 5 to 10-fold, 5 to 15-fold, 6 to 10-fold, 6 to 15-fold, 7 to 10-fold, 7 to 15-fold, 8 to 10-fold, 8 to 15-fold, 9 to 10-fold, 9 to 15-fold, 10 to 15-fold, 11 to 15-fold, 12 to 15-fold, 13 to 15-fold, or 14 to 15-fold guide to passenger strand ratio when processing is measured.

In one embodiment, the vector genome encoding the dsRNA comprises a sequence which is at least 60%, 65%, 70%, 75%, 80%, 85%, 90%, 95%, 99% or more than 99% of the full length of the construct. As a non-limiting example, the vector genome comprises a sequence which is at least 80% of the full-length sequence of the construct.

In one embodiment, the siRNA molecules may be used to silence wild type or mutant version of the gene of interest by targeting at least one exon on the gene of interest sequence. The exon may be exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, and/or exon 67.

Design and Sequences of siRNA Duplexes Targeting SOD1 Gene

The present invention provides small interfering RNA (siRNA) duplexes (and modulatory polynucleotides encoding them) that target SOD1 mRNA to interfere with SOD1 gene expression and/or SOD1 protein production.

The encoded siRNA duplex of the present invention contains an antisense strand and a sense strand hybridized together forming a duplex structure, wherein the antisense strand is complementary to the nucleic acid sequence of the targeted SOD1 gene, and wherein the sense strand is homologous to the nucleic acid sequence of the targeted SOD1 gene. In some aspects, the 5' end of the antisense strand has a 5' phosphate group and the 3' end of the sense strand contains a 3' hydroxyl group. In other aspects, there are none, one or 2 nucleotide overhangs at the 3' end of each strand.

Some guidelines for designing siRNAs have been proposed in the art. These guidelines generally recommend generating a 19-nucleotide duplexed region, symmetric 2-3 nucleotide 3' overhangs, 5'-phosphate and 3'-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA molecules essential for suppressing the SOD1 gene expression may be readily designed.

According to the present invention, siRNA molecules (e.g., siRNA duplexes or encoded dsRNA) that target the SOD1 gene are designed. Such siRNA molecules can specifically, suppress SOD1 gene expression and protein production. In some aspects, the siRNA molecules are designed and used to selectively "knock out" SOD1 gene variants in cells, i.e., mutated SOD1 transcripts that are identified in patients with ALS disease. In some aspects, the siRNA molecules are designed and used to selectively "knock down" SOD1 gene variants in cells. In other aspects, the siRNA molecules are able to inhibit or suppress both the wild type and mutated SOD1 gene.

In one embodiment, an siRNA molecule of the present invention comprises a sense strand and a complementary antisense strand in which both strands are hybridized together to form a duplex structure. The antisense strand has sufficient complementarity to the SOD1 mRNA sequence to direct target-specific RNAi, i.e., the siRNA molecule has a sequence sufficient to trigger the destruction of the target mRNA by the RNAi machinery or process.

In one embodiment, an siRNA molecule of the present invention comprises a sense strand and a complementary antisense strand in which both strands are hybridized together to form a duplex structure and where the start site of the hybridization to the SOD1 mRNA is between nucleotide 15 and 1000 on the SOD1 mRNA sequence. As a non-limiting example, the start site may be between nucleotide 15-25, 15-50, 15-75, 15-100, 100-150, 150-200, 200-250, 250-300, 300-350, 350-400, 400-450, 450-500, 500-550, 550-600, 600-650, 650-700, 700-70, 750-800, 800-850, 850-900, 900-950, and 950-1000 on the SOD1 mRNA sequence. As yet another non-limiting example, the start site may be nucleotide 26, 27, 28, 29, 30, 32, 33, 34, 35, 36, 37, 74, 76, 77, 78, 149, 153, 157, 160, 177, 192, 193, 195, 196, 197, 198, 199, 206, 209, 210, 239, 241, 261, 263, 264, 268, 269, 276, 278, 281, 284, 290, 291, 295, 296, 316, 317, 329, 330, 337, 350, 351, 352, 354, 357, 358, 364, 375, 378, 383, 384, 390, 392, 395, 404, 406, 417, 418, 469, 470, 475, 476, 480, 487, 494, 496, 497, 501, 504, 515, 518, 522, 523, 524, 552, 554, 555, 562, 576, 577, 578, 579, 581, 583, 584, 585, 587, 588, 589, 593, 594, 595, 596, 597, 598, 599, 602, 607, 608, 609, 610, 611, 612, 613, 616, 621, 633, 635, 636, 639, 640, 641, 642, 643, 644, 645, 654, 660, 661, 666, 667, 668, 669, 673, 677, 692, 698, 699, 700, 701, 706, 749, 770, 772, 775, 781, 800, 804, 819, 829, 832, 833, 851, 854, 855, 857, 858, 859, 861, 869, 891, 892, 906, 907, 912, 913, 934, 944, and 947 on the SOD1 mRNA sequence.

In some embodiments, the antisense strand and target SOD1 mRNA sequences have 100% complementarity. The antisense strand may be complementary to any part of the target SOD1 mRNA sequence.

In other embodiments, the antisense strand and target SOD1 mRNA sequences comprise at least one mismatch. As a non-limiting example, the antisense strand and the target SOD1 mRNA sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In one embodiment, an siRNA or dsRNA targeting SOD1 includes at least two sequences that are complementary to each other.

According to the present invention, the siRNA molecule targeting SOD1 has a length from about 10-50 or more nucleotides, i.e., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementarity to a target region. In one embodiment, each strand of the siRNA molecule has a length from about 19 to 25, 19 to 24 or 19 to 21 nucleotides. In one embodiment, at least one strand of the siRNA molecule is 19 nucleotides in length. In one embodiment, at least one strand of the siRNA molecule is 20 nucleotides in length. In one embodiment, at least one strand of the siRNA molecule is 21 nucleotides in length. In one embodiment, at least one strand of the siRNA molecule is 22 nucleotides in length. In one embodiment, at least one strand of the siRNA molecule is 23 nucleotides in length. In one embodiment, at least one strand of the siRNA molecule is 24 nucleotides in length. In one embodiment, at least one strand of the siRNA molecule is 25 nucleotides in length.

In some embodiments, the siRNA molecules of the present invention targeting SOD1 can be synthetic RNA duplexes comprising about 19 nucleotides to about 25 nucleotides, and two overhanging nucleotides at the 3'-end. In some aspects, the siRNA molecules may be unmodified RNA molecules. In other aspects, the siRNA molecules may contain at least one modified nucleotide, such as base, sugar or backbone modifications.

In one embodiment, the siRNA molecules of the present invention targeting SOD1 may comprise a nucleotide sequence such as, but not limited to, the antisense (guide) sequences in Table 2 or a fragment or variant thereof. As a non-limiting example, the antisense sequence used in the siRNA molecule of the present invention is at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% of a nucleotide sequence in Table 2. As another non-limiting example, the antisense sequence used in the siRNA molecule of the present invention comprises at least 3, 4, 5, 6, 7, 8, 9, 10, 11, 12, 13, 14, 15, 16, 17, 18, 19, 20, 21 or more than 21 consecutive nucleotides of a nucleotide sequence in Table 2. As yet another non-limiting example, the antisense sequence used in the siRNA molecule of the present invention comprises nucleotides 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 2 to 22, 2 to 21, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 3 to 22, 3 to 21, 3 to 20, 3 to 19, 3 to 18, 3 to 17, 3 to 16, 3 to 15, 3 to 14, 3 to 13, 3 to 12, 3 to 11, 3 to 10, 3 to 9, 3 to 8, 4 to 22, 4 to 21, 4 to 20, 4 to 19, 4 to 18, 4 to 17, 4 to 16, 4 to 15, 4 to 14, 4 to 13, 4 to 12, 4 to 11, 4 to 10, 4 to 9, 4 to 8, 5 to 22, 5 to 21, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 6 to 22, 6 to 21, 6 to 20, 6 to 19, 6 to 18, 6 to 17, 6 to 16, 6 to 15, 6 to 14, 6 to 13, 6 to 12, 6 to 11, 6 to 10, 7 to 22, 7 to 21, 7 to 20, 7 to 19, 7 to 18, 7 to 17, 7 to 16, 7 to 15, 7 to 14, 7 to 13, 7 to 12, 8 to 22, 8 to 21, 8 to 20, 8 to 19, 8 to 18, 8 to 17, 8 to 16, 8 to 15, 8 to 14, 8 to 13, 8 to 12, 9 to 22, 9 to 21, 9 to 20, 9 to 19, 9 to 18, 9 to 17, 9 to 16, 9 to 15, 9 to 14, 10 to 22, 10 to 21, 10 to 20, 10 to 19, 10 to 18, 10 to 17, 10 to 16, 10 to 15, 10 to 14, 11 to 22, 11 to 21, 11 to 20, 11 to 19, 11 to 18, 11 to 17, 11 to 16, 11 to 15, 11 to 14, 12 to 22, 12 to 21, 12 to 20, 12 to 19, 12 to 18, 12 to 17, 12 to 16, 13 to 22, 13 to 21, 13 to 20, 13 to 19, 13 to 18, 13 to 17, 13 to 16, 14 to 22, 14 to 21, 14 to 20, 14 to 19, 14 to 18, 14 to 17, 15 to 22, 15 to 21, 15 to 20, 15 to 19, 15 to 18, 16 to 22, 16 to 21, 16 to 20, 17 to 22, 17 to 21, or 18 to 22 of the sequences in Table 2.

TABLE 2

| Antisense Sequences | | |
|---|---|---|
| Antisense ID | Sequence | SEQ ID NO |
| A-4000 | UCACCACAAGCCAAACGACUU | 5 |
| A-4001 | UGAUUAAAGUGAGGACCUGUU | 6 |
| A-4002 | UAUUAAAGUGAGGACCUGCUU | 7 |
| A-4003 | UACACCACAAGCCAAACGAUU | 8 |
| A-4004 | GAUUAAAGUGAGGACCUGCUU | 9 |
| A-4005 | UCACCACAAGCCAAACGACUUU | 10 |
| A-4006 | UGCCAGCAGUCACAUUGCCUU | 11 |
| A-4007 | UAACAGAUGAGUUAAGGGGUU | 12 |
| A-4008 | UAUUAAAGUGAGGACCUGCdTdT | 13 |
| A-4009 | UACACCACAAGCCAAACGAdTdT | 14 |
| A-4010 | UUGUUUAUUGGGCGAUCCCdTdT | 15 |
| A-4011 | UGUUUAUUGGGCGAUCCCAdTdT | 16 |
| A-4012 | UCACCACAAGCCAAACGACdTdT | 17 |

TABLE 2-continued

Antisense Sequences

| Antisense ID | Sequence | SEQ ID NO |
|---|---|---|
| A-4013 | UGAUUAAAGUGAGGACCUGdTdT | 18 |
| A-4014 | UUUUAUUGGGCGAUCCCAAdTdT | 19 |
| A-4015 | UGUCAGCAGUCACAUUGCCdTdT | 20 |
| A-4016 | UGCGAUCCCAAUUACACCAdTdT | 21 |

In one embodiment, the siRNA molecules of the present invention targeting SOD1 may comprise a nucleotide sequence such as, but not limited to, the sense (passenger) sequences in Table 3 or a fragment or variant thereof. As a non-limiting example, the sense sequence used in the siRNA molecule of the present invention is at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% of a nucleotide sequence in Table 3. As another non-limiting example, the sense sequence used in the siRNA molecule of the present invention comprises at least 3, 4, 5, 6, 7, 8, 9, 10, 11, 12, 13, 14, 15, 16, 17, 18, 19, 20, 21 or more than 21 consecutive nucleotides of a nucleotide sequence in Table 3. As yet another non-limiting example, the sense sequence used in the siRNA molecule of the present invention comprises nucleotides 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 2 to 22, 2 to 21, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 3 to 22, 3 to 21, 3 to 20, 3 to 19, 3 to 18, 3 to 17, 3 to 16, 3 to 15, 3 to 14, 3 to 13, 3 to 12, 3 to 11, 3 to 10, 3 to 9, 3 to 8, 4 to 22, 4 to 21, 4 to 20, 4 to 19, 4 to 18, 4 to 17, 4 to 16, 4 to 15, 4 to 14, 4 to 13, 4 to 12, 4 to 11, 4 to 10, 4 to 9, 4 to 8, 5 to 22, 5 to 21, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 6 to 22, 6 to 21, 6 to 20, 6 to 19, 6 to 18, 6 to 17, 6 to 16, 6 to 15, 6 to 14, 6 to 13, 6 to 12, 6 to 11, 6 to 10, 7 to 22, 7 to 21, 7 to 20, 7 to 19, 7 to 18, 7 to 17, 7 to 16, 7 to 15, 7 to 14, 7 to 13, 7 to 12, 8 to 22, 8 to 21, 8 to 20, 8 to 19, 8 to 18, 8 to 17, 8 to 16, 8 to 15, 8 to 14, 8 to 13, 8 to 12, 9 to 22, 9 to 21, 9 to 20, 9 to 19, 9 to 18, 9 to 17, 9 to 16, 9 to 15, 9 to 14, 10 to 22, 10 to 21, 10 to 20, 10 to 19, 10 to 18, 10 to 17, 10 to 16, 10 to 15, 10 to 14, 11 to 22, 11 to 21, 11 to 20, 11 to 19, 11 to 18, 11 to 17, 11 to 16, 11 to 15, 11 to 14, 12 to 22, 12 to 21, 12 to 20, 12 to 19, 12 to 18, 12 to 17, 12 to 16, 13 to 22, 13 to 21, 13 to 20, 13 to 19, 13 to 18, 13 to 17, 13 to 16, 14 to 22, 14 to 21, 14 to 20, 14 to 19, 14 to 18, 14 to 17, 15 to 22, 15 to 21, 15 to 20, 15 to 19, 15 to 18, 16 to 22, 16 to 21, 16 to 20, 17 to 22, 17 to 21, or 18 to 22 of the sequences in Table 3.

TABLE 3

Sense Sequences

| Sense ID | Sequence | SEQ ID NO |
|---|---|---|
| S-4000 | GUCGUUUGGCUUGUGGUGGCU | 22 |
| S-4001 | CAGGUCCUCACUUUAAUCGCU | 23 |
| S-4002 | GCAGGUCCUCACUUUAAUGCC | 24 |
| S-4003 | GCAGGUCCUCACUUUAAUGCU | 25 |
| S-4004 | UCGUUUGGCUUGUGGUGUGCU | 26 |
| S-4005 | GCAGGUCCUCACUUUAAUCCC | 27 |
| S-4006 | GUCGUUUGGCUUGUGGUGGCC | 28 |
| S-4007 | CAGGUCCUCACUUUAAUCGCC | 29 |
| S-4008 | UCGUUUGGCUUGUGGUGUGCC | 30 |
| S-4009 | GGCAAUGUGACUGCUGGUGCC | 31 |
| S-4010 | GGCAAUGUGACUGCUGGUACC | 32 |
| S-4011 | GGCAAUGUGUCUGCUGGUACC | 33 |
| S-4012 | GGCAAUGUGACUGCUGGCCCC | 34 |
| S-4013 | GCAGGUCCUCACUUUAAUUCC | 35 |
| S-4014 | GCAGGUCCUGACUUUAAUCCC | 36 |
| S-4015 | CCCCUUAACUCAUUUGUUCCC | 37 |
| S-4016 | GCAGGUCCUCACUUUAAUCdTdT | 38 |
| S-4017 | UCGUUUGGCUUGUGGUGUCdTdT | 39 |
| S-4018 | GGGAUCGCCCAAUAAACACdTdT | 40 |
| S-4019 | UGGGAUCGCCCAAUAAACCdTdT | 41 |
| S-4020 | GUCGUUUGGCUUGUGGUGCdTdT | 42 |
| S-4021 | CAGGUCCUCACUUUAAUCCdTdT | 43 |
| S-4022 | UUGGGAUCGCCCAAUAAACdTdT | 44 |
| S-4023 | GGCAAUGUGACUGCUGACCdTdT | 45 |
| S-4024 | UGGUGUAAUUGGGAUCGCCdTdT | 46 |

In one embodiment, the siRNA molecules of the present invention targeting SOD1 may comprise an antisense sequence from Table 2 and a sense sequence from Table 3, or a fragment or variant thereof. As a non-limiting example, the antisense sequence and the sense sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In one embodiment, the siRNA molecules of the present invention targeting SOD1 may comprise the sense and antisense siRNA duplex as described in Table 4. As a non-limiting example, these siRNA duplexes may be tested for in vitro inhibitory activity on endogenous SOD1 gene expression.

TABLE 4

Sense and antisense strand sequences of SOD1 dsRNA

| siRNA Duplex ID | SS ID | Sense Strand Sequence (5'-3') | SS SEQ ID | AS ID | Antisense Strand Sequence (5'-3') | AS SEQ ID |
|---|---|---|---|---|---|---|
| D-4000 | S-4016 | GCAGGUCCUCACUUUAAUCdTdT | 38 | A-4008 | UAUUAAAGUGAGGACCUGCdTdT | 13 |
| D-4001 | S-4017 | UCGUUUGGCUUGUGGUGUCdTdT | 39 | A-4009 | UACACCACAAGCCAAACGAdTdT | 14 |
| D-4002 | S-4018 | GGGAUCGCCCAAUAAACACdTdT | 40 | A-4010 | UUGUUUAUUGGGCGAUCCCdTdT | 15 |
| D-4003 | S-4019 | UGGGAUCGCCCAAUAAACCdTdT | 41 | A-4011 | UGUUUAUUGGGCGAUCCCdTdT | 16 |
| D-4004 | S-4020 | GUCGUUUGGCUUGUGGUGCdTdT | 42 | A-4012 | UCACCACAAGCCAAACGACdTdT | 17 |
| D-4005 | S-4021 | CAGGUCCUCACUUUAAUCCdTdT | 43 | A-4013 | UGAUUAAAGUGAGGACCUGdTdT | 18 |
| D-4006 | S-4022 | UUGGGAUCGCCCAAUAAACdTdT | 44 | A-4014 | UUUUAUUGGGCGAUCCCAAdTdT | 19 |
| D-4007 | S-4023 | GGCAAUGUGACUGCUGACCdTdT | 45 | A-4015 | UGUCAGCAGUCACAUUGCCdTdT | 20 |
| D-4008 | S-4024 | UGGUGUAAUUGGGAUCGCCdTdT | 46 | A-4016 | UGCGAUCCCAAUUACACCAdTdT | 21 |
| D-4009 | S-4000 | GUCGUUUGGCUUGUGGUGGCU | 22 | A-4000 | UCACCACAAGCCAAACGACUU | 5 |
| D-4010 | S-4001 | CAGGUCCUCACUUUAAUCGCU | 23 | A-4001 | UGAUUAAAGUGAGGACCUGUU | 6 |
| D-4011 | S-4002 | GCAGGUCCUCACUUUAAUGCC | 24 | A-4002 | UAUUAAAGUGAGGACCUGCUU | 7 |
| D-4012 | S-4003 | GCAGGUCCUCACUUUAAUGCU | 25 | A-4002 | UAUUAAAGUGAGGACCUGCUU | 7 |
| D-4013 | S-4004 | UCGUUUGGCUUGUGGUGUGCU | 26 | A-4003 | UACACCACAAGCCAAACGAUU | 8 |
| D-4014 | S-4005 | GCAGGUCCUCACUUUAAUCCC | 27 | A-4004 | GAUUAAAGUGAGGACCUGCUU | 9 |
| D-4015 | S-4006 | GUCGUUUGGCUUGUGGUGGCC | 28 | A-4005 | UCACCACAAGCCAAACGACUUU | 10 |
| D-4016 | S-4007 | CAGGUCCUCACUUUAAUCGCC | 29 | A-4001 | UGAUUAAAGUGAGGACCUGUU | 6 |
| D-4017 | S-4008 | UCGUUUGGCUUGUGGUGUGCC | 30 | A-4003 | UACACCACAAGCCAAACGAUU | 8 |
| D-4018 | S-4009 | GGCAAUGUGACUGCUGGUGCC | 31 | A-4006 | UGCCAGCAGUCACAUUGCCUU | 11 |
| D-4019 | S-4010 | GGCAAUGUGACUGCUGGUACC | 32 | A-4006 | UGCCAGCAGUCACAUUGCCUU | 11 |
| D-4020 | S-4011 | GGCAAUGUGUCUGCUGGUACC | 33 | A-4006 | UGCCAGCAGUCACAUUGCCUU | 11 |
| D-4021 | S-4012 | GGCAAUGUGACUGCUGGCCCC | 34 | A-4006 | UGCCAGCAGUCACAUUGCCUU | 11 |

TABLE 4-continued

Sense and antisense strand sequences of SOD1 dsRNA

| siRNA Duplex ID | SS ID | Sense Strand Sequence (5'-3') | SS SEQ ID | AS ID | Antisense Strand Sequence (5'-3') | AS SEQ ID |
|---|---|---|---|---|---|---|
| D-4022 | S-4013 | GCAGGUCCUCAC UUUAAUUCC | 35 | A-4004 | GAUUAAAGUGA GGACCUGCUU | 9 |
| D-4023 | S-4014 | GCAGGUCCUGAC UUUAAUCCC | 36 | A-4004 | GAUUAAAGUGA GGACCUGCUU | 9 |
| D-4024 | S-4002 | GCAGGUCCUCAC UUUAAUGCC | 24 | A-4004 | GAUUAAAGUGA GGACCUGCUU | 9 |
| D-4025 | S-4015 | CCCCUUAACUCA UUUGUUCCC | 37 | A-4007 | UAACAGAUGAG UUAAGGGGUU | 12 |

In other embodiments, the siRNA molecules of the present invention targeting SOD1 can be encoded in plasmid vectors, AAV particles, viral genome or other nucleic acid expression vectors for delivery to a cell.

DNA expression plasmids can be used to stably express the siRNA duplexes or dsRNA of the present invention targeting SOD1 in cells and achieve long-term inhibition of the target gene expression. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

According to the present invention, AAV particles comprising the nucleic acids encoding the siRNA molecules targeting SOD1 mRNA are produced, the AAV serotypes may be any of the serotypes listed herein. Non-limiting examples of the AAV serotypes include, AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A, and/or AAV-PHP.B, AAVPHP.B2, AAVPHP.B3, AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3, AAVG2B4, AAVG2B5, and variants thereof.

In some embodiments, the siRNA duplexes or encoded dsRNA of the present invention suppress (or degrade) SOD1 mRNA. Accordingly, the siRNA duplexes or encoded dsRNA can be used to substantially inhibit SOD1 gene expression in a cell. In some aspects, the inhibition of SOD1 gene expression refers to an inhibition by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

According to the present invention, the siRNA molecules are designed and tested for their ability in reducing SOD1 mRNA levels in cultured cells. Such siRNA molecules may form a duplex such as, but not limited to, include those listed in Table 4. As a non-limiting example, the siRNA duplexes may be siRNA duplex IDs: D-4000 to D-4025.

In one embodiment, the siRNA molecules comprise a miRNA seed match for SOD1 located in the guide strand. In another embodiment, the siRNA molecules comprise a miRNA seed match for SOD1 located in the passenger strand. In yet another embodiment, the siRNA duplexes or encoded dsRNA targeting SOD1 gene do not comprise a seed match for SOD1 located in the guide or passenger strand.

In one embodiment, the siRNA duplexes or encoded dsRNA targeting SOD1 gene may have almost no significant full-length off target effects for the guide strand. In another embodiment, the siRNA duplexes or encoded dsRNA targeting SOD1 gene may have almost no significant full-length off target effects for the passenger strand. The siRNA duplexes or encoded dsRNA targeting SOD1 gene may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the passenger strand. In yet another embodiment, the siRNA duplexes or encoded dsRNA targeting SOD1 gene may have almost no significant full-length off target effects for the guide strand or the passenger strand. The siRNA duplexes or encoded dsRNA targeting SOD1 gene may have less than 1%, 2%, 3%, 4%, 5%, 6%, 7%, 8%, 9%, 10%,11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the guide or passenger strand.

In one embodiment, the siRNA duplexes or encoded dsRNA targeting SOD1 gene may have high activity in vitro. In another embodiment, the siRNA molecules may have low activity in vitro. In yet another embodiment, the siRNA duplexes or dsRNA targeting the SOD1 gene may have high guide strand activity and low passenger strand activity in vitro.

In one embodiment, the siRNA molecules targeting SOD1 have a high guide strand activity and low passenger strand activity in vitro. The target knock-down (KD) by the guide strand may be at least 40%, 50%, 60%, 65%, 70%, 75%, 80%, 85%, 90%, 95%, 99%, 99.5% or 100%. The target knock-down by the guide strand may be 40-50%, 45-50%, 50-55%, 50-60%, 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%. As a non-limiting example, the target knock-down (KD) by the guide strand is greater than 70%. As a non-limiting example, the target knock-down (KD) by the guide strand is greater than 60%.

In one embodiment, the siRNA duplex target SOD1 is designed so there is no miRNA seed match for the sense or antisense sequence to the non-SOD1 sequence.

In one embodiment, the $IC_{50}$ of the guide strand in the siRNA duplex targeting SOD1 for the nearest off target is greater than 100 multiplied by the $IC_{50}$ of the guide strand for the on-target gene, SOD1. As a non-limiting example, if the $IC_{50}$ of the guide strand for the nearest off target is greater than 100 multiplied by the $IC_{50}$ of the guide strand for the target then the siRNA molecules are said to have high guide strand selectivity for inhibiting SOD1 in vitro.

In one embodiment, the 5' processing of the guide strand of the siRNA duplex targeting SOD1 has a correct start (n) at the 5' end at least 75%, 80%, 85%, 90%, 95%, 99% or 100% of the time in vitro or in vivo. As a non-limiting example, the 5' processing of the guide strand is precise and has a correct start (n) at the 5' end at least 99% of the time in vitro. As a non-limiting example, the 5' processing of the guide strand is precise and has a correct start (n) at the 5' end at least 99% of the time in vivo. As a non-limiting example, the 5' processing of the guide strand is precise and has a correct start (n) at the 5' end at least 90% of the time in vitro. As a non-limiting example, the 5' processing of the guide strand is precise and has a correct start (n) at the 5' end at least 90% of the time in vivo. As a non-limiting example, the 5' processing of the guide strand is precise and has a correct start (n) at the 5' end at least 85% of the time in vitro. As a non-limiting example, the 5' processing of the guide strand is precise and has a correct start (n) at the 5' end at least 85% of the time in vivo.

In one embodiment, the 5' processing of the guide strand of the siRNA duplex targeting SOD1 has a correct start (n) at the 5' end in a range of 75-95%, 75-90%, 75-85%, 75-80%, 80-95%, 80-90%, 80-85%, 85-95%, 85-90%, or 90-95%. As a non-limiting example, the 5' processing of the guide strand of the siRNA duplex targeting SOD1 has a correct start (n) at the 5' end in a range of 75-95%.

In one embodiment, the 5' processing of the guide strand of the siRNA duplex targeting SOD1 has a correct start (n) at the 5' end for 75%, 75.1%, 75.2%, 75.3%, 75.4%, 75.5%, 75.6%, 75.7%, 75.8%, 75.9%, 76%, 76.1%, 76.2%, 76.3%, 76.4%, 76.5%, 76.6%, 76.7%, 76.8%, 76.9%, 77%, 77.1%, 77.2%, 77.3%, 77.4%, 77.5%, 77.6%, 77.7%, 77.8%, 77.9%, 78%, 78.1%, 78.2%, 78.3%, 78.4%, 78.5%, 78.6%, 78.7%, 78.8%, 78.9%, 79%, 79.1%, 79.2%, 79.3%, 79.4%, 79.5%, 79.6%, 79.7%, 79.8%, 79.9%, 80%, 80.1%, 80.2%, 80.3%, 80.4%, 80.5%, 80.6%, 80.7%, 80.8%, 80.9%, 81%, 81.1%, 81.2%, 81.3%, 81.4%, 81.5%, 81.6%, 81.7%, 81.8%, 81.9%, 82%, 82.1%, 82.2%, 82.3%, 82.4%, 82.5%, 82.6%, 82.7%, 82.8%, 82.9%, 83%, 83.1%, 83.2%, 83.3%, 83.4%, 83.5%, 83.6%, 83.7%, 83.8%, 83.9%, 84%, 84.1%, 84.2%, 84.3%, 84.4%, 84.5%, 84.6%, 84.7%, 84.8%, 84.9%, 85%, 85.1%, 85.2%, 85.3%, 85.4%, 85.5%, 85.6%, 85.7%, 85.8%, 85.9%, 86%, 86.1%, 86.2%, 86.3%, 86.4%, 86.5%, 86.6%, 86.7%, 86.8%, 86.9%, 87%, 87.1%, 87.2%, 87.3%, 87.4%, 87.5%, 87.6%, 87.7%, 87.8%, 87.9%, 88%, 88.1%, 88.2%, 88.3%, 88.4%, 88.5%, 88.6%, 88.7%, 88.8%, 88.9%, 89%, 89.1%, 89.2%, 89.3%, 89.4%, 89.5%, 89.6%, 89.7%, 89.8%, 89.9%, 90%, 90.1%, 90.2%, 90.3%, 90.4%, 90.5%, 90.6%, 90.7%, 90.8%, 90.9%, 91%, 91.1%, 91.2%, 91.3%, 91.4%, 91.5%, 91.6%, 91.7%, 91.8%, 91.9%, 92%, 92.1%, 92.2%, 92.3%, 92.4%, 92.5%, 92.6%, 92.7%, 92.8%, 92.9%, 93%, 93.1%, 93.2%, 93.3%, 93.4%, 93.5%, 93.6%, 93.7%, 93.8%, 93.9%, 94%, 94.1%, 94.2%, 94.3%, 94.4%, 94.5%, 94.6%, 94.7%, 94.8%, 94.9%, or 95% of the constructs expressed. As a non-limiting example, the 5' processing of the guide strand of the siRNA duplex targeting SOD1 has a correct start (n) at the 5' end for 81% of the constructs expressed. As a non-limiting example, the 5' processing of the guide strand of the siRNA duplex targeting SOD1 has a correct start (n) at the 5' end for 90% of the constructs expressed.

In one embodiment, a passenger-guide strand duplex for SOD1 is considered effective when the pri- or pre-microRNAs demonstrate, by methods known in the art and described herein, greater than 2-fold guide to passenger strand ratio when processing is measured. As a non-limiting examples, the pri- or pre-microRNAs demonstrate great than 2-fold, 3-fold, 4-fold, 5-fold, 6-fold, 7-fold, 8-fold, 9-fold, 10-fold, 11-fold, 12-fold, 13-fold, 14-fold, 15-fold, or 2 to 5-fold, 2 to 10-fold, 2 to 15-fold, 3 to 5-fold, 3 to 10-fold, 3 to 15-fold, 4 to 5-fold, 4 to 10-fold, 4 to 15-fold, 5 to 10-fold, 5 to 15-fold, 6 to 10-fold, 6 to 15-fold, 7 to 10-fold, 7 to 15-fold, 8 to 10-fold, 8 to 15-fold, 9 to 10-fold, 9 to 15-fold, 10 to 15-fold, 11 to 15-fold, 12 to 15-fold, 13 to 15-fold, or 14 to 15-fold guide to passenger strand ratio when processing is measured.

In one embodiment, the siRNA molecules may be used to silence wild type or mutant SOD1 by targeting at least one exon on the SOD1 sequence. The exon may be exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, and/or exon 67.

In one embodiment, the range of guide strands to the total endogenous pool of miRNAs is 0.001-0.6%, 0.005-0.6%, 0.01-0.6%, 0.015-0.6%, 0.02-0.6%, 0.025-0.6%, 0.03-0.6%, 0.035-0.6%, 0.04-0.6%, 0.045-0.6%, 0.05-0.6%, 0.055-0.6%, 0.06-0.6%, 0.065-0.6%, 0.07-0.6%, 0.075-0.6%, 0.08-0.6%, 0.085-0.6%, 0.09-0.6%, 0.095-0.6%, 0.1-0.6%, 0.15-0.6%, 0.2-0.6%, 0.25-0.6%, 0.3-0.6%, 0.35-0.6%, 0.4-0.6%, 0.45-0.6%, 0.5-0.6%, 0.55-0.6%, 0.001-0.5%, 0.005-0.5%, 0.01-0.5%, 0.015-0.5%, 0.02-0.5%, 0.025-0.5%, 0.03-0.5%, 0.035-0.5%, 0.04-0.5%, 0.045-0.5%, 0.05-0.5%, 0.055-0.5%, 0.06-0.5%, 0.065-0.5%, 0.07-0.5%, 0.075-0.5%, 0.08-0.5%, 0.085-0.5%, 0.09-0.5%, 0.095-0.5%, 0.1-0.5%, 0.15-0.5%, 0.2-0.5%, 0.25-0.5%, 0.3-0.5%, 0.35-0.5%, 0.4-0.5%, 0.45-0.5%, 0.001-0.4%, 0.005-0.4%, 0.01-0.4%, 0.015-0.4%, 0.02-0.4%, 0.025-0.4%, 0.03-0.4%, 0.035-0.4%, 0.04-0.4%, 0.045-0.4%, 0.05-0.4%, 0.055-0.4%, 0.06-0.4%, 0.065-0.4%, 0.07-0.4%, 0.075-0.4%, 0.08-0.4%, 0.085-0.4%, 0.09-0.4%, 0.095-0.4%, 0.1-0.4%, 0.15-0.4%, 0.2-0.4%, 0.25-0.4%, 0.3-0.4%, 0.35-0.4%, 0.001-0.3%, 0.005-0.3%, 0.01-0.3%, 0.015-0.3%, 0.02-0.3%, 0.025-0.3%, 0.03-0.3%, 0.035-0.3%, 0.04-0.3%, 0.045-0.3%, 0.05-0.3%, 0.055-0.3%, 0.06-0.3%, 0.065-0.3%, 0.07-0.3%, 0.075-0.3%, 0.08-0.3%, 0.085-0.3%, 0.09-0.3%, 0.095-0.3%, 0.1-0.3%, 0.15-0.3%, 0.2-0.3%, 0.25-0.3%, 0.001-0.2%, 0.005-0.2%, 0.01-0.2%, 0.015-0.2%, 0.02-0.2%, 0.025-0.2%, 0.03-0.2%, 0.035-0.2%, 0.04-0.2%, 0.045-0.2%, 0.05-0.2%, 0.055-0.2%, 0.06-0.2%, 0.065-0.2%, 0.07-0.2%, 0.075-0.2%, 0.08-0.2%, 0.085-0.2%, 0.09-0.2%, 0.095-0.2%, 0.1-0.2%, 0.15-0.2%, 0.001-0.1%, 0.005-0.1%, 0.01-0.1%, 0.015-0.1%, 0.02-0.1%, 0.025-0.1%, 0.03-0.1%, 0.035-0.1%, 0.04-0.1%, 0.045-0.1%, 0.05-0.1%, 0.055-0.1%, 0.06-0.1%, 0.065-0.1%, 0.07-0.1%, 0.075-0.1%, 0.08-0.1%, 0.085-0.1%, 0.09-0.1%, or 0.095-0.1%. As a non-limiting example, the range is 0.06-0.6%. As a non-limiting example, the range is 0.4-0.5%.

In one embodiment, the percent of guide strands to the total endogenous pool of miRNAs is 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, or 0.6%. As a non-limiting example, the percent is 0.06%. As a non-limiting example, the percent is 0.4%. As a non-limiting example, the percent is 0.5%.

siRNA Modification

In some embodiments, the siRNA molecules of the present invention, when not delivered as a precursor or DNA, may be chemically modified to modulate some features of RNA molecules, such as, but not limited to, increasing the stability of siRNAs in vivo. The chemically modified siRNA molecules can be used in human therapeutic applications and are improved without compromising the RNAi activity of the siRNA molecules. As a non-limiting example, the siRNA molecules modified at both the 3' and the 5' end of both the sense strand and the antisense strand.

In some aspects, the siRNA duplexes of the present invention may contain one or more modified nucleotides such as, but not limited to, sugar modified nucleotides, nucleobase modifications and/or backbone modifications. In some aspects, the siRNA molecule may contain combined modifications, for example, combined nucleobase and backbone modifications.

In one embodiment, the modified nucleotide may be a sugar-modified nucleotide. Sugar modified nucleotides include, but are not limited to 2'-fluoro, 2'-amino and 2'-thio modified ribonucleotides, e.g. 2'-fluoro modified ribonucleotides. Modified nucleotides may be modified on the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

In one embodiment, the modified nucleotide may be a nucleobase-modified nucleotide.

In one embodiment, the modified nucleotide may be a backbone-modified nucleotide. In some embodiments, the siRNA duplexes of the present invention may further comprise other modifications on the backbone. A normal "backbone", as used herein, refers to the repeating alternating sugar-phosphate sequences in a DNA or RNA molecule. The deoxyribose/ribose sugars are joined at both the 3'-hydroxyl and 5'-hydroxyl groups to phosphate groups in ester links, also known as "phosphodiester" bonds/linker (PO linkage). The PO backbones may be modified as "phosphorothioate" backbone (PS linkage). In some cases, the natural phosphodiester bonds may be replaced by amide bonds but the four atoms between two sugar units are kept. Such amide modifications can facilitate the solid phase synthesis of oligonucleotides and increase the thermodynamic stability of a duplex formed with siRNA complement. See e.g. Mesmaeker et al., *Pure & Appl. Chem.,* 1997, 3, 437-440; the content of which is incorporated herein by reference in its entirety.

Modified bases refer to nucleotide bases such as, for example, adenine, guanine, cytosine, thymine, uracil, xanthine, inosine, and queuosine that have been modified by the replacement or addition of one or more atoms or groups. Some examples of modifications on the nucleobase moieties include, but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any 0- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

In one embodiment, the modified nucleotides may be on just the sense strand.

In another embodiment, the modified nucleotides may be on just the antisense strand.

In some embodiments, the modified nucleotides may be in both the sense and antisense strands.

In some embodiments, the chemically modified nucleotide does not affect the ability of the antisense strand to pair with the target mRNA sequence.

In one embodiment, the AAV particle comprising a nucleic acid sequence encoding the siRNA molecules of the present invention may encode siRNA molecules which are polycistronic molecules. The siRNA molecules may additionally comprise one or more linkers between regions of the siRNA molecules.

Molecular Scaffold

In one embodiment, the siRNA molecules may be encoded in a modulatory polynucleotide which also comprises a molecular scaffold. As used herein a "molecular scaffold" is a framework or starting molecule that forms the sequence or structural basis against which to design or make a subsequent molecule.

In one embodiment, the molecular scaffold comprises at least one 5' flanking region. As a non-limiting example, the 5' flanking region may comprise a 5' flanking sequence which may be of any length and may be derived in whole or in part from wild type microRNA sequence or be a completely artificial sequence.

In one embodiment, the molecular scaffold comprises at least one 3' flanking region. As a non-limiting example, the 3' flanking region may comprise a 3' flanking sequence which may be of any length and may be derived in whole or in part from wild type microRNA sequence or be a completely artificial sequence.

In one embodiment, the molecular scaffold comprises at least one loop motif region. As a non-limiting example, the loop motif region may comprise a sequence which may be of any length.

In one embodiment, the molecular scaffold comprises a 5' flanking region, a loop motif region and/or a 3' flanking region.

In one embodiment, at least one siRNA, miRNA or other RNAi agent described herein, may be encoded by a modulatory polynucleotide which may also comprise at least one molecular scaffold. The molecular scaffold may comprise a 5' flanking sequence which may be of any length and may be derived in whole or in part from wild type microRNA sequence or be completely artificial. The 3' flanking sequence may mirror the 5' flanking sequence and/or a 3' flanking sequence in size and origin. Either flanking sequence may be absent. The 3' flanking sequence may optionally contain one or more CNNC motifs, where "N" represents any nucleotide.

Forming the stem of a stem loop structure is a minimum of the modulatory polynucleotide encoding at least one siRNA, miRNA or other RNAi agent described herein. In some embodiments, the siRNA, miRNA or other RNAi agent described herein comprises at least one nucleic acid sequence which is in part complementary or will hybridize to a target sequence. In some embodiments the payload is an siRNA molecule or fragment of an siRNA molecule.

In some embodiments, the 5' arm of the stem loop structure of the modulatory polynucleotide comprises a nucleic acid sequence encoding a sense sequence. Non-limiting examples of sense sequences, or fragments or variants thereof, which may be encoded by the modulatory polynucleotide are described in Table 3.

In some embodiments, the 3' arm of the stem loop of the modulatory polynucleotide comprises a nucleic acid sequence encoding an antisense sequence. The antisense sequence, in some instances, comprises a "G" nucleotide at the 5' most end. Non-limiting examples of antisense sequences, or fragments or variants thereof, which may be encoded by the modulatory polynucleotide are described in Table 2.

In other embodiments, the sense sequence may reside on the 3' arm while the antisense sequence resides on the 5' arm of the stem of the stem loop structure of the modulatory polynucleotide. Non-limiting examples of sense and antisense sequences which may be encoded by the modulatory polynucleotide are described in Tables 2 and 3.

In one embodiment, the sense and antisense sequences may be completely complementary across a substantial portion of their length. In other embodiments the sense sequence and antisense sequence may be at least 70, 80, 90, 95 or 99% complementarity across independently at least 50, 60, 70, 80, 85, 90, 95, or 99% of the length of the strands.

Neither the identity of the sense sequence nor the homology of the antisense sequence need to be 100% complementarity to the target sequence.

In one embodiment, separating the sense and antisense sequence of the stem loop structure of the modulatory polynucleotide is a loop sequence (also known as a loop motif, linker or linker motif). The loop sequence may be of any length, between 4-30 nucleotides, between 4-20 nucleotides, between 4-15 nucleotides, between 5-15 nucleotides, between 6-12 nucleotides, 6 nucleotides, 7 nucleotides, 8 nucleotides, 9 nucleotides, 10 nucleotides, 11 nucleotides, 12 nucleotides, 13 nucleotides, 14 nucleotides, and/or 15 nucleotides.

In some embodiments, the loop sequence comprises a nucleic acid sequence encoding at least one UGUG motif. In some embodiments, the nucleic acid sequence encoding the UGUG motif is located at the 5' terminus of the loop sequence.

In one embodiment, spacer regions may be present in the modulatory polynucleotide to separate one or more modules (e.g., 5' flanking region, loop motif region, 3' flanking region, sense sequence, antisense sequence) from one another. There may be one or more such spacer regions present.

In one embodiment, a spacer region of between 8-20, i.e., 8, 9, 10, 11, 12, 13, 14, 15, 16, 17, 18, 19, or 20 nucleotides may be present between the sense sequence and a flanking region sequence.

In one embodiment, the length of the spacer region is 13 nucleotides and is located between the 5' terminus of the sense sequence and the 3' terminus of the flanking sequence. In one embodiment, a spacer is of sufficient length to form approximately one helical turn of the sequence.

In one embodiment, a spacer region of between 8-20, i.e., 8, 9, 10, 11, 12, 13, 14, 15, 16, 17, 18, 19, or 20 nucleotides may be present between the antisense sequence and a flanking sequence.

In one embodiment, the spacer sequence is between 10-13, i.e., 10, 11, 12 or 13 nucleotides and is located between the 3' terminus of the antisense sequence and the 5' terminus of a flanking sequence. In one embodiment, a spacer is of sufficient length to form approximately one helical turn of the sequence.

In one embodiment, the molecular scaffold of the modulatory polynucleotide comprises in the 5' to 3' direction, a 5' flanking sequence, a 5' arm, a loop motif, a 3' arm and a 3' flanking sequence. As a non-limiting example, the 5' arm may comprise a nucleic acid sequence encoding a sense sequence and the 3' arm comprises a nucleic acid sequence encoding the antisense sequence. In another non-limiting example, the 5' arm comprises a nucleic acid sequence encoding the antisense sequence and the 3' arm comprises a nucleic acid sequence encoding the sense sequence.

In one embodiment, the 5' arm, sense and/or antisense sequence, loop motif and/or 3' arm sequence may be altered (e.g., substituting 1 or more nucleotides, adding nucleotides and/or deleting nucleotides). The alteration may cause a beneficial change in the function of the construct (e.g., increase knock-down of the target sequence, reduce degradation of the construct, reduce off target effect, increase efficiency of the payload, and reduce degradation of the payload).

In one embodiment, the molecular scaffold of the modulatory polynucleotides is aligned in order to have the rate of excision of the guide strand (also referred to herein as the antisense strand) be greater than the rate of excision of the passenger strand (also referred to herein as the sense strand). The rate of excision of the guide or passenger strand may be, independently, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99%. As a non-limiting example, the rate of excision of the guide strand is at least 80%. As another non-limiting example, the rate of excision of the guide strand is at least 90%.

In one embodiment, the rate of excision of the guide strand is greater than the rate of excision of the passenger strand. In one aspect, the rate of excision of the guide strand may be at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99% greater than the passenger strand.

In one embodiment, the efficiency of excision of the guide strand is at least 60%, 65%, 70%, 75%, 80%, 85%, 90%, 95%, 99% or more than 99%. As a non-limiting example, the efficiency of the excision of the guide strand is greater than 80%.

In one embodiment, the efficiency of the excision of the guide strand is greater than the excision of the passenger strand from the molecular scaffold. The excision of the guide strand may be 2, 3, 4, 5, 6, 7, 8, 9, 10 or more than 10 times more efficient than the excision of the passenger strand from the molecular scaffold.

In one embodiment, the molecular scaffold comprises a dual-function targeting modulatory polynucleotide. As used herein, a "dual-function targeting" modulatory polynucleotide is a polynucleotide where both the guide and passenger strands knock down the same target or the guide and passenger strands knock down different targets.

In one embodiment, the molecular scaffold of the modulatory polynucleotides described herein may comprise a 5' flanking region, a loop motif region and a 3' flanking region. Non-limiting examples of the sequences for the 5' flanking region, loop motif region (may also be referred to as a linker region) and the 3' flanking region which may be used, or fragments thereof used, in the modulatory polynucleotides described herein are shown in Tables 5-7.

TABLE 5

5' Flanking Regions for Molecular Scaffold

| 5' Flanking Region Name | 5' Flanking Region Sequence | 5' Flanking Region SEQ ID |
|---|---|---|
| 5F1 | CTCCCGCAGAACACCATGC GCTCCACGGAA | 47 |
| 5F2 | GAAGCAAAGAAGGGGCAGA GGGAGCCCGTGAGCTGAGT GGGCCAGGGACTGGGAGAA GGAGTGAGGAGGCAGGGCC GGCATGCCTCTGCTGCTGG CCAGA | 48 |

TABLE 5-continued

5' Flanking Regions for Molecular Scaffold

| 5' Flanking Region Name | 5' Flanking Region Sequence | 5' Flanking Region SEQ ID |
|---|---|---|
| 5F3 | GTGCTGGGCGGGGGCGGC GGGCCCTCCCGCAGAACAC CATGCGCTCTTCGGAA | 49 |

TABLE 6

Loop Motif Regions for Molecular Scaffold

| Loop Motif Region Name | Loop Motif Region Sequence | Loop Motif Region SEQ ID |
|---|---|---|
| L1 | GTGGCCACTGAGAAG | 50 |
| L2 | GTCTGCACCTGTCACTAG | 51 |
| L3 | TGTGACCTGG | 52 |
| L4 | TGTGATTTGG | 53 |

TABLE 7

3' Flanking Regions for Molecular Scaffold

| 3' Flanking Region Name | 3' Flanking Region Sequence | 3' Flanking Region SEQ ID |
|---|---|---|
| 3F1 | CTGAGGAGCGCCTTGACAGC AGCCATGGGAGGGCC | 54 |
| 3F2 | TGGCCGTGTAGTGCTACCCA GCGCTGGCTGCCTCCTCAGC ATTGCAATTCCTCTCCCATC TGGGCACCAGTCAGCTACCC TGGTGGGAATCTGGGTAGCC | 55 |
| 3F3 | GGCCGTGTAGTGCTACCCAG CGCTGGCTGCCTCCTCAGCA TTGCAATTCCTCTCCCATCT GGGCACCAGTCAGCTACCCT GGTGGGAATCTGGGTAGCC | 56 |
| 3F4 | CTGAGGAGCGCCTTGACAGC AGCCATGGGAGGGCCGCCCC CTACCTCAGTGA | 57 |
| 3F5 | CTGTGGAGCGCCTTGACAGC AGCCATGGGAGGGCCGCCCC CTACCTCAGTGA | 58 |

In one embodiment, the molecular scaffold may comprise at least one 5' flanking region, fragment or variant thereof listed in Table 5. As a non-limiting example, the 5' flanking region may be 5F1, 5F2, or 5F3.

In one embodiment, the molecular scaffold may comprise at least one 5F1 flanking region.

In one embodiment, the molecular scaffold may comprise at least one 5F2 flanking region.

In one embodiment, the molecular scaffold may comprise at least one 5F3 flanking region.

In one embodiment, the molecular scaffold may comprise at least one loop motif region, fragment or variant thereof listed in Table 6. As a non-limiting example, the loop motif region may be L1, L2, L3, or L4.

In one embodiment, the molecular scaffold may comprise at least one L1 loop motif region.

In one embodiment, the molecular scaffold may comprise at least one L2 loop motif region.

In one embodiment, the molecular scaffold may comprise at least one L3 loop motif region.

In one embodiment, the molecular scaffold may comprise at least one L4 loop motif region.

In one embodiment, the molecular scaffold may comprise at least one 3' flanking region, fragment or variant thereof listed in Table 7. As a non-limiting example, the 3' flanking region may be 3F1, 3F2, 3F3, 3F4, or 3F5.

In one embodiment, the molecular scaffold may comprise at least one 3F1 flanking region.

In one embodiment, the molecular scaffold may comprise at least one 3F2 flanking region.

In one embodiment, the molecular scaffold may comprise at least one 3F3 flanking region.

In one embodiment, the molecular scaffold may comprise at least one 3F4 flanking region.

In one embodiment, the molecular scaffold may comprise at least one 3F5 flanking region.

In one embodiment, the molecular scaffold may comprise at least one 5' flanking region, fragment or variant thereof, and at least one loop motif region, fragment or variant thereof, as described in Tables 5 and 6. As a non-limiting example, the 5' flanking region and the loop motif region may be 5F1 and L1, 5F1 and L2, 5F1 and L3, 5F1 and L4, 5F2 and L1, 5F2 and L2, 5F2 and L3, 5F2 and L4, 5F3 and L1, 5F3 and L2, 5F3 and L3, and 5F3 and L4.

In one embodiment, the molecular scaffold may comprise at least one 3' flanking region, fragment or variant thereof, and at least one motif region, fragment or variant thereof, as described in Tables 6 and 7. As a non-limiting example, the 3' flanking region and the loop motif region may be 3F1 and L1, 3F1 and L2, 3F1 and L3, 3F1 and L4, 3F2 and L1, 3F2 and L2, 3F2 and L3, 3F2 and L4, 3F3 and L1, 3F3 and L2, 3F3 and L3, 3F3 and L4, 3F4 and L1, 3F4 and L2, 3F4 and L3, 3F4 and L4, 3F5 and L1, 3F5 and L2, 3F5 and L3, and 3F5 and L4.

In one embodiment, the molecular scaffold may comprise at least one 5' flanking region, fragment or variant thereof, and at least one 3' flanking region, fragment or variant thereof, as described in Tables 5 and 7. As a non-limiting example, the flanking regions may be 5F1 and 3F1, 5F1 and 3F2, 5F1 and 3F3, 5F1 and 3F4, 5F1 and 3F5, 5F2 and 3F1, 5F2 and 3F2, 5F2 and 3F3, 5F2 and 3F4, 5F2 and 3F5, 5F3 and 3F1, 5F3 and 3F2, 5F3 and 3F3, 5F3 and 3F4, 5F3 and 3F5.

In one embodiment, the molecular scaffold may comprise at least one 5' flanking region, fragment or variant thereof, at least one loop motif region, fragment or variant thereof, and at least one 3' flanking region as described in Tables 5-7. As a non-limiting example, the flanking and loop motif regions may be 5F1, L1 and 3F1; 5F1, L1 and 3F2; 5F1, L1 and 3F3; 5F1, L1 and 3F4; 5F2, L1 and 3F1; 5F2, L1 and 3F2; 5F2, L1 and 3F3; 5F2, L1 and 3F4; 5F2, L1 and 3F5; 5F3, L1 and 3F1; 5F3, L1 and 3F2; 5F3, L1 and 3F3; 5F3, L1 and 3F4; 5F3, L1 and 3F5; 5F1, L2 and 3F1; 5F1, L2 and 3F2; 5F1, L2 and 3F3; 5F1, L2 and 3F4; 5F1, L2 and 3F5; 5F2, L2 and 3F1; 5F2, L2 and 3F2; 5F2, L2 and 3F3; 5F2, L2 and 3F4; 5F2, L2 and 3F5; 5F3, L2 and 3F1; 5F3, L2 and 3F2; 5F3, L2 and 3F3; 5F3, L2 and 3F4; 5F3, L2 and 3F5; 5F3; 5F1, L3 and 3F1; 5F1, L3 and 3F2; 5F1, L3 and 3F3; 5F1, L3 and 3F4; 5F1, L3 and 3F5; 5F2, L3 and 3F1; 5F2, L3 and 3F2; 5F2, L3 and 3F3; 5F2, L3 and 3F4; 5F2, L3 and 3F5; 5F3, L3 and 3F1; 5F3, L3 and 3F2; 5F3, L3 and 3F3; 5F3, L3 and 3F4; 5F3, L3 and 3F5; 5F1, L4 and 3F1; 5F1, L4 and 3F2; 5F1, L4 and 3F3; 5F1, L4 and 3F4; 5F1, L4 and 3F5; 5F2, L4 and 3F1; 5F2, L4 and 3F2; 5F2, L4 and 3F3; 5F2, L4 and 3F4; 5F2, L4 and 3F5; 5F3, L4 and 3F1; 5F3, L4 and 3F2; 5F3, L4 and 3F3; 5F3, L4 and 3F4; 5F3, L4 and 3F5.

In one embodiment, the molecular scaffold may be a natural pri-miRNA scaffold. As a non-limiting example, the molecular scaffold may be a scaffold derived from the human miR155 scaffold.

In one embodiment, the molecular scaffold may comprise one or more linkers known in the art. The linkers may separate regions or one molecular scaffold from another. As a non-limiting example, the molecular scaffold may be polycistronic.

Modulatory Polynucleotide Comprising Molecular Scaffold and siRNA Molecules Targeting SOD1

In one embodiment, the modulatory polynucleotide may comprise 5' and 3' flanking regions, loop motif region, and nucleic acid sequences encoding sense sequence and antisense sequence as described in Table 8. In Table 8, the DNA sequence identifier for the passenger and guide strands are described as well as the 5' and 3' Flanking Regions and the Loop region (also referred to as the linker region). In Table 8, the "miR" component of the name of the sequence does not necessarily correspond to the sequence numbering of miRNA genes (e.g., VOYSOD1miR-102 is the name of the sequence and does not necessarily mean that miR-102 is part of the sequence).

TABLE 8

SOD1 Modulatory Polynucleotide Sequence Regions (5' to 3')

| Modulatory Polynucleotide Construct Name | 5' Flanking to 3' Flanking SEQ ID NO | 5' Flanking SEQ ID NO | Passenger SEQ ID NO | Loop SEQ ID NO | Guide SEQ ID NO | 3' Flanking SEQ ID NO |
|---|---|---|---|---|---|---|
| VOYSOD1miR102-788 | 59 | 49 | 80 | 52 | 101 | 57 |
| VOYSOD1miR102-805c | 60 | 49 | 81 | 52 | 102 | 57 |
| VOYSOD1miR104-788 | 61 | 49 | 82 | 52 | 103 | 57 |
| VOYSOD1miR104-788.2 | 62 | 47 | 83 | 50 | 104 | 54 |
| VOYSOD1miR104-789 | 63 | 47 | 84 | 50 | 105 | 54 |
| VOYSOD1miR104-805c | 64 | 49 | 85 | 52 | 106 | 57 |
| VOYSOD1miR104-829 | 65 | 47 | 86 | 50 | 107 | 54 |
| VOYSOD1miR104-830 | 66 | 47 | 87 | 50 | 108 | 54 |
| VOYSOD1miR109-788 | 67 | 49 | 88 | 53 | 109 | 57 |

TABLE 8-continued

SOD1 Modulatory Polynucleotide Sequence Regions (5' to 3')

| Modulatory Polynucleotide Construct Name | 5' Flanking to 3' Flanking SEQ ID NO | 5' Flanking SEQ ID NO | Passenger SEQ ID NO | Loop SEQ ID NO | Guide SEQ ID NO | 3' Flanking SEQ ID NO |
|---|---|---|---|---|---|---|
| VOYSOD1miR109-805c | 68 | 49 | 89 | 53 | 110 | 57 |
| VOYSOD1miR114-788 | 69 | 49 | 90 | 52 | 111 | 58 |
| VOYSOD1miR114-805c | 70 | 49 | 91 | 52 | 112 | 58 |
| VOYSOD1miR116-788 | 71 | 49 | 92 | 52 | 113 | 58 |
| VOYSOD1miR116-805c | 72 | 49 | 93 | 52 | 114 | 58 |
| VOYSOD1miR127-788 | 73 | 48 | 94 | 51 | 115 | 55 |
| VOYSOD1miR127-788.2 | 74 | 48 | 95 | 51 | 116 | 55 |
| VOYSOD1miR127-789 | 75 | 48 | 96 | 51 | 117 | 55 |
| VOYSOD1miR127-805c | 76 | 48 | 97 | 51 | 118 | 55 |
| VOYSOD1miR127-829 | 77 | 48 | 98 | 51 | 119 | 56 |
| VOYSOD1miR127-830 | 78 | 48 | 99 | 51 | 120 | 55 |
| VOYSOD1miR127-860 | 79 | 48 | 100 | 51 | 121 | 55 |

AAV Particles Comprising Modulatory Polynucleotides

In one embodiment, the AAV particle comprises a viral genome with a payload region comprising a modulatory polynucleotide sequence. In such an embodiment, a viral genome encoding more than one polypeptide may be replicated and packaged into a viral particle. A target cell transduced with a viral particle comprising a modulatory polynucleotide may express the encoded sense and/or antisense sequences in a single cell.

In some embodiments, the AAV particles are useful in the field of medicine for the treatment, prophylaxis, palliation or amelioration of neurological diseases and/or disorders.

In one embodiment, the AAV particles comprising modulatory polynucleotide sequence which comprises a nucleic acid sequence encoding at least one siRNA molecule may be introduced into mammalian cells.

Where the AAV particle payload region comprises a modulatory polynucleotide, the modulatory polynucleotide may comprise sense and/or antisense sequences to knock down a target gene. The AAV viral genomes encoding modulatory polynucleotides described herein may be useful in the fields of human disease, viruses, infections veterinary applications and a variety of in vivo and in vitro settings.

In one embodiment, the AAV particle viral genome may comprise at least one inverted terminal repeat (ITR) region. The ITR region(s) may, independently, have a length such as, but not limited to, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, and 175 nucleotides. The length of the ITR region for the viral genome may be 75-80, 75-85, 75-100, 80-85, 80-90, 80-105, 85-90, 85-95, 85-110, 90-95, 90-100, 90-115, 95-100, 95-105, 95-120, 100-105, 100-110, 100-125, 105-110, 105-115, 105-130, 110-115, 110-120, 110-135, 115-120, 115-125, 115-140, 120-125, 120-130, 120-145, 125-130, 125-135, 125-150, 130-135, 130-140, 130-155, 135-140, 135-145, 135-160, 140-145, 140-150, 140-165, 145-150, 145-155, 145-170, 150-155, 150-160, 150-175, 155-160, 155-165, 160-165, 160-170, 165-170, 165-175, and 170-175 nucleotides. As a non-limiting example, the viral genome comprises an ITR that is about 105 nucleotides in length. As a non-limiting example, the viral genome comprises an ITR that is about 141 nucleotides in length. As a non-limiting example, the viral genome comprises an ITR that is about 130 nucleotides in length.

In one embodiment, the AAV particle viral genome may comprises two inverted terminal repeat (ITR) regions. Each of the ITR regions may independently have a length such as, but not limited to, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, and 175 nucleotides. The length of the ITR regions for the viral genome may be 75-80, 75-85, 75-100, 80-85, 80-90, 80-105, 85-90, 85-95, 85-110, 90-95, 90-100, 90-115, 95-100, 95-105, 95-120, 100-105, 100-110, 100-125, 105-110, 105-115, 105-130, 110-115, 110-120, 110-135, 115-120, 115-125, 115-140, 120-125, 120-130, 120-145, 125-130, 125-135, 125-150, 130-135, 130-140, 130-155, 135-140, 135-145, 135-160, 140-145, 140-150, 140-165, 145-150, 145-155, 145-170, 150-155, 150-160, 150-175, 155-160, 155-165, 160-165, 160-170, 165-170, 165-175, and 170-175 nucleotides. As a non-limiting example, the viral genome comprises an ITR that is about 105 nucleotides in length and 141 nucleotides in length. As a non-limiting example, the viral genome comprises an ITR that is about 105 nucleotides in length and 130 nucleotides in length. As a non-limiting example, the viral genome comprises an ITR that is about 130 nucleotides in length and 141 nucleotides in length.

In one embodiment, the AAV particle viral genome comprises two ITR sequence regions.

In one embodiment, the AAV particle viral genome may comprise at least one multiple filler sequence region. The filler region(s) may, independently, have a length such as, but not limited to, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3161, 3162, 3163, 3164, 3165, 3166, 3167, 3168, 3169, 3170, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, and 3250 nucleotides. The length of any filler region for the viral genome may be 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2050, 2050-2100, 2100-2150, 2150-2200, 2200-2250, 2250-2300, 2300-2350, 2350-2400, 2400-2450, 2450-2500, 2500-2550, 2550-2600, 2600-2650, 2650-2700, 2700-2750, 2750-2800, 2800-2850, 2850-2900, 2900-2950, 2950-3000, 3000-3050, 3050-3100, 3100-3150, 3150-3200, and 3200-3250 nucleotides. As a non-limiting example, the viral genome comprises a filler region that is about 55 nucleotides in length. As a non-limiting example, the viral genome comprises a filler region that is about 56 nucleotides in length. As a non-limiting example, the viral genome comprises a filler region that is about 97 nucleotides in length. As a non-limiting example, the viral genome comprises a filler region that is about 103 nucleotides in length. As a non-limiting example, the viral genome comprises a filler region that is about 105 nucleotides in length. As a non-limiting example, the viral genome comprises a filler region that is about 357 nucleotides in length. As a non-limiting example, the viral genome comprises a filler region that is about 363 nucleotides in length. As a non-limiting example, the viral genome comprises a filler region that is about 712 nucleotides in length. As a non-limiting example, the viral genome comprises a filler region that is about 714 nucleotides in length. As a non-limiting example, the viral genome comprises a filler region that is about 1203 nucleotides in length. As a non-limiting example, the viral genome comprises a filler region that is about 1209 nucleotides in length. As a non-limiting example, the viral genome comprises a filler region that is about 1512 nucleotides in length. As a non-limiting example, the viral genome comprises a filler region that is about 1519 nucleotides in length. As a non-limiting example, the viral genome comprises a filler region that is about 2395 nucleotides in length. As a non-limiting example, the viral genome comprises a filler region that is about 2403 nucleotides in length. As a non-limiting example, the viral genome comprises a filler region that is about 2405 nucleotides in length. As a non-limiting example, the viral genome comprises a filler region that is about 3013 nucleotides in length. As a non-limiting example, the viral genome comprises a filler region that is about 3021 nucleotides in length.

In one embodiment, the AAV particle viral genome may comprise at least one multiple filler sequence region. The filler region(s) may, independently, have a length such as, but not limited to, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2161, 2162, 2163, 2164, 2165, 2166, 2167, 2168, 2169, 2170, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2261, 2262, 2263, 2264, 2265, 2266, 2267, 2268, 2269, 2270, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3041, 3042, 3043, 3044, 3045, 3046, 3047, 3048, 3049, 3050, 3051, 3052, 3053, 3054, 3055, 3056, 3057, 3058, 3059, 3060, 3061, 3062, 3063, 3064, 3065, 3066, 3067, 3068, 3069, 3070, 3071, 3072, 3073, 3074, 3075, 3076, 3077, 3078, 3079, 3080, 3081, 3082, 3083, 3084, 3085, 3086, 3087, 3088, 3089, 3090, 3091, 3092, 3093, 3094, 3095, 3096, 3097, 3098, 3099, 3100, 3101, 3102, 3103, 3104, 3105, 3106, 3107, 3108, 3109, 3110, 3111, 3112, 3113, 3114, 3115, 3116, 3117, 3118, 3119, 3120, 3121, 3122, 3123, 3124, 3125, 3126, 3127, 3128, 3129, 3130, 3131, 3132, 3133, 3134, 3135, 3136, 3137, 3138, 3139, 3140, 3141, 3142, 3143, 3144, 3145, 3146, 3147, 3148, 3149, 3150, 3151, 3152, 3153, 3154, 3155, 3156, 3157, 3158, 3159, 3160, 3161, 3162, 3163, 3164, 3165, 3166, 3167, 3168, 3169, 3170, 3171, 3172, 3173, 3174, 3175, 3176, 3177, 3178, 3179, 3180, 3181, 3182, 3183, 3184, 3185, 3186, 3187, 3188, 3189, 3190, 3191, 3192, 3193, 3194, 3195, 3196, 3197, 3198, 3199, 3200, 3201, 3202, 3203, 3204, 3205, 3206, 3207, 3208, 3209, 3210, 3211, 3212, 3213, 3214, 3215, 3216, 3217, 3218, 3219, 3220, 3221, 3222, 3223, 3224, 3225, 3226, 3227, 3228, 3229, 3230, 3231, 3232, 3233, 3234, 3235, 3236, 3237, 3238, 3239, 3240, 3241, 3242, 3243, 3244, 3245, 3246, 3247, 3248, 3249, and 3250 nucleotides. The length of any filler region for the viral genome may be 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2050, 2050-2100, 2100-2150, 2150-2200, 2200-2250, 2250-2300, 2300-2350, 2350-2400, 2400-2450, 2450-2500, 2500-2550, 2550-2600, 2600-2650, 2650-2700, 2700-2750, 2750-2800, 2800-2850, 2850-2900, 2900-2950, 2950-3000, 3000-3050, 3050-3100, 3100-3150, 3150-3200, and 3200-3250 nucleotides. As a non-limiting example, the viral genome comprises a filler region that is about 55 nucleotides in length. As a non-limiting example, the viral genome comprises a filler region that is about 56 nucleotides in length. As a non-limiting example, the viral genome comprises a filler region that is about 97 nucleotides in length. As a non-limiting example, the viral genome comprises a filler region that is about 103 nucleotides in length. As a non-limiting example, the viral genome comprises a filler region that is about 105 nucleotides in length. As a non-limiting example, the viral genome comprises a filler region that is about 357 nucleotides in length. As a non-limiting example, the viral genome comprises a filler region that is about 363 nucleotides in length. As a non-limiting example, the viral genome comprises a filler region that is about 712 nucleotides in length. As a non-limiting example, the viral genome comprises a filler region that is about 714 nucleotides in length. As a non-limiting example, the viral genome comprises a filler region that is about 1203 nucleotides in length. As a non-limiting example, the viral genome comprises a filler region that is about 1209 nucleotides in length. As a non-limiting example, the viral genome comprises a filler region that is about 1512 nucleotides in length. As a non-limiting example, the viral genome comprises a filler region that is about 1519 nucleotides in length. As a non-limiting example, the viral genome comprises a filler region that is about 2395 nucleotides in length. As a non-limiting example, the viral genome comprises a filler region that is about 2403 nucleotides in length. As a non-limiting example, the viral genome comprises a filler region that is about 2405 nucleotides in length. As a non-limiting example, the viral genome comprises a filler region that is about 3013 nucleotides in length. As a non-limiting example, the viral genome comprises a filler region that is about 3021 nucleotides in length.

In one embodiment, the AAV particle viral genome may comprise at least one enhancer sequence region. The enhancer sequence region(s) may, independently, have a length such as, but not limited to, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, and 400 nucleotides. The length of the enhancer region for the viral genome may be 300-310, 300-325, 305-315, 310-320, 315-325, 320-330, 325-335, 325-350, 330-340, 335-345, 340-350, 345-355, 350-360, 350-375, 355-365, 360-370, 365-375, 370-380, 375-385, 375-400, 380-390, 385-395, and 390-400 nucleotides. As a non-limiting example, the viral genome comprises an enhancer region that is about 303 nucleotides in length. As a non-limiting example, the viral genome comprises an enhancer region that is about 382 nucleotides in length.

In one embodiment, the AAV particle viral genome may comprise at least one promoter sequence region. The promoter sequence region(s) may, independently, have a length such as, but not limited to, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, and 600 nucleotides. The length of the promoter region for the viral genome may be 4-10, 10-20, 10-50, 20-30, 30-40, 40-50, 50-60, 50-100, 60-70, 70-80, 80-90, 90-100, 100-110, 100-150, 110-120, 120-130, 130-140, 140-150, 150-160, 150-200, 160-170, 170-180, 180-190, 190-200, 200-210, 200-250, 210-220, 220-230, 230-240, 240-250, 250-260, 250-300, 260-270, 270-280, 280-290, 290-300, 300-310, 300-350, 310-320, 320-330, 330-340, 340-350, 350-360, 350-400, 360-370, 370-380, 380-390, 390-400, 400-410, 400-450, 410-420, 420-430, 430-440, 440-450, 450-460, 450-500, 460-470, 470-480, 480-490, 490-500, 500-510, 500-550, 510-520, 520-530, 530-540, 540-550, 550-560, 550-600, 560-570, 570-580, 580-590, and 590-600 nucleotides. As a non-limiting example, the viral genome comprises a promoter region that is about 4 nucleotides in length. As a non-limiting example, the viral genome comprises a promoter region that is about 17 nucleotides in length. As a non-limiting example, the viral genome comprises a promoter region that is about 204 nucleotides in length. As a non-limiting example, the viral genome comprises a promoter region that is about 219 nucleotides in length. As a non-limiting example, the viral genome comprises a promoter region that is about 260 nucleotides in length. As a non-limiting example, the viral genome comprises a promoter region that is about 303 nucleotides in length. As a non-limiting example, the viral genome comprises a promoter region that is about 382 nucleotides in length. As a non-limiting example, the viral genome comprises a promoter region that is about 588 nucleotides in length.

In one embodiment, the AAV particle viral genome may comprise at least one exon sequence region. The exon region(s) may, independently, have a length such as, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 nucleotides. The length of the exon region for the viral genome may be 2-10, 5-10, 5-15, 10-20, 10-30, 10-40, 15-20, 15-25, 20-30, 20-40, 20-50, 25-30, 25-35, 30-40, 30-50, 30-60, 35-40, 35-45, 40-50, 40-60, 40-70, 45-50, 45-55, 50-60, 50-70, 50-80, 55-60, 55-65, 60-70, 60-80, 60-90, 65-70, 65-75, 70-80, 70-90, 70-100, 75-80, 75-85, 80-90, 80-100, 80-110, 85-90, 85-95, 90-100, 90-110, 90-120, 95-100, 95-105, 100-110, 100-120, 100-130, 105-110, 105-115, 110-120, 110-130, 110-140, 115-120, 115-125, 120-130, 120-140, 120-150, 125-130, 125-135, 130-140, 130-150, 135-140, 135-145, 140-150, and 145-150 nucleotides. As a non-limiting example, the viral genome comprises an exon region that is about 53 nucleotides in length. As a non-limiting example, the viral genome comprises an exon region that is about 134 nucleotides in length.

In one embodiment, the AAV particle viral genome may comprise at least one intron sequence region. The intron region(s) may, independently, have a length such as, but not limited to, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, and 350 nucleotides. The length of the intron region for the viral genome may be 25-35, 25-50, 35-45, 45-55, 50-75, 55-65, 65-75, 75-85, 75-100, 85-95, 95-105, 100-125, 105-115, 115-125, 125-135, 125-150, 135-145, 145-155, 150-175, 155-165, 165-175, 175-185, 175-200, 185-195, 195-205, 200-225, 205-215, 215-225, 225-235, 225-250, 235-245, 245-255, 250-275, 255-265, 265-275, 275-285, 275-300, 285-295, 295-305, 300-325, 305-315, 315-325, 325-335, 325-350, and 335-345 nucleotides. As a non-limiting example, the viral genome comprises an intron region that is about 32 nucleotides in length. As a non-limiting example, the viral genome comprises an intron region that is about 172 nucleotides in length. As a non-limiting example, the viral genome comprises an intron region that is about 201 nucleotides in length. As a non-limiting example, the viral genome comprises an intron region that is about 347 nucleotides in length.

In one embodiment, the AAV particle viral genome may comprise at least one polyadenylation signal sequence region. The polyadenylation signal region sequence region(s) may, independently, have a length such as, but not limited to, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, and 600 nucleotides. The length of the polyadenylation signal sequence region for the viral genome may be 4-10, 10-20, 10-50, 20-30, 30-40, 40-50, 50-60, 50-100, 60-70, 70-80, 80-90, 90-100, 100-110, 100-150, 110-120, 120-130, 130-140, 140-150, 150-160, 150-200, 160-170, 170-180, 180-190, 190-200, 200-210, 200-250, 210-220, 220-230, 230-240, 240-250, 250-260, 250-300, 260-270, 270-280, 280-290, 290-300, 300-310, 300-350, 310-320, 320-330, 330-340, 340-350, 350-360, 350-400, 360-370, 370-380, 380-390, 390-400, 400-410, 400-450, 410-420, 420-430, 430-440, 440-450, 450-460, 450-500, 460-470, 470-480, 480-490, 490-500, 500-510, 500-550, 510-520, 520-530, 530-540, 540-550, 550-560, 550-600, 560-570, 570-580, 580-590, and 590-600 nucleotides. As a non-limiting example, the viral genome comprises a polyadenylation signal sequence region that is about 127 nucleotides in length. As a non-limiting example, the viral genome comprises a polyadenylation signal sequence region that is about 225 nucleotides in length. As a non-limiting example, the viral genome comprises a polyadenylation signal sequence region that is about 476 nucleotides in length. As a non-limiting example, the viral genome comprises a polyadenylation signal sequence region that is about 477 nucleotides in length.

In one embodiment, the AAV particle viral genome comprises more than one polyA signal sequence region.

Non-limiting examples of ITR to ITR sequences of AAV particles comprising a viral genome with a payload region comprising a modulatory polynucleotide sequence are described in Table 9.

TABLE 9

ITR to ITR Sequences of AAV Particles comprising Modulatory Polynucleotides

| ITR to ITR Construct Name | ITR to ITR SEQ ID NO | Modulatory Polynucleotide SEQ ID NO |
| --- | --- | --- |
| VOYSOD10 | 122 | 65 |
| VOYSOD11 | 123 | 63 |
| VOYSOD12 | 124 | 74 |
| VOYSOD13 | 125 | 62 |
| VOYSOD14 | 126 | 66 |
| VOYSOD15 | 127 | 73 |
| VOYSOD16 | 128 | 62 |
| VOYSOD17 | 129 | 65 |
| VOYSOD18 | 130 | 77 |
| VOYSOD19 | 131 | 75 |
| VOYSOD20 | 132 | 78 |
| VOYSOD21 | 133 | 64 |
| VOYSOD22 | 134 | 68 |
| VOYSOD23 | 135 | 72 |
| VOYSOD24 | 136 | 70 |
| VOYSOD25 | 137 | 60 |
| VOYSOD26 | 138 | 61 |
| VOYSOD27 | 139 | 76 |
| VOYSOD28 | 140 | 71 |
| VOYSOD29 | 141 | 69 |
| VOYSOD30 | 142 | 59 |
| VOYSOD31 | 143 | 67 |
| VOYSOD32 | 144 | 79 |
| VOYSOD33 | 145 | 62 |
| VOYSOD34 | 146 | 65 |

In one embodiment, the AAV particle comprises a viral genome which comprises a sequence which has a percent identity to any of SEQ ID NOs: 122-146. The viral genome may have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% identity to any of SEQ ID NOs: 122-146. The viral genome may have 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% to any of SEQ ID NOs: 122-146. As a non-limiting example, the viral genome comprises a sequence which as 80% identity to any of SEQ ID NO: 122-146. As another non-limiting example, the viral genome comprises a sequence which as 85% identity to any of SEQ ID NO: 122-146. As another non-limiting example, the viral genome comprises a sequence which as 90% identity to any of SEQ ID NO: 122-146. As another non-limiting example, the viral genome comprises a sequence which as 95% identity to any of SEQ ID NO: 122-146. As another non-limiting example, the viral genome comprises a sequence which as 99% identity to any of SEQ ID NO: 122-146.

AAV particles may be modified to enhance the efficiency of delivery. Such modified AAV particles comprising the nucleic acid sequence encoding the siRNA molecules of the present invention can be packaged efficiently and can be used to successfully infect the target cells at high frequency and with minimal toxicity.

In some embodiments, the AAV particle comprising a nucleic acid sequence encoding the siRNA molecules of the present invention may be a human serotype AAV particle. Such human AAV particle may be derived from any known serotype, e.g., from any one of serotypes AAV1-AAV11. As non-limiting examples, AAV particles may be vectors comprising an AAV1-derived genome in an AAV1-derived capsid; vectors comprising an AAV2-derived genome in an AAV2-derived capsid; vectors comprising an AAV4-derived genome in an AAV4 derived capsid; vectors comprising an AAV6-derived genome in an AAV6 derived capsid or vectors comprising an AAV9-derived genome in an AAV9 derived capsid.

In other embodiments, the AAV particle comprising a nucleic acid sequence for encoding siRNA molecules of the present invention may be a pseudotyped hybrid or chimeric AAV particle which contains sequences and/or components originating from at least two different AAV serotypes. Pseudotyped AAV particles may be vectors comprising an AAV genome derived from one AAV serotype and a capsid protein derived at least in part from a different AAV serotype. As non-limiting examples, such pseudotyped AAV particles may be vectors comprising an AAV2-derived genome in an AAV1-derived capsid; or vectors comprising an AAV2-derived genome in an AAV6-derived capsid; or vectors comprising an AAV2-derived genome in an AAV4-derived capsid; or an AAV2-derived genome in an AAV9-derived capsid. In like fashion, the present invention contemplates any hybrid or chimeric AAV particle.

In other embodiments, AAV particles comprising a nucleic acid sequence encoding the siRNA molecules of the present invention may be used to deliver siRNA molecules to the central nervous system (e.g., U.S. Pat. No. 6,180,613; the contents of which is herein incorporated by reference in its entirety).

In some aspects, the AAV particles comprising a nucleic acid sequence encoding the siRNA molecules of the present invention may further comprise a modified capsid including peptides from non-viral origin. In other aspects, the AAV particle may contain a CNS specific chimeric capsid to facilitate the delivery of encoded siRNA duplexes into the brain and the spinal cord. For example, an alignment of cap nucleotide sequences from AAV variants exhibiting CNS tropism may be constructed to identify variable region (VR) sequence and structure.

In other embodiments, the siRNA molecules of the present invention can be encoded in plasmid vectors, viral vectors (e.g., AAV vectors), genome or other nucleic acid expression vectors for delivery to a cell.

DNA expression plasmids can be used to stably express the siRNA duplexes or dsRNA of the present invention in cells and achieve long-term inhibition of target gene.

In one aspect, the sense and antisense strands of a siRNA duplex encoded by a SOD1 targeting polynucleotide are typically linked by a short spacer sequence leading to the expression of a stem-loop structure termed short hairpin RNA (shRNA). The hairpin is recognized and cleaved by Dicer, thus generating mature siRNA molecules.

According to the present invention, AAV vectors comprising the nucleic acids of the siRNA molecules targeting SOD1 mRNA are produced, the AAV vectors may be AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 and AAV-DJ, and variants thereof.

In some embodiments, the siRNA duplexes or dsRNA of the present invention when expressed suppress (or degrade) target mRNA (i.e. SOD1). Accordingly, the siRNA duplexes or dsRNA encoded by a SOD1 targeting polynucleotide can be used to substantially inhibit SOD1 gene expression in a cell, for example a motor neuron. In some aspects, the inhibition of SOD1 gene expression refers to an inhibition by at least about 20%, preferably by at least about 30%, 40%, 50%, 60%, 70%, 80%, 85%, 90%, 95% and 100%. Accordingly, the protein product of the targeted gene may be inhibited by at least about 20%, preferably by at least about 30%, 40%, 50%, 60%, 70%, 80%, 85%, 90%, 95% and 100%. The SOD1 gene can be either a wild type gene or a mutated SOD1 gene with at least one mutation. Accordingly, the protein is either wild type protein or a mutated polypeptide with at least one mutation.

Viral Production

The present disclosure provides a method for the generation of parvoviral particles, e.g. AAV particles, by viral genome replication in a viral replication cell comprising contacting the viral replication cell with an AAV polynucleotide or AAV genome.

The present disclosure provides a method for producing an AAV particle having enhanced (increased, improved) transduction efficiency comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, 5) harvesting and purifying the viral particle comprising a parvoviral genome.

In one embodiment, the present invention provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome.

Cells

The present disclosure provides a cell comprising an AAV polynucleotide and/or AAV genome.

Viral production disclosed herein describes processes and methods for producing AAV particles that contact a target cell to deliver a payload construct, e.g. a recombinant viral construct, which comprises a polynucleotide sequence encoding a payload molecule.

In one embodiment, the AAV particles may be produced in a viral replication cell that comprises an insect cell.

Growing conditions for insect cells in culture, and production of heterologous products in insect cells in culture are well-known in the art, see U.S. Pat. No. 6,204,059, the contents of which are herein incorporated by reference in their entirety.

Any insect cell which allows for replication of parvovirus and which can be maintained in culture can be used in accordance with the present invention. Cell lines may be used from *Spodoptera frugiperda*, including, but not limited to the Sf9 or Sf21 cell lines, *Drosophila* cell lines, or mosquito cell lines, such as *Aedes albopictus* derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, Methods in Molecular Biology, ed. Richard, Humana Press, N J (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.* 219:37-44 (1996); Zhao et al., Vir. 272:382-93 (2000); and Samulski et al., U.S. Pat. No. 6,204,059, the contents of each of which is herein incorporated by reference in its entirety.

The viral replication cell may be selected from any biological organism, including prokaryotic (e.g., bacterial) cells, and eukaryotic cells, including, insect cells, yeast cells and mammalian cells. Viral replication cells may comprise mammalian cells such as A549, WEH1, 3T3, 10T1/2, BHK, MDCK, COS 1, COS 7, BSC 1, BSC 40, BMT 10, VERO. W138, HeLa, HEK293, Saos, C2C12, L cells, HT1080, HepG2 and primary fibroblast, hepatocyte and myoblast cells derived from mammals. Viral replication cells comprise cells derived from mammalian species including, but not limited to, human, monkey, mouse, rat, rabbit, and hamster or cell type, including but not limited to fibroblast, hepatocyte, tumor cell, cell line transformed cell, etc.

Mammalian Cell (Small Scale) Production

Viral production disclosed herein describes processes and methods for producing AAV particles that contact a target cell to deliver a payload, e.g. a recombinant viral construct, which comprises a polynucleotide sequence encoding a payload.

In one embodiment, the AAV particles may be produced in a viral replication cell that comprises a mammalian cell.

Viral replication cells commonly used for production of recombinant AAV particles include, but are not limited to 293 cells, COS cells, HeLa cells, KB cells, and other mammalian cell lines as described in U.S. Pat. Nos. 6,156, 303, 5,387,484, 5,741,683, 5,691,176, and 5,688,676; U.S. patent application 2002/0081721, and International Patent Applications WO 00/47757, WO 00/24916, and WO 96/17947, the contents of each of which are herein incorporated by reference in their entireties.

In one embodiment, AAV particles are produced in mammalian-cells wherein all three VP proteins are expressed at a stoichiometry approaching 1:1:10 (VP1:VP2:VP3). The regulatory mechanisms that allow this controlled level of expression include the production of two mRNAs, one for VP1, and the other for VP2 and VP3, produced by differential splicing.

In another embodiment, AAV particles are produced in mammalian cells using a triple transfection method wherein a payload construct, parvoviral Rep and parvoviral Cap and a helper construct are comprised within three different constructs. The triple transfection method of the three components of AAV particle production may be utilized to produce small lots of virus for assays including transduction efficiency, target tissue (tropism) evaluation, and stability.

Baculovirus

Particle production disclosed herein describes processes and methods for producing AAV particles that contact a target cell to deliver a payload construct which comprises a polynucleotide sequence encoding a payload.

Briefly, the viral construct vector and the AAV payload construct vector are each incorporated by a transposon donor/acceptor system into a bacmid, also known as a baculovirus plasmid, by standard molecular biology techniques known and performed by a person skilled in the art. Transfection of separate viral replication cell populations produces two baculoviruses, one that comprises the viral construct expression vector, and another that comprises the AAV payload construct expression vector. The two baculoviruses may be used to infect a single viral replication cell population for production of AAV particles.

Baculovirus expression vectors for producing viral particles in insect cells, including but not limited to *Spodoptera frugiperda* (Sf9) cells, provide high titers of viral particle product. Recombinant baculovirus encoding the viral construct expression vector and AAV payload construct expression vector initiates a productive infection of viral replicating cells. Infectious baculovirus particles released from the primary infection secondarily infect additional cells in the culture, exponentially infecting the entire cell culture population in a number of infection cycles that is a function of the initial multiplicity of infection, see Urabe, M. et al., J Virol. 2006 February; 80 (4):1874-85, the contents of which are herein incorporated by reference in their entirety.

Production of AAV particles with baculovirus in an insect cell system may address known baculovirus genetic and physical instability. In one embodiment, the production system addresses baculovirus instability over multiple passages by utilizing a titerless infected-cells preservation and scale-up system. Small scale seed cultures of viral producing cells are transfected with viral expression constructs encoding the structural, non-structural, components of the viral particle. Baculovirus-infected viral producing cells are harvested into aliquots that may be cryopreserved in liquid nitrogen; the aliquots retain viability and infectivity for infection of large scale viral producing cell culture Wasilko D J et al., Protein Expr Purif. 2009 June; 65(2):122-32, the contents of which are herein incorporated by reference in their entirety.

A genetically stable baculovirus may be used to produce source of the one or more of the components for producing AAV particles in invertebrate cells. In one embodiment, defective baculovirus expression vectors may be maintained episomally in insect cells. In such an embodiment the bacmid vector is engineered with replication control elements, including but not limited to promoters, enhancers, and/or cell-cycle regulated replication elements.

In one embodiment, baculoviruses may be engineered with a (non-) selectable marker for recombination into the chitinase/cathepsin locus. The chia/v-cath locus is non-essential for propagating baculovirus in tissue culture, and the V-cath (EC 3.4.22.50) is a cysteine endoprotease that is most active on Arg-Arg dipeptide containing substrates. The Arg-Arg dipeptide is present in densovirus and parvovirus capsid structural proteins but infrequently occurs in dependovirus VP1.

In one embodiment, stable viral replication cells permissive for baculovirus infection are engineered with at least one stable integrated copy of any of the elements necessary for AAV replication and viral particle production including, but not limited to, the entire AAV genome, Rep and Cap genes, Rep genes, Cap genes, each Rep protein as a separate transcription cassette, each VP protein as a separate transcription cassette, the AAP (assembly activation protein), or at least one of the baculovirus helper genes with native or non-native promoters.

AAV particles described herein may be produced by triple transfection or baculovirus mediated virus production, or any other method known in the art. Any suitable permissive or packaging cell known in the art may be employed to produce the vectors. Mammalian cells are often preferred. Also preferred are trans-complementing packaging cell lines that provide functions deleted from a replication-defective helper virus, e.g., 293 cells or other E1a trans-complementing cells.

The gene cassette may contain some or all of the parvovirus (e.g., AAV) cap and rep genes. Preferably, however, some or all of the cap and rep functions are provided in trans by introducing a packaging vector(s) encoding the capsid and/or Rep proteins into the cell. Most preferably, the gene cassette does not encode the capsid or Rep proteins. Alternatively, a packaging cell line is used that is stably transformed to express the cap and/or rep genes.

Recombinant AAV virus particles are, in some cases, produced and purified from culture supernatants according to the procedure as described in US20160032254, the contents of which are incorporated by reference. Production may also involve methods known in the art including those using 293T cells, sf9 insect cells, triple transfection or any suitable production method.

In some cases, 293T cells (adhesion/suspension) are transfected with polyethylenimine (PEI) with plasmids required for production of AAV, i.e., AAV2 rep, an adenoviral helper construct and a ITR flanked transgene cassette. The AAV2 rep plasmid also contains the cap sequence of the particular virus being studied. Twenty-four hours after transfection (no medium changes for suspension), which occurs in DMEM/F17 with/without serum, the medium is replaced with fresh medium with or without serum. Three (3) days after transfection, a sample is taken from the culture medium of the 293 adherent cells. Subsequently cells are scraped, or suspension cells are pelleted, and transferred into a receptacle. For adhesion cells, after centrifugation to remove cellular pellet, a second sample is taken from the supernatant after scraping. Next, cell lysis is achieved by three consecutive freeze-thaw cycles (−80 C to 37 C) or adding detergent triton. Cellular debris is removed by centrifugation or depth filtration and sample 3 is taken from the medium. The samples are quantified for AAV particles by DNase resistant genome titration by DNA qPCR. The total production yield from such a transfection is equal to the particle concentration from sample 3.

AAV particle titers are measured according to genome copy number (genome particles per milliliter). Genome particle concentrations are based on DNA qPCR of the vector DNA as previously reported (Clark et al. (1999) Hum. Gene Ther., 10:1031-1039; Veldwijk et al. (2002) Mol. Ther., 6:272-278).

Large-Scale Production

In some embodiments, AAV particle production may be modified to increase the scale of production. Large scale viral production methods according to the present disclosure may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety. Methods of increasing viral particle production scale typically comprise increasing the number of viral replication cells. In some embodiments, viral replication cells comprise adherent cells. To increase the scale of viral particle production by adherent viral replication cells, larger cell culture surfaces are required. In some cases, large-scale production methods comprise the use of roller bottles to increase cell culture surfaces. Other cell culture substrates with increased surface areas are known in the art. Examples of additional adherent cell culture products with increased surface areas include, but are not limited to CELLSTACK®, CELLCUBE® (Corning Corp., Corning, N.Y.) and NUNC™ CELL FACTORY' (Thermo Scientific, Waltham, Mass.) In some cases, large-scale adherent cell surfaces may comprise from about 1,000 cm$^2$ to about 100,000 cm$^2$. In some cases, large-scale adherent cell cultures may comprise from about $10^7$ to about $10^9$ cells, from about $10^8$ to about $10^{10}$ cells, from about $10^9$ to about $10^{12}$ cells or at least $10^{12}$ cells. In some cases, large-scale adherent cultures may produce from about $10^9$ to about $10^{12}$, from about $10^{10}$ to about $10^{13}$, from about $10^{11}$ to about $10^{14}$, from about $10^{12}$ to about $10^{15}$ or at least $10^{15}$ viral particles.

In some embodiments, large-scale viral production methods of the present disclosure may comprise the use of suspension cell cultures. Suspension cell culture allows for significantly increased numbers of cells. Typically, the number of adherent cells that can be grown on about 10-50 cm$^2$ of surface area can be grown in about 1 cm$^3$ volume in suspension.

Transfection of replication cells in large-scale culture formats may be carried out according to any methods known in the art. For large-scale adherent cell cultures, transfection methods may include, but are not limited to the use of inorganic compounds (e.g. calcium phosphate), organic compounds [e.g. polyethyleneimine (PEI)] or the use of non-chemical methods (e.g. electroporation.) With cells grown in suspension, transfection methods may include, but are not limited to the use of calcium phosphate and the use of PEI. In some cases, transfection of large scale suspension cultures may be carried out according to the section entitled "Transfection Procedure" described in Feng, L. et al., 2008. Biotechnol Appl. Biochem. 50:121-32, the contents of which are herein incorporated by reference in their entirety. According to such embodiments, PEI-DNA complexes may be formed for introduction of plasmids to be transfected. In some cases, cells being transfected with PEI-DNA complexes may be 'shocked' prior to transfection. This comprises lowering cell culture temperatures to 4° C. for a period of about 1 hour. In some cases, cell cultures may be shocked for a period of from about 10 minutes to about 5 hours. In some cases, cell cultures may be shocked at a temperature of from about 0° C. to about 20° C.

In some cases, transfections may include one or more vectors for expression of an RNA effector molecule to reduce expression of nucleic acids from one or more AAV payload construct. Such methods may enhance the production of viral particles by reducing cellular resources wasted on expressing payload constructs. In some cases, such methods may be carried according to those taught in US Publication No. US2014/0099666, the contents of which are herein incorporated by reference in their entirety.

Bioreactors

In some embodiments, cell culture bioreactors may be used for large scale viral production. In some cases, bioreactors comprise stirred tank reactors. Such reactors generally comprise a vessel, typically cylindrical in shape, with a stirrer (e.g. impeller.) In some embodiments, such bioreactor vessels may be placed within a water jacket to control vessel temperature and/or to minimize effects from ambient temperature changes. Bioreactor vessel volume may range in size from about 500 ml to about 2 L, from about 1 L to about 5 L, from about 2.5 L to about 20 L, from about 10 L to about 50 L, from about 25 L to about 100 L, from about 75 L to about 500 L, from about 250 L to about 2,000 L, from about 1,000 L to about 10,000 L, from about 5,000 L to about 50,000 L or at least 50,000 L. Vessel bottoms may be rounded or flat. In some cases, animal cell cultures may be maintained in bioreactors with rounded vessel bottoms.

In some cases, bioreactor vessels may be warmed through the use of a thermocirculator. Thermocirculators pump heated water around water jackets. In some cases, heated water may be pumped through pipes (e.g. coiled pipes) that are present within bioreactor vessels. In some cases, warm air may be circulated around bioreactors, including, but not limited to air space directly above culture medium. Additionally, pH and $CO_2$ levels may be maintained to optimize cell viability.

In some cases, bioreactors may comprise hollow-fiber reactors. Hollow-fiber bioreactors may support the culture of both anchorage dependent and anchorage independent cells. Further bioreactors may include, but are not limited to, packed-bed or fixed-bed bioreactors. Such bioreactors may comprise vessels with glass beads for adherent cell attachment. Further packed-bed reactors may comprise ceramic beads.

In some cases, viral particles are produced through the use of a disposable bioreactor. In some embodiments, such bioreactors may include WAVE™ disposable bioreactors.

In some embodiments, AAV particle production in animal cell bioreactor cultures may be carried out according to the methods taught in U.S. Pat. Nos. 5,064,764, 6,194,191, 6,566,118, 8,137,948 or US Patent Application No. US2011/0229971, the contents of each of which are herein incorporated by reference in their entirety.

Cell Lysis

Cells of the invention, including, but not limited to viral production cells, may be subjected to cell lysis according to any methods known in the art. Cell lysis may be carried out to obtain one or more agents (e.g. viral particles) present within any cells of the invention. In some embodiments, cell lysis may be carried out according to any of the methods listed in U.S. Pat. Nos. 7,326,555, 7,579,181, 7,048,920, 6,410,300, 6,436,394, 7,732,129, 7,510,875, 7,445,930, 6,726,907, 6,194,191, 7,125,706, 6,995,006, 6,676,935, 7,968,333, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety. Cell lysis methods may be chemical or mechanical. Chemical cell lysis typically comprises contacting one or more cells with one or more lysis agent. Mechanical lysis typically comprises subjecting one or more cells to one or more lysis condition and/or one or more lysis force.

In some embodiments, chemical lysis may be used to lyse cells. As used herein, the term "lysis agent" refers to any agent that may aid in the disruption of a cell. In some cases, lysis agents are introduced in solutions, termed lysis solutions or lysis buffers. As used herein, the term "lysis solution" refers to a solution (typically aqueous) comprising one or more lysis agent. In addition to lysis agents, lysis solutions may include one or more buffering agents, solubilizing agents, surfactants, preservatives, cryoprotectants, enzymes, enzyme inhibitors and/or chelators. Lysis buffers are lysis solutions comprising one or more buffering agent. Additional components of lysis solutions may include one or more solubilizing agent. As used herein, the term "solubilizing agent" refers to a compound that enhances the solubility of one or more components of a solution and/or the solubility of one or more entities to which solutions are applied. In some cases, solubilizing agents enhance protein solubility. In some cases, solubilizing agents are selected based on their ability to enhance protein solubility while maintaining protein conformation and/or activity.

Exemplary lysis agents may include any of those described in U.S. Pat. Nos. 8,685,734, 7,901,921, 7,732,129, 7,223,585, 7,125,706, 8,236,495, 8,110,351, 7,419,956, 7,300,797, 6,699,706 and 6,143,567, the contents of each of which are herein incorporated by reference in their entirety. In some cases, lysis agents may be selected from lysis salts, amphoteric agents, cationic agents, ionic detergents and non-ionic detergents. Lysis salts may include, but are not limited to, sodium chloride (NaCl) and potassium chloride (KCl.) Further lysis salts may include any of those described in U.S. Pat. Nos. 8,614,101, 7,326,555, 7,579,181, 7,048,920, 6,410,300, 6,436,394, 7,732,129, 7,510,875, 7,445,930, 6,726,907, 6,194,191, 7,125,706, 6,995,006, 6,676,935 and 7,968,333, the contents of each of which are herein incorporated by reference in their entirety. Concentrations of salts may be increased or decreased to obtain an effective concentration for rupture of cell membranes. Amphoteric agents, as referred to herein, are compounds capable of reacting as an acid or a base. Amphoteric agents may include, but are not limited to lysophosphatidylcholine, 3-((3-Cholamidopropyl) dimethylammonium)-1-propanesulfonate (CHAPS), ZWITTERGENT® and the like, Cationic agents may include, but are not limited to, cetyltrimethylammonium bromide (C (16) TAB) and Benzalkonium chloride. Lysis agents comprising detergents may include ionic detergents or non-ionic detergents. Detergents may function to break apart or dissolve cell structures including, but not limited to cell membranes, cell walls, lipids, carbohydrates, lipoproteins and glycoproteins. Exemplary ionic detergents include any of those taught in U.S. Pat. Nos. 7,625,570 and 6,593,123 or US Publication No. US2014/0087361, the contents of each of which are herein incorporated by reference in their entirety. Some ionic detergents may include, but are not limited to, sodium dodecyl sulfate (SDS), cholate and deoxycholate. In some cases, ionic detergents may be included in lysis solutions as a solubilizing agent. Non-ionic detergents may include, but are not limited to octylglucoside, digitonin, lubrol, C12E8, TWEEN®-20, TWEEN®-80, Triton X-100 and Noniodet P-40. Non-ionic detergents are typically weaker lysis agents but may be included as solubilizing agents for solubilizing cellular and/or viral proteins. Further lysis agents may include enzymes and urea. In some cases, one or more lysis agents may be combined in a lysis solution in order to enhance one or more of cell lysis and protein solubility. In some cases, enzyme inhibitors may be included in lysis solutions in order to prevent proteolysis that may be triggered by cell membrane disruption.

In some embodiments, mechanical cell lysis is carried out. Mechanical cell lysis methods may include the use of one or more lysis condition and/or one or more lysis force. As used herein, the term "lysis condition" refers to a state or circumstance that promotes cellular disruption. Lysis conditions may comprise certain temperatures, pressures, osmotic purity, salinity and the like. In some cases, lysis conditions comprise increased or decreased temperatures. According to some embodiments, lysis conditions comprise changes in temperature to promote cellular disruption. Cell lysis carried out according to such embodiments may include freeze-thaw lysis. As used herein, the term "freeze-thaw lysis" refers to cellular lysis in which a cell solution is subjected to one or more freeze-thaw cycle. According to freeze-thaw lysis methods, cells in solution are frozen to induce a mechanical disruption of cellular membranes caused by the formation and expansion of ice crystals. Cell solutions used according freeze-thaw lysis methods, may further comprise one or more lysis agents, solubilizing agents, buffering agents, cryoprotectants, surfactants, preservatives, enzymes, enzyme inhibitors and/or chelators. Once cell solutions subjected to freezing are thawed, such components may enhance the recovery of desired cellular products. In some cases, one or more cryoprotectants are included in cell solutions undergoing freeze-thaw lysis. As used herein, the term "cryoprotectant" refers to an agent used to protect one or more substance from damage due to freezing. Cryoprotectants may include any of those taught in US Publication No. US2013/0323302 or U.S. Pat. Nos. 6,503,888, 6,180,613, 7,888,096, 7,091,030, the contents of each of which are herein incorporated by reference in their entirety. In some cases, cryoprotectants may include, but are not limited to dimethyl sulfoxide, 1,2-propanediol, 2,3-butanediol, formamide, glycerol, ethylene glycol, 1,3-propanediol and n-dimethyl formamide, polyvinylpyrrolidone, hydroxyethyl starch, agarose, dextrans, inositol, glucose, hydroxyethylstarch, lactose, sorbitol, methyl glucose, sucrose and urea. In some embodiments, freeze-thaw lysis may be carried out according to any of the methods described in U.S. Pat. No. 7,704,721, the contents of which are herein incorporated by reference in their entirety.

As used herein, the term "lysis force" refers to a physical activity used to disrupt a cell. Lysis forces may include, but are not limited to mechanical forces, sonic forces, gravitational forces, optical forces, electrical forces and the like. Cell lysis carried out by mechanical force is referred to herein as "mechanical lysis." Mechanical forces that may be used according to mechanical lysis may include high shear fluid forces. According to such methods of mechanical lysis, a microfluidizer may be used. Microfluidizers typically comprise an inlet reservoir where cell solutions may be applied. Cell solutions may then be pumped into an interaction chamber via a pump (e.g. high-pressure pump) at high speed and/or pressure to produce shear fluid forces. Resulting lysates may then be collected in one or more output reservoir. Pump speed and/or pressure may be adjusted to modulate cell lysis and enhance recovery of products (e.g. viral particles.) Other mechanical lysis methods may include physical disruption of cells by scraping.

Cell lysis methods may be selected based on the cell culture format of cells to be lysed. For example, with adherent cell cultures, some chemical and mechanical lysis methods may be used. Such mechanical lysis methods may include freeze-thaw lysis or scraping. In another example, chemical lysis of adherent cell cultures may be carried out through incubation with lysis solutions comprising surfactant, such as Triton-X-100. In some cases, cell lysates generated from adherent cell cultures may be treated with one more nuclease to lower the viscosity of the lysates caused by liberated DNA.

In one embodiment, a method for harvesting AAV particles without lysis may be used for efficient and scalable AAV particle production. In a non-limiting example, AAV particles may be produced by culturing an AAV particle lacking a heparin binding site, thereby allowing the AAV particle to pass into the supernatant, in a cell culture, collecting supernatant from the culture; and isolating the AAV particle from the supernatant, as described in US Patent Application 20090275107, the contents of which are incorporated herein by reference in their entirety.

Clarification

Cell lysates comprising viral particles may be subjected to clarification. Clarification refers to initial steps taken in purification of viral particles from cell lysates. Clarification serves to prepare lysates for further purification by removing larger, insoluble debris. Clarification steps may include, but are not limited to, centrifugation and filtration. During clarification, centrifugation may be carried out at low speeds to remove larger debris only. Similarly, filtration may be carried out using filters with larger pore sizes so that only larger debris is removed. In some cases, tangential flow filtration may be used during clarification. Objectives of viral clarification include high throughput processing of cell lysates and to optimize ultimate viral recovery. Advantages of including a clarification step include scalability for processing of larger volumes of lysate. In some embodiments, clarification may be carried out according to any of the methods presented in U.S. Pat. Nos. 8,524,446, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498, 7,491,508, US Publication Nos. US2013/0045186, US2011/0263027, US2011/0151434, US2003/0138772, and International Publication Nos. WO2002012455, WO1996039530, WO1998010088, WO1999014354, WO1999015685, WO1999047691, WO2000055342, WO2000075353 and WO2001023597, the contents of each of which are herein incorporated by reference in their entirety.

Methods of cell lysate clarification by filtration are well understood in the art and may be carried out according to a variety of available methods including, but not limited to passive filtration and flow filtration. Filters used may comprise a variety of materials and pore sizes. For example, cell lysate filters may comprise pore sizes of from about 1 µM to about 5 µM, from about 0.5 µM to about 2 µM, from about 0.1 µM to about 1 µM, from about 0.05 µM to about 0.05 µM and from about 0.001 µM to about 0.1µ.M. Exemplary pore sizes for cell lysate filters may include, but are not limited to, 2.0, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.22, 0.21, 0.20, 0.19, 0.18, 0.17, 0.16, 0.15, 0.14, 0.13, 0.12, 0.11, 0.1, 0.09, 0.08, 0.07, 0.06, 0.05, 0.04, 0.03, 0.02, 0.01, 0.02, 0.019, 0.018, 0.017, 0.016, 0.015, 0.014, 0.013, 0.012, 0.011, 0.01, 0.009, 0.008, 0.007, 0.006, 0.005, 0.004, 0.003, 0.002, 0.001 and 0.001 µM. In one embodiment, clarification may comprise filtration through a filter with 2.0 µM pore size to remove large debris, followed by passage through a filter with 0.45 µM pore size to remove intact cells.

Filter materials may be composed of a variety of materials. Such materials may include, but are not limited to, polymeric materials and metal materials (e.g. sintered metal and pored aluminum.) Exemplary materials may include, but are not limited to nylon, cellulose materials (e.g. cellulose acetate), polyvinylidene fluoride (PVDF), polyethersulfone, polyamide, polysulfone, polypropylene, and polyethylene terephthalate. In some cases, filters useful for clarification of cell lysates may include, but are not limited to ULTIPLEAT PROFILE™ filters (Pall Corporation, Port Washington, N.Y.), SUPOR™ membrane filters (Pall Corporation, Port Washington, N.Y.).

In some cases, flow filtration may be carried out to increase filtration speed and/or effectiveness. In some cases, flow filtration may comprise vacuum filtration. According to such methods, a vacuum is created on the side of the filter opposite that of cell lysate to be filtered. In some cases, cell lysates may be passed through filters by centrifugal forces. In some cases, a pump is used to force cell lysate through clarification filters. Flow rate of cell lysate through one or more filters may be modulated by adjusting one of channel size and/or fluid pressure.

According to some embodiments, cell lysates may be clarified by centrifugation. Centrifugation may be used to pellet insoluble particles in the lysate. During clarification, centrifugation strength [expressed in terms of gravitational units (g), which represents multiples of standard gravitational force] may be lower than in subsequent purification steps. In some cases, centrifugation may be carried out on cell lysates at from about 200 g to about 800 g, from about 500 g to about 1500 g, from about 1000 g to about 5000 g, from about 1200 g to about 10000 g or from about 8000 g to about 15000 g. In some embodiments, cell lysate centrifugation is carried out at 8000 g for 15 minutes. In some cases, density gradient centrifugation may be carried out in order to partition particulates in the cell lysate by sedimentation rate. Gradients used according to methods of the present disclosure may include, but are not limited to, cesium chloride gradients and iodixanol step gradients.

Purification: Chromatography

In some cases, AAV particles may be purified from clarified cell lysates by one or more methods of chromatography. Chromatography refers to any number of methods known in the art for separating out one or more elements from a mixture. Such methods may include, but are not limited to, ion exchange chromatography (e.g. cation exchange chromatography and anion exchange chromatography), immunoaffinity chromatography and size-exclusion chromatography. In some embodiments, methods of viral chromatography may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety.

In some embodiments, ion exchange chromatography may be used to isolate viral particles. Ion exchange chromatography is used to bind viral particles based on charge-charge interactions between capsid proteins and charged sites present on a stationary phase, typically a column through which viral preparations (e.g. clarified lysates) are passed. After application of viral preparations, bound viral particles may then be eluted by applying an elution solution to disrupt the charge-charge interactions. Elution solutions may be optimized by adjusting salt concentration and/or pH to enhance recovery of bound viral particles. Depending on the charge of viral capsids being isolated, cation or anion exchange chromatography methods may be selected. Methods of ion exchange chromatography may include, but are not limited to, any of those taught in U.S. Pat. Nos. 7,419,817, 6,143,548, 7,094,604, 6,593,123, 7,015,026 and 8,137,948, the contents of each of which are herein incorporated by reference in their entirety.

In some embodiments, immunoaffinity chromatography may be used. Immunoaffinity chromatography is a form of chromatography that utilizes one or more immune compounds (e.g. antibodies or antibody-related structures) to retain viral particles. Immune compounds may bind specifically to one or more structures on viral particle surfaces, including, but not limited to one or more viral coat protein. In some cases, immune compounds may be specific for a particular viral variant. In some cases, immune compounds may bind to multiple viral variants. In some embodiments, immune compounds may include recombinant single-chain antibodies. Such recombinant single chain antibodies may include those described in Smith, R. H. et al., 2009. Mol. Ther. 17(11):1888-96, the contents of which are herein incorporated by reference in their entirety. Such immune compounds are capable of binding to several AAV capsid variants, including, but not limited to AAV1, AAV2, AAV6 and AAV8.

In some embodiments, size-exclusion chromatography (SEC) may be used. SEC may comprise the use of a gel to separate particles according to size. In viral particle purification, SEC filtration is sometimes referred to as "polishing." In some cases, SEC may be carried out to generate a final product that is near-homogenous. Such final products may in some cases be used in pre-clinical studies and/or clinical studies (Kotin, R. M. 2011. Human Molecular Genetics. 20(1):R2-R6, the contents of which are herein incorporated by reference in their entirety.) In some cases, SEC may be carried out according to any of the methods taught in U.S. Pat. Nos. 6,143,548, 7,015,026, 8,476,418, 6,410,300, 8,476,418, 7,419,817, 7,094,604, 6,593,123, and 8,137,948, the contents of each of which are herein incorporated by reference in their entirety.

In one embodiment, the compositions comprising at least one AAV particle may be isolated or purified using the methods described in U.S. Pat. No. 6,146,874, the contents of which are herein incorporated by reference in its entirety.

In one embodiment, the compositions comprising at least one AAV particle may be isolated or purified using the methods described in U.S. Pat. No. 6,660,514, the contents of which are herein incorporated by reference in its entirety.

In one embodiment, the compositions comprising at least one AAV particle may be isolated or purified using the methods described in U.S. Pat. No. 8,283,151, the contents of which are herein incorporated by reference in its entirety.

In one embodiment, the compositions comprising at least one AAV particle may be isolated or purified using the methods described in U.S. Pat. No. 8,524,446, the contents of which are herein incorporated by reference in its entirety.

Introduction into Cells

To ensure the chemical and biological stability of siRNA duplexes, it is important to deliver polynucleotides encoding the siRNAs inside the target cells. The polynucleotides of the present invention may be introduced into cells using any of a variety of approaches.

In some embodiments, the polynucleotide of the present invention is introduced into a cell by contacting the cell with the polynucleotide. In some embodiments, the polynucleotide is introduced into a cell by contacting the cell with a composition comprising the polynucleotide and a lipophilic carrier. In other embodiments, the polynucleotide is introduced into a cell by transfecting or infecting the cell with a vector comprising nucleic acid sequences capable of producing the siRNA duplex when transcribed in the cell.

In some embodiments, the siRNA duplex is introduced into a cell by injecting into the cell a vector comprising nucleic acid sequences capable of producing the siRNA duplex when transcribed in the cell.

In other embodiments, the polynucleotides of the present invention may be delivered into cells by electroporation (e.g. U.S. Patent Publication No. 20050014264; the content of which is herein incorporated by reference in its entirety).

In addition, the siRNA molecules inserted into viral vectors (e.g. AAV vectors) may be delivered into cells by viral infection. These viral vectors are engineered and optimized to facilitate the entry of siRNA molecule into cells that are not readily amendable to transfection. Also, some synthetic viral vectors possess an ability to integrate the shRNA into the cell genome, thereby leading to stable siRNA expression and long-term knockdown of a target gene. In this manner, viral vectors are engineered as vehicles for specific delivery while lacking the deleterious replication and/or integration features found in wild-type virus.

In some embodiments, the cells may include, but are not limited to, cells of mammalian origin, cells of human origins, embryonic stem cells, induced pluripotent stem cells, neural stem cells, and neural progenitor cells.

Pharmaceutical Compositions and Formulation

In addition to the pharmaceutical compositions, e.g., siRNA duplexes (including the encoding plasmids or expression vectors, such as viruses, e.g., AAV) to be delivered, provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients or subjects. For the purposes of the present disclosure, the phrase "active ingredient" generally refers either to synthetic siRNA duplexes or to the viral vector carrying the siRNA duplexes, or to the siRNA molecule delivered by a viral vector as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered.

The siRNA duplexes or viral vectors encoding them can be formulated using one or more excipients to: (1) increase stability; (2) increase cell transfection or transduction; (3) permit the sustained or delayed release; or (4) alter the biodistribution (e.g., target the viral vector to specific tissues or cell types such as brain and motor neurons).

Formulations of the present invention can include, without limitation, saline, lipidoids, liposomes, lipid nanoparticles, polymers, lipoplexes, core-shell nanoparticles, peptides, proteins, cells transfected with viral vectors (e.g., for transplantation into a subject), nanoparticle mimics and combinations thereof. Further, the viral vectors of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the formulations described herein may contain at least one SOD1 targeting polynucleotide. As a non-limiting example, the formulations may contain 1, 2, 3, 4 or 5 polynucleotide that target SOD1 gene at different sites.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In some embodiments, the formulations may comprise at least one inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA).

Formulations of viral vectors carrying SOD1 targeting polynucleotides disclosed herein may include cations or anions. In one embodiment, the formulations include metal cations such as, but not limited to, Zn2+, Ca2+, Cu2+, Mg+ and combinations thereof.

As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., Journal of Pharmaceutical Science, 66, 1-19 (1977); the content of each of which is incorporated herein by reference in their entirety.

The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

According to the present invention, the SOD1 targeting polynucleotides, or AAV vectors comprising the same, may be formulated for CNS delivery. Agents that cross the brain blood barrier may be used. For example, some cell penetrating peptides that can target siRNA molecules to the brain blood barrier endothelium may be used to formulate the siRNA duplexes targeting SOD1 gene (e.g., Mathupala, *Expert Opin Ther Pat.*, 2009, 19, 137-140; the content of which is incorporated herein by reference in its entirety).

Administration

The SOD1 targeting polynucleotides of the present invention may be administered by any route which results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracomal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

In specific embodiments, compositions including AAV vectors comprising at least one SOD1 targeting polynucleotide may be administered in a way which allows them enter the central nervous system and penetrate into motor neurons.

In some embodiments, the therapeutics of the present invention may be administered by muscular injection. Rizvanov et al. demonstrated for the first time that siRNA molecules, targeting mutant human SOD1 mRNA, is taken up by the sciatic nerve, retrogradely transported to the perikarya of motor neurons, and inhibits mutant SOD1 mRNA in SOD1$^{G93A}$ transgenic ALS mice (Rizvanov A A et al., *Exp. Brain Res.*, 2009, 195(1), 1-4; the content of which is incorporated herein by reference in its entirety). Another study also demonstrated that muscle delivery of AAV expressing small hairpin RNAs (shRNAs) against the mutant SOD1 gene, led to significant mutant SOD1 knockdown in the muscle as well as innervating motor neurons (Towne C et al., *Mol Ther.*, 2011; 19(2): 274-283; the content of which is incorporated herein by reference in its entirety).

In some embodiments, AAV vectors that express siRNA duplexes of the present invention may be administered to a subject by peripheral injections and/or intranasal delivery. It was disclosed in the art that the peripheral administration of AAV vectors for siRNA duplexes can be transported to the central nervous system, for example, to the motor neurons (e.g., U.S. Patent Publication Nos. 20100240739; and 20100130594; the content of each of which is incorporated herein by reference in their entirety).

In other embodiments, compositions comprising at least one siRNA duplex of the invention may be administered to a subject by intracranial delivery (See, e.g., U.S. Pat. No. 8,119,611; the content of which is incorporated herein by reference in its entirety).

The SOD1 targeting polynucleotides of the present invention may be administered in any suitable forms, either as a liquid solution or suspension, as a solid form suitable for liquid solution or suspension in a liquid solution. They may be formulated with any appropriate and pharmaceutically acceptable excipient.

The SOD1 targeting polynucleotides of the present invention may be administered in a "therapeutically effective" amount, i.e., an amount that is sufficient to alleviate and/or prevent at least one symptom associated with the disease or provide improvement in the condition of the subject.

Dosing

The pharmaceutical compositions of the present invention may be administered to a subject using any amount effective for preventing and treating a SOD1 associated disorder (e.g., ALS). The exact amount required will vary from subject to subject, depending on the species, age, and general condition of the subject, the severity of the disease, the particular composition, its mode of administration, its mode of activity, and the like.

The compositions of the present invention are typically formulated in unit dosage form for ease of administration and uniformity of dosage. It will be understood, however, that the total daily usage of the compositions of the present invention may be decided by the attending physician within the scope of sound medical judgment. The specific therapeutically effectiveness for any particular patient will depend upon a variety of factors including the disorder being treated and the severity of the disorder; the activity of the specific compound employed; the specific composition employed; the age, body weight, general health, sex and diet of the patient; the time of administration, and route of administration; the duration of the treatment; drugs used in combination or coincidental with the specific compound employed; and like factors well known in the medical arts.

In some specific embodiments, the doses of AAV vectors for delivering siRNA duplexes of the present invention may be adapted dependent on the disease condition, the subject and the treatment strategy, etc. Typically, about $10^5$, $10^6$, $10^{12}$, $10^{13}$, $10^{14}$, $10^{15}$, $10^{16}$ viral genome (unit) may be administered per dose.

The desired dosage may be delivered three times a day, two times a day, once a day, every other day, every third day, every week, every two weeks, every three weeks, or every four weeks.

In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total daily dose into two or more doses, e.g., two or more administrations of the single unit dose. As used herein, a "single unit dose" is a dose of any modulatory polynucleotide therapeutic administered in one dose/at one time/single route/single point of contact, i.e., single administration event. As used herein, a "total daily dose" is an amount given or prescribed in 24 hr period. It may be administered as a single unit dose. In one embodiment, the viral vectors comprising the SOD1 targeting polynucleotides of the present invention are administered to a subject in split doses. They may be formulated in buffer only or in a formulation described herein.

Methods of treatment of ALS and/or Canine Degenerative Myelopathy (DM)

Provided in the present invention include methods for introducing the SOD1 targeting polynucleotides described herein into cells, the method comprising introducing into said cells any of the polynucleotides in an amount sufficient for degradation of target SOD1 mRNA to occur. In some aspects, the cells may be stem cells, neurons such as motor neurons, muscle cells and glial cells such as astrocytes.

Disclosed in the present invention also include methods for treating ALS associated with abnormal SOD1 function in a subject in need of treatment. The method optionally comprises administering to the subject a therapeutically effective amount of a composition comprising or encoding at least one siRNA duplex targeting SOD1 gene. Said siRNA duplex will silence SOD1 gene expression and inhibit SOD1 protein production, and reduce one or more symptoms of ALS in the subject such that ALS is therapeutically treated.

In some embodiments, the SOD1 targeting polynucleotide of the present invention or the composition comprising or encoding this polynucleotide is administered to the central nervous system of the subject. In other embodiments, the siRNA duplex of the present invention or the composition comprising it is administered to the muscles of the subject In particular, the SOD1 targeting polynucleotides may be delivered into specific types of targeted cells, including motor neurons; glial cells including oligodendrocytes, astrocytes and microglia; and/or other cells surrounding neurons such as T cells. Studies in human ALS patients and animal SOD1 ALS model implicated that glial cells play an early role in the dysfunction and death of ALS neurons. Normal SOD1 in the surrounding, protective glial cells can prevent the motor neurons from dying even though mutant SOD1 is present in motor neurons (e.g., reviewed by Philips and Rothstein, *Exp. Neurol.*, 2014, May 22. pii: S0014-4886(14) 00157-5; the content of which is incorporated herein by reference in its entirety).

In some specific embodiments, at least one siRNA duplex targeting SOD1 gene used as a therapy for ALS is inserted in a viral vector, such as an AAV vector.

In some embodiments, the present composition is administered as a single therapeutic or combination therapeutics for the treatment of ALS.

The viral vectors comprising or encoding siRNA duplexes targeting SOD1 gene may be used in combination with one or more other therapeutic, agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the SOD1 targeting polynucleotides of the present invention can be small molecule compounds which are antioxidants, anti-inflammatory agents, anti-apoptosis agents, calcium regulators, antiglutamatergic agents, structural protein inhibitors, and compounds involved in metal ion regulation.

Compounds used in combination for treating ALS may include, but are not limited to, agents that reduce oxidative stress, such as free radical scavengers, and/or Radicava (edaravone), antiglutamatergic agents: Riluzole, Topiramate, Talampanel, Lamotrigine, Dextromethorphan, Gabapentin and AMPA antagonist; Anti-apoptosis agents: Minocycline, Sodium phenylbutyrate and Arimoclomol; Anti-inflammatory agent: ganglioside, Celecoxib, Cyclosporine, Azathioprine, Cyclophosphamide, Plasmaphoresis, Glatiramer acetate and thalidomide; Ceftriaxone (Berry et al., *Plos One*, 2013, 8(4)); Beat-lactam antibiotics; Pramipexole (a dopamine agonist) (Wang et al., *Amyotrophic Lateral Scler.*, 2008, 9(1), 50-58); Nimesulide in U.S. Patent Publication No. 20060074991; Diazoxide disclosed in U.S. Patent Publication No. 20130143873); pyrazolone derivatives disclosed in US Patent Publication No. 20080161378; free radical scavengers that inhibit oxidative stress-induced cell death, such as bromocriptine (US. Patent Publication No. 20110105517); phenyl carbamate compounds discussed in PCT Patent Publication No. 2013100571; neuroprotective compounds disclosed in U.S. Pat. Nos. 6,933,310 and 8,399, 514 and US Patent Publication Nos. 20110237907 and 20140038927; and glycopeptides taught in U.S. Patent Publication No. 20070185012; the content of each of which is incorporated herein by reference in their entirety.

Therapeutic agents that may be used in combination therapy with the siRNA duplexes targeting SOD1 gene of the present invention may be hormones or variants that can protect neuron loss, such as adrenocorticotropic hormone (ACTH) or fragments thereof (e.g., U.S. Patent Publication No. 20130259875); Estrogen (e.g., U.S. Pat. Nos. 6,334,998 and 6,592,845); the content of each of which is incorporated herein by reference in their entirety.

Neurotrophic factors may be used in combination therapy with the siRNA duplexes targeting SOD1 gene of the present invention for treating ALS. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the AAV vector comprising at least one siRNA duplex targeting SOD1 gene may be co-administered with AAV vectors expressing neurotrophic factors such as AAV-IGF-I (Vincent et al., *Neuromolecular medicine*, 2004, 6, 79-85; the content of which is incorporated herein by reference in its entirety) and AAV-GDNF (Wang et al., J Neurosci., 2002, 22, 6920-6928; the content of which is incorporated herein by reference in its entirety).

In some embodiments, the composition of the present invention for treating ALS is administered to the subject in need intravenously, intramuscularly, subcutaneously, intraperitoneally, intrathecally and/or intraventricularly, allowing the siRNA duplexes or vectors comprising the siRNA duplexes to pass through one or both the blood-brain barrier and the blood spinal cord barrier. In some aspects, the method includes administering (e.g., intraventricularly administering and/or intrathecally administering) directly to the central nervous system (CNS) of a subject (using, e.g., an infusion pump and/or a delivery scaffold) a therapeutically effective amount of a composition comprising at least one siRNA duplex targeting SOD1 gene or AAV vectors comprising at least one siRNA duplex targeting SOD1 gene, silencing/suppressing SOD1 gene expression, and reducing one or more symptoms of ALS in the subject such that ALS is therapeutically treated.

In certain aspects, the symptoms of ALS including motor neuron degeneration, muscle weakness, muscle atrophy, the stiffness of muscle, difficulty in breathing, slurred speech, fasciculation development, frontotemporal dementia and/or premature death are improved in the subject treated. In other aspects, the composition of the present invention is applied to one or both of the brain and the spinal cord. In other aspects, one or both of muscle coordination and muscle function are improved. In other aspects, the survival of the subject is prolonged.

The compositions described herein may be tested in animal models. As a non-limiting example, the animal may be a rodent (e.g., a rat or mouse), or a mammal (e.g., a non-human primate or a dog). In one embodiment, the animal model is a dog with canine degenerative myelopathy (DM). Canine DM can be a model for ALS as the dogs have a comparable size and complexity in their nervous system and the dogs suffer from motor neuron loss and similar SOD1 chemistry levels. Canine DM is a late age onset disease (8 to 14 years) as a result of a SOD1 mutation (E40K, T18S), and there is currently no treatment available. Some benefits of using Canine DM as a disease model for ALS include, but are not limited to, the ability to have administration and therapy pharmacodynamics shared across species and to recapitulate disease measures in canine DM that are shared amongst transgenic rodent ALS models and human ALS.

In canine DM, there are 4 stages. Stage 1 (early stage) neurologic signs in DM dogs include, but are not limited to, progressive general proprioceptive ataxia, asymmetric spastic paraparesis, and/or intact spinal reflexes. Stage 2 (early stage) neurologic signs in DM dogs include, but are not limited to, mild to moderate loss of muscle mass, reduced to absent spinal reflexes in pelvic limbs, and/or urinary and fecal incontinence. Stage 3 (late stage) neurologic signs in DM dogs include, but are not limited to, signs of thoracic limb paresis, flaccid paraplegia, sever loss of muscle mass in pelvic limbs, and/or urinary and fecal incontinence. Stage 4 (late stage) neurologic signs in DM dogs include, but are not limited to, flaccid tetraplegia, difficulty with swallowing and tongue movements, reduced to absent cutaneous trunci reflex, generalized and sever loss of muscle mass, and/or urinary and fecal incontinence.

Various measurements may be used to track canine DM dogs and normal dogs used in the animal study. These measurements include, but are not limited to, neurophysiology tests (e.g., motor and sensory nerve conduction study (NCS), motor unit number estimation (MUNE), compound muscle action potential (CMAP), and electrical impedance myography (EIM)), neuropathy, neuroimaging (e.g., MRS, DTI, PET/CT), genomics (e.g., using genetic modifiers), profiling of samples (e.g., serum and CSF for SOD1, NF-H, and/or NF-L), natural history metrics and/or severity rating scales (e.g., Olby locomotor scale; see e.g., Olby N J et al. Am J Vet Res 2001, the contents of which are herein incorporated by reference in their entirety).

In one embodiment, a structural protein may be used as a biomarker to correlate disease progression and/or effect of treatment. The level of the structural protein in the blood and/or CSF of a subject may be used to determine disease progression and/or therapeutic effect.

In one embodiment, a neurofilament protein may be used as a biomarker to correlate disease progression and/or effect of treatment. The level of the neurofilament protein in the blood and/or CSF of a subject may be used to determine disease progression and/or therapeutic effect. As a non-limiting example, the neurofilament protein is neurofilament light chain (NF-L). As a non-limiting example, the neurofilament protein is neurofilament heavy chain (NF-H).

In one embodiment, a neurofilament light chain (NF-L) protein may be used as a biomarker to correlate disease progression and/or effect of treatment. The level of NF-L in the blood and/or CSF of a subject may be used to determine disease progression and/or therapeutic effect.

In one embodiment, a neurofilament heavy chain (NF-H) protein may be used as a biomarker to correlate disease progression and/or effect of treatment. The level of NF-H in the blood and/or CSF of a subject may be used to determine disease progression and/or therapeutic effect.

Definitions

Unless stated otherwise, the following terms and phrases have the meanings described below. The definitions are not meant to be limiting in nature and serve to provide a clearer understanding of certain aspects of the present invention.

As used herein, the term "nucleic acid", "polynucleotide" and 'oligonucleotide" refer to any nucleic acid polymers composed of either polydeoxyribonucleotides (containing 2-deoxy-D-ribose), or polyribonucleotides (containing D-ribose), or any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

As used herein, the term "small/short interfering RNA" or "siRNA" refers to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called siRNA duplex. According to the present invention, recombinant AAV vectors may encode one or more RNAi molecules such as an siRNA, shRNA, microRNA or precursor thereof.

As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the siRNA strand. According to the present invention, recombinant AAV vectors may encode a sense and/or antisense strand.

As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity.

As used herein, "targeting" means the process of design and selection of nucleic acid sequence that will hybridize to a target nucleic acid and induce a desired effect.

The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

As used herein, the term "mutation" refers to any changing of the structure of a gene, resulting in a variant (also called "mutant") form that may be transmitted to subsequent generations. Mutations in a gene may be caused by the alternation of single base in DNA, or the deletion, insertion, or rearrangement of larger sections of genes or chromosomes.

As used herein, the term "vector" means any molecule or moiety which transports, transduces or otherwise acts as a carrier of a heterologous molecule such as the SOD1 targeting polynucleotides of the invention. A "viral vector" is a vector which comprises one or more polynucleotide regions encoding or comprising a molecule of interest, e.g., a transgene, a polynucleotide encoding a polypeptide or multi-polypeptide or a modulatory nucleic acid such as small interfering RNA (siRNA). Viral vectors are commonly used to deliver genetic materials into cells. Viral vectors are often modified for specific applications. Types of viral vectors include retroviral vectors, lentiviral vectors, adenoviral vectors and adeno-associated viral vectors.

The term "adeno-associated virus" or "AAV" or "AAV vector" as used herein refers to any vector which comprises or derives from components of an adeno associated vector and is suitable to infect mammalian cells, preferably human cells. The term AAV vector typically designates an AAV type viral particle or virion comprising a nucleic acid molecule encoding a siRNA duplex. The AAV vector may be derived from various serotypes, including combinations of serotypes (i.e., "pseudotyped" AAV) or from various genomes (e.g., single stranded or self-complementary). In addition, the AAV vector may be replication defective and/or targeted.

As used herein, the phrase "inhibit expression of a gene" means to cause a reduction in the amount of an expression product of the gene. The expression product can be a RNA molecule transcribed from the gene (e.g., an mRNA) or a polypeptide translated from an mRNA transcribed from the gene. Typically, a reduction in the level of an mRNA results in a reduction in the level of a polypeptide translated therefrom. The level of expression may be determined using standard techniques for measuring mRNA or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "modified" refers to a changed state or structure of a molecule of the invention. Molecules may be modified in many ways including chemically, structurally, and functionally.

As used herein, the term "synthetic" means produced, prepared, and/or manufactured by the hand of man. Synthesis of polynucleotides or polypeptides or other molecules of the present invention may be chemical or enzymatic.

As used herein, the term "transfection" refers to methods to introduce exogenous nucleic acids into a cell. Methods of transfection include, but are not limited to, chemical methods, physical treatments and cationic lipids or mixtures. The list of agents that can be transfected into a cell is large and includes, but is not limited to, siRNA, sense and/or antisense sequences, AAV vectors or particles, DNA encoding one or more genes and organized into an expression plasmid, proteins, protein fragments, and more.

As used herein, "off target" refers to any unintended effect on any one or more target, gene, or cellular transcript.

As used herein, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "effective amount" of an agent is that amount sufficient to effect beneficial or desired results, for example, clinical results, and, as such, an "effective amount" depends upon the context in which it is being applied. For example, in the context of administering an agent that treats ALS, an effective amount of an agent is, for example, an amount sufficient to achieve treatment, as defined herein, of ALS, as compared to the response obtained without administration of the agent.

As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates such as chimpanzees and other apes and monkey species, and humans) and/or plants.

As used herein, the term "preventing" or "prevention" refers to delaying or forestalling the onset, development or progression of a condition or disease for a period of time, including weeks, months, or years.

The term "treatment" or "treating", as used herein, refers to the application of one or more specific procedures used for the cure or amelioration of a disease. In certain embodiments, the specific procedure is the administration of one or more pharmaceutical agents. In the context of the present invention, the specific procedure is the administration of one or more siRNA duplexes or dsRNA targeting SOD1 gene.

As used herein, the term "amelioration" or "ameliorating" refers to a lessening of severity of at least one indicator of a condition or disease. For example, in the context of neurodegeneration disorder, amelioration includes the reduction of neuron loss.

As used herein, the term "administering" refers to providing a pharmaceutical agent or composition to a subject.

As used herein, the term "neurodegeneration" refers to a pathologic state which results in neural cell death. A large number of neurological disorders share neurodegeneration as a common pathological state. For example, Alzheimer's disease, Parkinson's disease, Huntington's disease, and amyotrophic lateral sclerosis (ALS) all cause chronic neurodegeneration, which is characterized by a slow, progressive neural cell death over a period of several years, whereas acute neurodegeneration is characterized by a sudden onset of neural cell death as a result of ischemia, such as stroke, or trauma, such as traumatic brain injury, or as a result of axonal transection by demyelination or trauma caused, for example, by spinal cord injury or multiple sclerosis. In some neurological disorders, mainly one type of neuron cells is degenerating, for example, motor neuron degeneration in ALS.

EXAMPLES

Example 1. SOD1 Targeting Polynucleotide Design (siRNA)

siRNA design is carried out to identify siRNAs targeting human SOD1 gene. The design uses the SOD1 transcripts from human (NCBI Reference Sequence NM_000454.4; SEQ ID NO: 1), cynomolgus monkey (NCBI Reference Sequence NM_001285406.1; (SEQ ID NO: 2), rhesus monkey (NCBI Reference Sequence NM_001032804.1; SEQ ID NO: 2), and *canis lupus familiaris* (NCBI Reference Sequence NM_0013035; SEQ ID NO: 4), respectively (Table 10). The siRNA duplexes are designed with 100% identity to the human SOD1 transcript for positions 2-18 of the antisense strand, and partial or 100% identity to the non-human primate SOD1 transcript for positions 2-18 of the antisense strand. In all siRNA duplexes, position 1 of the antisense strand is engineered to a U and position 19 of the sense strand was engineered to a C, in order to unpair the duplex at this position.

TABLE 10

SOD1 gene sequences

| SOD1 transcripts | Access No. | SEQ ID NO. | Sequence |
|---|---|---|---|
| Human SOD1 cDNA (981 bp) | NM_000454.4 | 1 | GTTTGGGGCCAGAGTGGGCGAGGCGCGGAGGTCTGGCC TATAAAGTAGTCGCGGAGACGGGGTGCTGGTTTGCGTCG TAGTCTCCTGCAGCGTCTGGGGTTTCCGTTGCAGTCCTCG GAACCAGGACCTCGGCGTGGCCTAGCGAGTTATGGCGA CGAAGGCCGTGTGCGTGCTGAAGGGCGACGGCCCAGTG CAGGGCATCATCAATTTCGAGCAGAAGGAAAGTAATGG ACCAGTGAAGGTGTGGGGAAGCATTAAAGGACTGACTG AAGGCCTGCATGGATTCCATGTTCATGAGTTTGGAGATA ATACAGCAGGCTGTACCAGTGCAGGTCCTCACTTTAATC CTCTATCCAGAAAACACGGTGGGCCAAAGGATGAAGAG |

TABLE 10-continued

SOD1 gene sequences

| SOD1 transcripts | Access No. | SEQ ID NO. | Sequence |
|---|---|---|---|
| | | | AGGCATGTTGGAGACTTGGGCAATGTGACTGCTGACAA<br>AGATGGTGTGGCCGATGTGTCTATTGAAGATTCTGTGAT<br>CTCACTCTCAGGAGACCATTGCATCATTGGCCGCACACT<br>GGTGGTCCATGAAAAAGCAGATGACTTGGGCAAAGGTG<br>GAAATGAAGAAAGTACAAAGACAGGAAACGCTGGAAGT<br>CGTTTGGCTTGTGGTGTAATTGGGATCGCCCAATAAACA<br>TTCCCTTGGATGTAGTCTGAGGCCCCTTAACTCATCTGTT<br>ATCCTGCTAGCTGTAGAAATGTATCCTGATAAACATTAA<br>ACACTGTAATCTTAAAAGTGTAATTGTGTGACTTTTTCA<br>GAGTTGCTTTAAAGTACCTGTAGTGAGAAACTGATTTAT<br>GATCACTTGGAAGATTTGTATAGTTTTATAAAACTCAGT<br>TAAAATGTCTGTTTCAATGACCTGTATTTTGCCAGACTTA<br>AATCACAGATGGGTATTAAACTTGTCAGAATTTCTTTGT<br>CATTCAAGCCTGTGAATAAAAACCCTGTATGGCACTTAT<br>TATGAGGCTATTAAAAGAATCCAAATTCAAACTAAAAA<br>AAAAAAAAAAAA |
| cynomolgus SOD1 cDNA (465 bp) | NM_001285406.1 | 2 | ATGGCGATGAAGGCCGTGTGCGTGTTGAAGGGCGACAG<br>CCCAGTGCAGGGCACCATCAATTTCGAGCAGAAGGAAA<br>GTAATGGACCAGTGAAGGTGTGGGGAAGCATTACAGGA<br>TTGACTGAAGGCCTGCATGGATTCCATGTTCATCAGTTT<br>GGAGATAATACACAAGGCTGTACCAGTGCAGGTCCTCA<br>CTTTAATCCTCTATCCAGACAACACGGTGGGCCAAAGGA<br>TGAAGAGAGGCATGTTGGAGACCTGGGCAATGTGACTG<br>CTGGCAAAGATGGTGTGGCCAAGGTGTCTTTCGAAGATT<br>CTGTGATCTCGCTCTCAGGAGACCATTCCATCATTGGCC<br>GCACATTGGTGGTCCATGAAAAAGCAGATGACTTGGGC<br>AAAGGTGGAAATGAAGAAAGTAAAAAGACAGGAAACG<br>CTGGAGGTCGTCTGGCTTGTGGTGTAATTGGGATCGCCC<br>AATAA |
| rhesus SOD1 cDNA (465 bp) | NM_001032804.1 | 2 | ATGGCGATGAAGGCCGTGTGCGTGTTGAAGGGCGACAG<br>CCCAGTGCAGGGCACCATCAATTTCGAGCAGAAGGAAA<br>GTAATGGACCAGTGAAGGTGTGGGGAAGCATTACAGGA<br>TTGACTGAAGGCCTGCATGGATTCCATGTTCATCAGTTT<br>GGAGATAATACACAAGGCTGTACCAGTGCAGGTCCTCA<br>CTTTAATCCTCTATCCAGACAACACGGTGGGCCAAAGGA<br>TGAAGAGAGGCATGTTGGAGACCTGGGCAATGTGACTG<br>CTGGCAAAGATGGTGTGGCCAAGGTGTCTTTCGAAGATT<br>CTGTGATCTCGCTCTCAGGAGACCATTCCATCATTGGCC<br>GCACATTGGTGGTCCATGAAAAAGCAGATGACTTGGGC<br>AAAGGTGGAAATGAAGAAAGTAAAAAGACAGGAAACG<br>CTGGAGGTCGTCTGGCTTGTGGTGTAATTGGGATCGCCC<br>AATAA |
| Canis lupus familiaris SOD1 cDNA (474 bp) | NM_001003035 (GI: 50978673) | 4 | CGAGTCATGGAGATGAAGGCCGTGTGCGTGTTGAAGGG<br>CCAGGGCCCGGTGGAGGGCACCATCCACTTCGTGCAGA<br>AGGGAAGTGGGCCTGTTGTGGTATCAGGAACCATTACA<br>GGGCTGACTGAAGGCGAGCATGGATTCCACGTCCATCA<br>GTTTGAAGATAANACACAAGGCTGTACTAGTGCAGGTCC<br>TCACTTTAATCCTCTGTCCAAAAAACATGGTGGGCCAAA<br>AGATCAAGAGAGGCATGTTGGAGACCTGGGCAATGTGA<br>CTGCTGGCAAGGATGGCGTGGCCATTGTGTCCATAGAAG<br>ATTCTCTGATTGCACTCTCAGGAGACTATTCCATCATTGG<br>CCGCACCATGGTGGTCCACGAGAAACGAGATGACTTGG<br>GCAAAGGTGACAATGAAGAAAGTACACAGACAGGAAAC<br>GCCGGGAGTCGTTTGGCTTGTGGTGTCATTGGGATCGCC<br>CAATAAACATTC |

Example 2. ALS Animal Model

Dogs can be used to study the efficacy of AAV gene therapy targeting SOD1 for the treatment of ALS. Canine degenerative myelopathy (DM) is an ideal disease model as a naturally-occurring SOD1 mutation (E40K) is causative for canine DM, dogs have relatively large spinal cord/brain, DM-affected dogs have a homogenous pattern of disease progression and histopathologic findings and functional deficits in DM share similarities to some forms of upper motor neuron onset of human ALS (Awano et al. Genome-wide association analysis reveals a SOD1 mutation in canine degenerative myelopathy that resembles amyotrophic lateral sclerosis; PNAS February 2009; 106(8); 2794-2799, the contents of which are herein incorporated by reference in its entirety).

Canine DM is a naturally-occurring, adult-onset, progressive disease that, like ALS, leads to paralysis and death (Averill, D J. Degenerative myelopathy in the aging German Shepherd dog: clinical and pathologic findings. J Am Vet Med Assoc 1973; 162:1045-1051; the contents of which is herein incorporated by reference in its entirety). The earliest clinical signs begin when the dog is 8 years or older. DM affects many dog breeds with an overall prevalence of 0.19%

Disease onset and clinical progression are homogeneous across all breeds, representing degeneration of the sensory and upper and lower motor neurons. Clinical presentation has been categorized into four clinical disease stages (Coates J R, Wininger F A. Canine degenerative myelopathy. Vet Clin North Am Small Anim Pract 2010; 40:929-950 and Kanazono S, Pithua P, Johnson G C, et al. Clinical progression of canine degenerative myelopathy. 2013 American College of Veterinary Internal Medicine Annual Forum. Seattle, Wash. Jun. 16-18, 2013. J Vet Int Med 2013; 24(3):699; the contents of each of which are herein incorporated by reference in their entireties). Clinical signs emerge as an asymmetric spastic paraparesis and general proprioceptive ataxia (Stage I), progressing to non-ambulatory paraparesis/paraplegia with pelvic limb lower motor neuron signs within 1 year from disease onset (Stage II). Dog owners often elect euthanasia when their dog becomes nonambulatory in the pelvic limbs. Neurologic deficits progress to include thoracic limb weakness (Stage III) followed by flaccid tetraplegia, generalized muscle atrophy and brainstem dysfunction (Stage IV).

The pathologic features of DM are similar to those of ALS, including axonal loss, secondary demyelination and astroglial proliferation (sclerosis), that are most severe in the dorsal portion of the lateral funiculus and in the dorsal columns of the middle to lower thoracic region. Because owners of companion dogs with DM have their pets euthanized at different stages of disease progression, it is possible to study the disease at all stages of progression by examining tissues from these dogs collected at the time of euthanasia, and thereby gain a better understanding of the chronological relationships between the pathologies that develop in the spinal cord, peripheral nerves, and muscles. Significant sensory neuron degeneration also precedes any evidence of motor neuron pathology. Thus, the distribution of lesions and clinical disease progression in DM are similar to that reported for the UMN-onset ALS, with UMN signs in DM-affected dogs progressing later to LMN signs.

Preliminary data have shown that the median period for disease progression from Stage 1 (ambulatory, onset of signs) to 2 (nonambulatory) is 10 months (95% CI, 9 to 12 months) (Kanazono S, Pithua P, Johnson G C, et al. Clinical progression of canine degenerative myelopathy. 2013 American College of Veterinary Internal Medicine Annual Forum. Seattle, Wash. Jun. 16-18, 2013. J Vet Int Med 2013; 24(3):699; the contents of which is herein incorporated by reference in its entireties). There was no significant difference in time for transition from Stage 1 to 2 amongst different breeds. Thus, the homogeneous disease progression of DM will facilitate longitudinal measures and detection of therapeutic efficacy. When translating therapies for ALS from animals to humans or vice versa, sensitive and objective disease markers shared across species are necessary to diagnose and monitor disease progression so that therapeutic efficacy can be accurately.

Any of the AAVs targeting SOD1 described herein may be studied using the canine DM model.

Example 3. Methods for Measuring Canine DM

Overview

Reliable methods for measuring progression of damage to upper (brain and spinal cord) and lower (muscle and nerve) motor neurons will provide early diagnosis of DM, determine the contribution of the lesion to the clinical syndrome and serve as objective functional measures or biomarkers of disease progression in treatment trials. Moreover, these techniques could offer an outcome assessment for monitoring disease progression in therapeutic trials that parallel those in ALS patients. Our studies will evaluate IT delivered AAV.iSOD1 to slow disease progression. Significant differences in longitudinal disease between treated and nontreated groups would provide quantifiable measures of LMN and UMN preservation in DM affected dogs. Below is a brief summary of functional disease marker studies in canine DM for longitudinal monitoring of progression.

Neurofilament Proteins (NFs)

Neurofilament proteins (NFs) are the most abundant cytoskeletal proteins of myelinated axons, outnumbering microtubules 5 to 10-fold. NFs are obligate heteropolymers of neurofilament light (NF-L), medium (NF-M) and heavy (NF-H) proteins. In vivo NFs are required for the large increase in axonal diameter that occurs concomitantly with myelination. NF-L and NF-H levels in blood and CSF have been assayed as biomarkers in a variety of diseases. Specifically, for human ALS, assays for NFs in blood and CSF have focused on phosphorylated forms of NF-H (pNF-H)). pNF-H levels in CSF isolated from confirmed cases of ALS were inversely correlated with survival suggesting that pNF-H is a reliable marker of disease stage. Moreover, disease progression in ALS involves defined trajectories of longitudinally evaluated plasma NF-H levels, reflecting speed of neurological decline and survival.

Frozen serum and CSF samples are thawed and diluted threefold with a dilution buffer. The assay for pNF-H is performed according to Dr. Shaw's laboratory protocol with a commercial ELISA kit using human pNF-H antibody (BioVendor Research and Diagnostic Products, Modrice, Czech Republic); the standard curve is constructed by plotting mean absorbance of the standards against known concentrations on a logarithmic scale.

CSF and blood pNF-H should be reliable biomarkers of DM in dogs and can be used as minimally invasive, longitudinal measures of AAV-iSOD1 pharmacodynamics.

Magnetic Resonance Imaging (MRI)

Advanced Magnetic resonance imaging (MRI) including diffusion tensor imaging (DTI) and proton magnetic resonance spectroscopy (MRS) have potential as techniques for quantitative assessment of the UMN system in the analysis of ALS. DTI is able to characterize the diffusion properties of water molecules in vivo. DTI can quantitate the diffusion anisotropy in local microstructures in vivo by fractional anisotropy. Two DTI-based scalar indices have often been used to characterize microstructure of the local brain tissue: apparent diffusion coefficient (ADC) and fractional anisotropy (FA). ADC is a measure of the directionally averaged magnitude of diffusion and is related to the integrity of the local brain tissue. FA represents the degree of diffusion anisotropy and reflects the degree of alignment of cellular structures. It has been suggested that a reduction in anisotropy can reflect axonal fiber degeneration and myelin breakdown in both the peripheral and central nervous systems. It has been previously reported that reduced anisotropy is seen in the corticospinal tract (CST) and corpus callosum of patients with ALS, occurs early in the disease course, and relates to disease severity. The CST degeneration as a pathologic hallmark of ALS parallels the lateral funicular degeneration seen in DM-affected dogs. The lateral and dorsal funicular degeneration parallel the dorsal root ganglion degeneration (i.e., spinocerebellar tract degeneration) (March P A, Coates J R, Abyad R, et al. Degenerative Myelopathy in 18 Pembroke Welsh Corgi Dogs. Vet Pathol 2009; 241-250; the contents of which are herein incorporated by reference in its entirety).

MRS allows for measurement of the neurochemical profile of a particular region of the brain in vivo, and typically relies on the measurement of N-acetyl compound resonance (predominantly N-acetylaspartate (NAA)) a marker of neuronal integrity, expressed as the ratio of NAA to creatine (Cr). Several studies have demonstrated a decrease in NAA and NAA/Cr ratios at the level of the motor cortex of patients with ALS (Pioro E P, Majors A W, Mitsumoto H, et al. H-MRS evidence of neurodegeneration and excess glutamate+glutamine in ALS medulla. Neurology 1999; 53:71-79 and Rooney W D, Miller R G, Gelinas D, et al. Decreased N-acetylaspartate in motor cortex and corticospinal tract in ALS. Neurology 1998; 50:1800-1805; the contents of each of which are herein incorporated by reference in its entirety). While DM is predominantly thought to be a spinal cord disease, its otherwise strong resemblance to ALS merits investigation into the presence of the neurochemical changes that may be also occurring in the brain. It is possible that these neurochemical changes are present in the absence of other microstructural changes identifiable on histopathology.

MRI may be used to study the effects of IT administration of AAV-iSO1 including the differences between treated and nontreated DM affected dogs in dampening the decreased level of anisotropy on DTI and a decreased level of NAA in CNS regions of interests.

Motor Unit Number Estimation (MUNE)

Motor unit number estimation (MUNE), is a non-invasive electrophysiologic technique for quantifying loss of LMNs or motor units. MUNE has been used to demonstrate loss of LMN function prior to the onset of clinical signs and as a predictor of progression in ALS. MUNE is determined by dividing the supramaximal compound muscle action potential (CMAP) by the average single motor unit potential (SMUP) (McComas A J, Fawcett P R, Campbell M J, Sica R E P. Electrophysiological estimation of the number of motor units within a human muscle. J Neurol Neurosurg Psychiatry 1971; 34:121-131; the contents of which are herein incorporated by reference in its entirety). Negative peak area or amplitude may be used to calculate SMUP and CMAP. The calculation results in a unitless number that estimates the number of motor axons innervating that muscle group. Studies have shown that a decrease in the MUNE counts correlates well with disease progression in ALS patients (Shefner J M, Cudkowicz M E, Zhang H, et al. The use of statistical MUNE in a multicenter clinical trial. Muscle Nerve 2004; 30:463-469; the contents of which is herein incorporated by reference in its entirety). The value in longitudinal monitoring of patients with early signs of ALS is its rate of change over time, thus may require sequential measurements. MUNE techniques differ in how the average SMUP is obtained. In modified incremental stimulation, the stimulating electrode remains in the same position and applies graded electrical stimuli to a peripheral nerve to obtain sequential incremental evoked potentials (McComas et al., 1971). A modified incremental stimulation MUNE technique for the extensor digitorum brevis muscle may be used in a longitudinal study in DM-affected dogs. Utilizing MUNE in canine DM with other clinical criteria in a dynamic study of DM will provide sensitive and specific measures (markers) not only of disease progression of the LMN but also of response to therapy that parallels a surrogate marker utilized in ALS patients.

Semi-Quantitative Locomotor Scale

Semi-quantitative procedures may score the function of an animal along an ordinal locomotor rating scale. Olby et al. adapted the BBB scale, an expanded locomotor scale used in rodents (Olby N J, De Risio L, Munana K R et al. Development of a functional scoring system in dogs with acute spinal cord injuries. Am J Vet Res. 2001; 62:1624-1628; the contents of which is herein incorporated by reference in its entirety). The scale was validated to evaluate for recovery of pelvic limb and tail functions (motor and sensory) in paralyzed dogs after acute spinal cord injury (Olby N J, Harris T, Burr J et al. Recovery of pelvic limb function in dogs following acute intervertebral disc herniations. J Neurotrauma. 2004; 21:49-59; the contents of which are herein incorporated by reference in its entirety). Recovery was divided into 14 different grades. The Olby Locomotor Rating Scale can be modified in order to evaluate the ambulatory status in DM affected dogs. For intraobserver reliability, the videos were reviewed by 5 observers who scored the segments 3 times each over a period of 2 weeks with at least 48 hours in between repeat observations. The mean and SD of the scores allocated for each dog were used to calculate the intraobserver and interobserver coefficient of variabilities by using Fleiss Kappa-statistics. There was moderate agreement for ratings into categories 1 and 2, and substantial agreement in categories 3 to 5 [bias corrected value: Kappa (95% CI)=0.670 (0.53-0.796)]. This modified locomotor rating scale will serve to longitudinally evaluate the gait from ambulatory (Stage 1) to nonambulatory status (Stage 2) in a more sensitive manner. This rating scale can be used to more finely monitor severity of ambulation e.g. a score of 9 equates to the time point of 10 months when dogs become nonambulatory.

Electrical Impedance Myography (EIM)

Electrical impedance myography (EIM) is a non-invasive electrophysiological technique of measuring localized tissue impedance. All impedance methods rely upon the basic principle that if an alternating current of high frequency and low-intensity is applied to a substance, energy will be dissipated as it travels through it, thus producing a measurable voltage. Therefore, electrical impedance can be used to measure the effect of tissue on the applied current. Impedance can be described mathematically based on Ohm's law $V_{voltage} = I_{current} \times R_{resistance}$ or $V = I \times Z$, where Z represents the complex impedance of the circuit, a combination of its inherent resistance and its reactance (X); the latter is the obstruction to current flow produced by the presence of capacitors and/or inductors in the circuit. Skeletal muscle possesses a unique feature of strong anisotropy or directional dependence on current flow. Myocytes are cylindrical, which allow for current to readily flow across with different impedance values depending on the direction of the current. The lipid bilayers of the myocyte membrane act as the capacitors, the source of the reactance (X), and the intra- and extracellular fluids act as the resistors, the source of its resistance (R). The major EIM outcome variable is the phase angle ($\Theta$), using the relationship $\Theta = \arctan(X/R)$. Measurements are taken using multiple electrodes spanning the region of interest or spatially averaged value $\Theta_{avg}$, a principal outcome value/variable.

In diseased muscle, changes in structure and composition will be reflected in alterations in the localized impedance of the muscle. Diseased muscle can be manifested by atrophy of myofibers, increased endomysial connective tissue and fat, and edema; all can influence resistance and reactance. Based largely on the postmortem examination of tissues from ALS and DM patients, it is widely believed that the muscle atrophy characteristic of ALS is secondary to degeneration of motor neurons. However, muscle atrophy may be occurring to a large extent independently of and even prior to motor neuron degeneration in both ALS and DM. For identifying patterns of disease change, EIM parameters can serve as markers of disease progression and outcome measures. Lower $\ominus_{avg}$ values reflect more serious disease based on studies of radiculopathy and inflammatory myopathy. Long-term studies of ALS patients and transgenic ALS rats have shown a steady decline in $\ominus_{avg}$ values (Wang L L, Spieker A J, Li J, Rutkove S B. Electrical impedance myography for monitoring motor neuron loss in the SOD1 G93A amyotrophic lateral sclerosis rat. Clin Neurophysiol. 2011 December; 122(12):2505-11; Tarulli A W, Garmirian L P, Fogerson P M, Rutkove S B. Localized muscle impedance abnormalities in amyotrophic lateral sclerosis. J Clin Neuromuscul Dis. 2009; 10(3):90-6; the contents of each of which are herein incorporated by reference in its entirety), and correlation with survival and other conventional measures, i.e. forced vital capacity and ALS Functional Rating Scale. Currently such data on the use of EIM is lacking in DM-affected dogs. Application of EIM has a major advantage in that it is easily performed in awake animals, whereas most other diagnostic markers discussed thus far require general anesthesia. Dogs affected with DM should have changes in EIM values similar to human ALS patients, and that treatment with AAV.iSOD1 will impact these values.

Example 4. Targeting SOD1 for the Treatment of ALS

Overview

AAV gene therapy targeting SOD1 for the treatment of ALS will be studied using the gene therapy approach on canine degenerative myelopathy (DM) which is a naturally-occurring disease of companion dogs that is similar to some forms of ALS. The study will evaluate dosing paradigms in order to determine a homogenous distribution of gene transfer to target regions. Intrathecal (IT) administration of AAV has previously shown greater CNS distribution including prominent transduction of motor neurons, less peripheral tissue exposure and reduced immune responses than system dosing. The safety, pharmacology (including distribution) and efficacy of AAV gene therapy targeting SOD1 with IT administration in normal dogs and a naturally-occurring animal model of ALS, canine DM, can be evaluated.

Selection of Construct, Capsid and Dosing Paradigm

To identify an optimal RNAi sequence, 169 sequences selectively targeting SOD1 were designed, synthesized and tested in vitro in HeLa cells. At 100 pM approximately 25 sequences inhibited SOD1 mRNA by more than 80%.

Dosing

The AAV needs to be delivered with a dosing paradigm that provides a relatively homogenous distribution of gene transfer along the rostral-caudal axis of the CNS. This distribution should show a therapeutic translation to treat human ALS. Parameters such as volume, rate and duration of infusion can be varied in order to have the optimal distribution of transgene expression for the treatment of ALS.

Example 5. Pharmacology Study of AAV Targeting SOD1 in Normal Does

Dosing Regimen

AAV targeting SOD1 (AAV.iSOD1) is produced using triple transfection in HEK293 cells. The AAV.iSOD1 is tested prior to testing the dogs to ensure it is pharmacologically active in vivo by assessing SOD1 suppression in hSOD1 transgenic mice (Tg(SOD1)3Cje/J; The Jackson Laboratory) after direct CNS administration.

Up to approximately 80 male mongrel dogs (Marshall BioResources, North Rose, N.Y., USA) will be screened for pre-existing immunity to the AAV capsid by evaluating serum samples in an in vitro neutralizing antibody assay. Animals with antibody titers of <1:10 will be candidates for the study. 16 male mongrel dogs (including 2 alternates) will be surgically implanted with catheters. Dogs will be divided into four treatment groups and administered with AAV.iSOD1 or vehicle by IT dosing as shown in Table 11. The site will be either lumbar or cerebellomedullary cistern.

TABLE 11

Study Design

| Group # | Test Article | Rate | Dose (vg) | Conc. (vg/ml) | Volume (ml) | No. of animals | Day of Necropsy |
|---|---|---|---|---|---|---|---|
| 1 | AAV.iSOD1 | Infusion - rate TBD | $3 \times 10^{13}$ | $1 \times 10^{13}$ | 3 | 4 | D 28 |
| 2 | AAV.iSOD1 | Bolus (1 mL/minute) | $3 \times 10^{13}$ | $1 \times 10^{13}$ | 3 | 4 | D 28 |
| 3 | AAV.iSOD1 | Infusion - rate TBD | $1 \times 10^{14}$ | $1 \times 10^{13}$ | 10 | 4 | D 28 |
| 4 | Vehicle | Infusion to match groups 1 and 3 | 0 | 0 | 3 | 2 | D 28 |

After a pre-determined interval the dogs will be evaluated for clinical observations, body weight, functional observational batteries, neurological examinations, clinical pathology, organ weights, gross pathology, histopathology (H&E, expanded neuropathy panel), distribution of SOD1 suppression and vector genomes in spinal cord and other tissues and potential biomarkers in CSF.

Safety and Pharmacology

Male Mongrel dogs (Marshall BioResources, North Rose, N.Y., USA) weighing 15-30 kg at the time of injection will be used. After dosing, each dog will be monitored for changes in general appearance and behavior. Animals will be observed at least twice daily for morbidity and mortality beginning on the first day of dosing. Clinical signs will be recorded at least twice daily post-surgery throughout the study period. Any animal(s) determined to be moribund during the study period will be sacrificed. A comprehensive neurological examination will be performed weekly. Body weights will be recorded on all animals prior to surgery, on the day of surgery, weekly during the study and at necropsy. Food consumption will be collected daily beginning prior to surgery and continuing throughout the treatment period.

Blood and urine samples will be collected from fasted animals for clinical pathology (pre-dose on Day 1, Day 3 and just prior to necropsy on Day 28), serum antibody analysis (pre-dose on Day 1, Day 3 and just prior to necropsy on Day 28) and cytokine analysis (pre-dose on Day 1 and just prior to necropsy on Day 28). CSF samples will be collected just prior to dosing and on Day 28 for antibody analysis and potential biomarker assays. Four weeks after AAV administration, all animals will be euthanized and perfused with saline followed by collection of tissues including brain, spinal cord, dorsal root ganglion, liver, heart, spleen, kidney, and other organs. Organ weight and gross pathology will be recorded.

At the time of euthanasia, the brain will be cut in a brain matrix at 3 mm coronal slice thickness. The left hemisphere brain slices will be snap-frozen and stored at −60° C. or below until shipment. The spinal cord will be cut into approximately 25 segments including cervical, thoracic, lumbar and sacral segments. Selected segments will be snap-frozen and stored at −60° C. or below until shipment. Spinal nerve roots and dorsal root ganglia (DRG) will also be collected. The right hemisphere brain slices and selected spinal cord segments (e.g. C1, C7, T8 and L6/7) and pairs of DRGs with spinal nerves corresponding to C1, C7, T8, L6 and S2 will be immersion fixed in chilled 4% paraformaldehyde (PFA) and kept at 1-8° C. for 72 hours with agitation. Tissues will then be transferred to 30% sucrose in 0.1M phosphate buffered saline and refrigerated (2-8° C.) until shipment. Fresh frozen tissues will be used for analyses that may include quantification of vector genomes, mRNA and/or transgene expression. Post-fixed tissues will be used for histopathology including hematoxylin and eosin (H&E) staining, and an expanded neuropathology panel.

Clinical Pathology

Clinical pathology will be conducted will include hematology, serum biochemistry, CSF analysis, urinalysis and coagulation evaluation. Although any parameters outside of reference range will be noted, mean hepatic enzymes ALT, GGT and ALP, indexes of hepatic function (albumin, glucose, cholesterol, bilirubin, blood urea nitrogen (BUN)), and creatine will be compared statistically using ANOVA. If any hepatic enzyme is outside of laboratory-established reference range, fasting blood ammonia concentration will be assayed to evaluate liver function in that dog. In addition to BUN and creatinine, urine specific gravity, urine protein and urine casts will be used to evaluate renal function. If proteinuria is detected at greater than trace amounts, protein:creatine ratio will be performed. Prothrombin time, partial thromboplastin time and buccal mucosal bleeding time will be evaluated for coagulation abnormality. The CSF will be evaluated for protein concentration, cellularity and cell type.

Antibody Analysis

Analysis of serum and CSF for neutralizing antibodies will be performed using an in vitro cell-based assay to assess the serum or CSF sample for functional inhibition of transduction by AAV using a reporter.

Cytokine Analysis

Cytokine analysis of blood and CSF will be performed using canine specific assays. Cytokines that will be evaluated include IL-1 beta, IL-1RA, IL-6, IFN-gamma, and TNF-alpha.

Histological Procedures

Histological procedures and evaluation will be performed. The spinal cord and other tissue samples will be will be trimmed, embedded in paraffin, and sectioned (approximately 5 microns), and stained with H&E and an expanded neuropathology panel. H&E staining will be used for evaluating general histopathological changes, while Fluoro-Jade B and immunohistochemistry for cell-type specific markers (e.g. NeuN, GFAP, Iba1) will be used for assessing neuropathological changes.

SOD1 mRNA Quantitation

SOD1 suppression in spinal cord, DRG and other tissue samples will be assessed using quantitative RT-PCR to measure mRNA levels. Briefly, mRNA levels of SOD1, and endogenous GAPDH and/or beta-actin mRNA will be determined by qRT-PCR, using standard methods. The mean level of SOD1 mRNA will be normalized to the mean level of endogenous control mRNA for each sample. Samples will include cross-sections of spinal cord and whole DRG, as well as motor neurons, astrocytes and large sensory neurons identified by morphology and immunohistochemical markers such as choline acetyltransferase, GFAP and parvalbumin, respectively, and then collected by laser capture microdissection.

SOD1 Protein Assay

SOD1 suppression in spinal cord and other tissue samples will be assessed using Western blot analysis. Standard methods will be employed.

Vector Genome Quantitation

Vector genomes in spinal cord and other tissue samples will be assessed using quantitative PCR. Briefly, the copies of vector genomes and host diploid genomes will be determined by quantitative PCR, using standard methods. The mean level of the copies of vector genomes will be normalized to the copies of host diploid genomes for each sample.

Biomarker Assays

Biomarkers may be evaluated in CSF samples. For subsequent isolation of CSF exosomes, samples will be processed by centrifugation and filtration immediately following collection, and then snap-frozen and stored at −60° C. or below until shipment.

Example 6. Efficacy Study of AAV Targeting SOD1 in DM-Affected Dogs

Selection of Animals for Study

DM-affected companion dogs (n=20) in early Stage 1 of DM based on signs of mild general proprioceptive ataxia will be selected for the study. Diagnosis of DM will be based on clinical signs, normal MRI of the entire spinal cord and CSF analysis, lack of electrophysiologic abnormalities and homozygosity for the SOD1:c.118A allele. Dogs will also be screened for other major physical diseases.

Dosing Regimen

AAV targeting SOD1 (AAV.iSOD1) is produced by either the baculo/Sf9 system or triple transfection in HEK293 cell methods. The AAV.iSOD1 is tested prior to testing in the dogs to ensure it is pharmacologically active in vivo by assessing SOD1 suppression in hSOD1 transgenic mic (Tg (SOD1)3Cje/J; The Jackson Laboratory) after direct CNS administration.

DM-affected dogs will be screened for pre-existing immunity to the AAV capsid by evaluating serum samples in an in vitro neutralizing antibody assay. Animals with antibody titers of <1:10 will be candidates for the study. Dogs will be divided into two treatment groups and administered either AAV.iSOD1 or vehicle using an IT dosing paradigm (rate, dose and volume) that was shown to be safe and pharmacologically active in the normal dog study (See Example 5). Table 12 shows the study design for the DM-affected dogs. The site will be either lumbar or cerebellomedullary cistern.

TABLE 12

Study Design

| Group # | Test Article | Rate | Dose (vg) | Conc. (vg/ml) | Volume (ml) | No. of animals |
|---|---|---|---|---|---|---|
| 1 | AAV.iSOD1 | TBD | TBD | $1 \times 10^{13}$ | TBD | 15 |
| 2 | Vehicle | TBD | 0 | 0 | TBD | 5 |

After a pre-determined interval, the dogs will be evaluated for neurologic deficits, time from onset of clinical signs to non-ambulatory paraparesis, gait grading scale, nerve conduction studies, electromyography, motor unit number estimation (MUNE), electrical impedance myography (EIM), magnetic resonance imaging (MRI), clinicopathology studies, potential CSF biomarkers, and histopathology.

Monitoring of DM-Affected Dogs

The animals will be evaluated 2 to 3 months (baseline and up to 4 times) for physical and neurologic examinations, bloodwork, CSF sampling and urinalysis, and for longitudinal assessments and every month the gait of the animal will be reviewed. Times for assessments are outlined in Table 13 below:

TABLE 13

Assessments

| Disease Measure | Baseline | 3 months | 6 months | 9 months | 11 months |
|---|---|---|---|---|---|
| pNF-H | X | X | X | X | X |
| DTI/MRS | X | — | X | — | X |
| Electrodiagnostic MUNE | X | X | X | X | X |
| EIM | X | X | X | X | X |

Monitoring Gait and Neurologic Outcome

Disease progression will be monitored from Stage 1 (ambulatory, onset of signs) to 2 (nonambulatory). Nontreated DM-affected dogs will likely progress from Stage 1 to Stage 2 by 10 months (95% CI, 9-12). The Kaplan-Meier (KM) plots will be used to track the progression of DM across the cohort, and possibly the proportion of cohort transitioning from DM Stage 1 to 2. Therefore, proportion (and the associated one-sided 95% CI) of dogs not progressing to Stage 2 will be calculated. The gait of dogs between disease Stages 1 and 2 will be video-taped and graded by 2 experienced observers using the modified Olby Locomotor Rating Scale. Still dogs will be monitored during their entire disease course until euthanasia.

pNF-H pNF-H will be monitored in the serum and CSF of the treated and nontreated DM-affected dogs. Serum and CSF samples will be collected at the designated times and at the time of euthanasia. All samples will be batched and sent to EnCor (Gainesville, Fla.) for assay and analysis. Comparisons between treatment groups will be made by repeated measures ANOVA followed by Holm-Sidak pairwise comparisons.

Cytokine Analysis

Cytokine analysis of blood and CSF will be performed using canine specific assays. Cytokines that will be evaluated include IL-1β, IL-1RA, IL-6, IFN-γ, and TNF-α.

DTI and MRS

At 3 time points MRIs will be performed on AAV.iSOD1 treated dogs. All MRI studies of the brain will be performed using a 3 Tesla Toshiba scanner with previously established canine parameters. DTI will be performed in 30 directions for superior resolution. In addition to standard 3D T1 anatomic imaging using an MPRAGE sequence, FA, ADC and color maps will be generated for data analysis. Single and multivoxel MRS acquisition will be performed on the brain of all dogs with previously established protocols, focusing on the thalamus, red nucleus and caudate nucleus as the regions of interest.

Descriptive statistics of mean, median and standard deviation for ADC, FA, NAA concentrations and NAA/Cr will be calculated. Differences between these values in the DM-affected versus unaffected dogs will be evaluated with a paired student's t test (P<0.05). Correlation coefficients will be established to compare MR values with disease severity.

Electrodiagnostic Testing and MUNE

Prospective electrodiagnostic evaluations will be performed at specified time points. Testing will be done using a Cadwell SIERRA-WAVE™ electrodiagnostic machine. Since disease onset is often asymmetric, the modified incremental stimulation MUNE technique of the EDB muscle will be applied to both pelvic limbs. Once sub-threshold level is established, stimulus increments will be applied until a different evoked potential is observed. 10 evoked potentials will be recorded and used as single motor unit potentials (SMUPs). Mean SMUP divided into supramaximal compound muscle action potential will yield MUNE. Two consecutive trials will be performed per session and averaged to decrease variability. Routine whole-body EMG and nerve conduction studies (including F waves) of the ulnar and sciatic-peroneal nerve will also be performed.

Frequency distribution plots will be generated to check the normality of MUNE data in DM-affected treated and nontreated dogs at disease Stages 1 and 2 and compared to age-matched normal dogs. Longitudinal declination of MUNE will be assessed for each limb. Raw data that are not normally distributed will be log transformed. Mean MUNE within each disease Stage (1-2) will be calculated and differences between groups (treated vs. nontreated dogs) and disease Stages (1-2) compared using 2-sample t tests. Bonferroni's adjustments will be applied to account for multiple comparisons of estimated MUNE averages between DM stages. Values of the means corresponding with each clinical stage will constitute the quantitative markers for disease progression in DM-affected dogs.

Electrical Impedance Myography (EDI)

EIM measurements by techniques will be performed as described in the art and as described in the protocol of the device (DF50 (Impedimed, Inc., San Diego Calif.)). The impedance measuring system consists of a multi-frequency lock-in amplifier coupled with a very low capacitance active probe providing data from 0.5-1000 kHz. Selected muscles will include the cranial tibialis and biceps femoris of the pelvic limb; the extensor carpi radialis and triceps of the thoracic limb; and tongue. Hair will be removed over overlying the area of interest for each limb muscles. To ensure similar positioning of voltage and current electrodes over the muscles of interest between evaluation times, a pinpoint tattoo will be applied as a reference point. Values obtained will include resistance (R) and reactance (X) from which the third parameter, phase (θ). Reactance-slope, phase-slope and the resistance log-slope will be calculated at different frequencies. The procedure will be performed at the designated time points and correlated with time at onset of signs to non-ambulatory status, gait scoring and MUNE values.

Frequency distribution plots will be generated to evaluate for normality of data. If raw data are not normally distributed, log transformation will be utilized to normalize the data. Thus, overall mean MUNE quantitative outcomes within each disease Stage (1-2) will be calculated and differences between disease Stages (1-2) and normal dogs using 2-sample t tests. Bonferroni's adjustments will be made to account for potential problems due to multiple comparisons of MUNE and EIM means between DM stages. EIM and MUNE data will be compared to each other and with time from onset of signs to non-ambulatory status and gait score. For all correlation analyses, Spearman rank correlations will be performed. Two-group comparisons will be made using the Mann-Whitney test. Statistical significance will be $p<0.05$. Power analysis will be performed at the conclusion of the experiment to determine the number of additional samples required for significance and group size for future studies. Dr. Rutkove will assist with data interpretation and statistical comparisons.

Example 7. In Vitro Study of Constructs Targeting Dog SOD1

A. Screen of siRNAs Targeting Dog SOD1

Seven siRNA constructs (10 nM) targeting dog SOD1 (dSOD1) and vehicle (negative control) were transfected in D-17 cells (ATCC cat #ATCC® CRL-1430™) or cf2Th cells (ATCC cat #ATCC® CRL-183™). The cell culture medium for both types of cells was DMEM/F-12 containing 2mMGlutaMAX™ supplement, 1×MEM non-essential amino acids solution, 10 mM HEPES and 10% FBS (all reagents from Life Technologies).

After 24 hours the cultures were harvested for measuring SOD1 and GAPDH mRNA by RT-qPCR. SOD1 mRNA levels were normalized to GAPDH mRNA levels, and then the normalized SOD1 mRNA levels were expressed relative to the vehicle (negative control) group. The relative SOD1 mRNA levels for both cell types after treatment with SOD1 siRNA (siSOD1) are shown in Table 14.

TABLE 14

Relative SOD1 mRNA level in D-17 and cf2Th cells after SOD1 siRNA construct transfection

| Duplex ID | Relative dSOD1 mRNA Level (% of vehicle) | |
|---|---|---|
| | D-17 | Cf2Th |
| D-4000 | 43 ± 8 | 43 ± 3 |
| D-4001 | 35 ± 4 | 40 ± 5 |
| D-4002 | 84 ± 3 | 100 ± 12 |
| D-4003 | 77 ± 8 | 87 ± 8 |
| D-4004 | 36 ± 3 | 40 ± 2 |
| D-4005 | 36 ± 1 | 49 ± 2 |
| D-4006 | 95 ± 8 | 100 ± 15 |
| Control | 100 ± 9 | 100 ± 10 |

Treatment with SOD1 siRNA constructs having the duplex ID D-4000, D-4001, D-4004, and D-4005 resulted in greater than 50% suppression of dSOD1 mRNA levels in both D-17 cells and cf2Th cells.

B. Pharmacological Evaluation of Self-Complimentary Vectors

For this study, self-complementary vectors encoding siRNA constructs targeting dog SOD1 (dSOD1) were packaged in AAV2. For this study, degenerative myelopathy (DM) dog primary brain astrocytes, DM dog primary spinal cord astrocytes, and D-17 cells (ATCC cat #ATCC® CRL-1430™) were used to test the constructs. The cell culture medium for D-17 cells was DMEM/F-12 containing 2 mM GlutaMAX supplement, 1×MEM non-essential amino acids solution, 10 mM HEPES and 10% FBS (all reagents from Life Technologies). The cell culture medium for primary astrocytes was AGM™ astrocyte growth medium (cat #: CC-3186, Lonza). Cells were plated into 96-well plates and infected with AAV2-dSOD1 miRNA vectors in triplicate ($1-2 \times 10^4$ cells/well in 200 ul cell culture medium).

Dog SOD1 and GAPDH mRNA were measured by RT-qPCR 48 hours after infection with the vectors. SOD1 mRNA levels were normalized to GAPDH mRNA levels, and then expressed relative to the negative control group.

Table 15 shows the relative dSOD1 mRNA levels in DM dog primary brain astrocytes, DM dog primary spinal cord astrocytes, and D-17 cells after infection with scAAV2-dSOD1 miR vectors at a MOI of $1 \times 10^5$.

TABLE 15

Relative SOD1 mRNA level after infection with scAAV2-dSOD1 miR vectors

| Construct | Relative dSOD1 mRNA Level (%) (Normalized to control) | | |
|---|---|---|---|
| | DM dog primary brain astrocytes | Dog primary spinal cord astrocytes | DM dog primary brain astrocytes |
| VOYSOD1mir104-788.2 | 18 ± 2 | 18 ± 1 | 12 ± 3 |
| VOYSOD1miR104-829 | 39 ± 6 | 34 ± 2 | 22 ± 3 |
| VOYSOD1miR104-789 | 31 ± 3 | 26 ± 3 | 11 ± 1 |
| VOYSOD1miR127-788.2 | 32 ± 2 | 22 ± 3 | 10 ± 2 |
| VOYSOD1miR104-830 | 26 ± 3 | 25 ± 4 | 9 ± 1 |
| VOYSOD1mir127-788 | 54 ± 0 | 40 ± 0 | 20 ± 0 |
| VOYSOD1miR127-829 | 68 ± 5 | 56 ± 2 | 41 ± 7 |
| VOYSOD1miR127-789 | 73 ± 9 | 45 ± 4 | 19 ± 2 |
| VOYSOD1miR127-830 | 60 ± 11 | 41 ± 2 | 20 ± 3 |

Treatment with constructs VOYSOD1mir104-788.2, VOYSOD1miR104-829, VOYSOD1miR104-789, VOYSOD1miR127-788.2, VOYSOD1miR104-830, and VOYSOD1mir127-788 packaged in AAV2 were effective in suppressing dSOD1 mRNA in all three cell types by at least 45%.

Table 16 shows the relative dSOD1 mRNA levels in DM dog primary spinal cord astrocytes after infection with scAAV2-dSOD1 miR vectors at different MOIs ($1 \times 10^2$, $1 \times 10^3$, $1 \times 10^4$, or $1 \times 10^5$), containing constructs VOYSOD1mir104-788.2, VOYSOD1miR104-789, VOYSOD1miR127-788.2, or VOYSOD1miR104-830. A control AAV2.eGFP vector was also evaluated at these MOIs.

TABLE 16

Relative SOD1 mRNA levels in DM dog primary spinal cord astrocytes after infection
with scAAV2-dSOD1 miR vectors or control vector (AAV2.eGFP) - dose-response Relative dSOD1 mRNA Level (%) (Normalized to control)

| MOI | VOYSOD1miR104-788.2 | VOYSOD1miR104-789 | VOYSOD1miR127-788.2 | VOYSOD1miR104-830 | eGFP |
|---|---|---|---|---|---|
| $1 \times 10^2$ | 61 ± 11 | 91 ± 5 | 86 ± 3 | 72 ± 3 | 105 ± 3 |
| $1 \times 10^3$ | 24 ± 2 | 32 ± 8 | 42 ± 6 | 33 ± 2 | 83 ± 2 |
| $1 \times 10^4$ | 16 ± 2 | 23 ± 4 | 22 ± 3 | 17 ± 2 | 110 ± 4 |
| $1 \times 10^5$ | 15 ± 3 | 21 ± 6 | 17 ± 4 | 19 ± 2 | 103 ± 6 |

C. Screen of SOD1 Constructs

Four siRNA constructs targeting dog SOD1 (D-4000, D-4007, D-4008, D-4002) were transfected in cf2Th cells (ATCC cat #ATCC® CRL-183) ($2 \times 10^4$ cells/well in 96-well plate, triplicate for each condition). The cell culture medium was DMEM/F-12 containing 2mMGlutaMAX™ supplement, 1×MEM non-essential amino acids solution, 10 mM HEPES and 10% FBS (all reagents from Life Technologies).

After 48 hours, the cultures were harvested for measuring SOD1 and GAPDH mRNA levels. dSOD1 mRNA levels were normalized to GAPDH mRNA levels, and then expressed relative to the negative control group. These relative dSOD1 mRNA levels are shown in Table 17.

TABLE 17

Relative SOD1 mRNA levels in cf2Th cells after transfection
of dog SOD1 siRNAs at different doses

| Dose of dog SOD1 siRNA (nM) | Relative dSOD1 mRNA Level (Fold) (Normalized to control) | | | |
|---|---|---|---|---|
| | D-4000 | D-4007 | D-4008 | D-4002 |
| 0 | 1.00 ± 0.11 | 1.01 ± 0.18 | 1.01 ± 0.12 | 1.00 ± 0.02 |
| 0.31 | 0.69 ± 0.07 | 0.83 ± 0.20 | 0.86 ± 0.06 | 0.93 ± 0.08 |
| 0.62 | 0.66 ± 0.09 | 0.63 ± 0.09 | 0.74 ± 0.04 | 0.73 ± 0.09 |
| 1.25 | 0.66 ± 0.13 | 0.70 ± 0.08 | 0.81 ± 0.06 | 0.78 ± 0.07 |
| 2.5 | 0.52 ± 0.07 | 0.48 ± 0.03 | 0.68 ± 0.09 | 0.72 ± 0.06 |
| 5 | 0.47 ± 0.04 | 0.57 ± 0.02 | 0.75 ± 0.07 | 0.75 ± 0.05 |
| 10 | 0.39 ± 0.02 | 0.45 ± 0.09 | 0.67 ± 0.04 | 0.74 ± 0.06 |
| 20 | 0.36 ± 0.02 | 0.43 ± 0.06 | 0.66 ± 0.05 | 0.7 ± 0.06 |

The transfection of D-4000, D-4007, D-4008 or D-4002 caused dose-dependent SOD1 silencing in cf2Th cells. D-4000 provided the maximum suppression of dSOD1 mRNA (~64% suppression).

Seven siRNA constructs targeting dog SOD1 (dSOD1) and a control were transfected (10 nM) into HEK293T, cf2Th, D-17, and dog primary spinal cord astrocyte cells. After 24 hours the cultures were harvested for measuring SOD1 mRNA levels. The relative dSOD1 mRNA levels are shown in Table 18.

TABLE 18

Relative SOD1 mRNA level

| | Relative dSOD1 mRNA Level (% of control) | | | |
|---|---|---|---|---|
| Duplex ID | HEK293T | cf2Th | D-17 | Dog primary spinal cord astrocytes |
| D-4000 | 12 ± 9 | 43 ± 3 | 43 ± 8 | 69 ± 8 |
| D-4001 | 7 ± 2 | 40 ± 5 | 35 ± 4 | 57 ± 3 |
| D-4002 | 12 ± 2 | 100 ± 12 | 84 ± 3 | 105 ± 15 |

TABLE 18-continued

Relative SOD1 mRNA level

| | Relative dSOD1 mRNA Level (% of control) | | | |
|---|---|---|---|---|
| Duplex ID | HEK293T | cf2Th | D-17 | Dog primary spinal cord astrocytes |
| D-4003 | 8 ± 1 | 87 ± 8 | 77 ± 8 | 94 ± 3 |
| D-4004 | 17 ± 1 | 40 ± 2 | 36 ± 3 | 65 ± 5 |
| D-4005 | 21 ± 1 | 49 ± 2 | 36 ± 1 | 87 ± 7 |
| D-4006 | 24 ± 2 | 100 ± 15 | 95 ± 8 | 97 ± 8 |
| Control | 100 ± 3 | 100 ± 10 | 100 ± 9 | 100 ± 11 |

In HEK293T cells, all dog SOD1 siRNAs (10 nM) led to robust suppression of SOD1 mRNA levels (suppression by 75-95%). In cf2Th cells, transfection of dog SOD1 siRNAs (D-4000, D-4005, D-4004, D-4001) at 10 nM led to 50-60% suppression of SOD1 mRNA levels. In D-17 cells, transfection of dog SOD1 siRNAs (D-4000, D-4005, D-4004, D-4001) at 10 nM led to 55-65% knock-down of SOD1. In dog primary spinal cord astrocytes, transfection of dog SOD1 siRNAs (D-4000, D-4004, D-4001) at 10 nM led to 30-45% suppression of SOD1 mRNA levels. Duplexes D-4000, D-4001, D-4004, and D-4005 were selected for further studies.

D. Evaluation of AAV2 Vectors in HEK293T

For this study, AAV vectors with siRNA constructs targeting dog SOD1 (dSOD1) were packaged in AAV2. HEK293T cells were plated into 96-well plates and infected with AAV2-dSOD1 miRNA vectors at a MOI of $1 \times 10^5$, $1 \times 10^4$ or a control, in triplicate ($4 \times 10^4$ cells/well in 200 ul cell culture medium).

Dog SOD1 and GAPDH mRNA levels were measured by RT-qPCR 48 hours after infection with the vectors. SOD1 mRNA levels were normalized to GAPDH mRNA levels, and then expressed relative to the negative control group.

Table 19 shows the relative SOD1 mRNA levels in HEK293T cells after infection with scAAV2-dSOD1 miR vectors as MOI of $1 \times 10^5$.

TABLE 19

Relative SOD1 mRNA levels in HEK293T cells
after AAV Infection at a MOI of $1 \times 10^5$

| Construct Name | Relative SOD1 mRNA Level (% of control) HEK293T |
|---|---|
| VOYSOD1miR104-805c | 109.7 ± 6.8 |
| Iodixanol/Control | 100.4 ± 4.4 |
| VOYSOD1miR109-805c | 82.5 ± 2.7 |
| VOYSOD1miR116-805c | 78.4 ± 3.2 |
| VOYSOD1miR114-805c | 74.7 ± 1.8 |
| VOYSOD1mir102-805c | 69.0 ± 1.3 |

TABLE 19-continued

Relative SOD1 mRNA levels in HEK293T cells
after AAV Infection at a MOI of 1 × $10^5$

| Construct Name | Relative SOD1 mRNA Level (% of control) HEK293T |
|---|---|
| VOYSOD1miR104-788 | 48.7 ± 1.0 |
| VOYSOD1miR127-805c | 37.0 ± 1.6 |
| VOYSOD1miR116-788 | 31.7 ± 1.9 |
| VOYSOD1miR114-788 | 31.6 ± 0.7 |
| VOYSOD1miR102-788 | 27.5 ± 0.7 |
| VOYSOD1miR109-788 | 26.1 ± 1.0 |
| VOYSOD1miR127-788 | 0.2 ± 0.0 |

Table 20 shows the relative SOD1 mRNA levels in HEK293T cells after infection with scAAV2-dSOD1 miR vectors at MOI of 1×$10^4$. Dog SOD1 and GAPDH mRNA levels were measured by RT-qPCR 48 hours after infection with the vectors. SOD1 mRNA levels were normalized to GAPDH mRNA levels, and then expressed relative to the negative control group.

TABLE 20

Relative SOD1 mRNA levels in HEK293T cells
after AAV Infection at MOI of 1 × $10^4$

| Construct Name | Relative SOD1 mRNA Level (% of control) HEK293T |
|---|---|
| VOYSOD1miR104-788-2 | 3.9 ± 0.2 |
| VOYSOD1miR104-789 | 5.0 ± 9.2 |
| VOYSOD1miR104-829 | 11.9 ± 0.5 |
| VOYSOD1miR104-830 | 1.1 ± 0.0 |
| VOYSOD1miR127-788-2 | 7.9 ± 0.3 |
| VOYSOD1miR127-789 | 43.5 ± 0.5 |
| VOYSOD1miR127-829 | 32.0 ± 1.2 |
| VOYSOD1miR127-830 | 15.0 ± 0.3 |
| dsCherry (ITR to ITR sequence provided as SEQ ID NO: 147) | 100.0 ± 0.8 |
| VOYSOD1miR127-860 positive control | 2.1 ± 0.1 |
| uninfected | 61.7 ± 1.5 |

At a MOI of 1×$10^5$, VOYSOD1miR127-805c, VOYSOD1miR116-788, VOYSOD1miR114-788, VOYSOD1miR102-788, VOYSOD1miR109-788, and VOYSOD1miR127-788 provided at least 60% reduction of SOD1 mRNA in HEK293 cells. VOYSOD1miR127-788 led to 99% reduction of SOD1 mRNA in HEK293T cells. At a MOI of 1E4, VOYSOD1miR127-789 and VOYSOD1miR127-829 lead to 57-68% reduction of SOD1 mRNA, and VOYSOD1miR104-788-2, VOYSOD1miR104-789, VOYSOD1miR104-829, VOYSOD1miR104-830, and VOYSOD1miR127-830 lead to 85-99% reduction of SOD1 mRNA.

E. Evaluation of Constructs Packaged in AAV2 siRNA constructs targeting dog SOD1 (dSOD1) were packaged in AAV2 and infected in cf2Th, D-17 cells, dog spinal cord astrocytes and fibroblasts. The cell culture medium for D-17 cells and cf2Th cells was DMEM/F-12 containing 2mMGlutaMAX™ supplement, 1×MEM non-essential amino acids solution, 10 mM HEPES and 10% FBS (all reagents were ordered from Life Technologies). The cell culture medium for primary astrocytes was AGM™ astrocyte growth medium (cat #: CC-3186, Lonza). The cell culture medium for fibroblasts was DMEM/F-12 containing 2mMGlutaMAX™ supplement, 1×MEM Non-Essential Amino Acids Solution, 10 mM HEPES and 10% FBS, 2 ng/ml human FGF-2 and 5 ug/ml human insulin (all reagents ordered from Life Technologies). Cells were plated into 96-well plates and infected with AAV2-dSOD1 miRNA vectors in triplicate (1-2E4 cells/well in 200 ul cell culture medium).

Dog SOD1 and GAPDH mRNAs were measured by RT-qPCR 48 hours after infection with the vectors at MOI of 1×$10^5$ or 1×$10^6$. dSOD1 mRNA levels were normalized to GAPDH mRNA levels, and then expressed relative to the negative control group.

Tables 21 and 22 shows the relative dSOD1 mRNA levels after infection with scAAV2-dSOD1 miR vectors at an MOI of 1×$10^5$.

TABLE 21

Relative dSOD1 mRNA levels in cf2Th, D-17, dog spinal cord astrocytes
and dog fibroblasts after AAV Infection at a MOI of 1 × $10^5$

| | Relative dSOD1 mRNA Level (% of mCherry) | | | |
|---|---|---|---|---|
| Construct Name | cf2Th | D-17 | Dog Spinal Cord Astrocytes | Dog Fibroblasts |
| mCherry | 101 ± 6 | 101 ± 5 | 103 ± 6 | 101 ± 8 |
| VOYSOD1miR109-805c | 86 ± 3 | 84 ± 2 | 96 ± 3 | 99 ± 2 |
| VOYSOD1miR114-805c | 85 ± 2 | 83 ± 3 | 94 ± 3 | 98 ± 3 |
| VOYSOD1miR102-805c | 82 ± 3 | 81 ± 2 | 94 ± 2 | 97 ± 7 |
| VOYSOD1miR104-805c | 81 ± 5 | 80 ± 3 | 93 ± 4 | 97 ± 3 |
| VOYSOD1miR116-805c | 74 ± 2 | 74 ± 3 | 85 ± 3 | 96 ± 3 |
| VOYSOD1miR104-788 | 68 ± 3 | 64 ± 3 | 84 ± 3 | 93 ± 2 |
| VOYSOD1miR114-788 | 63 ± 4 | 59 ± 3 | 82 ± 3 | 89 ± 3 |
| VOYSOD1miR127-805c | 62 ± 4 | 59 ± 2 | 79 ± 4 | 86 ± 3 |
| VOYSOD1miR109-788 | 61 ± 3 | 58 ± 2 | 72 ± 2 | 85 ± 2 |
| VOYSOD1miR102-788 | 59 ± 7 | 57 ± 1 | 72 ± 2 | 80 ± 3 |
| VOYSOD1miR116-788 | 55 ± 3 | 54 ± 4 | 71 ± 4 | 78 ± 3 |
| VOYSOD1miR127-788 | 31 ± 4 | 19 ± 2 | 54 ± 2 | 65 ± 1 |

In cf2Th and D17 cells, infection with scAAV2-dSOD1 miR vectors containing VOYSOD1miR104-788, VOYSOD1miR114-788, VOYSOD1miR127-805c, VOYSOD1miR109-788, VOYSOD1miR102-788, or VOYSOD1miR116-788 at a MOI of 1×$10^5$ resulted in suppression of SOD1 mRNA levels by ~30-45%. However, infection with scAAV2-dSOD1 miR vector containing VOYSOD1miR127-788 at a MOI of 1×$10^5$ resulted in ~70-80% suppression of SOD1 mRNA levels. In dog primary cells (spinal cord astrocytes and fibroblasts), VOYSOD1miR127-788 led to ~35-45% knock-down of SOD1 mRNA at a MOI of 1×$10^5$.

TABLE 22

Relative dSOD1 mRNA levels in dog brain astrocytes,
D-17 cells, dog spinal cord astrocytes and dog fibroblasts
after AAV infection at a MOI of 1 × $10^5$

| | Relative dSOD1 mRNA Level (% of mCherry) | | | |
|---|---|---|---|---|
| Construct Name | Dog Brain Astrocytes | D-17 | Dog Spinal Cord Astrocytes | Dog Fibroblasts |
| mCherry | 100 ± 4 | 100 ± 3 | 100 ± 3 | 100 ± 3 |
| VOYSOD1miR127-829 | 68 ± 2 | 41 ± 3 | 56 ± 1 | 74 ± 3 |
| VOYSOD1miR127-789 | 73 ± 4 | 19 ± 1 | 45 ± 2 | 74 ± 2 |
| VOYSOD1miR127-830 | 60 ± 4 | 20 ± 1 | 41 ± 1 | 73 ± 2 |
| VOYSOD1miR104-829 | 39 ± 2 | 22 ± 1 | 34 ± 1 | 51 ± 1 |
| VOYSOD1miR104-789 | 31 ± 1 | 11 ± 0 | 26 ± 1 | 50 ± 1 |
| VOYSOD1miR127-788.2 | 32 ± 1 | 10 ± 1 | 22 ± 1 | 41 ± 1 |

TABLE 22-continued

Relative dSOD1 mRNA levels in dog brain astrocytes,
D-17 cells, dog spinal cord astrocytes and dog fibroblasts
after AAV infection at a MOI of 1 × 10⁵

Relative dSOD1 mRNA Level (% of mCherry)

| Construct Name | Dog Brain Astrocytes | D-17 | Dog Spinal Cord Astrocytes | Dog Fibroblasts |
|---|---|---|---|---|
| VOYSOD1miR104-830 | 26 ± 1 | 9 ± 0 | 25 ± 2 | 37 ± 1 |
| VOYSOD1miR104-788.2 | 18 ± 1 | 12 ± 1 | 18 ± 0 | 21 ± 1 |

In dog brain astrocytes, dog spinal cord astrocytes, dog fibroblasts and D-17 cells, infection with scAAV2-dSOD1 miR vectors containing VOYSOD1miR104-829, VOYSOD1miR104-789, VOYSOD1miR127-788.2, VOYSOD1miR104-830, or VOYSOD1miR104-788.2 showed at least approximately 50% SOD1 mRNA suppression.

Table 23 shows the relative dSOD1 mRNA levels after infection with scAAV2-dSOD1 miR vectors at an MOI of 1×10⁶.

TABLE 23

Relative dSOD1 mRNA levels in dog brain astrocytes,
D-17 cells, dog spinal cord astrocytes and dog fibroblasts
after AAV infection at a MOI of 1 × 10⁶

Relative dSOD1 mRNA Level (% of mCherry)

| Construct Name | D-17 | Dog Brain Astrocytes | Dog Spinal Cord Astrocytes | Dog Fibroblasts |
|---|---|---|---|---|
| mCherry | 100 ± 2 | 100 ± 3 | 100 ± 2 | 100 ± 4 |
| VOYSOD1miR109-805c | 91 ± 2 | 101 ± 3 | 110 ± 3 | 112 ± 4 |
| VOYSOD1miR114-805c | 79 ± 5 | 90 ± 6 | 102 ± 4 | 106 ± 3 |
| VOYSOD1miR102-805c | 76 ± 4 | 103 ± 7 | 92 ± 3 | 101 ± 4 |
| VOYSOD1miR104-805c | 91 ± 3 | 98 ± 3 | 107 ± 4 | 101 ± 1 |
| VOYSOD1miR116-805c | 86 ± 8 | 94 ± 3 | 100 ± 3 | 104 ± 2 |
| VOYSOD1miR104-788 | 76 ± 6 | 87 ± 5 | 84 ± 2 | 109 ± 2 |
| VOYSOD1miR114-788 | 43 ± 1 | 80 ± 4 | 79 ± 1 | 102 ± 4 |
| VOYSOD1miR127-805c | 62 ± 7 | 83 ± 2 | 91 ± 4 | 97 ± 3 |
| VOYSOD1miR109-788 | 59 ± 5 | 91 ± 7 | 80 ± 4 | 104 ± 3 |
| VOYSOD1miR102-788 | 71 ± 3 | 92 ± 2 | 82 ± 4 | 105 ± 4 |
| VOYSOD1miR116-788 | 51 ± 4 | 88 ± 4 | 82 ± 2 | 99 ± 4 |
| VOYSOD1miR127-788 | 10 ± 1 | 42 ± 4 | 33 ± 1 | 56 ± 1 |

In D17 cells, infection with scAAV2-dSOD1 miR vector containing VOYSOD1miR127-788 resulted in the maximal suppression (by ~90%) of SOD1 mRNA at a MOI of 1×10⁶. In dog primary cells, VOYSOD1miR127-788 led to 44-67% suppression of SOD1 mRNA at a MOI of 1×10⁶.

A dose-response study was conducted with infection with scAAV2-dSOD1 miR vector containing VOYSOD1miR104-788.2, VOYSOD1miR104-789, VOYSOD1miR104-829, VOYSOD1miR104-830, or VOYSOD1miR127-788.2 at MOIs of 1×10², 1×10³, 1×10⁴, 1×10⁵, and 1×10⁶ in spinal cord astrocytes and D-17 cells. With scAAV2-dSOD1 miR vector containing VOYSOD1miR104-788.2, VOYSOD1miR104-789, VOYSOD1miR104-829, VOYSOD1miR104-830 and VOYSOD1miR127-788.2, dose-dependent SOD1 mRNA silencing in D-17 cells and spinal cord astrocytes and 50% SOD1 mRNA knock-down was achieved by infection of AAV SOD1 miRNA vectors at a MOI of 1×10² and 1×10³ in both cell types.

A further dose-response study was conducted with scAAV2-dSOD1 miR vector containing VOYSOD1miR127-788 at a MOI of 1×10², 1×10³, 1×10⁴, 1×10⁵, and 1×10⁶ in dog brain astrocytes, spinal cord astrocytes, cf2Th cells, and D-17 cells. In cf2Th cells, D-17 cells and spinal cord astrocytes, 50% knock-down of SOD1 mRNA was achieved at a MOI of 1×10³ and 1×10⁴. In dog brain astrocytes, 50% knock-down of SOD1 mRNA was achieved with an MOI of at least 1×10⁵.

Example 8. In Vivo Study of Constructs

A. In Vivo Selection Study in Mouse

Transgenic mice expressing human wild-type SOD1 (C57BL/6-Tg(SOD1)3Cje/J) were administered one of six candidates (VOYSOD1miR104-829, VOYSOD1miR104-789, VOYSOD1miR127-788.2, VOYSOD1miR104-788.2, VOYSOD1miR104-830, VOYSOD1miR127-788) packaged in AAVDJ, or vehicle by unilateral intrastriatal infusion of 5 uL test article at 0.5 uL/min. Vector concentrations were 1.5×10¹² vg/mL corresponding to a total administered dose of 7.5×10⁹ vg.

Four weeks after dosing, striatal tissues from the site of administration were evaluated for SOD1 mRNA suppression by RT-qPCR relative to the vehicle group, and for pri-miRNA processing by deep sequencing.

Shown in Table 24 are the SOD1 mRNA levels normalized to glyceraldehyde-3-phosphate dehydrogenase (GAPDH) and then expressed relative to the vehicle group (n=5 per group).

TABLE 24

Suppression of hSOD1 mRNA in Human Wild-Type SOD1
Mice by Pri-miRNA Constructs Packaged in AAVDJ

| Construct Name | hSOD1 mRNA (normalized to mGAPDH) (fold change relative to vehicle) (Average ± SD) |
|---|---|
| VOYSOD1miR104-829 | 0.31 ± 0.06 |
| VOYSOD1miR104-789 | 0.53 ± 0.19 |
| VOYSOD1miR127-788.2 | 0.70 ± 0.09 |
| VOYSOD1miR104-788.2 | 0.38 ± 0.05 |
| VOYSOD1miR104-830 | 0.45 ± 0.17 |
| VOYSOD1miR127-788 | 0.33 ± 0.11 |
| Vehicle | 1 ± 0.11 |

VOYSOD1miR104-788.2 and VOYSOD1miR104-829 were also evaluated using next generation sequencing to assess precision and efficiency of pri-miRNA processing; the results are shown in Table 25. In Table 25, G/P ratio means guide/passenger strand ratio.

TABLE 25

Precision and Efficacy of pri-miRNA Processing in Human Wild-
Type SOD1 Mice after AAVDJ.CB6.miRSOD1 Administration

| Construct Name | G/P Ratio | Abundance relative to endogenous miRNAs (%) | 5'-End processing precision (% N) |
|---|---|---|---|
| VOYSOD1miR104-788.2 | 314 | 11.1 | 89 |
| VOYSOD1miR104-829 | 434 | 16.4 | 78 |

B. In Vivo Pharmacology and Safety Study in Normal Dog

AAV vectors for these studies were generated using the triple transfection method in HEK293 cells.

Normal dogs were dosed intrathecally with scAAVrh10.H1.miR104-788.2 (ITR to ITR sequence provided as SEQ ID NO: 145) or scAAVrh10.H1.miR104-829 (ITR to ITR sequence provided as SEQ ID NO: 146) at a dose of $2\times10^{13}$ vg or $6\times10^{13}$ vg, or vehicle (n=4 per group). Animals were euthanized after 4 weeks and samples were collected for further analysis.

Dorsal root ganglia (DRG) from L5, T7 or C4 were assessed by RT-qPCR for levels of canine SOD1 (dSOD1), GAPDH, alanyl-tRNA synthetase (AARS) and X-prolyl aminopeptidase 1 (XPNPEP1) mRNA. dSOD1 mRNA levels were normalized to the geometric mean of the housekeeping genes (GAPDH, AARS, and XPNPEP1), and then expressed relative to the vehicle group. Shown in Table 26 are the relative SOD1 mRNA levels in DRG for scAAVrh10.H1.miR104-788.2 with and without immunosuppression. Shown in Table 27 are the relative SOD1 mRNA levels in DRG for scAAVrh10.H1.miR104-829 with immunosuppression.

TABLE 26

SOD1 mRNA expression in DRG after treatment with scAAVrh10.H1.miR104-788.2

| Immunosuppression | Dose (vg) | SOD mRNA normalized to geomean (GAPDH, AARS and XPNPEP1) (relative to vehicle) (Average ± SD) | | |
|---|---|---|---|---|
| | | L5 DRG | T7 DRG | C4 DRG |
| With Immunosuppression | $2 \times 10^{13}$ | 0.54 ± 0.10 | 0.66 ± 0.07 | 0.74 ± 0.08 |
| | $6 \times 10^{13}$ | 0.30 ± 0.09 | 0.34 ± 0.06 | 0.40 ± 0.21 |
| | vehicle | 1 ± 0.27 | 1 ± 0.26 | 1 ± 0.24 |
| Without Immunosuppression | $6 \times 10^{13}$ | 0.40 ± 0.12 | 0.43 ± 0.06 | 0.39 ± 0.11 |
| | vehicle | 1 ± 0.25 | 1 ± 0.14 | 1 ± 0.12 |

TABLE 27

SOD1 mRNA expression in DRG after treatment with scAAVrh10.H1.miR104-829

| Immunosuppression | Dose (vg) | SOD mRNA normalized to geomean (GAPDH, AARS and XPNPEP1) (relative to vehicle) | | |
|---|---|---|---|---|
| | | L5 DRG | T7 DRG | C4 DRG |
| With Immunosuppression | $2 \times 10^{13}$ | 0.87 ± 0.16 | 0.74 ± 0.10 | 0.61 ± 0.09 |
| | $6 \times 10^{13}$ | 0.64 ± 0.27 | 0.57 ± 0.08 | 0.74 ± 0.40 |
| | vehicle | 1 ± 0.25 | 1 ± 0.14 | 1 ± 0.12 |

The levels of dSOD1 mRNA were evaluated in the liver and the results are shown in Table 28 for scAAVrh10.H1.miR104-788.2.

TABLE 28

SOD1 mRNA expression in liver after treatment with scAAVrh10.H1.miR104-788.2

| Immunosuppression | Dose (vg) | SOD mRNA normalized to geomean (GAPDH, AARS and XPNPEP1) (relative to vehicle) Liver |
|---|---|---|
| With Immunosuppression | $2 \times 10^{13}$ | 0.23 ± 0.16 |
| | $6 \times 10^{13}$ | 0.17 ± 0.07 |
| | vehicle | 1 ± 0.15 |
| Without Immunosuppression | $6 \times 10^{13}$ | 0.42 ± 0.14 |
| | vehicle | 1 ± 0.15 |

For dSOD1 mRNA levels in the spinal cord, scAAVrh10.H1.miR104-788.2 at a dose of $6\times10^{13}$ vg (with immunosuppression) resulted in a suppression of 41±9% (average±standard deviation) relative to vehicle (spinal cord ventral horn mRNA levels of dSOD1 were normalized to the geometric mean of GAPDH, AARS, and XPNPEP1).

Using DuplexRNAscope in situ hybridization for co-detection of vg and dSOD1 mRNA in the ventral horn of the spinal cord, a reduction of SOD1 mRNA in vg+ cells was seen in the ventral horn for scAAVrh10.H1.miR104-788.2 at a dose of $6\times10^{13}$ vg, relative to the vehicle group.

scAAVrh10.H1.miR104-788.2 at a dose of $6\times10^{13}$ vg also had a high guide/passenger strand ratio (170 in DRG and 373 in spinal cord ventral horn), precise processing at the 5' end of the guide strand (>90%), and a low level of guide and passenger strands relative to the total endogenous pool of miRNAs (6.7+/−5.1% for DRGs and 0.9+/−0.6% for the spinal cord ventral horn.

scAAVrh10.H1.miR104-788.2, with and without immunosuppression, was well-tolerated in all animals. No significant vector-related effects on body weight, clinical signs, clinical pathology (days 15 and 29), cerebrospinal fluid (CSF) chemistry (day 29) or CSF total cell counts (day 29). There were no gross lesions and the histopathology of the DRG, spinal cord and brain showed no significant vector-related findings.

scAAVrh10.H1.miR104-788.2 was selected for additional studies as it demonstrated safety, dose-dependent knock-down in vitro, 62% knock-down of SOD1 mRNA in human wild-type SOD1 transgenic mice, and knock-down in normal dogs of SOD1 in the DRG of up to 74% and in the spinal cord of up to 41%.

Example 9. Tolerability and Distribution of AAV in Normal Dog

Distribution of AAVrh10 capsids had not been previously reported, therefore studies needed to be conducted to confirm that AAVrh10 distributes to motor neurons and DRG neurons of the dog, as in other species. The primary objective of this pilot study was to assess the acute tolerability of AAV lumbar IT delivery in a canine model. No neuropathology or clinical pathology/toxicology analysis was conducted.

Six adult male beagles aged 13 mo (10-13 kg) were pre-screened for serum neutralizing antibody titers to AAVrh10 and AAV9. Six animals were implanted with an intrathecal (IT) catheter with the tip located at the upper lumbar spine and which terminated in a subcutaneous access port. Prior to dosing, the animals were immunosuppressed using cyclosporine and mycophenolate. While sedated, the animals were administered three 1-mL injections (1 mL/minute) of test article (dose $2.7\times10^{13}$ vg) at 1-hour intervals for a total time of approximately 2.5 hours. The sixth animal (Group 4) was used for the collection of control tissues. Table 29 shows the study design. In Table 29 under test article, "sc" means self-complementary, CBA is the CBA promoter, hFXN is human Frataxin, and HA is the HA tag.

TABLE 29

Study Design

| Group | n | Test Article | Rate (mL/min) | Total Vol. (mL) | Conc. (vg/mL) | Dose (vg) |
|---|---|---|---|---|---|---|
| 1 | 1 | Vehicle | 1 | 3 | 0 | 0 |
| 2 | 2 | scAAV9-CBA-hFXN-HA | 1 | 3 | $9.0 \times 10^{12}$ | $2.7 \times 10^{13}$ |
| 3 | 2 | scAAVrh10-CBA-hFXN-HA | 1 | 3 | $9.0 \times 10^{12}$ | $2.7 \times 10^{13}$ |
| 4 | 1 | n/a | n/a | n/a | n/a | n/a |

The animals were injected with AAV vectors (scAAVx-CBA-hFXN-HA) using either AAV9 or AAVrh10 capsids. After 2.5 weeks, the animals were perfused with saline and spinal cord, DRGs, and brain were processed for analysis. Half of the samples were post-fixed in 4% paraformaldehyde for 72-96 hrs whereas the other half was fresh frozen.

In-life observations and measurements for animals in Groups 1 through 3 included body weight, food consumption, and clinical observations. There were no test article-related clinical signs during this study. There were no test article-related changes in body weight or food consumption. There were no test article-related gross lesions observed at necropsy.

Histological evaluation of the spinal cord and DRGs with HA-immunohistochemistry demonstrated motor neuron transduction that was most prominent in the L5 spinal cord in all animals. A gradient pattern was observed with rostral levels exhibiting less motor neuron staining (C1<T4<L5), independent of treatment group. Sensory neuron transduction was observed in DRGs from all levels (cervical, thoracic and lumbar) in both treatment groups. In summary, IT delivery of both AAV9 and AAVrh10 constructs resulted in positive anti-HA immunoreactivity in both spinal cord and DRG neurons. These results showed that an IT dosing paradigm consisting of three ~1 mL lumbar injections every hour achieved target levels of transduction particularly in the more caudal regions of the spinal cord, with less transduction in more rostral regions of the spinal cord.

Example 10. CSF and Serum Neurofilament Light Chain Levels as a Biomarker

Background

Canine degenerative myelopathy (DM) is a late-onset, progressive neurodegenerative disease affecting many pure and mixed-breed dogs. Clinical signs are the result of multisystem neurodegeneration involving the central and peripheral nervous systems. DM initially manifests as spastic upper motor neuron paraparesis and general proprioceptive ataxia (stage 1). Progressive neurodegeneration results in non-ambulatory paraparesis/paraplegia (stage 2) and thoracic limb paresis (stage 3). End-stage disease culminates in flaccid tetraplegia, widespread muscle atrophy and bulbar dysfunction (stage 4). Superoxide dismutase 1 gene (SOD1) mutations (SOD1:c.118A, SOD1: c.52T) are risk factors for DM, with most cases resulting from autosomal recessive inheritance. The disease is considered to be similar in cause, progression, and prognosis to some forms of human amyotrophic lateral sclerosis (ALS). Diagnosis is based on exclusion of other mimicking diseases and a definitive diagnosis of DM can, at this point, only be made postmortem by histopathologic examination of the spinal cord. Neurofilament light chain (NF-L), an abundant structural protein of myelinated motor axons, is a promising fluid biomarker of animal and human motor neuron diseases, including ALS. Blood and CSF NF-L levels have diagnostic value in ALS, and may correlate with disease progression and thereby serve as a biomarker of treatment effect. A study was conducted to assess serum and CSF NF-L levels as a potential biomarker for diagnosis and disease progression in DM dogs.

Study Design

Serum samples and CSF samples from three types of dogs were analyzed for this study. Group 1 included young (1 to 5 years) and aged (>9 years) normal control dogs (n=13-17), Group 2 included DM-affected dogs (homozygous for the SOD1c.118A allele) of stage 1 through 4 (n=22-25), and Group 3 included aged asymptomatic dogs (homozygous for the SOD1c.118A allele).

Analysis and Results: Normal Dogs

Prior to sample testing, the digital ELISA was assessed for dilution linearity, stability and spike recovery of NFL in CSF and serum of normal dogs. Commercially available digital ELISA (Quanterix) for human NF-L (which is 98% conserved with canine NFL) was used for the analysis. FIG. 1. shows a representative NF-L calibration curve for the Quanterix Simoa hNF-L (Beta) assay. The limit of detection (LOD) was calculated as the NF-L level at an average enzyme per bead (AEB) equal to the average of the zero calibrator+2.5SD.

Dilution linearity of a digital ELISA for NF-L was tested in CSF of eight normal dogs. As shown in Table 30, concentrations within ±20% were observed at a dilution of 1:100 compared to 1:40. Subsequent assays were performed at a minimal dilution of 1:100 for dog CSF. In Table 30, N/A means no number was available and * denotes a sample that reads outside Standard Curve range.

TABLE 30

Dilution Concentration and Linearity (1:40) for CSF in Normal Dog

| Dog CSF Sample (CSF) | Dilution | Dilution Corrected Concentration (pg/mL) | % Linearity (1:40) |
|---|---|---|---|
| 1 | 1:4 | 10316* | — |
|   | 1:10 | 16005* | — |
|   | 1:40 | 18037 | — |
|   | 1:100 | 19349 | 107% |
| 2 | 1:4 | N/A* | — |
|   | 1:10 | 20091* | — |
|   | 1:40 | 20347 | — |
|   | 1:100 | 19536 | 96% |
| 3 | 1:4 | 8070* | — |
|   | 1:10 | 9909* | — |
|   | 1:40 | 11775 | — |
|   | 1:100 | 11230 | 95% |
| 4 | 1:4 | N/A* | — |
|   | 1:10 | 19548* | — |
|   | 1:40 | 21483* | — |
|   | 1:100 | 21731 | 101% |
| 5 | 1:4 | N/A* | — |
|   | 1:10 | 25275* | — |
|   | 1:40 | 33277 | — |
|   | 1:100 | 36038 | 108% |
| 6 | 1:4 | 7259* | — |
|   | 1:10 | 8449* | — |
|   | 1:40 | 7977 | — |
|   | 1:100 | 7339 | 92% |
| 7 | 1:4 | 6090* | — |
|   | 1:10 | 7440* | — |
|   | 1:40 | 7875 | — |
|   | 1:100 | 8073 | 103% |

TABLE 30-continued

Dilution Concentration and Linearity (1:40) for CSF in Normal Dog

| Dog CSF Sample (CSF) | Dilution | Dilution Corrected Concentration (pg/mL) | % Linearity (1:40) |
|---|---|---|---|
| 8 | 1:4 | 3129* | — |
|   | 1:10 | 3613 | — |
|   | 1:40 | 4001 | — |
|   | 1:100 | 4323 | 108% |

Dilution linearity of a digital ELISA for NFL was tested in serum of three normal dogs. As shown in Table 31, concentrations within ±20% were observed at a dilution of 1:200 compared to 1:100. Subsequent assays were performed at a minimal dilution of 1:200 for dog blood serum.

TABLE 31

Dilution Concentration and Linearity (1:40, 1:100, 1:200) for Blood Serum in Normal Dog

| Dog Serum Sample (S) | Dog Serum Samples Dilution | Dilution Corrected Concentration | Linearity (1:40) | Linearity (1:100) | Linearity (1:200) |
|---|---|---|---|---|---|
| 1 | 1:40 | 90.4 | — | — | — |
|   | 1:100 | 116 | 128% | — | — |
|   | 1:200 | 131 | 145% | 113% | — |
|   | 1:400 | 154 | 170% | 133% | 118% |
| 5 | 1:40 | 247 | — | — | — |
|   | 1:100 | 266 | 108% | — | — |
|   | 1:200 | 310 | 125% | 116% | — |
|   | 1:400 | 319 | 129% | 120% | 103% |
| 6 | 1:40 | 231 | — | — | — |
|   | 1:100 | 245 | 106% | — | — |
|   | 1:200 | 268 | 116% | 109% | — |
|   | 1:400 | 320 | 139% | 131% | 119% |

Figure 2A:
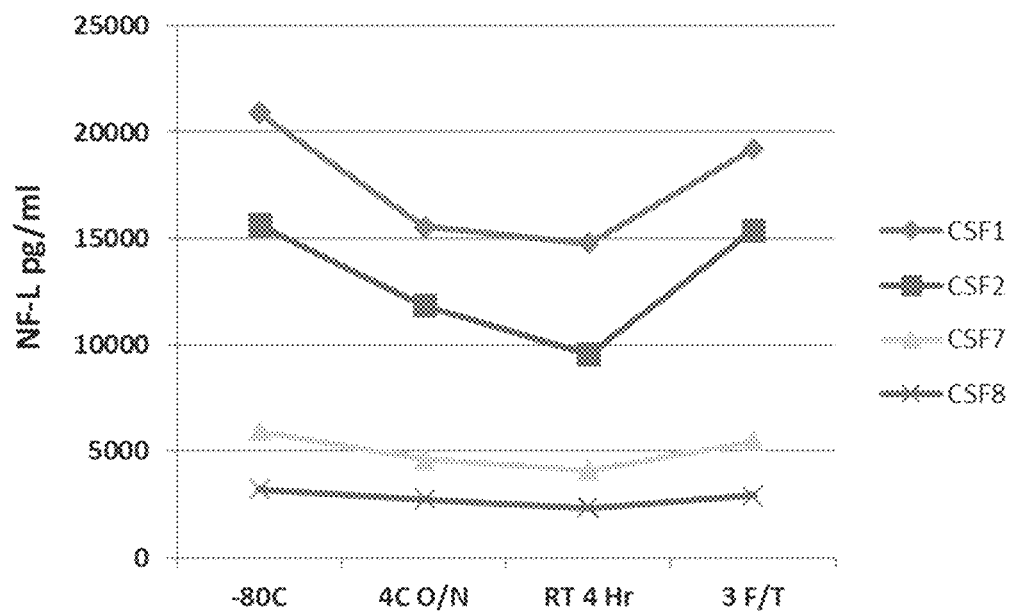
FIG. 2A and FIG. 2B show the stability of NF-L in CSF of normal dogs.
Figure 2B:
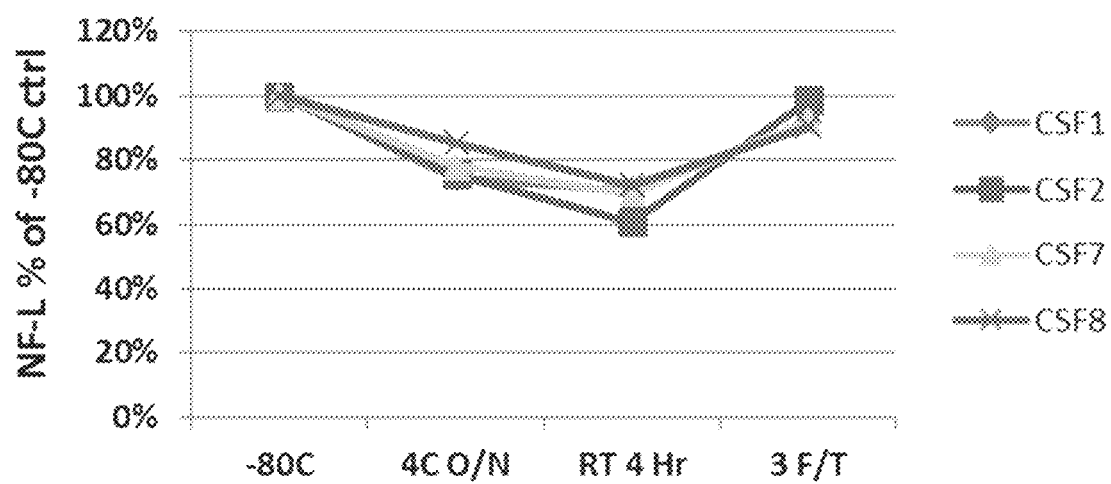
Figure 3A:
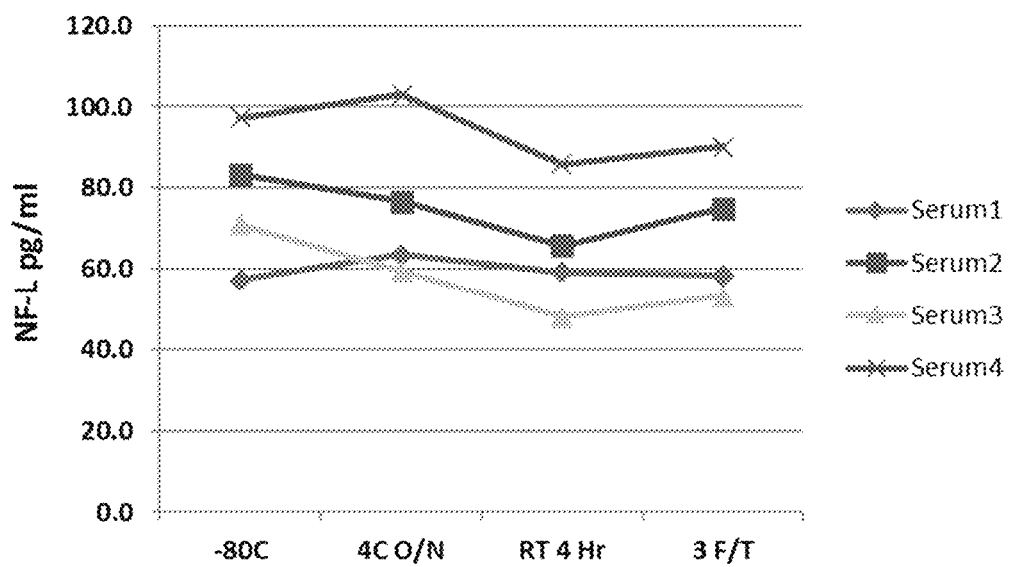
FIG. 3A and FIG. 3B show the stability of NF-L in blood serum of normal dogs.
Figure 3B:
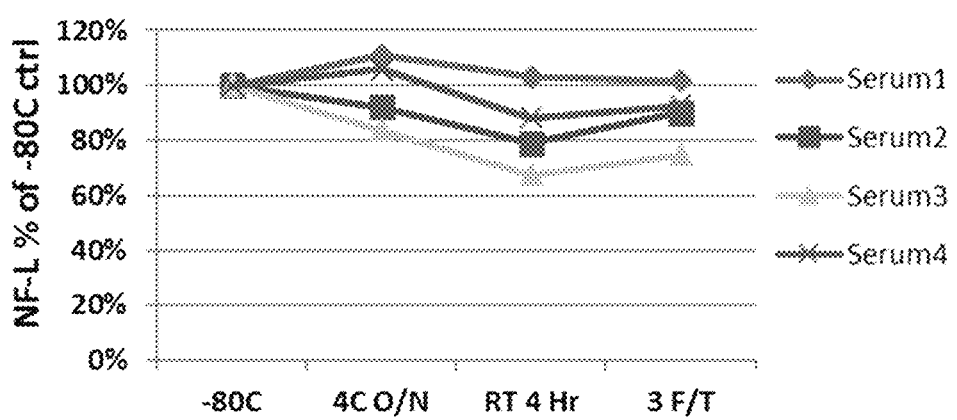

Sample stability for NF-L was tested in CSF (data shown in FIGS. 2A and 2B) and blood serum (data shown in FIGS. 3A and 3B) of four normal dogs. Samples were submitted to different treatment conditions including −80° C., 4° C. overnight, room temperature for 4 hours, or 3 freeze/thaw cycles. In FIGS. 2A, 2B, 3A, and 3B O/N=Over night, RT=Room temperature, F/T=Freeze/thaw cycles. NFL concentrations were determined by digital ELISA (Quanterix) in duplicate. Three F/T cycles had only minor effect on sample NF-L concentration. FIG. 2B shows the data in FIG. 2A expressed as percent of −80° C. control and FIG. 3B shows the data in FIG. 3A expressed as percent of −80° C. control. Samples appeared stable for duration of experimental procedure if stored on ice.

Spike recovery for NF-L was tested by supplementing buffer control, CSF or serum of two normal dogs with increasing concentrations of recombinant human NF-L. CSF samples were assayed at 1:100 dilution, serum samples were assayed at 1:400. As shown in Table 32, the average spike recovery was close to or within acceptance criteria, but significant variability was observed between spike levels. In Table 32, "CSF" in the NF-L sample column refers to a CSF sample, and "S" refers to a serum sample.

TABLE 32

NF-L Recovery in Dog CSF and Serum

| NF-L Sample | Spike (pg/ml) | Dilution Corrected Concentration (pg/ml) | Recovery | Buffer Corrected Recovery | Ave. Recovery |
|---|---|---|---|---|---|
| Buffer | 100 | 51.0 | 51% | — | — |
|   | 500 | 387 | 77% | — |   |
|   | 1000 | 716 | 72% | — |   |
|   | 5000 | 3703 | 74% | — |   |
|   | 10000 | 7473 | 75% | — |   |
| CSF 7 | 0 | 4978 | — | — | 122% |
|   | 1000 | 5964 | 99% | 138% |   |
|   | 5000 | 9227 | 85% | 115% |   |
|   | 10000 | 13527 | 85% | 114% |   |
| CSF 8 | 0 | 2949 | — | — | 106% |
|   | 1000 | 3796 | 85% | 118% |   |
|   | 5000 | 7038 | 82% | 110% |   |
|   | 10000 | 9678 | 67% | 90% |   |
| S 5 | 0 | 102 | — | — | 88% |
|   | 100 | 166 | 65% | 127% |   |
|   | 500 | 363 | 52% | 67% |   |
|   | 1000 | 599 | 50% | 69% |   |
| S 6 | 0 | 116 | — | — | 94% |
|   | 100 | 183 | 67% | 131% |   |
|   | 500 | 396 | 56% | 72% |   |
|   | 1000 | 689 | 57% | 80% |   |

Analysis and Results: DM Dogs

Figure 4A:
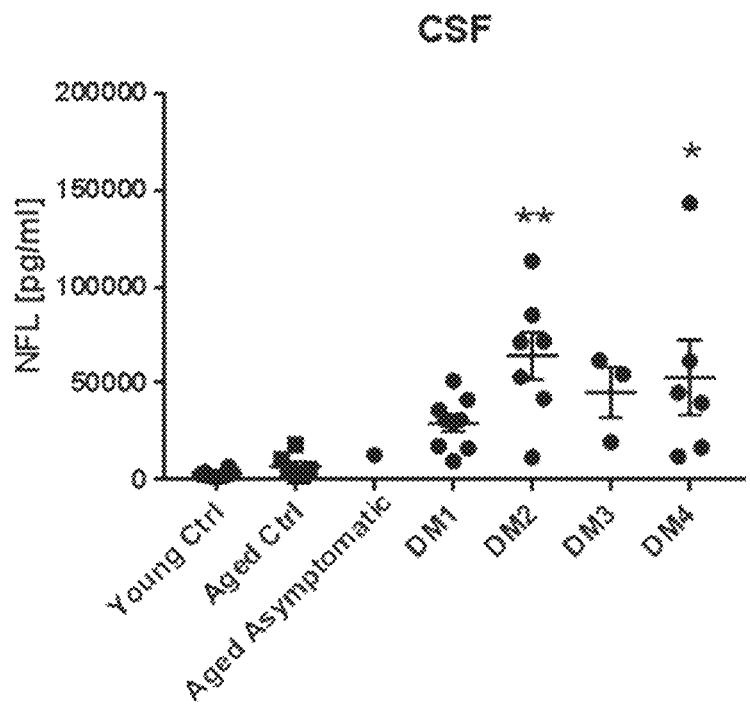
FIG. 4A and FIG. 4B are histograms showing NF-L levels in DM dogs.

NF-L concentrations in the CSF of DM dogs and control dogs were compared and the results (average for each animal) are shown in FIG. 4A. Samples were analyzed at 1:500 dilution in duplicate (% CV values ranged from 0-10%; error as SEM; one-way ANOVA with Tukey's multiple comparison test; *$p<0.05$, **$p<0.01$ vs. aged control).

DM dogs of all stages showed a strong increase in CSF NF-L compared to aged (>9 years old) and young (1-5 years old) control groups. Combined DM cohorts display average NF-L concentration of 47,068 pg/ml compared to 6,864 pg/ml in the aged control group (human CSF is 2100 pg/ml). The increase in NF-L appears most pronounced at initial disease stages and increases were seen with severity. Group DM2 tended have increased NF-L levels as compared to group DM1 ($p=0.1$) Additionally, canine aged control group showed higher levels of NF-L as compared the young control group (6864 pg/ml vs. 3053 pg/m) suggesting age-dependent NF-L increase in the CSF of normal dogs.

Figure 4B:
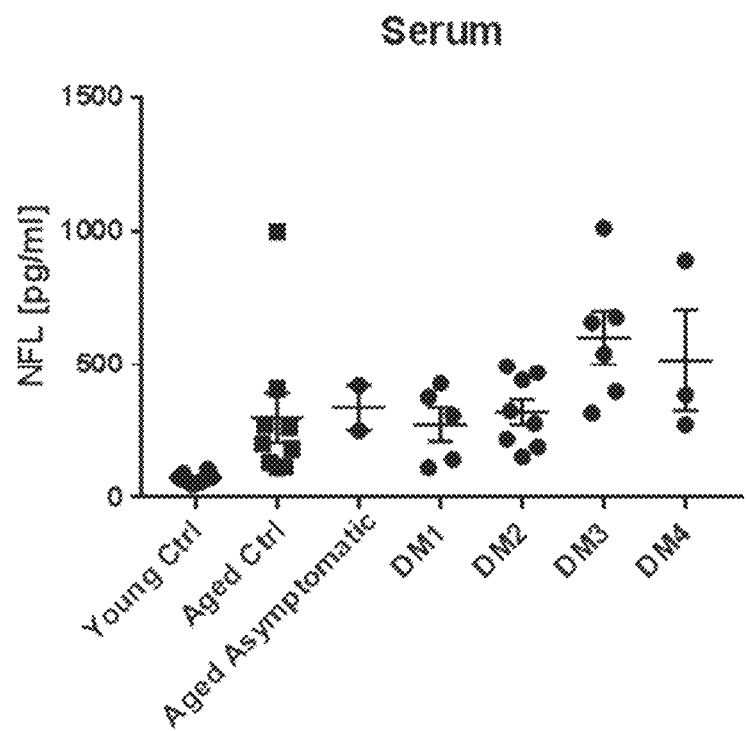

NF-L concentrations in the serum of DM and control dogs were compared and the results (average for each animal) are shown in FIG. 4B. Samples were analyzed at 1:200 dilution in duplicate (Error as SEM; One-way ANOVA with Tukey's multiple comparison test).

There was an apparent increase in serum NF-L in the aged control group (297 pg/ml) as compared to the young control group (72 pg/ml), suggesting age-dependent increase in normal dogs. Unlike CSF, serum of DM dogs at any stage did not show a significant increase in NF-L compared to aged control group. However, average NF-L levels might increase from combined DM1/2 stages (302 pg/ml) to combined DM3/4 stages (572 pg/ml). As the young control group NF-L level is about 10 fold higher than normal human serum NF-L (72 pg/ml v~8 pg/ml), low serum NF-L levels in humans will be difficult to detect compared to dog.

Correlation plots for NF-L in serum and CSF of control and DM dogs showed that there was no apparent linear correlation when all groups were combined, but combined data from the young control and the aged control group suggested a linear correlation of serum with CSF NF-L levels.

Summary

A digital ELISA assay for hNFL (Quanterix Simoa platform) was optimized to meet pre-defined acceptance criteria for dilution linearity, stability and hNFL spike recovery in CSF and serum of normal dogs. Using this ELISA assay, CSF and serum levels from normal and DM dogs were analyzed.

CSF NF-L levels were elevated substantially in DM-affected dogs of stages 1-4 compared to aged controls and the CSF NF-L increase was most pronounced at initial disease stages.

Unlike CSF, serum of DM dogs at any stage did not show a significant increase in NF-L compared to aged control group. A substantial increase in serum NF-L was observed in the aged control group versus the young control group suggesting age-dependent increase in normal dogs. A similar relative increase was demonstrated in CSF. In control dogs, CSF and serum NFL levels might be linearly correlated.

Therefore, it is likely that NF-L concentrations in serum and CSF increase with aging and are elevated in DM dogs compared to aged control dogs. CSF NFL concentrations may also represent a biomarker for early disease progression.

Example 11. Phosphorylated Neurofilament Heavy Chain Levels as a Biomarker

DM initially manifests as spastic upper motor neuron paraparesis and general proprioceptive ataxia (stage 1). Progressive neurodegeneration results in non-ambulatory paraparesis/paraplegia (stage 2) and thoracic limb paresis (stage 3). End-stage disease culminates in flaccid tetraplegia, widespread muscle atrophy and bulbar dysfunction (stage 4). The disease is considered to be similar in cause, progression, and prognosis to some forms of human amyotrophic lateral sclerosis (ALS). Phosphorylated neurofilament heavy (pNF-H) has potential as a cross-species biomarker for DM and ALS. Increased pNF-H concentrations in blood and CSF have shown high diagnostic performance and association with disease progression in patients diagnosed with ALS. In DM-affected dogs, CSF pNF-H is a sensitive biomarker for diagnosis with high specificity and has a determined cut-off value >20.25 ng/mL that is 80.4% sensitive (CI 66.09-90.64%) and 93.6% specific (CI 78.5-99.21%).

Figure 5A:
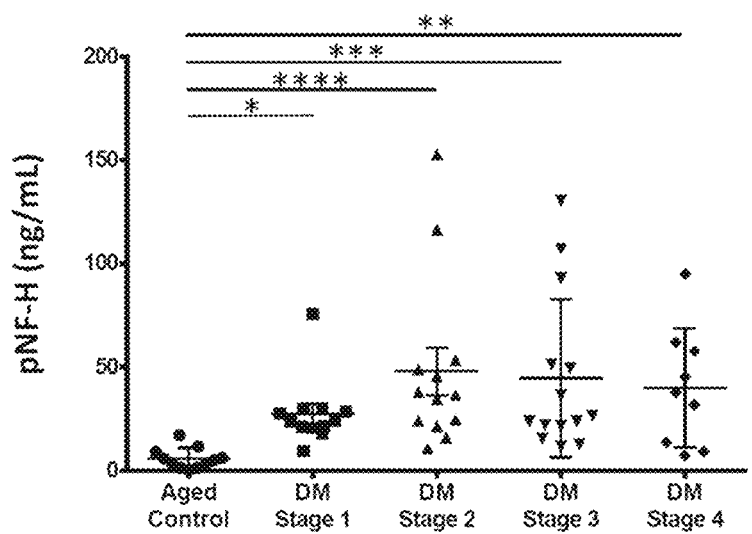
FIG. 5A, FIG. 5B, and FIG. 5C are histograms showing pNF-H levels in DM dogs.
Figure 5B:
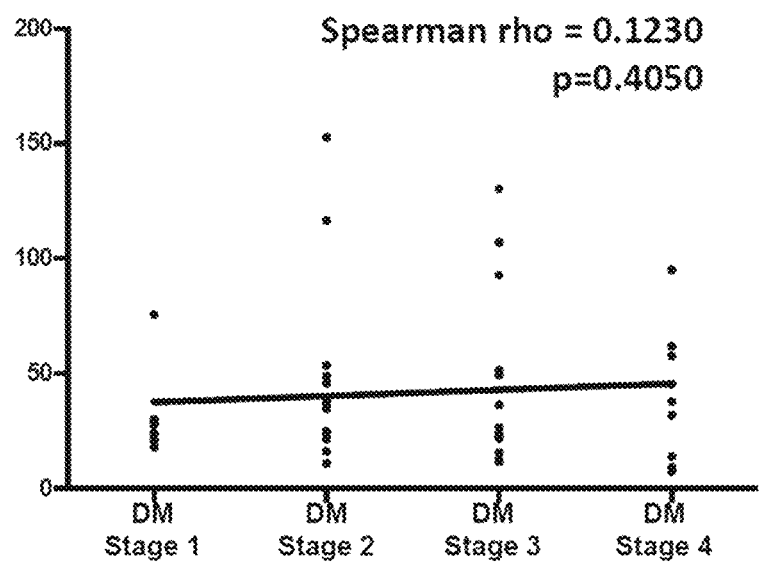
Figure 5C:
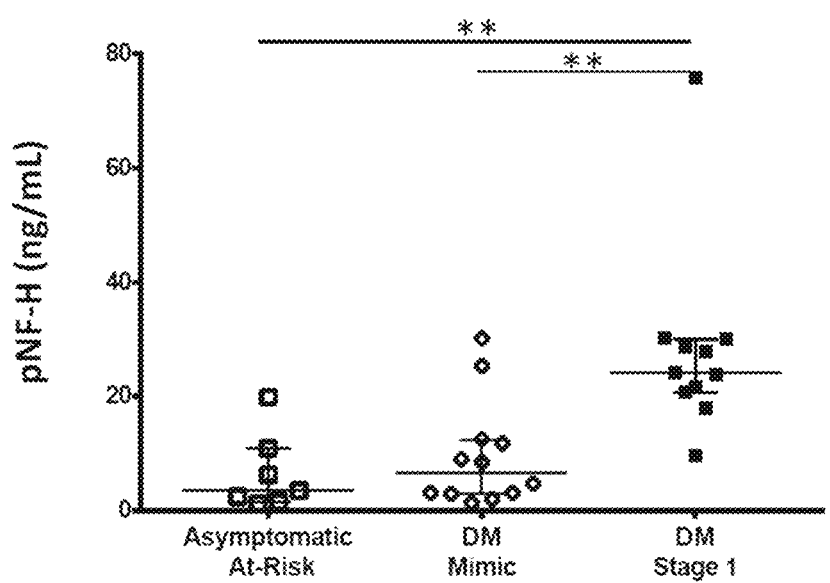

As shown in FIG. 5A, FIG. 5B, and FIG. 5C, pNF-H is increased in the CSF of DM-affected dogs. FIG. 5A shows that the median CSF pNF-H is increased in DM-affected dogs at all disease stages (Stage 1, n=10, p<0.05; Stage 2, n=13, p<0.0001; Stage 3, n=14, p<0.001; Stage 4 n=9, p<0.01) as compared to normal dogs (Comparisons based on a Kruskal-Wallis ANOVA on Ranks with post hoc Dunn's method; bars represent group median and interquartile range). FIG. 5B show that there is no correlation between single time-point CSF pNF-H concentration and DM disease stage (p=0.4050). FIG. 5C suggests that pNF-H may be a useful biomarker of disease progression as CSF pNF-H concentration increases over time in longitudinal paired samples from DM-affected dogs.

Significant differences in pNF-H results between treated and non-treated groups will provide a quantifiable measure in DM-affected dogs.

Example 12. In Vivo Study in DM-Affected Dogs

In order to study the therapeutic efficacy of AAV targeting SOD1, DM dogs are dosed intrathecally (CM and lumbar) with AAV SOD1 constructs, produced either by baculoviral or triple transfection production methods. Groups of 5 dogs will be used for this study (n=3 for dosing with AAV and n=2 for vehicle). In order to be included in this study, animals will need to be in an early stage of DM, undergo a NSF health screen, have normal CSF levels, a normal EMG, undergo a NSF T-L spinal cord MRI, have A/A genotype, and/or have AAV natural antibodies of less than 1:10. Prior to administration of the AAV or vehicle only, baseline fluid samples will be collected and the animals will be administered an immunosuppressant.

Toxicology and a longitudinal study will be conducted for approximately 12 months (can be extended) and then the animals will be euthanized. The toxicology study will include, but is not limited to, a physical exam, CBC levels, blood biochemistry analysis, urinalysis, and/or CSF analysis. The longitudinal study will include, but is not limited to, neurologic exams, video gait scoring, CSF pNF-H levels, collection and storage (optimally at −80° C.) of CSF, serum, and urine samples. An exemplary screening chart is shown below as Table 33.

TABLE 33

Analysis Timeline

| Analysis Conducted/ Sample Collected | Evaluation for Entry into Study | Day 0 | Month 1, 3, 6, 9, 12 | Every 3 months recheck until end of study | End of Study |
|---|---|---|---|---|---|
| Physical and Neuro Exams | X | X | X | X | X |
| Video-record Gait | X | X | X | X | X |
| CBC | X | X | X | | X |
| Chemistry Panel | X | X | X | | X |
| Urinalysis | X | X | X | | X |
| Thoracic Radiographs | X | | | | |
| Abdominal Ultrasound | X | | | | |
| MRI Spinal Cord | X | | | | |
| CSF Collection (Analysis/Store) | X | X | X | | X |
| Serum, Plasma Collect (Store) | X | X | X | | X |
| AAV Titers | X | | | | |

It is expected that AAV treated animals will have an extension of median time from onset to non-ambulatory state and a stabilized to lower CSF pNF-H level.

Equivalents and Scope

Those skilled in the art will recognize, or be able to ascertain, using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

We claim:

1. A modulatory polynucleotide which interferes with expression of a superoxide dismutase 1 (SOD1) gene, the modulatory polynucleotide comprising a sense strand sequence and an antisense strand sequence of an siRNA duplex, wherein each of the sense strand sequence and each of the antisense strand sequence is 30 nucleotides or less in length, and wherein
   (a) the sense strand sequence comprises the nucleotide sequence of SEQ ID NO: 25; and
   (b) the antisense strand sequence comprises the nucleotide sequence of SEQ ID NO: 7.

2. The modulatory polynucleotide of claim 1, wherein the nucleotide sequence encoding the sense strand sequence comprises the nucleotide sequence of SEQ ID NO: 83, and wherein the nucleotide sequence encoding the antisense strand sequence comprises the nucleotide sequence of SEQ ID NO: 104.

3. The modulatory polynucleotide of claim 1, wherein the sense strand sequence and the antisense strand sequence are, independently, 21 nucleotides in length.

4. The modulatory polynucleotide of claim 1, wherein at least one of the sense strand sequence and the antisense strand sequence comprise a 3' overhang of at least 1 or 2 nucleotides.

5. An adeno-associated virus (AAV) viral genome comprising a nucleic acid sequence positioned between two inverted terminal repeats (ITRs), wherein said nucleic acid sequence encodes the modulatory polynucleotide of claim 1.

6. A recombinant adeno-associated virus (AAV) comprising the AAV viral genome of claim 5, and an AAV capsid protein.

7. The recombinant AAV of claim 6, wherein the AAV capsid protein is an AAVrh10 capsid protein or a variant thereof, an AAV5 capsid protein or a variant thereof, or an AAV9 capsid protein or a variant thereof.

8. A pharmaceutical composition comprising the recombinant AAV of claim 6, and a pharmaceutically acceptable excipient.

9. The modulatory polynucleotide of claim 1, which further comprises:
   (a) a 5' flanking region;
   (b) a loop region; and/or
   (c) a 3' flanking region.

10. The modulatory polynucleotide of claim 9, wherein:
   (i) the 5' flanking region comprises the nucleotide sequence of SEQ ID NO: 47;
   (ii) the loop region comprises the nucleotide sequence of SEQ ID NO: 50; and
   (iii) the 3' flanking region comprises the nucleotide sequence of SEQ ID NO: 54.

11. The modulatory polynucleotide of claim 1, wherein the nucleotide sequence encoding the modulatory polynucleotide comprises the nucleotide sequence of SEQ ID NO: 62.

12. The AAV viral genome of claim 5, which further comprises:
   (i) a promoter;
   (ii) an enhancer;
   (iii) an intron;
   (iv) a filler sequence; and/or
   (v) a poly A signal sequence.

13. The AAV viral genome of claim 12, wherein the promoter comprises an H1 promoter.

14. A cell comprising the AAV viral genome of claim 5.

15. The cell of claim 14, wherein the cell is an insect cell, a mammalian cell, or a bacterial cell.

16. A vector comprising the AAV viral genome of claim 5.

* * * * *